(12) United States Patent
Tseng et al.

(10) Patent No.: US 11,078,259 B2
(45) Date of Patent: Aug. 3, 2021

(54) METHODS AND COMPOSITIONS FOR PROMOTING THERMOGENIC POTENTIAL

(71) Applicant: Joslin Diabetes Center, Inc., Boston, MA (US)

(72) Inventors: Yu-Hua Tseng, Newton, MA (US); Matthew Lynes, Brookline, MA (US); Ruidan Xue, Shanghai (CN)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 15/579,885

(22) PCT Filed: Jun. 3, 2016

(86) PCT No.: PCT/US2016/035669
§ 371 (c)(1),
(2) Date: Dec. 5, 2017

(87) PCT Pub. No.: WO2016/196895
PCT Pub. Date: Dec. 8, 2016

(65) Prior Publication Data
US 2018/0362623 A1    Dec. 20, 2018

Related U.S. Application Data

(60) Provisional application No. 62/171,619, filed on Jun. 5, 2015.

(51) Int. Cl.
*C07K 16/18* (2006.01)
*A61K 35/35* (2015.01)
*A61K 38/17* (2006.01)
*A61K 38/46* (2006.01)
*C12N 5/077* (2010.01)
*C07K 14/705* (2006.01)
*A61K 35/545* (2015.01)
(Continued)

(52) U.S. Cl.
CPC .......... *C07K 16/18* (2013.01); *A61K 31/7088* (2013.01); *A61K 35/35* (2013.01); *A61K 35/545* (2013.01); *A61K 38/177* (2013.01); *A61K 38/1719* (2013.01); *A61K 38/1761* (2013.01); *A61K 38/1796* (2013.01); *A61K 38/465* (2013.01); *C07K 14/705* (2013.01); *C12N 5/0653* (2013.01); *C12N 15/11* (2013.01); *C12Q 1/6883* (2013.01); *C12Y 301/03048* (2013.01); *G01N 33/5091* (2013.01); *C07K 2317/75* (2013.01); *C07K 2317/76* (2013.01); *C12N 2310/20* (2017.05); *C12N 2800/80* (2013.01); *C12Q 2600/118* (2013.01)

(58) Field of Classification Search
CPC .. C07K 16/18; C07K 14/705; C07K 2317/75; C07K 2317/76; C12Q 1/6883; C12Q 2600/118; G01N 33/5091; A61K 31/7088; A61K 38/1761; A61K 35/545; A61K 38/465; A61K 38/1796; A61K 38/177; A61K 38/1719; A61K 35/35; C12N 15/11; C12N 5/0653; C12N 2310/20; C12N 2800/80; C12Y 301/03048
See application file for complete search history.

(56) References Cited

U.S. PATENT DOCUMENTS 5,399,163 A * 3/1995 Peterson .................. A61M 5/30
 604/140
5,750,370 A * 5/1998 Li ...................... C07K 14/70571
 435/252.3
(Continued)

FOREIGN PATENT DOCUMENTS

WO WO-2005103681 A1 * 11/2005 ........... G01N 33/566
WO WO-2006063465 A1 * 6/2006 ............... A61P 7/04
(Continued)

OTHER PUBLICATIONS

Onate, B et al. Stem cells isolated from adipose tissue of obese patients show changes in their transcriptomic profile that indicate loss in stemcellness and increased commitment to an adipocyte-like phenotype. BMC Genomics. 2013. 14: 625. 12 pages. (Year: 2013).*
(Continued)

*Primary Examiner* — David W Berke-Schlessel
*Assistant Examiner* — Susan E. Fernandez
(74) *Attorney, Agent, or Firm* — Womble Bond Dickinson (US) LLP; Cristin Cowles; Kevin A. Piala

(57) ABSTRACT

The invention provides methods and compositions relating to molecular targets identified as being capable of increasing or decreasing thermogenic potential in cells, including pre-adipocytes. Included in the invention are methods and compositions relating to inhibiting or suppressing the activity of an uncoupling protein 1 (UCP1) negative regulator, such as cardiac actin 1 (ACTC1), somatostatin receptor 1 (SSTR1), FAT atypical cadherin 1 (FAT1), and protein tyrosine phosphatase receptor type B (PTPRB). Also included in the invention are methods and compositions relating to activating a UCP1 positive regulator, such as phosphatidylinositol-3,4,5-triphosphate-dependent Rac exchange factor 1 (PREX1), cortactin binding protein 2 (CTTNBP2), doublesex and mab-3-related transcription factor-like family A1 (DMRTA1), and endothelin receptor type B (ENDRB). The invention also provides methods and compositions relating to enrichment of cells having thermogenic potential based on cell surface markers, e.g., CD29, identified as being predictive of such.

5 Claims, 28 Drawing Sheets
Specification includes a Sequence Listing.

(51) Int. Cl.
  *A61K 31/7088* (2006.01)
  *C12N 15/11* (2006.01)
  *C12Q 1/6883* (2018.01)
  *G01N 33/50* (2006.01)

(56) References Cited

U.S. PATENT DOCUMENTS

| | | | |
|---|---|---|---|
| 2006/0223826 A1* | 10/2006 | Abe | C07D 209/20 514/254.09 |
| 2010/0021900 A1* | 1/2010 | Gong | G01N 33/6863 435/6.11 |
| 2011/0104133 A1 | 5/2011 | Tseng et al. | |
| 2012/0129711 A1* | 5/2012 | Mosser | C12Q 1/6886 506/9 |
| 2013/0123231 A1* | 5/2013 | Harriman | A61P 35/00 514/210.18 |
| 2013/0331433 A1* | 12/2013 | Thibonnier | C12N 15/113 514/44 A |
| 2015/0011429 A1 | 1/2015 | Zhang et al. | |

FOREIGN PATENT DOCUMENTS

| | | |
|---|---|---|
| WO | 2011/126790 A1 | 10/2011 |
| WO | 2015/171928 A2 | 11/2015 |

OTHER PUBLICATIONS

International Search Report and Written Opinion, issued in corresponding International Application No. PCT/US2016/035669 dated Dec. 8, 2016; 11 pages.

International Preliminary Report on Patentability, issued in corresponding International Patent Application No. PCT/US2016/035669 dated Dec. 5, 2017; 8 pages.

Onate et al., "Stem cells isolated from adipose tissue of obese patients show changes in their transcriptomic profile that indicate loss in stemcellness and increased commitment to an adipocyte-lke phenotype," BMC Genomics, Sep. 16, 2013 (Sep. 16, 2013), vol. 14, No. 625, pp. 1-12, entire document.

Xue et al., "Clonal analyses and gene profiling identify genetic biomarkers of human brown and white preadipocyte thermogenic potential," Nat Med, Jun. 15, 2015 (Jun. 15, 2015), vol. 21, No. 7, pp. 760-768, entire document.

* cited by examiner

| | Nile Red Staining | | |
|---|---|---|---|
| Adipogenic Capacity | Nile Red Score | % of lipid laden cells | Microscope picture |
| − | <0.2 | <20% | |
| + | 0.2-0.4 | 20-70% | |
| ++ | >0.4 | >70% | |

FIG. 9

| UCP1 level | Luciferase Score | % of GFP+ cells | Luciferase Activity | |
|---|---|---|---|---|
| | | | Microscope picture | |
| | | | GFP | Merge |
| Negative | <10 | <5% |  |  |
| Low | 10-50 | 5-30% |  |  |
| Medium | 50-100 | 30-70% |  |  |
| High | >100 | >70% |  |  |

METHODS AND COMPOSITIONS FOR PROMOTING THERMOGENIC POTENTIAL

RELATED APPLICATIONS

This application is a U.S. national stage filing under 35 U.S.C. § 371(c), of International Application No. PCT/US2016/035669, filed on Jun. 3, 2016, which in turn claims priority to U.S. Provisional Application No. 62/171,619, filed Jun. 5, 2015. The entire contents of the foregoing applications are incorporated herein by reference.

GOVERNMENT RIGHTS

This invention was made with Government support under Grant Nos. RO1 DK077097 and P30 DK036836 awarded by the National Institutes of Health. The Government has certain rights in the invention.

BACKGROUND OF THE INVENTION

In mammals, there are two functionally distinct types of fat tissue: white adipose tissue (WAT), which is specialized for energy storage, and brown adipose tissue (BAT), which dissipates energy for thermogenesis (Cannon B. et al., *Physiol. Rev.* 84:277-359, 2004; Schulz T. J. et al., *Biochem J* 453:167-178, 2013) via uncoupling protein 1(UCP1). In addition to the classical brown adipocytes, which form a discrete depot and exert a high level of basal thermogenic capacity, UCP1-positive "beige" or "brite" adipocytes can be recruited within WAT upon chronic cold or β-adrenergic stimulation (Guerra C. et al., *J. Clin. Invest.* 102:412-420, 1998; Petrovic N. et al., *J. Biol. Chem.* 285:7153-7164, 2010; Harms, M. & Seale, P. *Nat Med* 19, 1252-1263, 2013; and Nedergaard J. et al., *Cell. Metab.* 13:238-240, 2011).

Owing to the immense capacity of BAT to combust fuels for heat production (Bartelt, A., et al. *Nat Med* 17, 200-205, 2011; Stanford, K. I., et A. *J Clin Invest* 123, 215-223, 2013) and the presence of BAT in adult humans (Nedergaard, J. et al., *Am J Physiol Endocrinol Metab* 293, E444-E452, 2007; Cypess, A. M., et al. *N Engl J Med* 360, 1509-1517, 2009; van Marken, L. W., et al. *N Engl J Med* 360, 1500-1508, 2009; Virtanen, K. A., et al. *N Engl J Med* 360, 1518-1525, 2009; Saito, M., et al. *Diabetes* 58, 1526-1531, 2009; Zingaretti, M. C., et al. *Faseb J* 23, 3113-3120, 2009), increasing the amount or activity of brown/beige fat has been considered as an appealing approach for the treatment or prevention of obesity and related metabolic disorders. Indeed, several lines of evidence using rodent models have demonstrated that activation of brown/beige fat can promote energy expenditure, reduce adiposity and protect from diet-induced obesity (Harms, M. & Seale, P. *Nat Med* 19, 1252-1263, 2013; Nedergaard, J. & Cannon, B. *Cell Metab* 20, 396-407, 2014; Himms-Hagen, J., et al. *Am J Physiol* 266, R1371-R1382, 1994). In humans, BAT mass or activity is inversely correlated to body mass index and percent body fat (Cypess, A. M., et al. *N Engl J Med* 360, 1509-1517, 2009; van Marken, L. W., et al. *N Engl J Med* 360, 1500-1508, 2009; Virtanen, K. A., et al. *N Engl J Med* 360, 1518-1525, 2009). Cold exposure in humans can elevate BAT volume and activity and increase energy expenditure, pointing towards a therapeutic potential of BAT in humans (Yoneshiro, T., et al. *J Clin Invest* 123, 3404-3408, 2013; van der Lans, A. A., et al. *J Clin Invest* 123, 3395-3403, 2013).

Recent data indicate that the neck, clavicular and spinal cord regions of adult humans contain significant deposits of UCP1-positive adipocytes (Wu, J., et al. *Cell* 150, 366-376, 2012; Cypess, A. M., et al. *Nat Med* 19, 635-639, 2013; Lidell, M. E., et al. *Nat Med* 19, 631-634, 2013; Jespersen, N. Z., et al. *Cell Metab* 17, 798-805, 2013). The presence of brown, beige, and white adipocytes as well as perhaps other unidentified adipose cell types highlights the heterogeneity of adipose tissue depots, which potentially links to their diverse functions in energy metabolism. Both inter-subject differences and various cellular compositions within a fat tissue contribute to the heterogeneity of human BAT and affect thermogenic potential. In rodents, lineage tracing and cell sorting analyses demonstrate that the various types of fat cells arise from discrete pools of progenitors, which express distinct molecular markers (Wu, J., et al. *Cell* 150, 366-376, 2012; Schulz, T. J., et al. *Proc Natl Acad Sci USA* 108, 143-148, 2011; Lee, Y. H., et al. *Cell Metab* 15, 480-491, 2012; Berry, R. & Rodeheffer, *Nat Cell Biol* 15, 302-308, 2013; Wang, W., et al. *Proc Natl Acad Sci USA* 111, 14466-14471, 2014). However, whether these markers identified in murine cells can unambiguously define different types of human adipose progenitors is currently unknown.

Given the unique property of BAT to be able to mediate energy expenditure and thermogenesis, markers that can predict thermogenic potential may be able to provide new avenues for the development of therapies to treat obesity and other metabolic disorders. Further, there is a need in the art for methods for identifying cells with thermogenic potential and genes for modulating the thermogenic potential for use in therapies for obesity, metabolic disorders, diabetes and related disorders.

SUMMARY OF THE INVENTION

The present invention is based, at least in part, on the finding that certain molecular targets that regulate the expression level of uncoupling protein 1 (UCP1) can increase or decrease thermogenic potential in thermogenically competent cells, such as preadipocytes. Thus, the invention includes in one embodiment methods and compositions for inhibiting or suppressing the activity of an UCP1 negative regulator e.g. ACTC1, SSTR1, FAT1, PTPRB, in order to promote energy consumption. Another embodiment of the invention includes methods and compositions for activating a UCP1 positive regulator, e.g. PREX1, CTTNBP2, DMRTA1, and ENDRB to promote energy consumption. Such energy consumption—usually attributed to BAT but determined herein to be possible in preadipocytes and WAT—can be used therapeutically to treat metabolic disorders, such as obesity, diabetes, or metabolic syndrome. In addition, in a further embodiment, the invention includes methods and compositions relating to identifying cells having thermogenic potential based on cell surface markers e.g., CD29.

One aspect of the invention provides methods of promoting thermogenic capacity in a thermogenically competent cell, the method comprising contacting the thermogenically competent cell with an inhibitor of a uncoupling protein 1 (UCP1) negative regulator, such that thermogenic capacity is promoted, wherein the UCP1 negative regulator is selected from the group consisting of cardiac actin 1 (ACTC1), somatostatin receptor 1 (SSTR1), FAT atypical cadherin 1 (FAT1) and protein tyrosine phosphatase receptor type B (PTPRB), or combinations thereof. Other examples of UCP1 negative regulators are described in Table 4.

In one embodiment of the invention, the inhibitor of the UCP1 negative regulator is selected from the group consisting of a small molecule inhibitor, an antagonist antibody, or antigen-binding fragment thereof, and an inhibitory nucleic acid targeting the UCP1 negative regulator. In another embodiment, the inhibitory nucleic acid targeting the UCP1 negative regulator is a small interfering RNA (siRNA) that binds to an mRNA encoding the UCP1 negative regulator. In another embodiment, the inhibitory nucleic acid targeting the UCP1 negative regulator is associated with the CRISPR/Cas system which binds the UCP1 negative regulator.

One aspect of the invention provides methods of promoting thermogenic capacity in a thermogenically competent cell, the method comprising contacting the thermogenically competent cell with either an activator of a uncoupling protein 1 (UCP1) positive regulator or a UCP1 positive regulator, such that thermogenic capacity is promoted, wherein the UCP1 positive regulator is selected from the group consisting of phosphatidylinositol-3,4,5-triphosphate-dependent Rac exchange factor 1 (PREX1), cortactin binding protein 2 (CTTNBP2), doublesex and mab-3-related transcription factor-like family A1 (DMRTA1) and endothelin receptor type B (ENDRB), or combinations thereof. Other examples of UCP1 positive regulators are described in Table 4.

In one embodiment of the invention, the activator of the UCP1 positive regulator is a small molecule activator or an agonist antibody. In another embodiment, the method comprises contacting the cell with the UCP1 positive regulator protein or a nucleic acid molecule encoding the UCP1 positive regulator. In a further embodiment, the activator of the UCP1 positive regulator is a polynucleotide associated with the CRISPR/Cas system which binds the UCP1 positive regulator and activates the transcription of the UCP1 positive regulator.

In a further embodiment, the invention provides a method of determining whether a human subject has or is at risk of having a metabolic disorder or obesity, said method comprising comparing a pre-determined level of a UCP1 negative regulator from a sample comprising preadipocytes from the subject, with a known standard level of the UCP1 negative regulator associated with the metabolic disorder or obesity; and assessing whether the subject's UCP1 negative regulator level is equal to or greater than the known standard level of the UCP1 negative regulator, wherein an equal or greater level of UCP1 negative regulator level from the subject relative to the known standard level indicates that the subject has or is at risk of having a metabolic disorder or obesity.

In a further embodiment, the invention provides a method of determining whether a human subject has or is at risk of having a metabolic disorder or obesity, said method comprising comparing a pre-determined level of a UCP1 positive regulator from a sample comprising preadipocytes from the subject, with a known standard level of the UCP1 positive regulator associated with a subject who is not obese or has a metabolic disorder; and assessing whether the subject's UCP1 negative regulator level is equal to or greater than the known standard level of the UCP1 negative regulator, wherein an equal or greater level of UCP1 positive regulator level from the subject relative to the known standard level indicates that the subject does not have or is not at risk of having a metabolic disorder or obesity.

In one embodiment, the thermogenic capacity is promoted by increasing UCP1 gene expression. In another embodiment, the thermogenic capacity is promoted by increasing brown adipocyte tissue (BAT) or cells.

In one embodiment, the thermogenically competent cell comprises a preadipocyte. In another embodiment, the thermogenically competent cell comprises a brown preadipocyte. In yet another embodiment, the thermogenically competent cell comprises a white preadipocyte.

In one embodiment, the method is in vitro. In another embodiment, the method is in vivo. In another embodiment, the method is ex vivo. In a particular embodiment, the method is in vivo in a human subject.

In one embodiment, the UCP1 negative regulator is selected from the group consisting of human ACTC1, human SSTR1, human FAT1, and human PTPRB. Other examples of UCP1 negative regulators are described in Table 4.

In one embodiment, the UCP1 positive regulator is selected from the group consisting of human PREX1, human CTTNBP2, human DMRTA1, and human ENDRB. Other examples of UCP1 positive regulators are described in Table 4.

In certain embodiments, the method of the invention includes use of a UCP1 negative regulator and a UCP1 positive regulator to achieve increased thermogenesis is a cell or subject.

One aspect of the invention provides methods of treating a human subject having a disorder that would benefit from metabolic control, said method comprising administering a therapeutically effective amount of an inhibitor of a UCP1 negative regulator to the human subject, such that the disorder is treated, wherein the UCP1 negative regulator is selected from the group consisting of ACTC1, SSTR1, FAT1, and PTPRB.

Another aspect of the invention provides methods of decreasing the weight of a human subject, said method comprising administering a therapeutically effective amount of an inhibitor of a UCP1 negative regulator to the human subject, such that the weight of the human subject is decreased, wherein the UCP1 negative regulator is selected from the group consisting of ACTC1, SSTR1, FAT1, and PTPRB.

In one embodiment of the invention, the inhibitor of the UCP1 negative regulator is selected from the group consisting of a small molecule inhibitor, an antagonist antibody, and an inhibitory nucleic acid targeting the UCP1 negative regulator. In another embodiment, the inhibitory nucleic acid targeting the UCP1 negative regulator is a small interfering RNA (siRNA) that binds to an mRNA encoding the UCP1 negative regulator. In another embodiment, the inhibitory nucleic acid targeting the UCP1 negative regulator is associated with the CRISPR/Cas system which binds the UCP1 negative regulator.

In one embodiment, the methods and compositions of the invention are useful for increasing UCP1 gene expression. In another embodiment, the methods and compositions of the invention are useful for increasing UCP1 protein expression.

One aspect of the invention provides methods of treating a human subject having a disorder that would benefit from metabolic control, said method comprising administering a therapeutically effective amount of either an activator of a UCP1 positive regulator or a UCP1 positive regulator to the human subject, such that the disorder is treated, wherein the UCP1 positive regulator is selected from the group consisting of ACTC1, SSTR1, FAT1, and PTPRB.

Another aspect of the invention provides methods of decreasing the weight of a human subject, said method comprising administering a therapeutically effective amount of an inhibitor of either an activator of a UCP1 positive regulator or a UCP1 positive regulator to the human subject, such that the weight of the human subject is decreased, wherein the UCP1 positive regulator is selected from the group consisting of ACTC1, SSTR1, FAT1, and PTPRB.

In one embodiment of the invention, the activator of the UCP1 positive regulator is a small molecule activator or an agonist antibody. In a further embodiment, the method comprises administering an UCP1 positive regulator protein or administering a nucleic acid molecule encoding any UCP1 positive regulator. In a further embodiment, the activator of the UCP1 positive regulator is a polynucleotide associated with the CRISPR/Cas system which binds the UCP1 positive regulator and activates the transcription of the UCP1 positive regulator. In a particular embodiment, the nucleic acid molecule is administered to the subject via a viral vector.

In one embodiment of the invention, the inhibitor of the UCP1 negative regulator, the activator of the UCP1 positive regulator, and/or the UCP1 positive regulator is administered to adipose tissue of the human subject.

In one embodiment of the invention, the disorder is selected from the group consisting of a disease that would benefit from glucose control, a disease that would benefit from weight control, a disease that would benefit from cholesterol control, and a fatty acid metabolism disorder. In another embodiment, the disease that would benefit from glucose control is selected from the group consisting of insulin resistance, diabetes, and hyperglycemia. In yet another embodiment, the disease that would benefit from weight control is selected from the group consisting of liver disease, dyslipidemia, a glycemic control disorder, cardiovascular disease and obesity. In one embodiment, the disease that would benefit from cholesterol control is heart disease. In a particular embodiment, the disorder is metabolic syndrome.

In one embodiment of the invention, the subject has, or is at risk of developing, insulin resistance or type 2 diabetes mellitus. In another embodiment, the subject is, or is at risk of becoming, obese. In yet another embodiment, the subject is human.

One aspect of the invention provides methods of selecting thermogenically competent precursor cells from a plurality of cells, the method comprising contacting said cells with a binding protein that binds CD29 and/or integrin alpha 10 (ITGA10), and selecting cells bound by the binding protein, thereby selecting thermogenically competent precursor cells.

In one embodiment of the invention, the binding protein is an anti-CD29 antibody, or antigen-binding portion thereof, or an anti-ITGA10 antibody, or antigen-binding portion thereof. In one embodiment, the cells are selected using fluorescence-activated-cell-sorting (FACS). In another embodiment, the plurality of cells is derived from white adipose tissue.

One aspect of the invention provides compositions of an enriched plurality of thermogenically competent cells, e.g., preadipocytes, comprising CD29 high (CD29$^{high}$) cells and/or integrin alpha 10 high (ITGA10$^{high}$) cells.

In one embodiment of the invention, the enriched plurality of thermogenically competent cells, e.g., preadipocytes, comprises at least about 20% CD29$^{high}$ cells and/or ITGA10$^{high}$ cells. In another embodiment, the enriched plurality of thermogenically competent cells comprises at least about 25% CD29$^{high}$ cells and/or ITGA10$^{high}$ cells. In yet another embodiment, the enriched plurality of thermogenically competent cells comprises over 30% CD29$^{high}$ cells and/or ITGA10$^{high}$ cells.

One aspect of the invention provides compositions of an enriched plurality of thermogenically competent cells, e.g., preadipocytes, comprising CD29 low (CD29$^{low}$) cells and/or integrin alpha 10 low (ITGA10$^{low}$) cells.

In one embodiment of the invention, the enriched plurality of thermogenically competent cells, e.g., preadipocytes, comprises 15% or less CD29$^{low}$ cells and/or ITGA10$^{low}$ cells. In another embodiment, the enriched plurality of thermogenically competent cells comprises 10% or less CD29$^{low}$ cells and/or ITGA10$^{low}$ cells. In yet another embodiment, the enriched plurality of thermogenically competent cells comprises 5% or less CD29$^{low}$ cells and/or ITGA10$^{low}$ cells. In a further embodiment, the enriched plurality of thermogenically competent cells comprises 1% or less CD29$^{low}$ cells and/or ITGA10$^{low}$ cells.

In one embodiment of the invention, the thermogenically competent cell is a preadipocyte. In another embodiment, the thermogenically competent cell is an embryonic stem cell. In yet another embodiment, the thermogenically competent cell is an inducible pluripotent stem cell. In one embodiment, the thermogenically competent cell is a fibroblast cell. In another embodiment, the thermogenically competent cell is a white adipocyte. In yet another embodiment, the thermogenically competent cell is a brown adipocyte. In another embodiment, the thermogenically competent cell is a beige adipocyte. In one embodiment of the invention, the preadipocyte is a brown preadipocyte. In another embodiment, the preadipocyte is a white preadipocyte.

One aspect of the invention provides methods of treating a metabolic disorder in a human subject, comprising administering the enriched plurality of cells as described herein to the human subject. In one embodiment of the invention, the disorder is selected from the group consisting of a disease that would benefit from glucose control, a disease that would benefit from weight control, a disease that would benefit from cholesterol control, and a fatty acid metabolism disorder. In a particular embodiment, the disease that would benefit from glucose control is selected from the group consisting of insulin resistance, diabetes, and hyperglycemia. In another embodiment, the disease that would benefit from weight control is selected from the group consisting of liver disease, dyslipidemia, a glycemic control disorder, cardiovascular disease and obesity. In yet another embodiment, the disease that would benefit from cholesterol control is heart disease. In a particular embodiment, the disorder is metabolic syndrome.

One aspect of the invention provides methods of treating a human subject who has, or is at risk of developing, insulin resistance or type 2 diabetes mellitus, comprising administering the enriched plurality of cells as described herein to the human subject.

One aspect of the invention provides methods of treating a human subject who is, or is at risk of becoming, obese, comprising administering the enriched plurality of cells as described herein to the human subject.

One aspect of the invention provides methods of identifying a compound which modulates thermogenic capacity, the method comprising contacting the compound with the enriched plurality of cells as described herein and determining the thermogenic capacity of the enriched plurality of cells.

One aspect of the invention provides methods of predicting whether a human subject has or is at risk of having a metabolic disorder or obesity, said method comprising contacting a sample comprising adipocytes from said human subject with a binding protein that binds CD29 and/or a binding protein that binds integrin alpha 10 (ITGA10), and determining the level of adipocytes bound by the binding protein(s), wherein either a level of adipocytes bound by the binding protein which correlates with a known standard for a subject who does not have or is not at risk of having a metabolic disorder or obesity indicates that the subject is not at risk for having a metabolic disorder or obesity, or, alternatively, a level of adipocytes bound by the binding protein which correlates with a known standard for a subject who has or is at risk of having a metabolic disorder or obesity indicates that the subject is at risk for having a metabolic disorder or obesity.

BRIEF DESCRIPTION OF THE DRAWINGS

FIG. 2A depicts light microscopic images of immortalized human WAT progenitors (hWAT-SVF) and human BAT progenitors (hBAT-SVF) at day 0 and day 18 from 4 subjects (Sub1, Sub2, Sub3 and Sub4). Immortalized progenitor cells were grown to confluence in growth medium for 6 days and then incubated in adipogenic induction medium for 12 days. Lipid droplets in differentiated cells at day 18 were stained with Oil Red O. Representative images from three independent experiments are shown. Scale bar, 100 μm. FIGS. 2B and 2C depict quantitative reverse transcription polymerase chain reaction (Q-RT-PCR) analysis for UCP1 and LEPTIN mRNA expression in fully differentiated adipocytes from hWAT-SVF and hBAT-SVF (referred as hWA and hBA, respectively) of 4 subjects (Sub1 hWA; Sub1 hBA; Sub2 hWA; Sub2 hBA; Sub3 hWA; Sub3 hBA; Sub4 hWA; Sub4 hBA). Data are presented as fold changes relative to Sub1 hWA (mean±s.e.m., n=3; RQ, relative quotient). Asterisks depict statistically significant differences between hWA and hBA groups in each subject. Two-tailed Student's t-test was used to determine P values (*P<0.05, P<0.01, *P<0.001). A representative experiment from a total of three independent studies is shown. FIG. 2D depicts Western blot analysis of UCP1 protein level in hWA and hBA differentiated from progenitors of Sub1 and Sub2. α-Tubulin serves as a loading control. Representative blots of four independent experiments are shown. FIG. 2E depicts oxygen consumption rate (OCR) measured by the Seahorse extracellular flux analyzer in hWA and hBA from Sub1 (Left) and Sub2 (Right). Equal numbers of progenitors were plated and differentiated. Quantifications of OCR in the absence (Basal respiration, Basal Res.) and presence of oligomycin (Proton Leak) or FCCP (Maximal respiration, Max. Res.) are shown. The same numbers of cells were used and data are presented as mean±s.e.m. (n=10). Asterisks depict statistically significant differences between hWA and hBA groups in each subject (two-tailed Student's t-test; P<0.05, P<0.01, *P<0.001). A representative experiment from three independent studies is shown. FIG. 2F depicts glucose uptake measured using $^3$H 2-deoxy-glucose in hWA and hBA from Sub1 (Left) and Sub2 (Right). The cells were stimulated with 100 nM insulin for 30 min (Ins100) or unstimulated (Ins0) before assay. The same numbers of cells were used in the assay and data were normalized to protein content. Data are presented as mean±s.e.m. (n=3; two-tailed Student's t-test; *P<0.05, P<0.01, *P<0.001). A representative experiment from three independent studies is shown. FIG. 2G depicts fatty acid uptake (FAU) and fatty acid oxidation (FAO) measured using $^{14}$C-palmitic acid in hWA and hBA from Sub1 (Left) and Sub2 (Right). The same numbers of cells were used in the assay and data were normalized to protein content. Data are presented as a fold change compared to hWA (mean±s.e.m., n=3; two-tailed Student's t-test; *P<0.05, P<0.01, *P<0.001). A representative experiment from two independent studies is shown. FIG. 2H depicts Q-RT-PCR analysis for UCP1 and PPARγ mRNA expression in hWA and hBA from Sub1 (Left) and Sub2 (Right). hWAT-SVF and hBAT-SVF progenitors were pre-treated with BMP7 or vehicle (Veh) for 6 days and then differentiated into mature adipocytes for another 12 days. Data are presented as fold changes compared to vehicle-hWA for each subject (mean±s.e.m., n=3). Asterisks depict statistically significant differences between Veh and BMP7 groups (two-tailed Student's t-test; N.S., not significant; *P<0.05, P<0.01, *P<0.001). A representative experiment from a total of three independent studies is shown.

Figure 6A:
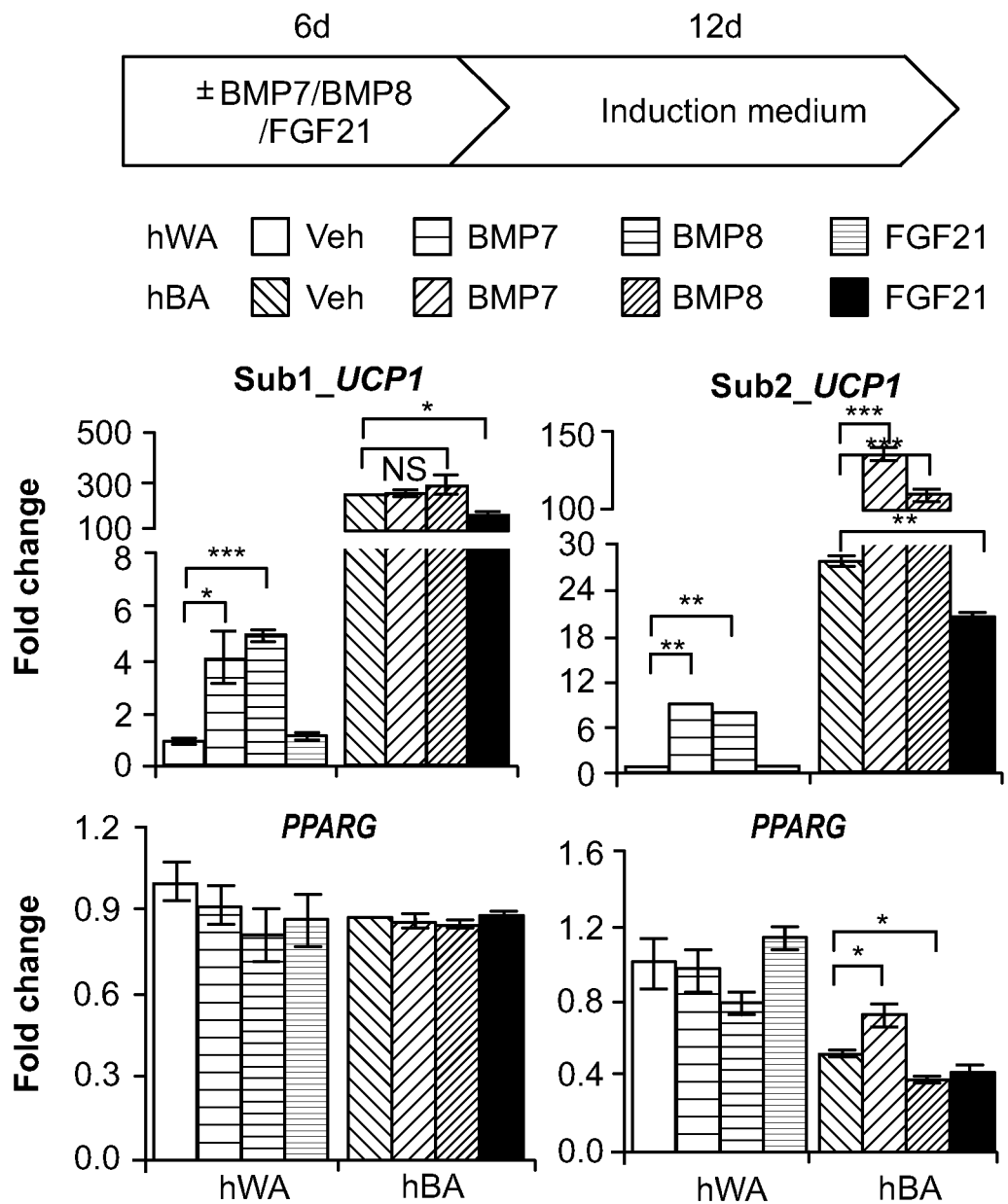
FIG. 6A depicts Q-RT-PCR analysis for UCP1 and PPARγ mRNA expression in differentiated hWA and hBA from Sub1 and Sub2 that were pre-treated with 3.3 nM BMP7, 3.3 nM BMP8 and 50 nM FGF21 for 6 days and then differentiation into mature adipocytes. Data are presented as a fold change compared to vehicle (Veh) treatment of hWA in each subject (mean±s.e.m., n=3; two-tailed Student's t-test; *P<0.05, P<0.01, *P<0.001). A representative experiment from a total of three independent studies is shown.
Figure 6B:
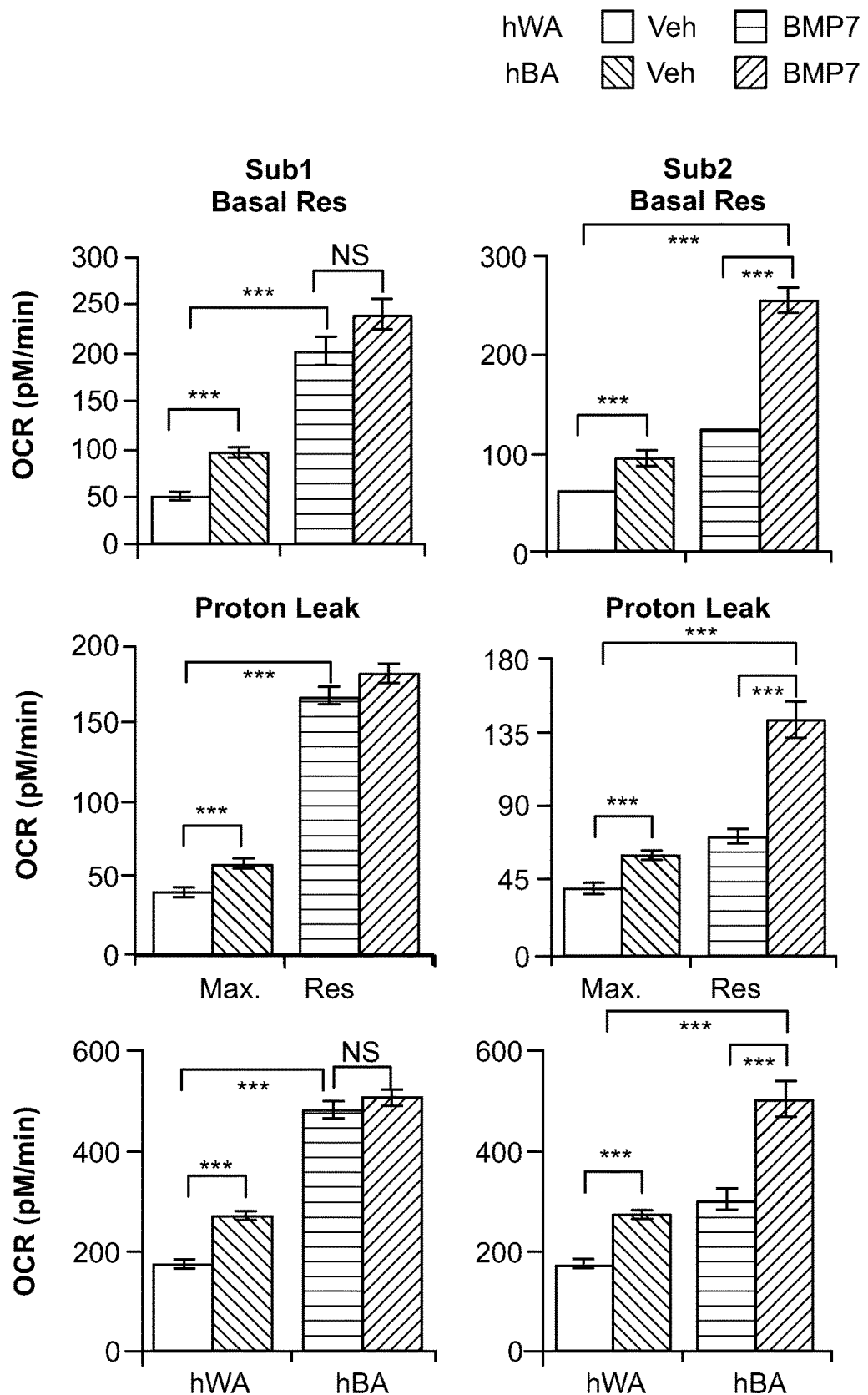
Figure 6C:
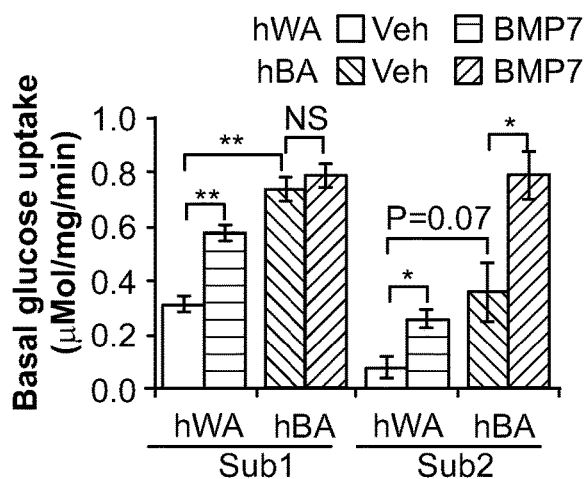
Figure 6D:
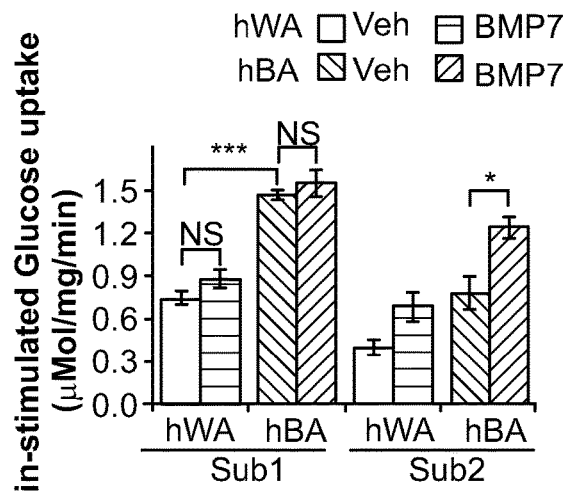
Figure 6E:
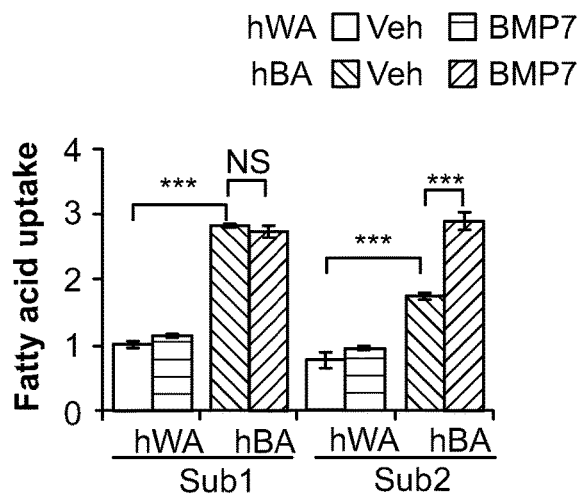
Figure 6F:
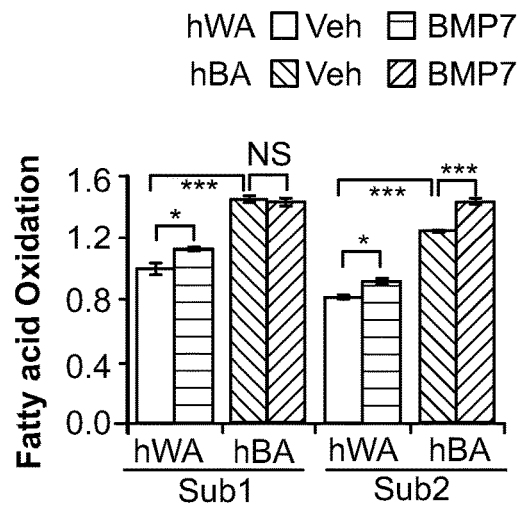
Figure 6G:
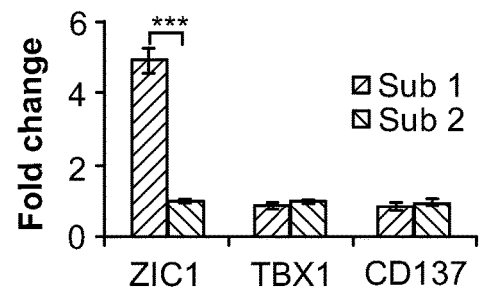

FIG. 6B depicts OCR assayed using the Seahorse extracellular flux analyzer in differentiated hWA and hBA from Sub1 and Sub2 that were pre-treated with 3.3 nM BMP7 or vehicle (Veh) for 6 days and then differentiation into mature adipocytes. Equal numbers of progenitors were plated and differentiated. Quantification of OCR in the absence (Basal Res.) and presence of oligomycin (Proton Leak) or FCCP (Max. Res.) are shown. Data are presented as mean±s.e.m. (n=10; two-tailed Student's t-test; *P<0.05, P<0.01, *P<0.001). A representative experiment from a total of two independent studies is shown. Data are represented in the same order as appeared in the legend. FIGS. 6C and 6D depict measurement of glucose uptake using $^3$H 2-Deoxy-Glucose in differentiated hWA and hBA from Sub1 and Sub2 that were pre-treated with 3.3 nM BMP7 or vehicle (Veh) for 6 days and then differentiation into mature adipocytes. The cells were stimulated in the absence (shown on FIG. 6C) and presence (shown on FIG. 6D) of 100 nM insulin for 30 min before assay. The same number of cells was used in the assay and data was normalized to protein content. Data are presented as mean±s.e.m. (n=3; two-tailed Student's t-test; *P<0.05, P<0.01, *P<0.001). A representative experiment from a total of three independent studies is shown. FIGS. 6E and 6F depict determination of fatty acid uptake (FIG. 6E) and fatty acid oxidation (FIG. 6F) using $^{14}$C-palmitic acid in differentiated hWA and hBA from Sub1 and Sub2 that were pre-treated with 3.3 nM BMP7 or vehicle (Veh) for 6 days and then differentiation into mature adipocytes. The same number of cells was used in the assay and data was normalized to protein content. Data are presented as a fold change compared to vehicle (Veh) treatment of Sub1 hWA (mean±s.e.m., n=3; two-tailed Student's t-test; *P<0.05, P<0.01, *P<0.001). A representative experiment from a total of two independent studies is shown. FIG. 6G depicts Q-RT-PCR analysis for ZIC1, TBX1 and CD137 expression in undifferentiated (Day 0) hBAT—SVF from 2 subjects. Data are presented as fold changes relative to subject 2 (mean±s.e.m., n=3). A representative experiment from a total of two independent studies is shown. Two-tailed Student's t-test was used to determine P values (*P<0.05, P<0.01, *P<0.001).

Figure 7A:
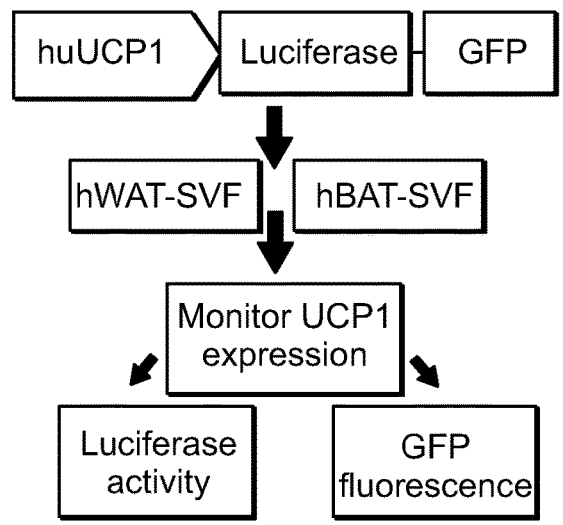
Figure 7B:
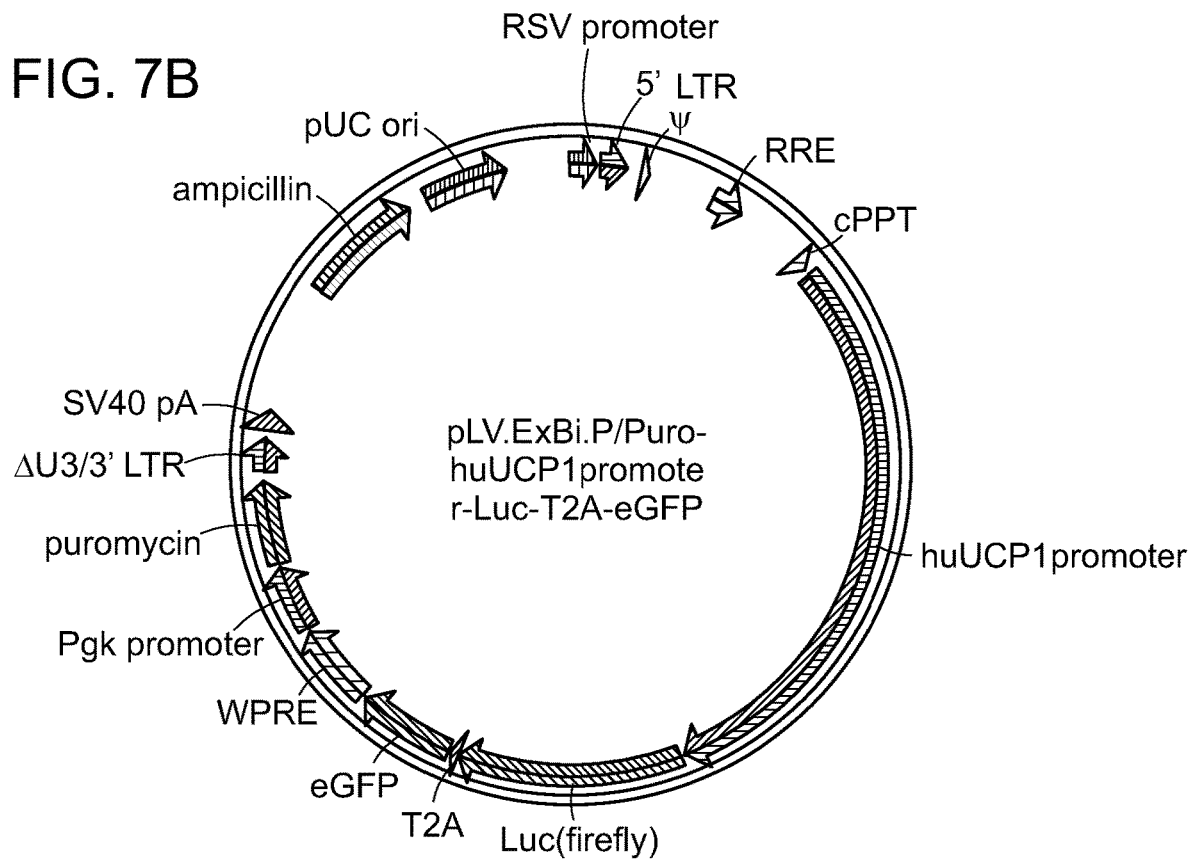
Figure 7C:
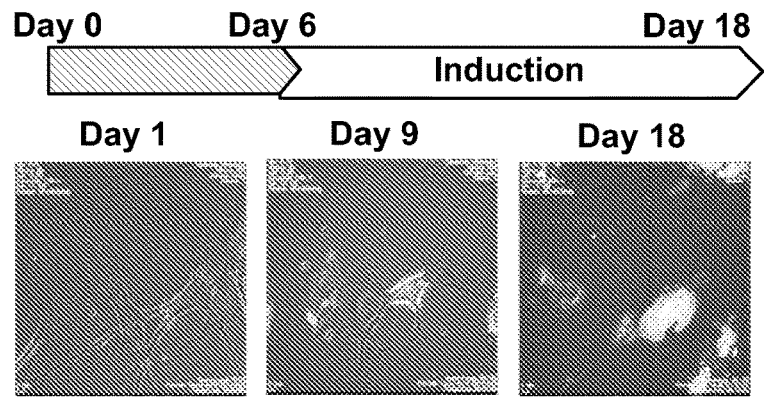
Figure 7D:
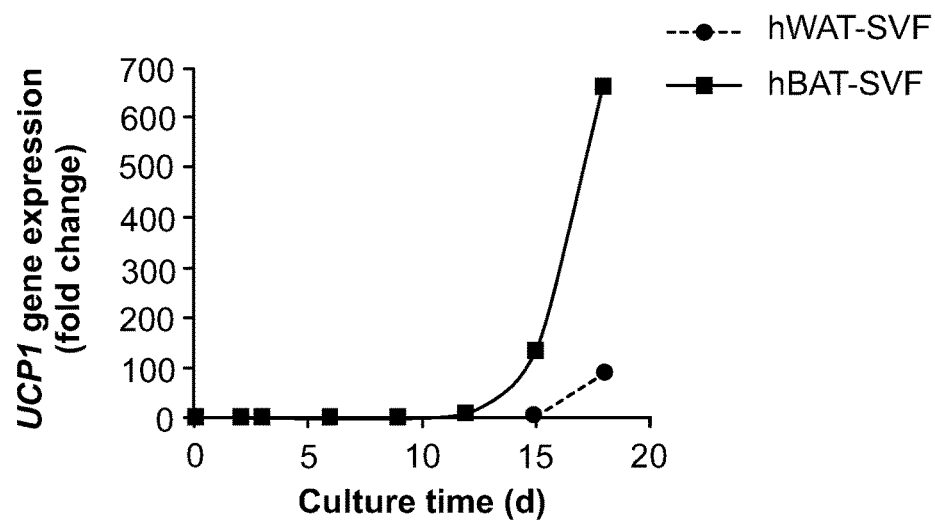
Figure 7D:
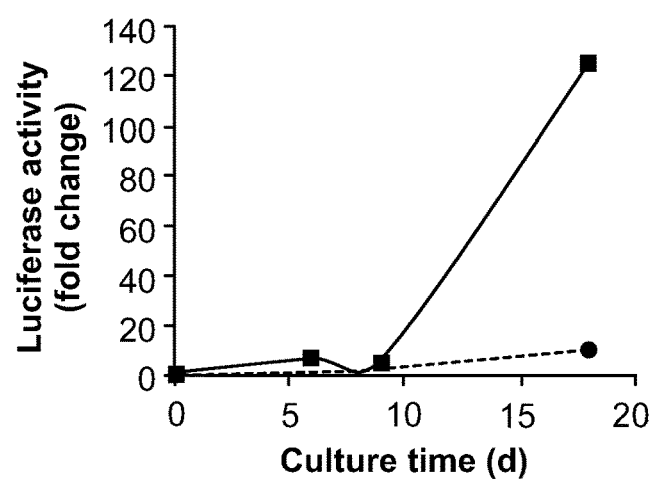
Figure 7E:
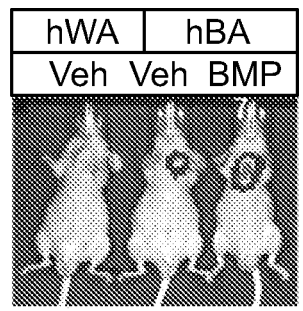
Figure 7F:
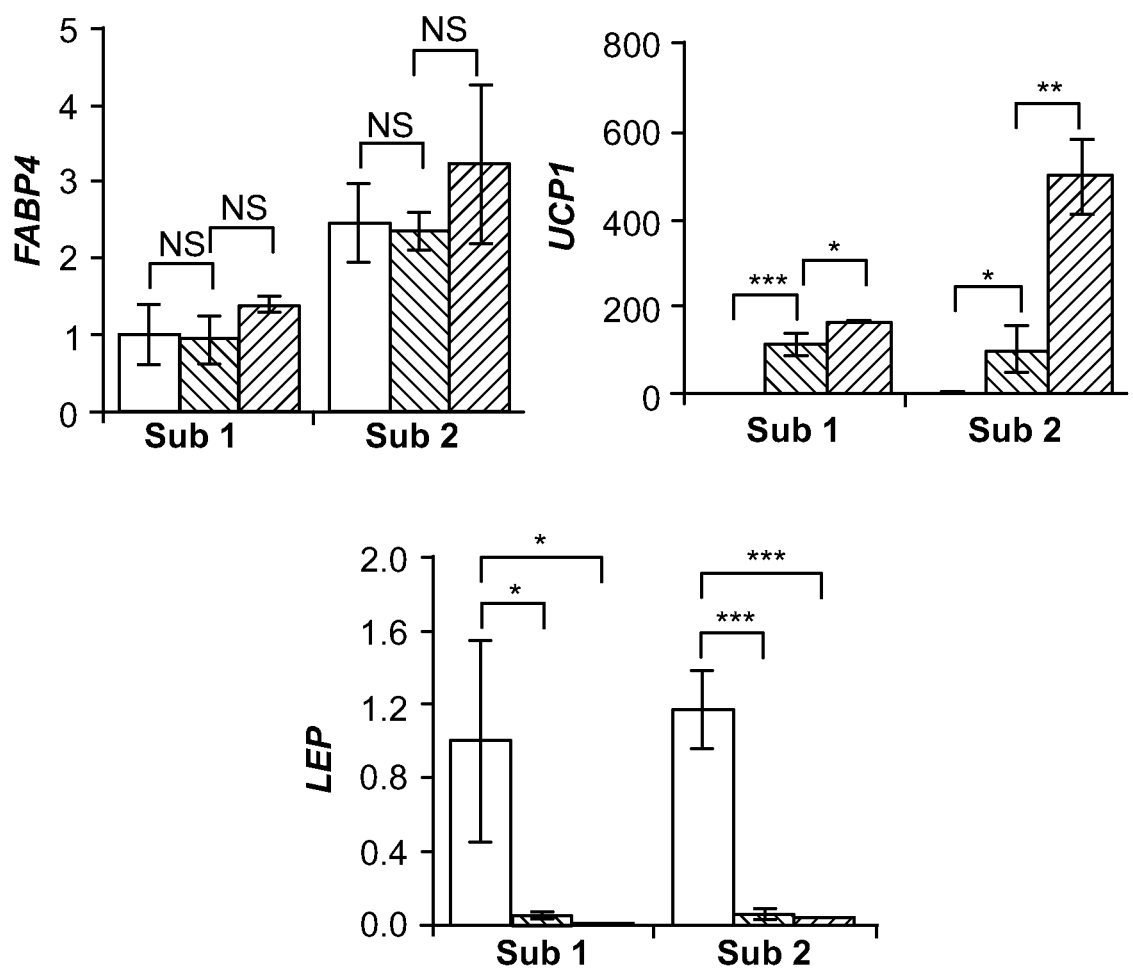

FIG. 7A depicts a transgenic UCP1 reporter system for measuring UCP1 gene expression. A bicistronic luciferase and green fluorescent protein (GFP) reporter was coupled to a 4.1 kb human UCP1 promoter fragment. FIG. 7B depicts the organization of plasmid pLV.ExBi.P/Puro-hUCP1promoter-Luc(firefly)-T2A-hrGFP, which contains the UCP1 reporter system described in FIG. 7A. FIG. 7C depicts time-lapse microscopy of differentiating hBAT-SVF cells containing the UCP1 reporter system. UCP1 expression was monitored by visualization of GFP. FIG. 7D depicts that in hBAT-SVF and hWAT-SVF cells stably expressing the reporter construct, luciferase activity (Right) was strongly correlated with endogenous UCP1 gene expression (Left) during the course of differentiation (see FIG. 2A and Methods). For determination of UCP1 mRNA levels, total RNAs were isolated on day 0, 2, 3, 5, 9, 12, 15 and 18; for luciferase activity assay, cell lysates were collected on day 0, 6, 9 and 18. Data are presented as fold changes compared to hWAT-SVF on day 0 (mean±s.e.m., n=3). A representative experiment from a total of two independent studies is shown. Data are represented in the same order as presented in the legend. FIG. 7E presents the results of bioluminescent imaging to measure UCP1 reporter activity in vivo following transplantation of progenitor cells into immune-deficient nude mice. Luciferase activity was high in mice implanted with hBAT progenitors, and conversely, mice receiving transplanted hWAT progenitors displayed almost no detectable luciferase activity. UCP1 levels in differentiated hBA were increased further by pretreatment of progenitors with bone morphogenetic protein 7 (BMP7), an inducer of brown adipogenesis. FIG. 7F depicts qRT-PCR analysis for expression of FABP4, UCP1 and LEP in fat pads developed from the transplanted cells. Data are presented as fold changes compared to fat pads developed from hWAT-SVF cells with vehicle treatment (mean±s.e.m.). *P<0.05, P<0.01, *P<0.001 by two-tailed Student's t-test. A representative experiment from a total of two independent studies is shown.

Figure 8:
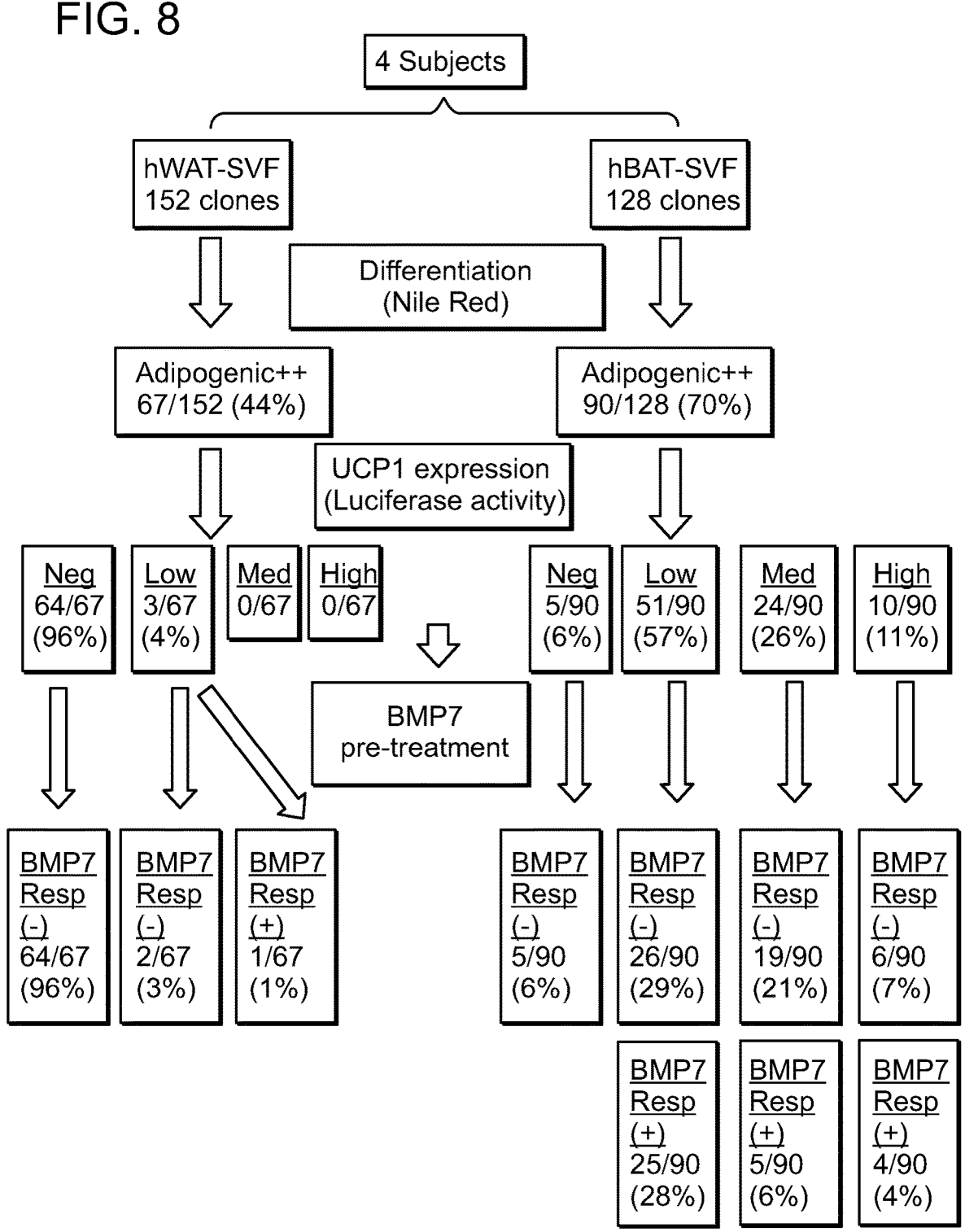

FIG. 8 depicts clonal analysis of human brown and white fat progenitors. Specifically, the strategy of clonal analysis of hWAT-SVF and hBAT-SVF progenitors is shown as a dendrogram. 152 clones from hWAT-SVF and 128 clones from hBAT-SVF were derived by limiting dilution from 4 subjects. Adipogenic capacity was determined by Nile red staining and UCP1 level was determined by luciferase activity on day 18. Detailed selection criteria are described in FIGS. 9 and 10. Selected highly adipogenic clones (adipogenic++) were pre-treated with 3.3 nM BMP7 for 6 days and then differentiated into mature adipocytes in a 96-well plate. Luciferase activity was measured on day 18 and divided into different levels (negative, Neg; low; medium, Med; high) after normalized to protein content. The positive response (+) to BMP7 pretreatment was defined by more than 1.5-fold increase of luciferase activity between BMP7-pretreated and vehicle groups.

FIG. 9 depicts Nile red staining used to determine clone's adipogenic capacity. Fluorescence intensity of Nile red staining was detect at Ex/Em=552/636 nm, and was divided into different levels (adipogenic–: fluorescence intensity <0.2; adipogenic+: fluorescence intensity 0.2-0.4; adipogenic++: fluorescence intensity >0.4) after normalized to protein content. Representative microscope views of Nile red staining on day 18 were shown on right. Scale bar, 100 μm.

Figure 10:
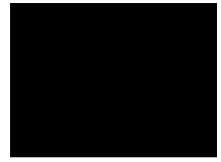
Figure 10:
Figure 10:
Figure 10:
Figure 10:
Figure 10:
Figure 10:
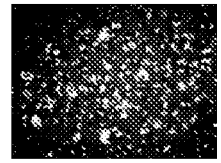
Figure 10:

FIG. 10 depicts definition of different UCP1 level (negative; low; medium; high) in human fat progenitor clones by both luciferase activity and GFP expression on day 18. Luciferase activity was measured and normalized to protein content, as indicated: negative <10; low 10-50; medium 50-100; high >100. And the indicated luciferase activity level is consistent with GFP expression in the same clone on day 18. The microscope views of GFP and merge with light picture are shown on right panel. Scale bar, 50 μm.

Figure 11A:
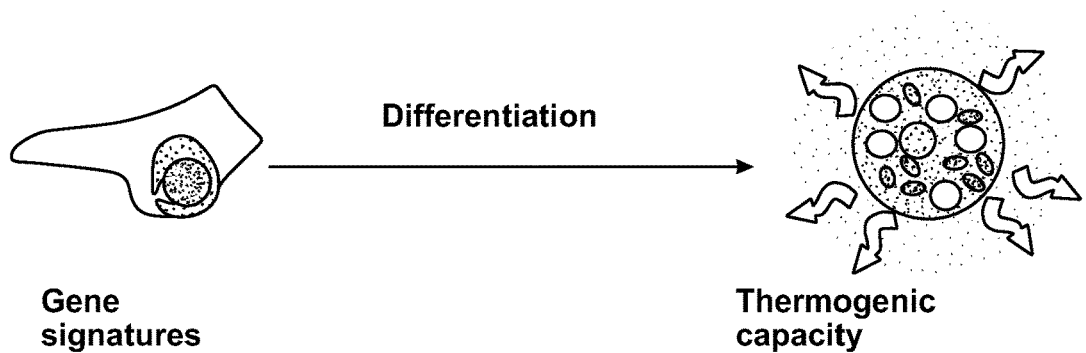
Figure 11A:
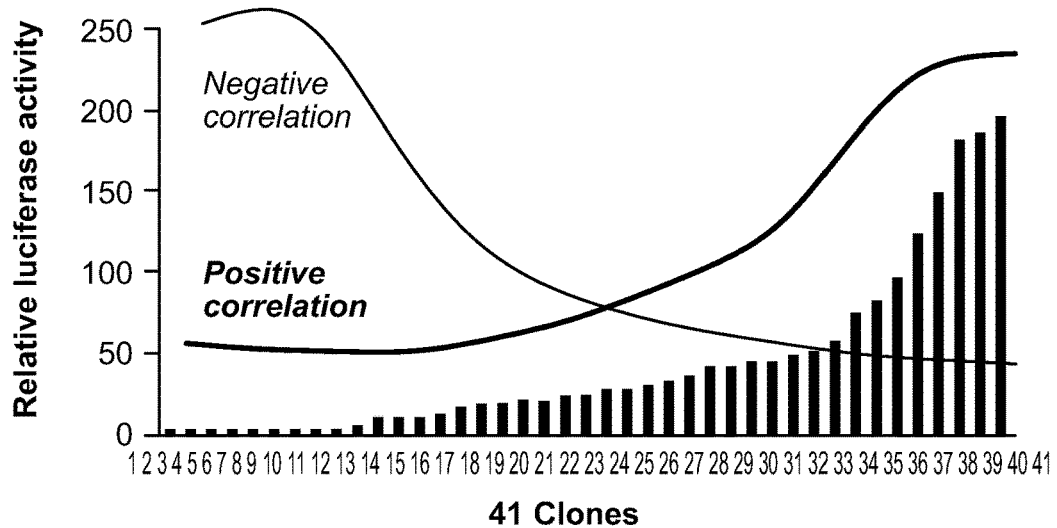
Figure 11B:
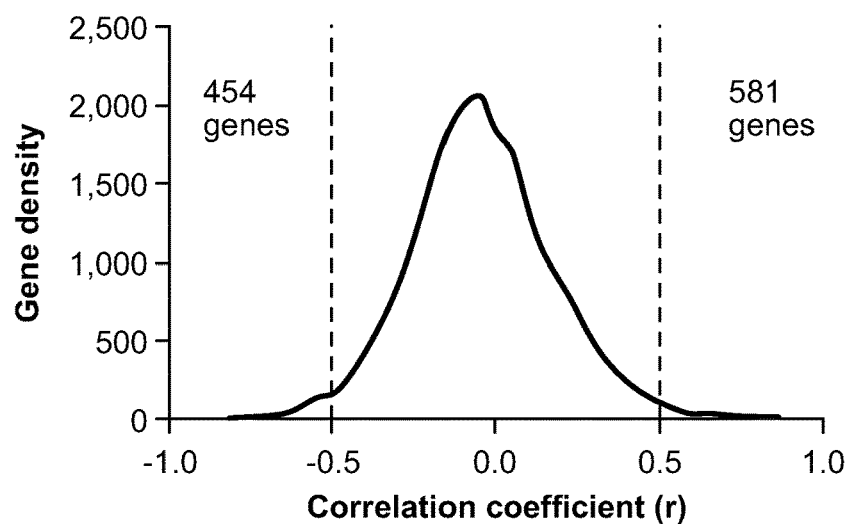
Figure 11C:
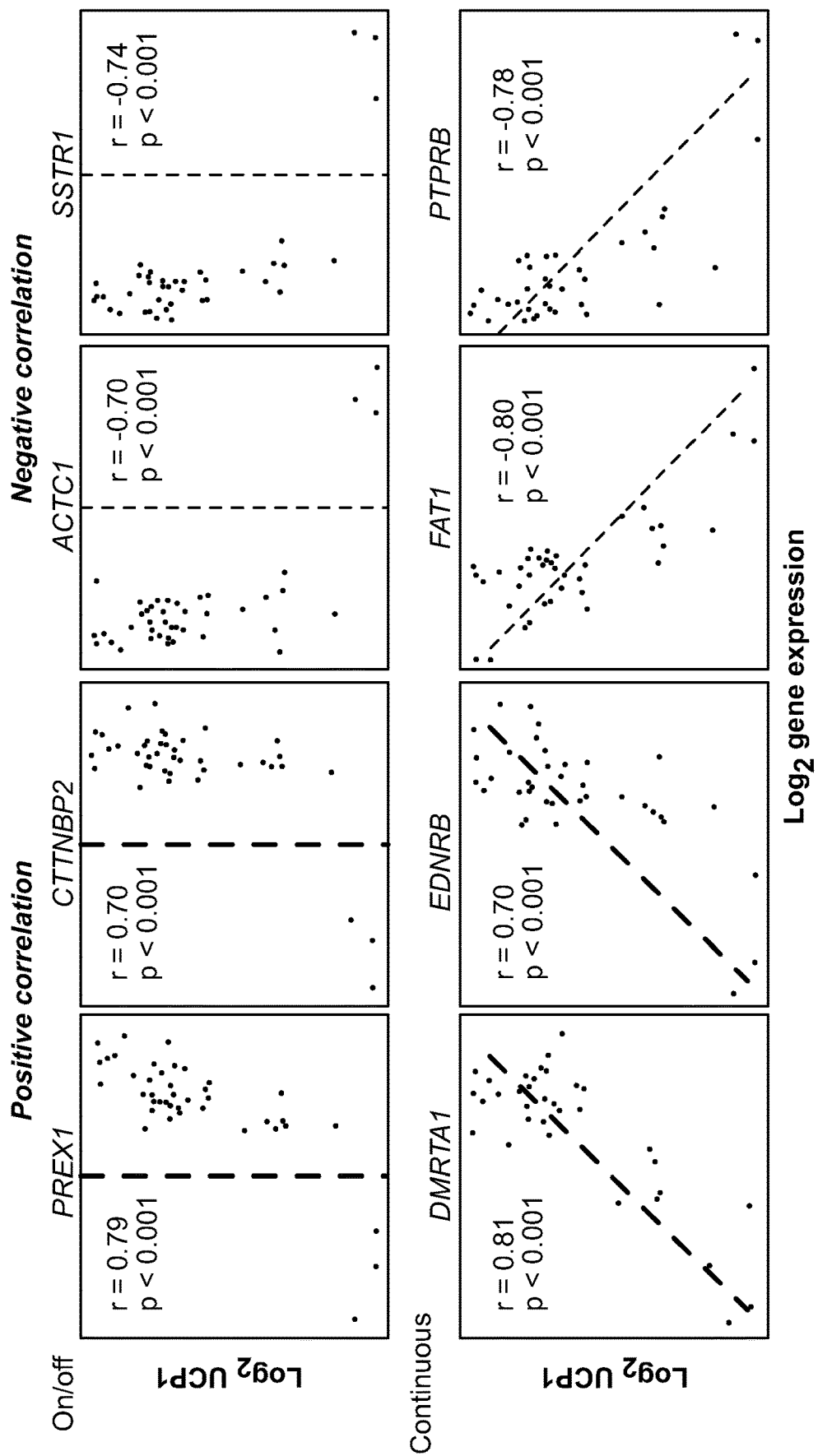

FIGS. 11A-11C depicts a graphic of gene expression profiles in adipose progenitors which predict the thermogenic capacity of mature adipocytes. Specifically, FIG. 11A depicts a schematic presentation outlining the strategy utilized to identify the genes in preadipocytes with positive or negative correlation with UCP1 levels in mature adipocytes. Microarray analyses were done in 41 selected highly adipogenic clones from 4 subjects (8 clones from hWAT-SVF and 33 clones from hBAT-SVF). FIG. 11B depicts a histogram showing the distribution of genes that are positively and negatively correlated with UCP1 levels (determined by luciferase activities). P-value <0.001 was used as the cutoff to prioritize candidate genes (two-tailed alternative with function cor.test). The correlation coefficient (R) is shown in the X-axis and gene frequency is shown in the Y-axis. FIG. 11C depicts a scatter plot showing the positive and negative correlations between the UCP1-luciferase levels and expression levels of candidate genes from microarrays. The $\log_2$ gene expression level of progenitor (day 0) is shown in the X-axis. The Y-axis represents the $\log_2$ of UCP1 luciferase level of mature adipocyte (day 18).

Figure 12A:
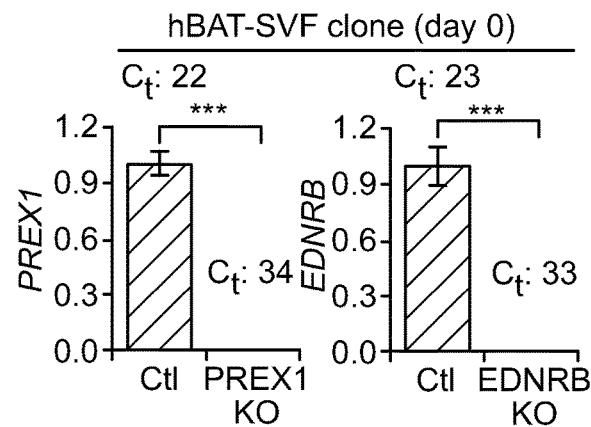
Figure 12B:
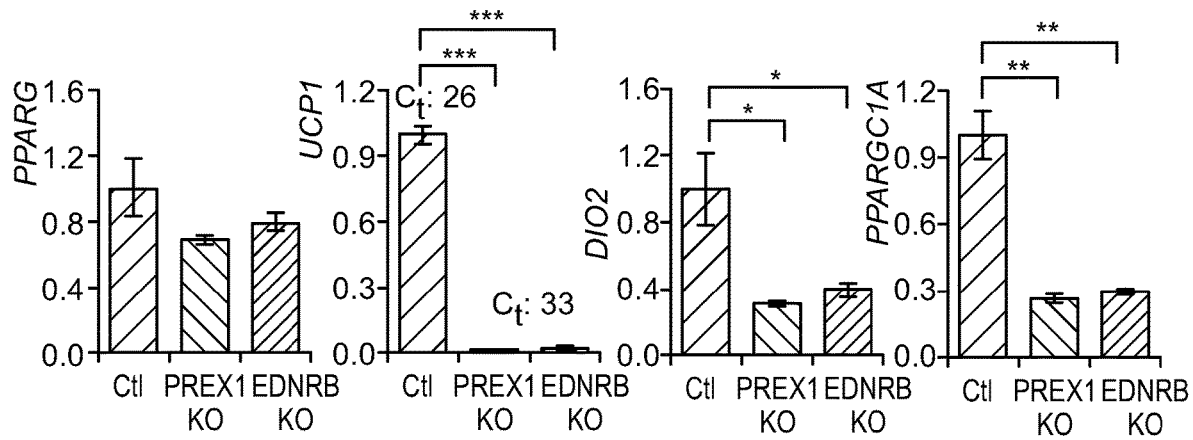
Figures 12C, 12D:
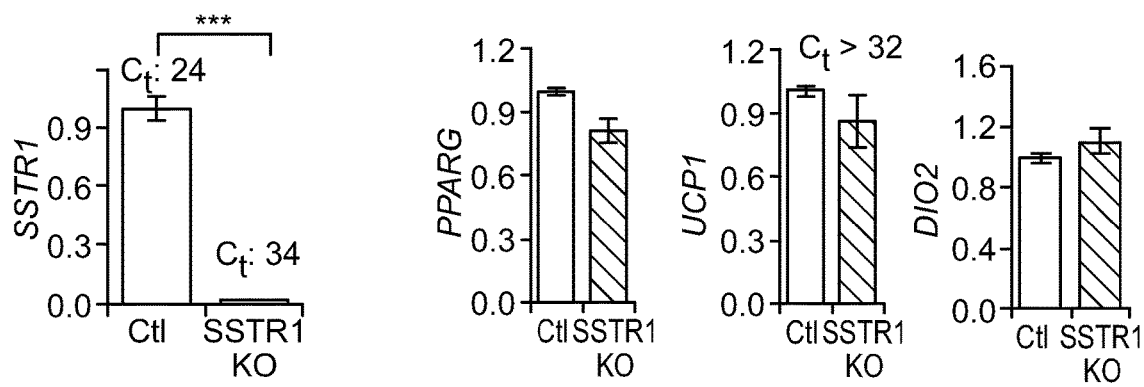

FIGS. 12A-12D depict that PREX1 and EDNRB are required for determining thermogenic competency. Specifically, FIG. 12A depicts the use of CRISPRs to knockout PREX1 (PREX1 KO) and EDNRB (EDNRB KO) in a hBAT-SVF clone. Levels of PREX1 and EDNRB mRNA were measured by Q-RT-PCR. The Ct values (Ct) from Q-RT-PCR are indicated to reflect the actual levels of gene expression. Data are presented as fold changes compared to control vector transfected cells (Ctl) (mean±s.e.m., n=3; two-tailed Student's t-test; *P<0.05, P<0.01, *P<0.001). The experiments were verified in another progenitor clone. FIG. 12B depicts Q-RT-PCR analysis performed for PPARγ and brown-fat-specific markers (UCP1, DIO2 and PGC1α) in differentiated PREX1 KO and EDNRB KO hBAT-SVF cells. Results are shown as mean±s.e.m.; two-tailed Student's t-test; *P<0.05, P<0.01, *P<0.001. FIG. 12C depicts the use of CRISPRs to knockout SSTR1 (SSTR1 KO) in a hWAT-SVF clone. SSTR1 level was detected by Q-RT-PCR on day 0. Data are presented as fold changes compared to control vector transfected cells (Ctl) (mean±s.e.m., n=3; two-tailed Student's t-test; *P<0.05, P<0.01, *P<0.001). The experiments were verified in another progenitor clone. FIG. 12D depicts Q-RT-PCR analysis performed for PPARγ and brown-fat-specific markers (UCP1 and DIO2) in differentiated SSTR1 KO clone. The $C_t$ values (CO from Q-RT-PCR are indicated to reflect the actual levels of gene expression. Data are presented as fold changes compared to control vector transfected cells (Ctl) (mean±s.e.m., n=3; two-tailed Student's t-test; *P<0.05, P<0.01, *P<0.001).

Figure 13:
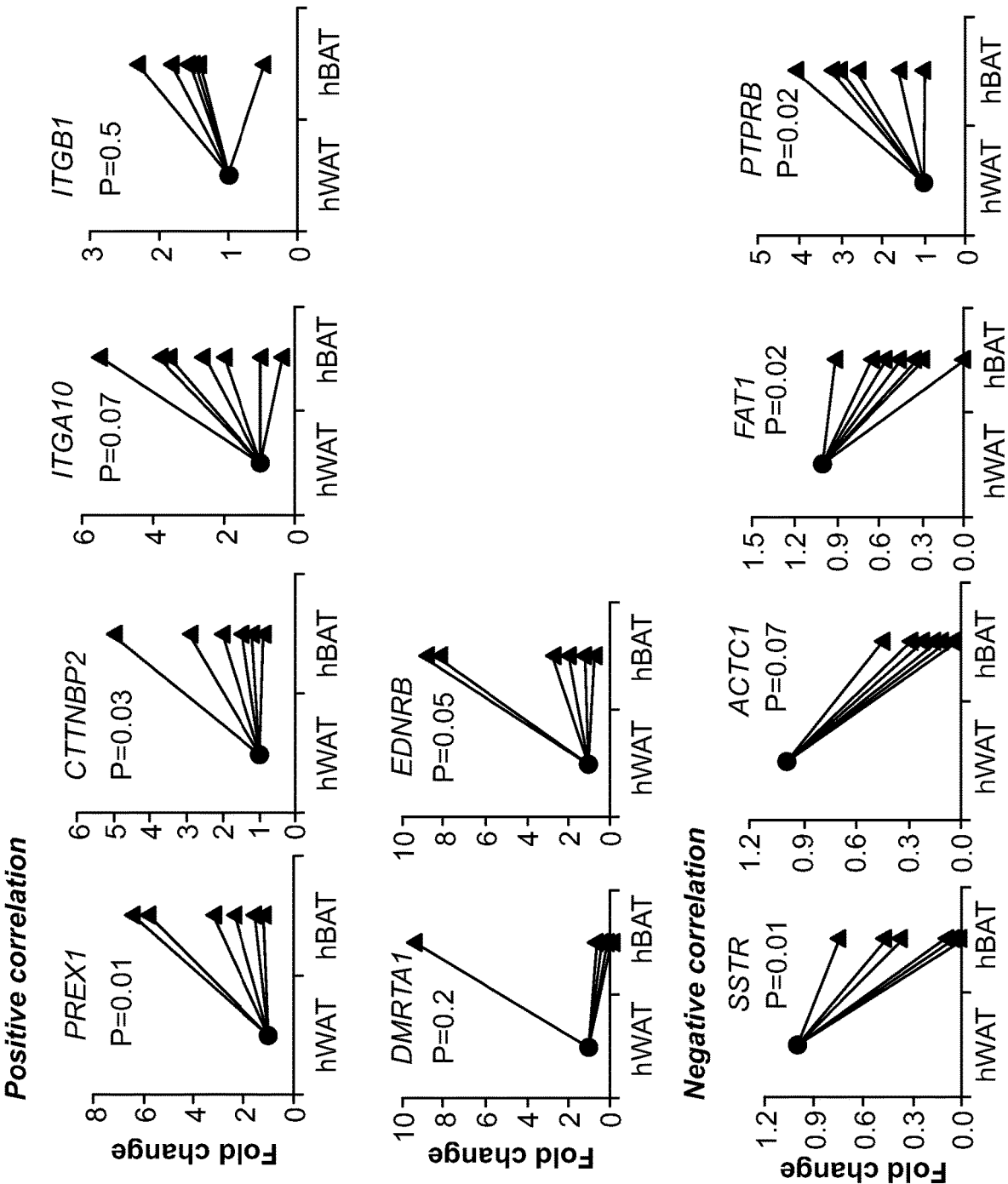

FIG. 13 depicts expression of positively and negatively correlated candidate genes in human neck fat derived from 7 subjects. Fat was resected from 7 patients undergone neck surgery. Q-RT-PCR analysis was performed for the expression of positive and negative correlation candidate genes that were normalized to 18 s. The subcutaneous fat was used as control, white adipose tissues (hWAT), and the deeper fat from each patients that had the highest expression levels of UCP1 was chosen for the human brown adipose tissues (hBAT) sample. P value was analyzed using Wilcoxon matched-pairs signed-ranks test.

Figure 14A:
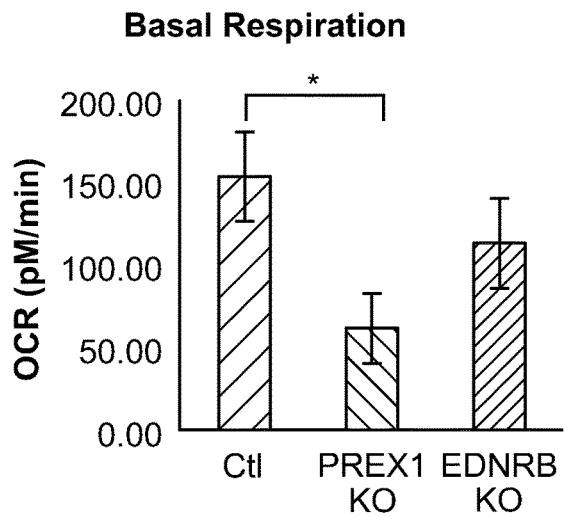
Figure 14B:
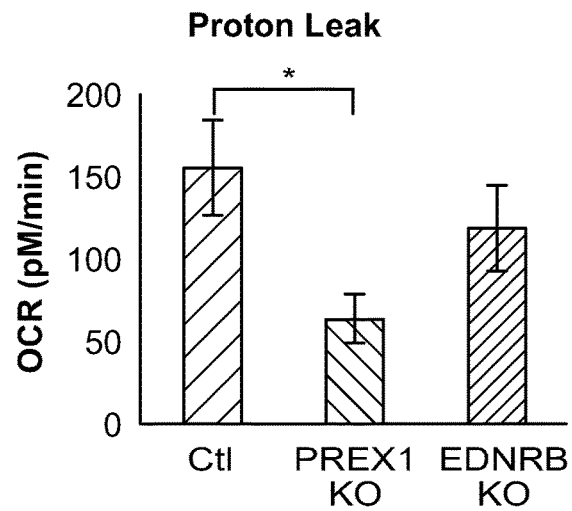
Figure 14C:
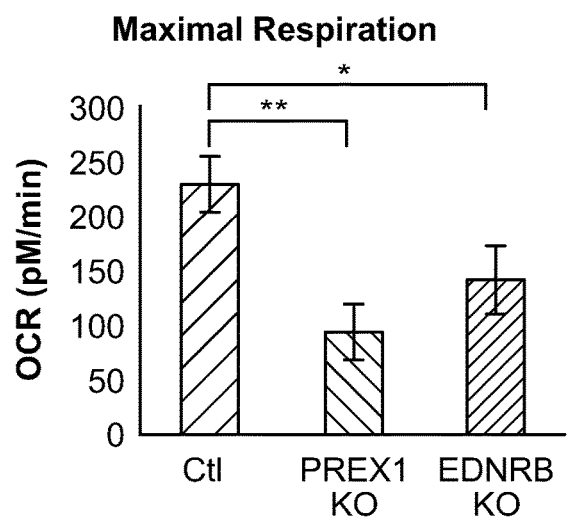
Figure 14D:
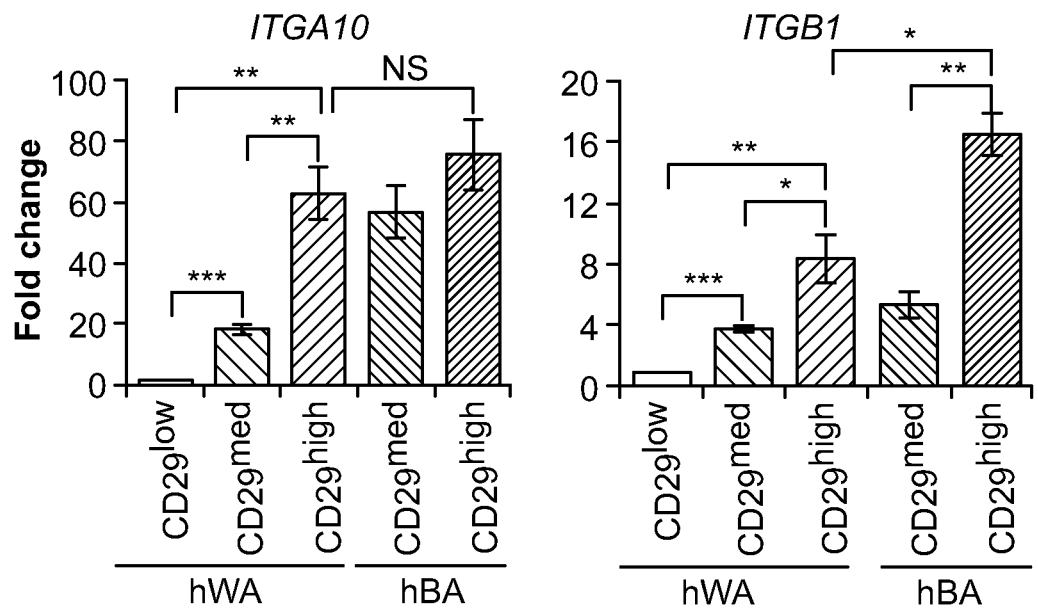
Figure 14E:
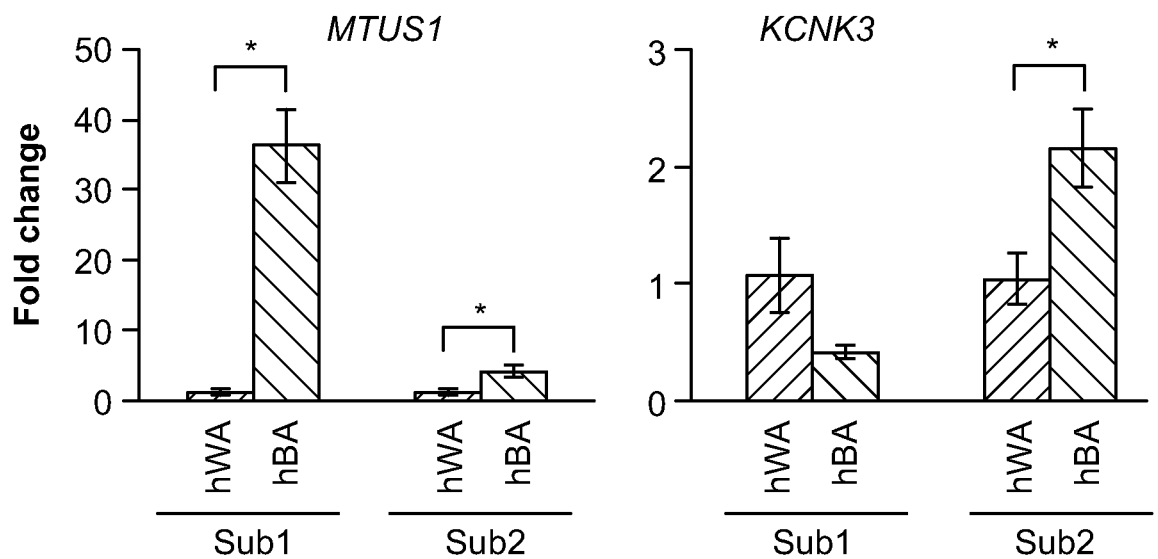

FIGS. 14A-14E depict functional analysis of PREX1 and EDNRB knockout cells and expression of potential brown fat markers in hWA and hBA. Oxygen consumption rate (OCR) was measured using the Seahorse extracellular flux analyzer in wild type control, PREX1 and EDNRB knockout hBA. Equal numbers of progenitors were plated and differentiated. FIG. 14A depicts quantifications of OCR in the absence (Basal respiration Basal Res.) and FIG. 14B depicts quantifications of OCR in the presence of oligomycin (Proton Leak). FIG. 14C depicts quantifications of OCR in the presence of FCCP (Maximal respiration, Max Res.). Data were normalized to DNA content and are presented as mean±s.e.m., n=7. Asterisks depict statistically significant differences between wild type and each knockout. A representative experiment from three independent studies is shown. FIG. 14D depicts mRNA expression of ITGA10 and ITGB1 in sorted subpopulation with different expression level of CD29 on day 0. Data are shown as a fold change compared to CD29low subpopulation from hWAT-SVF (mean±s.e.m., n=3). FIG. 14E depicts mRNA expression of MTUS1 and KCNK3 in the differentiated brown and white fat cells derived from pooled progenitors of Subject 1 and Subject 2. Two-tailed Student's t-test was used to determine P values (*P<0.05, P<0.01, *P<0.001).

Figure 15A:
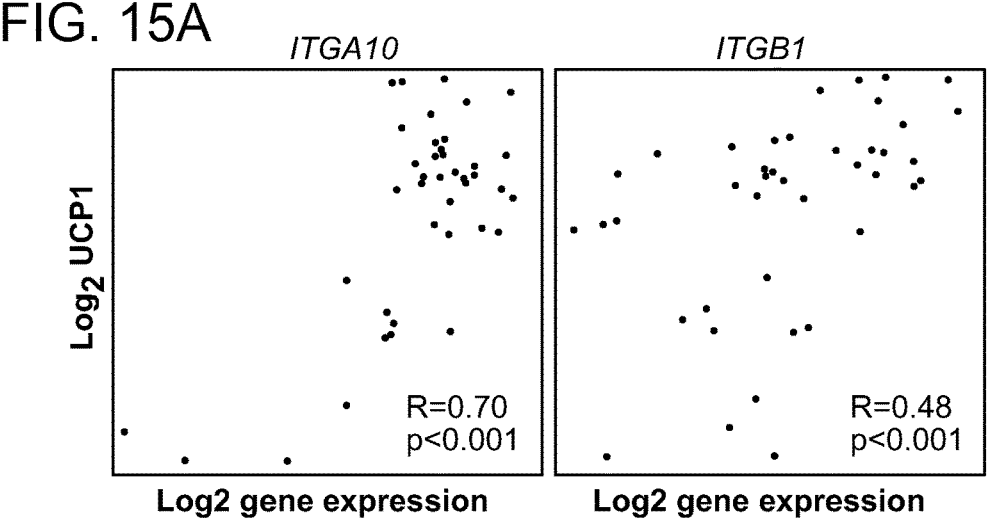
Figure 15B:
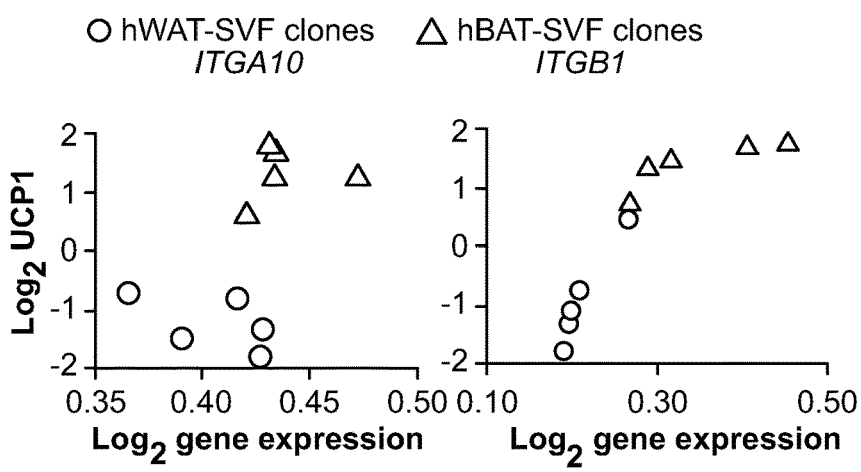
Figure 15C:
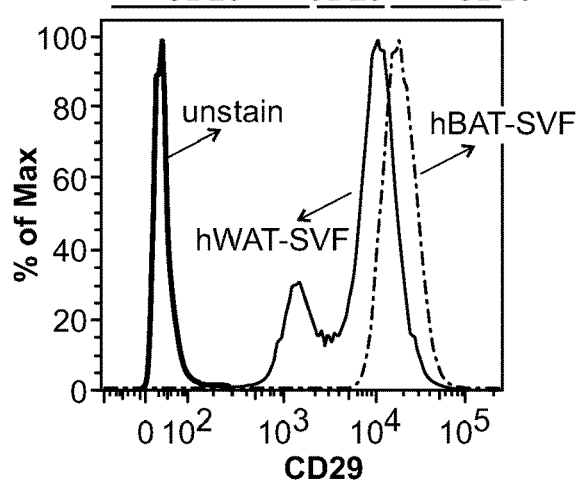
Figure 15D:
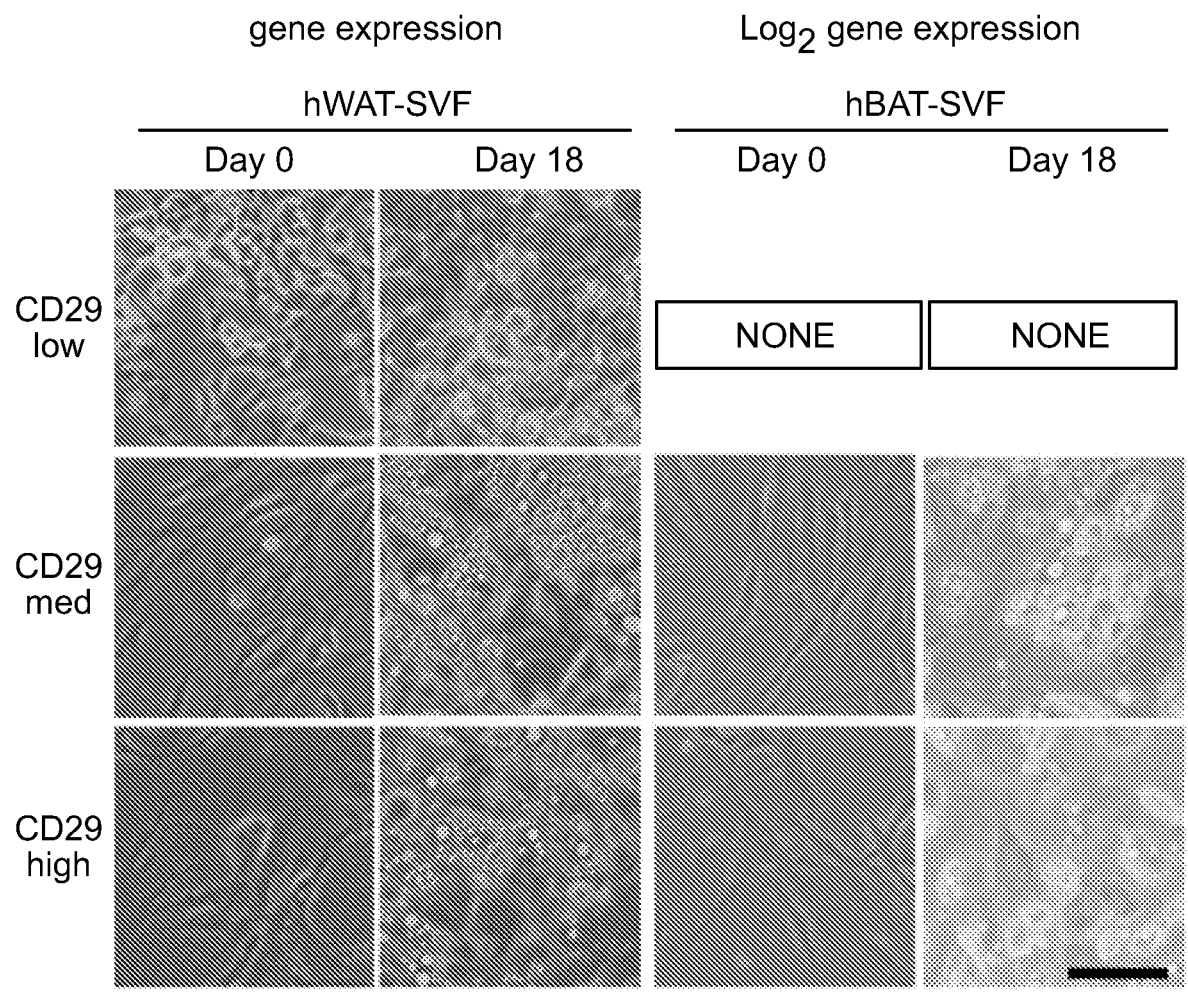

FIGS. 15A-15F depict isolation of progenitors possessing thermogenic potential using a cell surface marker. Specifically, FIG. 15A depicts scatter plots showing positive correlation between the UCP1-luciferase levels on day 18 and expression levels of ITGA10 and ITGB1 on day 0 from microarray analyses. The $\log_2$ gene expression level is shown in the X-axis. The Y-axis represents the $\log_2$ of UCP1 luciferase level. FIG. 15B depicts correlation between the mRNA levels of ITGA10 and ITGB1 on day 0 and UCP1 mRNA levels on day 18, in 10 independent hWAT-SVF and hBAT-SVF clones. Levels of mRNA expression were quantified by Q-RT-PCR. The $\log_2$ gene expression level is shown in the X-axis. The Y-axis represents the $\log_2$ of UCP1 mRNA levels. FIG. 15C depicts a histogram displaying subpopulations with differential levels of CD29 from hWAT-SVF and hBAT-SVF. Fluorescence-activated cell sorting was used to isolate subpopulations of cells with different level of CD29 from pooled hWAT-SVF and hBAT-SVF. FIG. 15D depicts sorted subpopulation with different level of CD29 ($CD29^{low}$, $CD29^{med}$ and $CD29^{high}$) cultured and induced to differentiation in adipogenic induction medium for 18 days. Microscopic views of cells on day 0 and day 18 are shown. Note that we couldn't sort enough numbers of $CD29^{low}$ from pooled hBAT-SVF, and thus results from this subpopulation are not shown. Scale bar, 100 μm. A representative experiment from a total of two independent studies is shown.

Figure 15F:
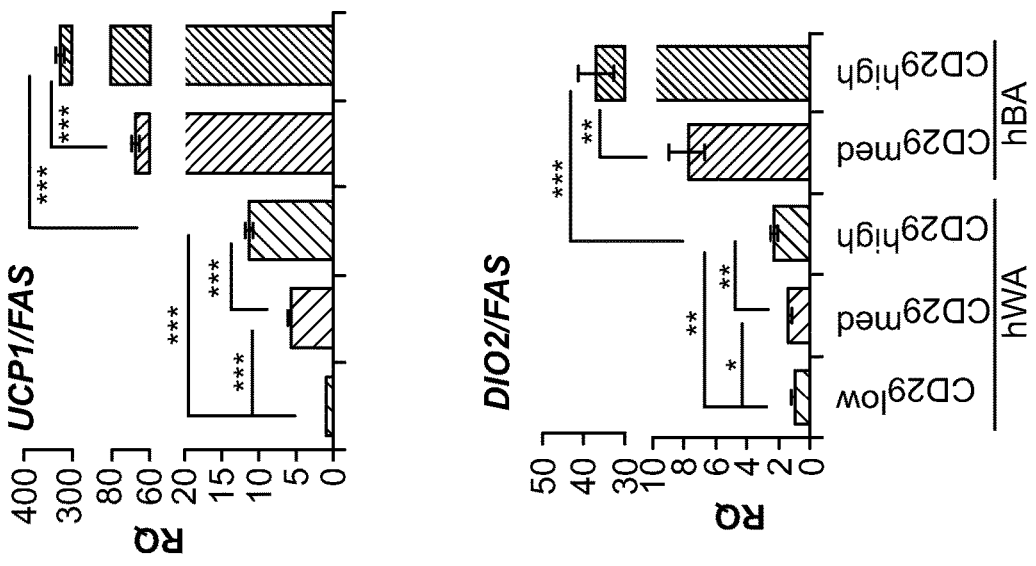
Figure 15E:
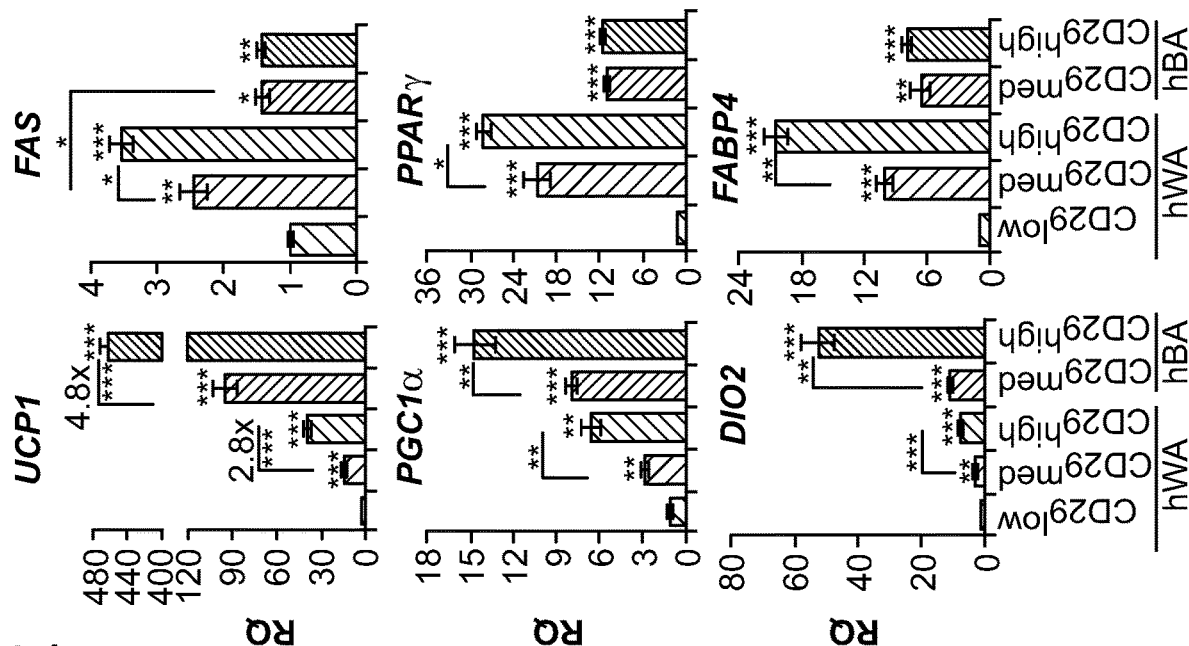

FIG. 15E depicts Q-RT-PCR analysis performed for selected markers. Specifically, RNA was isolated from cells differentiated for 18 days, and Q-RT-PCR analysis was performed for the adipocyte markers (FAS, PPARγ and FABP4) and brown-fat-specific markers (UCP1, PGC1α and DIO2) on the indicated populations: $CD29^{low}$, $CD29^{med}$ and $CD29^{high}$. Data are shown as a fold change compared to $CD29^{low}$ subpopulation from hWAT-SVF (mean±s.e.m., n=3; two-tailed Student's t-test; *P<0.05, P<0.01, *P<0.001). FIG. 15F depicts expression levels of brown fat markers UCP1 and DIO2 normalized to the level of mature adipocyte marker, FAS. To correct the impact of different degrees of adipogenesis on gene expression measured in FIG. 14E, expression levels of brown fat markers UCP1 and DIO2 were normalized to the level of mature adipocyte marker, FAS. Data are presented as mean±s.e.m. (n=3; two-tailed Student's t-test; *P<0.05, P<0.01, *P<0.001).

DETAILED DESCRIPTION OF THE INVENTION

The present invention provides, in one embodiment, methods and compositions for promoting thermogenic capacity in a cell or tissue by contacting a thermogenically competent cell, e.g., a preadipocyte, with an inhibitor of an uncoupling protein 1 negative regulator, an activator of a UCP1 positive regulator, a UCP1 positive regulator, or combinations thereof. The present invention also features, in one embodiment, methods and compositions for treating a disorder that would benefit from metabolic control, e.g., obesity or diabetes, comprising administering an inhibitor of a UCP1 negative regulator, an activator of a UCP1 positive regulator or a UCP1 positive regulator to a subject in need thereof. In addition, the present invention provides, in another embodiment, methods and compositions for selecting thermogenically competent preadipocytes from a plurality of cells, based on cell surface markers, e.g., CD29.

In order that the present invention may be more readily understood, certain terms are first defined.

I. Definitions

As used herein, "UCP", "UCP1" or "uncoupling protein 1", is intended to refer to a 32 kDa inner mitochondrial transmembrane protein (or the gene which encodes the protein) expressed in brown adipocytes. UCP1 allows protons in the mitochondrial intermembrane space to re-enter the mitochondrial matrix without generating ATP, i.e., uncoupling.

It should be noted that throughout, molecule names, e.g., UCP1 or PREX1, include both the gene and protein, unless otherwise specified. Thus, the term "UCP1" when used in reference to the molecule includes UCP1 protein and the UCP1 gene.

As used herein, the term "UCP1 expression", refers to transcription of the gene encoding uncoupling protein 1 (UCP1), i.e., UCP1 mRNA or translation of UCP1 mRNA, i.e., UCP1 protein. Thus, UCP1 expression, as used herein, refers to the presence of UCP1 in either protein or nucleic acid form, unless otherwise specified.

As used herein, the term "uncoupling protein 1 negative regulator" or "UCP1 negative regulator" refers to a gene or protein that is capable of negatively impacting UCP1 expression (transcription or translation) or a gene or protein that is capable of acting, directly or indirectly, such that UCP1 biological function, e.g., mitochondrial transport, is impaired. Examples of UCP1 negative regulators include, but are not limited to, cardiac actin 1 (ACTC1), somatostatin receptor 1 (SSTR1), FAT atypical cadherin 1, (FAT1), protein tyrosine phosphatase, receptor type B (PTPRB), contactin 3 (CNTN3), and genes listed in Table 4 such as ST6GALNAC3, S1PR3, SVIL, C17orf60, MASP1, PXK, C10orf90, TBC1D19, DNASE1L1, GPCR5A, ITGA10, ETFDH, MORN4, MRPS6, SETDB2, WRB, SYNRG, and ANP32A.

As used herein, the term "inhibitor of a uncoupling protein 1 negative regulator" or an "inhibitor of a UCP1 negative regulator" refers to an agent which directly or indirectly interferes with a UCP1 negative regulator and reduces the activity of the UCP1 negative regulator. In one embodiment, the inhibitor of a UCP1 negative regulator acts directly on the UCP1 negative regulator, e.g., an antagonist antibody which binds to the UCP1 negative regulator and inhibits its function. In another embodiment, the inhibitor of a UCP1 negative regulator acts indirectly on the UCP1 negative regulator (e.g., through a another molecule) resulting in increased UCP1 expression.

As used herein, the term "uncoupling protein 1 positive regulator" or "UCP1 positive regulator", refers to a gene or protein which positively impacts UCP1 expression or a gene or protein that is capable of acting, directly or indirectly, such that UCP1 biological function, e.g., mitochondrial transport, is increased. Examples of UCP1 positive regulators include, but are not limited to, phosphatidylinositol-3,4,5-triphosphate-dependent Rac exchange factor 1 (PREX1), cortactin binding protein 2 (CTTNBP2), doublesex and mab-3-related transcription factor-like family A1, (DMRTA1), Endothelin receptor type B, Receptor Type B (EDNRB), SESTD1, TXLNG, G-protein-coupled receptor 56 (GPR56) and WW domain containing transcription regulator 1 (WWTR1 (TAZ). Other examples include the genes listed in Table 4, such as TEK, CDH13, EPB41L3, KRT-CAP2, NUCB2, SMYD2, PSME4, TJP1, ZNF518B, GRIK2, ANTXR1, SLC7A6, THBS1, TOM1L1, CSRP2, STXBP6, SHROOM3, WNT2, HAPLN1, COL12A1, NALCN, PLCXD3.

As used herein, the term "activator of a uncoupling protein 1 positive regulator" or an "activator of a UCP1 positive regulator" refers to an agent which acts on a UCP1 positive regulator in order to increase UCP1 expression. In one embodiment, the activator of a UCP1 positive regulator acts directly on the UCP1 positive regulator. In another embodiment, the activator of a UCP1 positive regulator acts indirectly on the UCP1 positive regulator (e.g., through another molecule) resulting in increased UCP1 expression.

As used herein, the term "thermogenic capacity" when used in reference to a cell or tissue indicates the level of energy consumption via thermogenesis by the cell or tissue. In one embodiment, the thermogenic capacity is promoted by increasing UCP1 expression or increasing brown adipocyte tissue or cells.

The term "cell", as used herein, refers to an animal cell and not a plant cell.

As used herein, the term "thermogenically competent cell" refers to any cell in which UCP1 expression can be induced such that the cell has increased levels of mitochondrial respiration, such as basal respiration, ATP turnover, proton leak, and respiratory capacity. The levels of mitochondrial respiration of an energy consuming cell may be relative to a baseline respiration measure when UCP1 is not induced in the same cell type. In one embodiment, the level of UCP1 expressed in the cell is increased by at least about 3-fold, 4-fold, 5-fold, 6-fold, 10-fold, 15-fold, 20-fold, 25-fold, 30-fold, 35-fold, 40-fold, 45-fold, 50-fold, 75-fold, 100-fold, 200-fold, 300-fold, 400-fold, 500-fold, 1000-fold, 1500-fold, 2000-fold, 2500-fold, 3000-fold, 3500-fold, 4000-fold, 4500-fold, 5000-fold, 5500-fold, 6000-fold, 7000-fold, 8000-fold, 9000-fold or 10000-fold over baseline levels of the same type of cell in which UCP1 is not induced. In one embodiment, a thermogenically competent cell is an undifferentiated cell. Examples of thermogenically competent cells include, but are not limited to, preadipocytes, brown adipocytes, embryonic stem cells, induced pluripotent stem cells (iPS cells or iPSCs), undifferentiated fibroblast cells, and muscle derived progenitor cells.

As used herein, the term "undifferentiated cell" refers to a cell that has not yet assumed a morphological or functional feature of a mature cell (a mature cell being the cell type at the end of a cell lineage). In one embodiment, an undifferentiated cell is a pluripotent cell that is capable of differentiating into cells of functionally distinct lineages. In one embodiment, the undifferentiated cell is an undifferentiated fibroblast cell. In yet another embodiment, an undifferentiated cell is a preadipocyte. In one embodiment, an undifferentiated cell is a cell committed to adipocyte lineage (general adipocyte lineage and determination is known in the art, e.g., general lineage is described in FIG. 3 of Tseng, Cypress, and Kahn (2010) Nat Rev Drugs and Dis. 9:465-482). As used herein, the term "cell committed to adipocyte lineage" refers to a cell which becomes an adipocyte when exposed to factors that induce adipogenic differentiation. In one embodiment, when the cell committed to adipocyte lineage is exposed to factors that induce, for example myogenic or osteogenic differentiation, it does not become a myocyte or an osteocyte, respectively.

As used herein, a "preadipocyte" refers to an adipocyte precursor cell that can proliferate and differentiate to form mature adipocytes. In one embodiment, a preadipocyte is a brown preadipocyte (e.g., WT-1 cell). In one embodiment, a preadipocyte is a white preadipocyte. In one embodiment, a preadipocyte can mature into a beige (also known as brite) adipocyte. The term "progenitor" is also used herein to describe a preadipocyte when used in the context of fat cells.

As used herein, "brown adipocytes", "brown adipose tissue" or "BAT", refers to a mature cell (or tissue thereof) characterized by multiple small lipid droplets and abundant mitochondria that oxidizes nutrients and generates heat. Central to the thermogenic activity of BAT is the expression of UCP1.

As used herein, the term "differentiated cell" refers to a cell that is a mature cell, or a cell that has a defined morphology. An example of a differentiated cell includes, but is not limited to, a mature adipocyte.

As used herein, the term "unstained", when used in the context of flow cytometry, refers to a cell that is not exposed to an antibody during flow cytometry assay. Thus, an unstained cell serves as a control.

As used herein, the term "CD29$^{low}$" refers to a cell which is obtained using an anti-CD29 antibody in flow cytometry, where the cell has a 1000 fold or less increase in fluorescent intensity relative to cell obtained using an unstained sample as determined by flow cytometry. Similarly, the term "ITGA10$^{low}$" refers to a cell which is obtained using an anti-ITGA10 antibody in flow cytometry, where the cell has a 1000 fold or less increase in fluorescent intensity relative to cell obtained using an unstained sample as determined by flow cytometry.

As used herein, the term "CD29$^{med}$" refers to a cell which is obtained using an anti-CD29 antibody in flow cytometry, where the cell has more than a 1000 fold but less than a 10,000 fold increase in fluorescent intensity relative to cell obtained using an unstained sample as determined by flow cytometry. Similarly, the term "ITGA10$^{med}$" refers to a cell which is obtained using an anti-ITGA10 antibody in flow cytometry, where the cell has more than a 1000 fold but less than a 10,000 fold increase in fluorescent intensity relative to cell obtained using an unstained sample as determined by flow cytometry.

As used herein, the term "CD29$^{high}$" refers to a cell which is obtained using an anti-CD29 antibody in flow cytometry, where the cell has a 10,000 fold increase or more in fluorescent intensity relative to cell obtained using an unstained sample as determined by flow cytometry. Similarly, the term "ITGA10$^{high}$" refers to a cell which is obtained using an anti-ITGA10 antibody in flow cytometry, where the cell has a 10,000 fold increase or more in fluorescent intensity relative to cell obtained using an unstained sample as determined by flow cytometry.

As used herein, the term "enriched plurality" refers to population of cells that have undergone a selection process whereby the population has an increase in cells expressing CD29 and/or integrin alpha 10 expressed on the surface of the cells relative to a starting population of cells (an unenriched plurality of cells) which has not undergone the selection process. In one embodiment, the enriched plurality of cells is obtained through flow cytometry using a binding protein to CD29 and/or integrin alpha 10.

In certain embodiments, the term "control", as used herein, is intended to refer to a cell which is not contacted with an inhibitor of a UCP1 negative regulator, a UCP1 positive regulator, and/or an activator of a UCP1 positive regulator. For example, a control may include a brown fat progenitor cell cultured using the same cell culture conditions, including the same culture media, but which is not contacted with a UCP1 positive regulator. The control may be used as a baseline in determining whether UCP1 expression is increased.

As used herein, the term "isolated" refers to a molecule, e.g., a protein or nucleic acid, which is separated from other molecules that are present in the natural source of the molecule. In one embodiment, an "isolated" molecule is substantially free of other cellular material, or culture media when produced by recombinant techniques, or, in the alternative, substantially free of chemical precursors or other chemicals when chemically synthesized.

As used herein, the term "vector" refers to a nucleic acid molecule capable of transporting another nucleic acid to which it has been linked.

As used herein, the term "mimetic" when made in reference to a protein refers to a molecular structure which serves as a substitute for a UCP1 negative regulator or a UCP1 positive regulator protein used in the present invention (see Morgan el al. (1989) *Ann. Reports Med. Chem.* 24:243-252 for a review of peptide numerics). In one embodiment, a mimetic may be an organic compound that imitates the binding site of a specific UCP1 negative regulator or a UCP1 positive regulator, and, therefore, the functionality of a UCP1 negative regulator or a UCP1 positive regulator, e.g., inducing expression of UCP1 in a cell.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH 1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR1, CDR2, FR3, CDR3, FR4.

The term "antigen-binding portion" or "antigen-binding fragment" of an antibody (or simply "antibody portion"), as used herein, refers to a portion of a full-length antibody, generally the target binding or variable region. Examples of antibody fragments include Fab, Fab', F(ab')$_2$ and Fv fragments. The phrase "functional fragment" of an antibody is a compound having qualitative biological activity in common with a full-length antibody. For example, a functional fragment of a UCP1 positive regulator antibody is one which can bind to a UCP1 positive regulator in such a manner so as to activate UCP1 expression in the cell. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Collectively, the six CDRs confer target binding specificity to the antibody. However, even a single variable domain (or half of an Fv comprising only three CDRs specific for a target) has the ability to recognize and bind target, although at a lower affinity than the entire binding site.

The term "subject" as used herein interchangeably, refers to either a human or non-human animal. In one embodiment, the subject is a human subject. In another embodiment, the subject is a mammal.

As used herein "a disorder that would benefit from metabolic control" is intended to refer to diseases, disorders or conditions, lacking in metabolic regulation. A disorder that would benefit from metabolic control includes conditions where catabolism and/or anabolism are not effective in a subject (relative to known medical standards for a healthy population).

The term "dose," as used herein, refers to an amount of an inhibitor of a UCP1 negative regulator, an activator of a UCP1 positive regulator or a UCP1 positive regulator (e.g., an inhibitory nucleic acid targeting the UCP1 negative regulator, an antagonist antibody of a UCP1 negative regulator, or antigen-binding fragment thereof, an agonist antibody for the UCP1 positive regulator, or antigen-binding fragment thereof, a UCP1 positive regulator, a nucleic acid molecule encoding the UCP1 positive regulator, or a polynucleotide associated with the CRISPR/Cas system which binds the UCP1 positive regulator and activates the transcription of the UCP1 positive regulator) or a cell in which UCP1 has been induced via contact with an inhibitor of a UCP1 negative regulator, an activator of a UCP1 positive regulator or a UCP1 positive regulator, which is administered to a subject.

The term "dosing", as used herein, refers to the administration of a substance to achieve a therapeutic objective (e.g., the treatment of a disorder of glucose control, a disorder of weight control, a disorder of appetite control or obesity).

The term "kit" as used herein refers to a packaged product comprising components for administering a cell in which UCP1 expression has been induced via contact with an inhibitor of a UCP1 negative regulator, an activator of a UCP1 positive regulator or a UCP1 positive regulator (e.g., an inhibitory nucleic acid targeting the UCP1 negative regulator, an antagonist antibody of a UCP1 negative regulator, or antigen-binding fragment thereof, an agonist antibody for the UCP1 positive regulator, or antigen-binding fragment thereof, a UCP1 positive regulator, a nucleic acid molecule encoding the UCP1 positive regulator, or a polynucleotide associated with the CRISPR/Cas system which binds the UCP1 positive regulator and activates the transcription of the UCP1 positive regulator) of the invention for treatment of disorders that would benefit from metabolic control, e.g., diabetes or obesity. The kit preferably comprises a box or container that holds the components of the kit. The box or container is affixed with a label or a Food and Drug Administration approved protocol. The box or container holds components of the invention that are preferably contained within plastic, polyethylene, polypropylene, ethylene, or propylene vessels. The vessels can be capped-tubes or bottles. The kit can also include instructions for administering the cell or an inhibitor of a UCP1 negative regulator, an activator of a UCP1 positive regulator or a UCP1 positive regulator for use in the methods of the invention.

II. Methods and Compositions of the Invention

A. UCP1 Activators and Inhibitors

The capacity of thermogenically competent cells, such as preadipocytes, to consume energy is due, in large part, to the expression of UCP1. The present invention is based, at least in part, on the discovery that expression (or repression) of certain molecular targets in thermogenically competent cells (such as preadipocytes) correlates with the expression of UCP1 in the differentiated mature state of a cell (such as an adipocyte). As such, modulating the expression or activity of these molecular targets can be used as a way to regulate, particularly increase, the thermogenic potential in cells or tissues. Thus, the methods of the invention include, but are not limited to, contacting a thermogenically competent cell, such as a preadipocyte, with an inhibitor of a UCP1 negative regulator, an activator of a UCP1 positive regulator, or a UCP1 positive regulator, or combinations thereof, such that the thermogenic capacity of the cell is promoted.

The methods of the invention may be used to increase the thermogenic capacity of a cell or tissue through the modulation of genes identified as activators or repressors of UCP1. In certain embodiments, the present invention is based on the ability of a thermogenically competent cell, such as a preadipocyte, to dissipate energy and regulate triglyceride and glucose metabolism upon expression of UCP1 through exposure to a UCP1 positive regulator, an activator of a positive regulator, and/or an inhibitor of a UCP1 negative regulator.

The invention includes modulation of UCP1 (and, therefore, modulation of thermogenesis) in a cell, wherein the cell is a thermogenically competent cell. A thermogenically competent cell is a cell in which UCP1 expression can be induced such that the cell has increased levels of mitochondrial respiration. Mitochondrial respiration may be measured according to standard methods known in the art, including basal respiration, ATP turnover, proton leak, and respiratory capacity. Thermogenic capacity of a cell or tissue may be characterized by an increase in UCP1 gene expression and/or an increase in brown adipocyte tissue (BAT).

Conversion to an energy consuming cell can be determined by measuring mitochondrial metabolism. For example, following contact of the thermogenically competent cell with the inhibitor of the UCP1 negative regulator, a UCP1 positive regulator, or an activator of a UCP1 positive regulator, the cell may demonstrate increased mitochondrial metabolism. To assess mitochondrial metabolism, mitochondrial activity can be measured using, for example, a Seahorse Bioanalyzer. For example, cells are provided with abundant nutrients (e.g., 10 mM glucose, 0.5 mM carnitine, and 1 mM palmitate-BSA) and a profile of cellular respiration is developed by utilizing well-characterized mitochondrial toxins. Basal respiration is measured, followed by injection of oligomycin, an inhibitor of ATP synthase, which allows measurement of ATP turnover. The uncoupler FCCP is injected to measure respiratory capacity, followed by the complex 1 inhibitor rotenone, which prevents electron transfer activity and leaves only non-mitochondrial activity to be measured. This allows the bioenergetic profile (i.e., mitochondrial metabolism), comprising basal respiration, ATP turnover, proton leak and respiratory capacity, of energy consuming cells to be measured. In one embodiment, exposure of a thermogenically competent cell to an inhibitor of a UCP1 negative regulator, a UCP1 positive regulator, or an activator of a UCP1 positive regulator demonstrates levels or amounts of mitochondrial metabolism that are about 1.5-fold, 2-fold, 2.5-fold, 3-fold, 3.5-fold, 4-fold, 5-fold, 6-fold, 7-fold, 8-fold, 9-fold, 10-fold, 12-fold, 15-fold, 18-fold, 20-fold, 22-fold or 25-fold higher than in a control cell (i.e., a cell not contacted with the inhibitor of a UCP1 negative regulator, UCP1 positive regulator, or activator of a UCP1 positive regulator).

Ranges within one or more of the preceding values e.g., about 1.5-fold to about 3-fold, about 2-fold to about 6-fold, about 3-fold to about 10-fold, about 5-fold to about 15-fold, about 12-fold to about 20-fold, about 15-fold to about 25-fold or about 1.5-fold to about 25-fold are contemplated by the invention.

In another embodiment, the thermogenically competent cell demonstrates levels or amounts of mitochondrial metabolism resulting from an increase in any one of basal respiration, ATP turnover, proton leak and/or respiratory capacity following exposure to an inhibitor of a UCP1 negative regulator, a UCP1 positive regulator, or an activator of a UCP1 positive regulator. For example, any one of basal respiration, ATP turnover, proton leak and/or respiratory capacity is increased by at least about 1.5-fold, 2-fold, 2.5-fold, 3-fold, 3.5-fold, 4-fold, 5-fold, 6-fold, 7-fold, 8-fold, 9-fold, 10-fold, 12-fold, 15-fold, 18-fold, 20-fold, 22-fold or 25-fold as compared to a control cell. Ranges within one or more of the preceding values e.g., about 1.5-fold to about 3-fold, about 2-fold to about 6-fold, about 3-fold to about 10-fold, about 5-fold to about 15-fold, about 12-fold to about 20-fold, about 15-fold to about 25-fold or about 1.5-fold to about 25-fold are contemplated by the invention.

In one embodiment, a thermogenically competent cell is a preadipocyte, including either a brown or white preadipocyte. In one embodiment, a thermogenically competent cell is an undifferentiated cell or an embryonic stem cell. In one embodiment, a thermogenically competent cell is an inducible pluripotent stem cell. In one embodiment, a thermogenically competent cell is a muscle derived progenitor cell.

UCP1 Negative Regulators

In one embodiment, the methods and compositions of the invention are based on the identification of uncoupling protein 1 (UCP1) negative regulators whose activity in a thermogenically competent cell represses or inhibits UCP1 expression. By inhibiting any one of these UCP1 negative regulators, a thermogenically competent cell, such as a preadipocyte, can express UCP1 and promote thermogenic capacity. Examples of UCP1 negative regulators include, but are not limited to, cardiac actin 1 (ACTC1), somatostatin receptor 1 (SSTR1), and FAT atypical cadherin 1 (FAT1), protein tyrosine phosphatase receptor type B (PTPRB) and Contactin 3 (CNTN3). Other examples are provided in Table 4, including TEK, CDH13, EPB41L3, KRTCAP2, NUCB2, SMYD2, PSME4, TJP1, ZNF518B, GRIK2, ANTXR1, SLC7A6, THBS1, TOM1L1, CSRP2, STXBP6, SHROOM3, WNT2, HAPLN1, COL12A1, NALCN, PLCXD3 and CNTN3.

ACTC1 has been identified herein as a negative regulator of UCP1. ACTC1 is also known as Cardiac actin 1, Actin, alpha, cardiac muscle 1, LVNC4, ASD5, CMD1R and CMH11. The sequence of a human ACTC1 mRNA can be found at GenBank Accession GI:113722123 (NM_005159.4; SEQ ID NO: 1). The sequence of a human ACTC1 polypeptide sequence can be found at GenBank Accession No. GI:4885049 (NP_005150.1; SEQ ID NO: 2). Thus, in one embodiment, the invention features a method of inhibiting ACTC1 activity in a cell or tissue such that UCP1 expression occurs in the cell or tissue and thermogenesis is promoted.

SSTR1 has been identified herein as a negative regulator of UCP1. SSTR1 is also known as Somatostatin receptor 1, SRIF-2, SS1R, Somatostatin Receptor Type 1. SSTR1 encodes a protein which is a member of the superfamily of somatostatin receptors having seven transmembrane segments. The sequence of a human SSTR1 mRNA is set forth at GenBank Accession GI:33946330 (NM_001049.2; SEQ ID NO: 3). The sequence of human SSTR1 polypeptide sequence is set forth at GenBank Accession No. GI:4557857 (NP_001040.1; SEQ ID NO: 4). Thus, in one embodiment, the invention features a method of inhibiting SSTR1 activity in a cell or tissue such that UCP1 expression occurs in the cell or tissue and thermogenesis is promoted.

FAT1 has been identified herein as a negative regulator of UCP1. FAT1 is also known as FAT atypical cadherin 1, Cadherin-related family member 8, CDHR8, cadherin family member 7, CDHF7, cadherin-related tumor suppressor homolog, Protein Fat Homolog, FAT tumor suppressor homolog 1, ME5, Cadherin ME5, FAT tumor suppressor 1, Protocadeherin Fat 1. FAT1 is a member of the cadherin superfamily, a group of integral membrane proteins characterized by the presence of cadherin-type repeats. In addition to containing 34 tandem cadherin-type repeats, the FAT1 protein has five epidermal growth factor (EGF)-like repeats and one laminin A-G domain. FAT1 is among the top-ranking genes described herein whose expression level in preadipocytes is negatively correlated with UCP1 levels in mature cells. FAT1 is a tumor suppressor essential for controlling cell proliferation during Drosophila development. As a member of the cadherin superfamily, FAT1 may function as an adhesion molecule or signaling receptor during development and cell communication. The sequence of the human FAT1 mRNA can be found at GenBank Accession GI:75813622 (NM_005245.3; SEQ ID NO: 5). The sequence of the human FAT1 polypeptide sequence is set forth at GenBank Accession No. GI:66346693 (NP_005236.2; SEQ ID NO: 6). Thus, in one embodiment, the invention features a method of inhibiting FAT1 activity in a cell or tissue such that UCP1 expression occurs in the cell or tissue and thermogenesis is promoted.

PTPRB has been identified herein as a negative regulator of UCP1. PTPRB is also known as Protein tyrosine phosphatase, receptor type B, vascular endothelial protein tyrosine phosphatase, VEPTP, HPTP-BETA, protein tyrosine phosphatase, receptor type, beta polypeptide, receptor-type tyrosine-protein phosphatase beta, R-PTP-beta, protein-tyrosine phosphatase beta. PTPRB is a member of the protein tyrosine phosphatase (PTP) family. The sequence of a human PTPRB mRNA is set forth as GenBank Accession GI:332800996 (NM_001109754.2; SEQ ID NO: 7). The sequence of a human PTPRB polypeptide sequence is set forth in GenBank Accession No. GI:157952215 (NP_001103224.1; SEQ ID NO: 8). Thus, in one embodiment, the invention features a method of inhibiting ACTC1 activity in a cell or tissue such that UCP1 expression occurs in the cell or tissue and thermogenesis is promoted.

TEK has been identified herein as a negative regulator of UCP1. TEK is also known as TEK receptor tyrosine kinase, TIE2, VMCM, TIE-2, VMCM1, and CD202B. TEK is a member of the protein tyrosine kinase Tie2 family. In one embodiment, TEK is human TEK (Gene ID: 7010). In one embodiment, the sequence of a human TEK mRNA is set forth as GENBANK Accession Nos. NM_000459.4, GI:587651915 (isoform 1 precursor). Under this embodiment, the sequence of a human TEK polypeptide sequence is set forth in GENBANK Accession No. NP_000450.2, GI:88758596 (isoform 1 precursor). In another embodiment, the sequence of a human TEK mRNA is set forth as GENBANK Accession Nos. NM_001290077.1, GI:587651916 (isoform 2 precursor). Under this embodiment, the sequence of a human TEK polypeptide sequence is set forth in GENBANK Accession Nos. NP_001277006.1, GI:587651917 (isoform 2 precursor). In yet another embodiment, the sequence of a human TEK mRNA is set forth as GENBANK Accession Nos. NM_001290078.1, GI:587651918 (isoform 3 precursor). Under this embodiment, the sequence of a human TEK polypeptide sequence is set forth in GENBANK Accession No. NP_001277007.1, GI:587651919 (isoform 3 precursor). Thus, in one embodiment, the invention features a method of inhibiting TEK activity in a cell or tissue such that UCP1 expression occurs in the cell or tissue and thermogenesis is promoted.

CDH13 has been identified herein as a negative regulator of UCP1. CDH13 is also known as cadherin 13, CDHH, and P105. CDH13 is a member of the cadherin superfamily and acts as a negative regulator of axon growth during neural differentiation and it also protects vascular endothelial cells from apoptosis due to oxidative stress. In one embodiment, CDH13 is human CDH13 (Gene ID:1012). In one embodiment, the sequence of a human CDH13 mRNA is set forth as GENBANK Accession Nos. NM_001257.4, GI:333944011 (variant 1). Under this embodiment, the sequence of a human CDH13 polypeptide sequence is set forth in GENBANK Accession Nos. NP_001248.1, GI:4502719 (variant 1). In a second embodiment, the sequence of a human CDH13 mRNA is set forth as GENBANK Accession Nos. NM_001220488.1, GI:333944014 (variant 2). Under this embodiment, the sequence of a human CDH13 polypeptide sequence is set forth in GENBANK Accession Nos. NP_001207417.1, GI:333944015 (variant 2). In a third embodiment, the sequence of a human CDH13 mRNA is set forth as GENBANK Accession Nos. NM_001220489.1, GI:333944017 (variant 3). Under this embodiment, the sequence of a human CDH13 polypeptide sequence is set forth in GENBANK Accession Nos. NP_001207418.1, GI:333944018 (variant 3). In a fourth embodiment, the sequence of a human CDH13 mRNA is set forth as GENBANK Accession Nos. NM_001220490.1, GI:333944019 (variant 4). Under this embodiment, the sequence of a human CDH13 polypeptide sequence is set forth in GENBANK Accession Nos. NP_001207419.1, GI:333944020 (variant 4). In a fifth embodiment, the sequence of a human CDH13 mRNA is set forth as GENBANK Accession Nos. NM_001220491.1, GI:333944021 (variant 5). Under this embodiment, the sequence of a human CDH13 polypeptide sequence is set forth in GENBANK Accession Nos. NP_001207420.1, GI:333944022 (variant 5). In a sixth embodiment, the sequence of a human CDH13 mRNA is set forth as GENBANK Accession Nos. NM_001220492.1, GI:333944023 (variant 6). Under this embodiment, the sequence of a human CDH13 polypeptide sequence is set forth in GENBANK Accession Nos. NP_001207421.1, GI:333944024 (variant 6). Accordingly, in one embodiment, the invention features a method of inhibiting CDH13 activity in a cell or tissue such that UCP1 expression occurs in the cell or tissue and thermogenesis is promoted.

EPB41L3 has been identified herein as a negative regulator of UCP1. EPB41L3 is also known as erythrocyte membrane protein band 4.1 like 3, 4.1B, DAL1, and DAL-1. EPB41L3 is a tumor suppressor that inhibits cell proliferation and promotes apoptosis and modulates the activity of protein arginine N-methyltransferases, including PRMT3 and PRMT5. In one embodiment, EPB41L3 is human EPB41L3 (Gene ID: 23136). In one embodiment, the sequence of a human EPB41L3 mRNA is set forth as GENBANK Accession Nos. NM_012307.3, GI:528281417 (isoform 1). Under this embodiment, the sequence of a human EPB41L3 polypeptide sequence is set forth in GENBANK Accession Nos. NP_036439.2, GI:32490572 (isoform 1). In a second embodiment, the sequence of a human EPB41L3 mRNA is set forth as GENBANK Accession Nos. NM_001281533.1, GI:528281418 (isoform 2). Under this embodiment, the sequence of a human EPB41L3 polypeptide sequence is set forth in GENBANK Accession Nos. NP_001268462.1, GI:528281419 (isoform 2). In a third embodiment, the sequence of a human EPB41L3 mRNA is set forth as GENBANK Accession Nos. NM_001281534.1, GI:528281420 (isoform 3). Under this embodiment, the sequence of a human EPB41L3 polypeptide sequence is set forth in GENBANK Accession Nos. NP_001268463.1, GI:528281421 (isoform 3). In a fourth embodiment, the sequence of a human EPB41L3 mRNA is set forth as GENBANK Accession Nos. NM_001281535.1, GI:528281422 (isoform 4). Under this embodiment, the sequence of a human EPB41L3 polypeptide sequence is set forth in GENBANK Accession Nos. NP_001268464.1, GI:528281423 (isoform 4). Thus, in one embodiment, the invention features a method of inhibiting EPB41L3 activity in a cell or tissue such that UCP1 expression occurs in the cell or tissue and thermogenesis is promoted.

KRTCAP2 has been identified herein as a negative regulator of UCP1. KRTCAP2 is also known as keratinocyte associated protein 2 and KCP2. KRTCAP2 is a component of the oligosaccharyltransferase (OST) complex. In one embodiment, KRTCAP2 is human KRTCAP2 (Gene ID: 200185). In one embodiment, the sequence of a human KRTCAP2 mRNA is set forth as GENBANK Accession Nos. NM_173852.3, GI:56676325. Under this embodiment, the sequence of a human KRTCAP2 polypeptide sequence is set forth in GENBANK Accession Nos. NP_776251.1, GI:27777661. Thus, in one embodiment, the invention features a method of inhibiting KRTCAP2 activity in a cell or tissue such that UCP1 expression occurs in the cell or tissue and thermogenesis is promoted.

NUCB2 has been identified herein as a negative regulator of UCP1. NUCB2 is also known as nucleobindin 2, NEFA, and HEL-S-109. NUCB2 is a calcium-binding protein with a suggested role in calcium level maintenance, eating regulation in the hypothalamus, and release of tumor necrosis factor from vascular endothelial cells. In one embodiment, NUCB2 is human NUCB2 (Gene ID: 4925). In one embodiment, the sequence of a human NUCB2 mRNA is set forth as GENBANK Accession Nos. NM_005013.2, GI:116063564. Under this embodiment, the sequence of a human NUCB2 polypeptide sequence is set forth in GENBANK Accession Nos. NP_005004.1, GI:4826870. Thus, in one embodiment, the invention features a method of inhibiting NUCB2 activity in a cell or tissue such that UCP1 expression occurs in the cell or tissue and thermogenesis is promoted.

SMYD2 has been identified herein as a negative regulator of UCP1. SMYD2 is also known as SET and MYND domain containing 2, KMT3C, HSKM-B, and ZMYND14. SMYD2 is a member of SET-domain-containing protein family that catalyze the methylation of lysine. In one embodiment, SMYD2 is human SMYD2 (Gene ID: 56950). In one embodiment, the sequence of a human SMYD2 mRNA is set forth as GENBANK Accession Nos. NM_020197.2, GI:188035870. Under this embodiment, the sequence of a human SMYD2 polypeptide sequence is set forth in GENBANK Accession Nos. NP_064582.2, GI:188035871. Thus, in one embodiment, the invention features a method of inhibiting SMYD2 activity in a cell or tissue such that UCP1 expression occurs in the cell or tissue and thermogenesis is promoted.

PSME4 has been identified herein as a negative regulator of UCP1. PSME4 is also known as proteasome activator subunit 4 and PA200. PSME4 is a component of the proteasome that specifically recognizes acetylated histones and promotes ATP- and ubiquitin-independent degradation of core histones during spermatogenesis and DNA damage response. In one embodiment, PSME4 is human PSME4 (Gene ID: 23198). In one embodiment, the sequence of a human PSME4 mRNA is set forth as GENBANK Accession Nos. NM_014614.2, GI:163644282. Under this embodiment, the sequence of a human PSME4 polypeptide sequence is set forth in GENBANK Accession Nos. NP_055429.2, GI:163644283. Thus, in one embodiment, the invention features a method of inhibiting PSME4 activity in a cell or tissue such that UCP1 expression occurs in the cell or tissue and thermogenesis is promoted.

TJP1 has been identified herein as a negative regulator of UCP1. TJP1 is also known as tight junction protein 1 and ZO-1. TJP1 is a protein found in tight junctions and plays a role in the regulation of cell migration by targeting CDC42BPB to the leading edge of migrating cells. In one embodiment, TJP1 is human TJP1 (Gene ID: 7082). In one embodiment, the sequence of a human TJP1 mRNA is set forth as GENBANK Accession Nos. NM_003257.4, GI:666335592 (isoform a). Under this embodiment, the sequence of a human TJP1 polypeptide sequence is set forth in GENBANK Accession Nos. NP_003248.3, GI:116875767 (isoform a). In a second embodiment, the sequence of a human TJP1 mRNA is set forth as GENBANK Accession Nos. NM_175610.3, GI:666335567 (isoform b). Under this embodiment, the sequence of a human TJP1 polypeptide sequence is set forth in GENBANK Accession Nos. NP_783297.2, GI:116875765 (isoform b). In a third embodiment, the sequence of a human TJP1 mRNA is set forth as GENBANK Accession Nos. NM_001301025.1, GI:666335568 (isoform c). Under this embodiment, the sequence of a human TJP1 polypeptide sequence is set forth in GENBANK Accession Nos. NP_001287954.1, GI:666335569 (isoform c). In a fourth embodiment, the sequence of a human TJP1 mRNA is set forth as GENBANK Accession Nos. NM_001301026.1, GI:666335593 (isoform d). Under this embodiment, the sequence of a human TJP1 polypeptide sequence is set forth in GENBANK Accession Nos. NP_001287955.1, GI:666335594 (isoform d). Thus, in one embodiment, the invention features a method of inhibiting TJP1 activity in a cell or tissue such that UCP1 expression occurs in the cell or tissue and thermogenesis is promoted.

ZNF518B has been identified herein as a negative regulator of UCP1. ZNF518B is also known as zinc finger protein 518B. ZNF518B is a zinc-finger containing DNA-binding protein postulated to be involved in transcriptional regulation. In one embodiment, ZNF518B is human ZNF518B (Gene ID: 85460). In one embodiment, the sequence of a human ZNF518B mRNA is set forth as GENBANK Accession Nos. NM_053042.2, GI:58761534. Under this embodiment, the sequence of a human ZNF518B polypeptide sequence is set forth in GENBANK Accession Nos. NP_444270.2, GI:58761535. Thus, in one embodiment, the invention features a method of inhibiting ZNF518B activity in a cell or tissue such that UCP1 expression occurs in the cell or tissue and thermogenesis is promoted.

GRIK2 has been identified herein as a negative regulator of UCP1. GRIK2 is also known as glutamate ionotropic receptor kainate type subunit 2, EAA4, GLR6, MRT6, GLUK6, GLUR6, and GluK2. GRIK2 is a member of the family of glutamate receptors, which are composed of four subunits and function as ligand-activated ion channels (i.e., excitatory neurotransmitter receptors). In one embodiment, GRIK2 is human GRIK2 (Gene ID: 2898). In one embodiment, the sequence of a human GRIK2 mRNA is set forth as GENBANK Accession Nos. NM_021956.4, GI:261278359 (isoform 1). Under this embodiment, the sequence of a human GRIK2 polypeptide sequence is set forth in GENBANK Accession Nos. NP_068775.1, GI:11386137 (isoform 1). In a second embodiment, the sequence of a human GRIK2 mRNA is set forth as GENBANK Accession Nos. NM_175768.3, GI:261278360 (isoform 2). Under this embodiment, the sequence of a human GRIK2 polypeptide sequence is set forth in GENBANK Accession Nos. NP_786944.1, GI:28559003 (isoform 2). In a third embodiment, the sequence of a human GRIK2 mRNA is set forth as GENBANK Accession Nos. NM_001166247.1, GI:261278361 (isoform 3). Under this embodiment, the sequence of a human GRIK2 polypeptide sequence is set forth in GENBANK Accession Nos. NP_001159719.1, GI:261278362 (isoform 3). Thus, in one embodiment, the invention features a method of inhibiting GRIK2 activity in a cell or tissue such that UCP1 expression occurs in the cell or tissue and thermogenesis is promoted.

ANTXR1 has been identified herein as a negative regulator of UCP1. ANTXR1 is also known as anthrax toxin receptor 1, ATR, GAPO, and TEM8. ANTXR1 is a type I transmembrane protein that serves as a docking protein or receptor for *Bacillus anthracis* toxin, the causative agent of the disease, anthrax and is also a tumor-specific endothelial marker that has been implicated in colorectal cancer. In one embodiment, ANTXR1 is human ANTXR1 (Gene ID: 84168). In one embodiment, the sequence of a human ANTXR1 mRNA is set forth as GENBANK Accession Nos. NM_032208.2, GI:208022654 (isoform 1). Under this embodiment, the sequence of a human ANTXR1 polypeptide sequence is set forth in GENBANK Accession Nos. NP_115584.1, GI:14149904 (isoform 1). In a second embodiment, the sequence of a human ANTXR1 mRNA is set forth as GENBANK Accession Nos. NM_053034.2, GI:208022655 (isoform 2). Under this embodiment, the sequence of a human ANTXR1 polypeptide sequence is set forth in GENBANK Accession Nos. NP_444262.1, GI:16933551 (isoform 2). Yet in a third embodiment, the sequence of a human ANTXR1 mRNA is set forth as GENBANK Accession Nos. NM_018153.3, GI:208022656 (isoform 3). Under this embodiment, the sequence of a human ANTXR1 polypeptide sequence is set forth in GENBANK Accession Nos. NP_060623.2, GI:16933553 (isoform 3). Thus, in one embodiment, the invention features a method of inhibiting ANTXR1 activity in a cell or tissue such that UCP1 expression occurs in the cell or tissue and thermogenesis is promoted.

SLC7A6 has been identified herein as a negative regulator of UCP1. SLC7A6 is also known as solute carrier family 7 member 6, LAT3, LAT-2, and y+LAT-2. SLC7A6 is a member of the solute carrier family of proteins and is involved in the sodium-independent uptake of dibasic amino acids and sodium-dependent uptake of some neutral amino acids. In one embodiment, SLC7A6 is human EPB41L3 (Gene ID: 9057). In one embodiment, the sequence of a human SLC7A6 mRNA is set forth as GENBANK Accession Nos. NM_001076785.2, GI:342672033 (variant 1). Under this embodiment, the sequence of a human SLC7A6 polypeptide sequence is set forth in GENBANK Accession Nos. NP_001070253.1, GI:115648063 (variant 1). In a second embodiment, the sequence of a human SLC7A6 mRNA is set forth as GENBANK Accession Nos. NM_003983.5, GI:342672034 (variant 2). Under this embodiment, the sequence of a human SLC7A6 polypeptide sequence is set forth in GENBANK Accession Nos. NP_003974.2, GI:115648022 (variant 2). Thus, in one embodiment, the invention features a method of inhibiting SLC7A6 activity in a cell or tissue such that UCP1 expression occurs in the cell or tissue and thermogenesis is promoted.

THBS1 has been identified herein as a negative regulator of UCP1. THBS1 is also known as thrombospondin 1, TSP, THBS, TSP1, TSP-1, and THBS-1. THBS1 is an adhesive glycoprotein that mediates cell-to-cell and cell-to-matrix interactions by binding to fibrinogen, fibronectin, laminin, type V collagen and integrins alpha-V/beta-1. In one embodiment, THBS1 is human THBS1 (Gene ID: 7057). In one embodiment, the sequence of a human THBS1 mRNA is set forth as GENBANK Accession Nos. NM_003246.3, GI:769468216. Under this embodiment, the sequence of a human THBS1 polypeptide sequence is set forth in GENBANK Accession Nos. NP_003237.2, GI:40317626. Thus, in one embodiment, the invention features a method of inhibiting THBS1 activity in a cell or tissue such that UCP1 expression occurs in the cell or tissue and thermogenesis is promoted.

TOM1L1 has been identified herein as a negative regulator of UCP1. TOM1L1 is also known as target of myb1 like 1 membrane trafficking protein and SRCASM. TOM1L1 is an adapter protein involved in signaling pathways. In one embodiment, TOM1L1 is human TOM1L1 (Gene ID: 10040). In one embodiment, the sequence of a human TOM1L1 mRNA is set forth as GENBANK Accession Nos. NM_005486.2, GI:191252811 (isoform 1). Under this embodiment, the sequence of a human TOM1L1 polypeptide sequence is set forth in GENBANK Accession Nos. NP_005477.2, GI:191252812 (isoform 1). In a second embodiment, the sequence of a human TOM1L1 mRNA is set forth as GENBANK Accession Nos. NM_001321173.1, GI:1007382087 (isoform 2). Under this embodiment, the sequence of a human TOM1L1 polypeptide sequence is set forth in GENBANK Accession Nos. NP_001308102.1, GI:1007382088 (isoform 2). In a third embodiment, the sequence of a human TOM1L1 mRNA is set forth as GENBANK Accession Nos. NM_001321174.1, GI:1007376790 (isoform 3). Under this embodiment, the sequence of a human TOM1L1 polypeptide sequence is set forth in GENBANK Accession Nos. NP_001308103.1, GI:1007376791 (isoform 3). In another embodiment, the sequences of human TOM1L1 isoform 3 are set forth as GENBANK Accession Nos. NM_001321175.1, GI:1007375183 (variant 4 mRNA) and NP_001308104.1, GI:1007375184 (variant 4 protein). Yet in another embodiment, the sequences of human TOM1L1 isoform 3 are set forth as GENBANK Accession Nos. NM_001321176.1, GI:1007377888 (variant 5 mRNA) and NP_001308105.1, GI:1007377889 (variant 5 protein) Thus, in one embodiment, the invention features a method of inhibiting TOM1L1 activity in a cell or tissue such that UCP1 expression occurs in the cell or tissue and thermogenesis is promoted.

CSRP2 has been identified herein as a negative regulator of UCP1. CSRP2 is also known as cysteine and glycine rich protein 2, CRP2, LMOS, and SmLIM. CSRP2 is a member of the LIM domain proteins, which may be involved in regulatory processes important for development and cellular differentiation. In one embodiment, CSRP2 is human CSRP2 (Gene ID: 1466). In one embodiment, the sequence of a human CSRP2 mRNA is set forth as GENBANK Accession Nos. NM_001321.2, GI:665821265 (variant 1). Under this embodiment, the sequence of a human CSRP2 polypeptide sequence is set forth in GENBANK Accession Nos. NP_001312.1, GI:4503101 (variant 1). In a second embodiment, the sequence of a human CSRP2 mRNA is set forth as GENBANK Accession Nos. NM_001300965.1, GI:665821266 (variant 2). Under this embodiment, the sequence of a human CSRP2 polypeptide sequence is set forth in GENBANK Accession Nos. NP_001287894.1, GI:665821267 (variant 2). Thus, in one embodiment, the invention features a method of inhibiting CSRP2 activity in a cell or tissue such that UCP1 expression occurs in the cell or tissue and thermogenesis is promoted.

STXBP6 has been identified herein as a negative regulator of UCP1. STXBP6 is also known as syntaxin binding protein 6, amisyn, and HSPC156. STXBP6 binds to soluble N-ethylmaleimide-sensitive factor (NSF) attachment protein receptor (SNARE) and may be involved in regulating SNARE complex formation. In one embodiment, STXBP6 is human STXBP6 (Gene ID: 29091). In one embodiment, the sequence of a human STXBP6 mRNA is set forth as GENBANK Accession Nos. NM_014178.7, GI:751130457 (variant 1). In a second embodiment, the sequence of a human STXBP6 mRNA is set forth as GENBANK Accession Nos. NM_001304476.1, GI:751247009 (variant 2). In a third embodiment, the sequence of a human STXBP6 mRNA is set forth as GENBANK Accession Nos. NM_001304477.1, GI:751247025 (variant 3). Under these embodiments, the sequences of a human STXBP6 polypeptide encoded by the aforementioned mRNA variants is set forth in GENBANK Accession Nos. NP_054897.4, GI:21426793 (product of variant 1) or NP_001291405.1, GI:751247010 (product of variant 2) or NP_001291406.1, GI:751247026 (product of variant 3). Thus, in one embodiment, the invention features a method of inhibiting STXBP6 activity in a cell or tissue such that UCP1 expression occurs in the cell or tissue and thermogenesis is promoted.

SHROOM3 has been identified herein as a negative regulator of UCP1. SHROOM3 is also known as shroom family member 3, SHRM, APXL3, ShrmL, and MSTP013. SHROOM3 is a member of the Shroom-related proteins and may be involved in regulating cell shape in certain tissues. In one embodiment, SHROOM3 is human SHROOM3 (Gene ID: 57619). In one embodiment, the sequence of a human SHROOM3 mRNA is set forth as GENBANK Accession Nos. NM_020859.3, GI:203098097. Under this embodiment, the sequence of a human SHROOM3 polypeptide sequence is set forth in GENBANK Accession Nos. NP_065910.3, GI:203098098. Thus, in one embodiment, the invention features a method of inhibiting SHROOM3 activity in a cell or tissue such that UCP1 expression occurs in the cell or tissue and thermogenesis is promoted.

WNT2 has been identified herein as a negative regulator of UCP1. WNT2 is also known as Wnt family member 2, IRP, and INT1L1. WNT2 is among the top-ranking genes described herein whose expression level in preadipocytes is negatively correlated with UCP1 levels in mature cells. WNT2 is a member of the WNT family of proteins and has been implicated in oncogenesis and in several developmental processes, including regulation of cell fate and patterning during embryogenesis. WNT2 may regulate a large variety of modeling and remodeling processes, including cell polarity, cell differentiation, and cell migration. While other members of the WNT family have been shown to directly inhibit adipogenesis, the role of WNT2 in regulation of adipocyte function and energy metabolism was previously unknown. In one embodiment, WNT2 is human WNT2 (Gene ID: 7472). In one embodiment, the sequence of a human WNT2 mRNA is set forth as GENBANK Accession Nos. NM_003391.2, GI:195230749 (coding transcript). Under this embodiment, the sequence of a human WNT2 polypeptide sequence is set forth in GENBANK Accession Nos. NP_003382.1, GI:4507927 (protein product). In a second embodiment, the sequence of a human WNT2 mRNA is set forth as GENBANK Accession Nos. NR_024047.1, GI:195230751 (non-coding transcript). Thus, in one embodiment, the invention features a method of inhibiting WNT2 activity in a cell or tissue such that UCP1 expression occurs in the cell or tissue and thermogenesis is promoted.

HAPLN1 has been identified herein as a negative regulator of UCP1. HAPLN1 is also known as hyaluronan and proteoglycan link protein 1, CRT1, and CRTL1. HAPLN1 is a protein that stabilizes the aggregates of proteoglycan monomers with hyaluronic acid in the extracellular cartilage matrix. In one embodiment, HAPLN1 is human HAPLN1 (Gene ID: 1404). In one embodiment, the sequence of a human HAPLN1 mRNA is set forth as GENBANK Accession Nos. NM_001884.3, GI:194018435. Under this embodiment, the sequence of a human HAPLN1 polypeptide sequence is set forth in GENBANK Accession Nos. NP_001875.1, GI:4503053. Thus, in one embodiment, the invention features a method of inhibiting HAPLN1 activity in a cell or tissue such that UCP1 expression occurs in the cell or tissue and thermogenesis is promoted.

COL12A1 has been identified herein as a negative regulator of UCP1. COL12A1 is also known as collagen type XII alpha 1 chain, UCMD2, BTHLM2, COL12A1L, BA209D8.1, and DJ234P15.1. COL12A1 encodes the alpha chain of type XII collagen, a member of FACIT (fibril-associated collagens with interrupted triple helices) collagen family of proteins and is thought to modify the interactions between collagen I fibrils and the surrounding matrix. In one embodiment, COL12A1 is human COL12A1 (Gene ID: 1303). In one embodiment, the sequence of a human COL12A1 mRNA is set forth as GENBANK Accession Nos. NM_004370.5, GI:93141046 (long chain). Under this embodiment, the sequence of a human COL12A1 polypeptide sequence is set forth in GENBANK Accession Nos. NP_004361.3, GI:93141047 (long chain). In a second embodiment, the sequence of a human COL12A1 mRNA is set forth as GENBANK Accession Nos. NM_080645.2, GI:93141048 (short chain). Under this embodiment, the sequence of a human COL12A1 polypeptide sequence is set forth in GENBANK Accession Nos. NP_542376.2, GI:93141049 (short chain). Thus, in one embodiment, the invention features a method of inhibiting COL12A1 activity in a cell or tissue such that UCP1 expression occurs in the cell or tissue and thermogenesis is promoted.

NALCN has been identified herein as a negative regulator of UCP1. NALCN is also known as sodium leak channel, non-selective, IHPRF, INNFD, Canlon, IHPRF1, VGCNL1, CLIFAHDD, and bA430M15.1. NALCN is a voltage-independent, nonselective, non-inactivating cation channel permeable to Na+, K+, and Ca(2+) and is responsible for the neuronal background sodium leak conductance. In one embodiment, NALCN is human NALCN (Gene ID: 259232). In one embodiment, the sequence of a human NALCN mRNA is set forth as GENBANK Accession Nos. NM_052867.2, GI:93277089. Under this embodiment, the sequence of a human NALCN polypeptide sequence is set forth in GENBANK Accession Nos. NP_443099.1, GI:24119274. Thus, in one embodiment, the invention features a method of inhibiting NALCN activity in a cell or tissue such that UCP1 expression occurs in the cell or tissue and thermogenesis is promoted.

PLCXD3 has been identified herein as a negative regulator of UCP1. PLCXD3 is also known as phosphatidylinositol specific phospholipase C X domain containing 3. PLCXD3 may participate in lipid catabolism and is postulated to have phosphoric diester hydrolase activity and signal transducer activity. In one embodiment, PLCXD3 is human PLCXD3 (Gene ID: 345557). In one embodiment, the sequence of a human PLCXD3 mRNA is set forth as GENBANK Accession Nos. NM_001005473.2, GI:111548664. Under this embodiment, the sequence of a human PLCXD3 polypeptide sequence is set forth in GENBANK Accession Nos. NP_001005473.1, GI:53828920. Thus, in one embodiment, the invention features a method of inhibiting PLCXD3 activity in a cell or tissue such that UCP1 expression occurs in the cell or tissue and thermogenesis is promoted.

CNTN3 has been identified herein as a negative regulator of UCP1. CNTN3 is also known as Contactin 3, Brain-Derived Immunoglobulin Superfamily Protein 1, Plasmacytoma-Associated Neuronal Glycoprotein, BIG-1, PANG, KIAA1496 and PCS. CNTN3 is a contactin which mediates cell surface interactions during nervous system development. Diseases associated with CNTN3 include plasmacytoma and taylor's syndrome. The sequence of the human CNTN3 mRNA can be found at GenBank Accession GI:735997413 (NM_020872.2; SEQ ID NO: 25). The sequence of the human CNTN3 polypeptide sequence is set forth at GenBank Accession No. GI:75709184 (NP_065923.1; SEQ ID NO: 26). Thus, in one embodiment, the invention features a method of inhibiting CNTN3 activity in a cell or tissue such that UCP1 expression occurs in the cell or tissue and thermogenesis is promoted.

In some embodiments, UCP1 negative regulators are cell surface molecules. Exemplary UCP1 negative regulators that are cell surface markers include, but are not limited to, GRIK2, ANTXR1, and SSTR1.

In other embodiments, UCP1 negative regulators are involved in the Hippo signaling pathway. The Hippo pathway contains a network of proteins that controls organ/cell size through regulation of cell proliferation, apoptosis and differentiation. Expression levels of several negative regulators of this pathway were coordinately correlated with UCP1 levels by Ingenuity pathway analysis, as described herein. In particular, LATS1/2, DLG1-5, and PP1, which negatively regulate the Hippo pathway, were identified as UCP1 negative regulators. Expression of one of the key activators/mediators of this pathway, WWTR1 (also known as TAZ), in preadipocytes is positively and significantly correlated with UCP1 levels in mature fat cells, as described below. An overall increase in the activity of the Hippo signaling pathway (e.g., by inhibiting the UCP1 negative regulators LATS1/2, DLG1-5, and/or PP1) will lead to enhanced thermogenic capacity of mature brown/beige fat cells.

One embodiment of the invention features a method of promoting thermogenic capacity in a cell or tissue by contacting a cell having thermogenic competency, such as a preadipocyte, with an inhibitor of a UCP1 negative regulator, such that the cell is able to express UCP1 and promote thermogenesis. Examples of inhibitors that may be used in the methods described herein include, but are not limited to, an inhibitory nucleic acid targeting the UCP1 negative regulator, (e.g., siRNA or CRISPR based inhibitory nucleic acids), an antagonist antibody, or antigen-binding fragment thereof, or a small molecule inhibitor. Examples of inhibitors of UCP1 negative regulators are described in more detail below.

UCP1 Positive Regulators

In one embodiment, the invention features a method of promoting thermogenic capacity in a thermogenically competent cell, such as a preadipocyte, by contacting the thermogenically competent cell with either an activator of a UCP1 positive regulator or a UCP1 positive regulator itself. Examples of UCP1 positive regulators include phosphatidylinositol-3,4,5-triphosphate-dependent Rac exchange factor 1 (PREX1), cortactin binding protein 2 (CTTNBP2), doublesex and mab-3-related transcription factor-like family A1 (DMRTA1), endothelin receptor type B (ENDRB), G protein-coupled receptor 56 (GPR56), and WW domain containing transcription regulator 1 (WWTR1), or combinations thereof. Table 4 further provides additional examples of UCP1 positive regulators such as ST6GALNAC3, S1PR3, SVIL, C17orf60, MASP1, PXK, C10orf90, TBC1D19, DNASE1L1, GPCR5A, ITGA10, ETFDH, MORN4, MRPS6, SETDB2, WRB, SYNRG, ANP32A, and DMRTA1, or a combination thereof.

PREX1 has been identified herein as an activator of UCP1. PREX1 is also known as Phosphatidylinositol-3,4,5-triphosphate-dependent Rac exchange factor 1, PtdIns(3,4,5)-Dependent Rac Exchanger 1, KIAA1415 and Phosphatidylinositol 3,4,5-Trisphosphate-Dependent Rac Exchanger 1 Protein. PREX1 encodes a protein which acts as a guanine nucleotide exchange factor for the RHO family of small GTP-binding proteins (RACs). It has been shown to bind to and activate RAC1 by exchanging bound GDP for free GTP. PREX1 regulates cytoskeletal reorganization and cell migration. PREX1 promotes Glut4 trafficking in 3T3-L1 adipocytes. SNPs near PREX1 are linked to susceptibility to Type 2 diabetes through its potential effect on adiposity. The sequence of a human PREX1 mRNA can be found at GenBank Accession GI:112789552 (NM_020820.3; SEQ ID NO: 9). The sequence of a human PREX1 polypeptide sequence can be found at GenBank Accession No. GI:34452732 (NP_065871.2; SEQ ID NO: 10). Thus, in one embodiment, the invention includes a method of contacting either PREX1 or a PREX1 activator with a thermogenically competent cell or tissue such that UCP1 expression occurs in the cell or tissue and thermogenesis is promoted.

CTTNBP2 has been identified herein as an activator of UCP1. CTTNBP2 is also known as Cortactin binding protein 2, KIAA1758, CORTBP2, C7orf8 and Orf4. CTTNBP2 encodes a protein with six ankyrin repeats and several proline-rich regions. The sequence of a human CTTNBP2 mRNA can be found at GenBank Accession GI:92091570 (NM_033427.2; SEQ ID NO: 11). The sequence of a human CTTNBP2 polypeptide sequence can be found at GenBank Accession No. GI:16975496 (NP_219499.1; SEQ ID NO: 12). Thus, in one embodiment, the invention includes a method of contacting either CTTNBP2 or a CTTNBP2 activator with a thermogenically competent cell or tissue such that UCP1 expression occurs in the cell or tissue and thermogenesis is promoted.

DMRTA1 has been identified herein as an activator of UCP1. DMRTA1 is also known as Doublesex and mab-3-related transcription factor-like family A1, DMO, and DMRT4. The sequence of a human DMRTA1 mRNA can be found at GenBank Accession GI:170763514 (NM_022160.2; SEQ ID NO: 13). The sequence of a human DMRTA1 polypeptide sequence can be found at GenBank Accession No. GI:170763515 (NP_071443.2; SEQ ID NO: 14). Thus, in one embodiment, the invention includes a method of contacting either DMRTA1 or an activator of DMRTA1 with a thermogenically competent cell or tissue, such that UCP1 expression occurs in the cell or tissue and thermogenesis is promoted. EDNRB has been identified herein as a UCP1 activator. EDNRB is also known as Endothelin receptor type B, Receptor Type B, ETRB, HSCR2, HSCR, ABCDS, WS4A, Receptor Non-Selective Type, ETB, ETBR, B Receptor. EDNRB encodes a G protein-coupled receptor which activates a phosphatidylinositol-calcium second messenger system. Its ligand, endothelin, consists of a family of three potent vasoactive peptides: ET1, ET2, and ET3. Endothelin can modulateintracellular calcium and cAMP levels, stimulate glucose uptake, and activate lipolysis in adipocytes. The sequence of a human EDNRB mRNA can be found at GenBank Accession GI:319655693 (NM_000115.3; SEQ ID NO: 15). The sequence of a human EDNRB polypeptide sequence can be found at GenBank Accession No. GI:4557547 (NP_000106.1; SEQ ID NO: 16). Thus, in one embodiment, the invention includes a method of contacting either EDNRB or an activator of EDNRB with a thermogenically competent cell or tissue, such that UCP1 expression occurs in the cell or tissue and thermogenesis is promoted.

GPR56 has been identified herein as a UCP1 activator. GPR56 is also known as G Protein-Coupled Receptor 56, Adhesion G Protein-Coupled Receptor G1, TM7LN4, TM7XN1, 7-Transmembrane Protein With No EGF-Like N-Terminal Domains-1, BFPP and BPPR. GPR45 is a member of the G protein-coupled receptor family and regulates brain cortical patterning. The encoded protein binds specifically to transglutaminase 2, a component of tissue and tumor stroma implicated as an inhibitor of tumor progression. Mutations in this gene are associated with a brain malformation known as bilateral frontoparietal polymicrogyria. The sequence of the human GPR56 mRNA can be found at GenBank Accession GI:589269188 (NM_005682.6; SEQ ID NO: 21). The sequence of the human FAT1 polypeptide sequence is set forth at GenBank Accession No. GI:41584200 (NP_005673.3; SEQ ID NO: 20). Thus, in one embodiment, the invention includes a method of contacting a thermogenically competent cell or tissue with either GPR56 or an activator of GPR56, such that UCP1 expression occurs in the cell or tissue and thermogenesis is promoted.

WWTR1 has been identified herein as a UCP1 activator. WWTR1 is also known as WW Domain Containing Transcription Regulator 1, Transcriptional Coactivator With PDZ-Binding Motif and TAZ. WWTR1 is a transcriptional coactivator which acts as a downstream regulatory target in the Hippo signaling pathway that plays a pivotal role in organ size control and tumor suppression by restricting proliferation and promoting apoptosis. Diseases associated with WWTR1 include epithelioid hemangioendothelioma and histiocytoid hemangioma. The sequence of the human WWTR1 mRNA can be found at GenBank Accession GI:270132687 (NM_015472.4; SEQ ID NO: 23). The sequence of the human WWTR1 polypeptide sequence is set forth at GenBank Accession No. GI:13346498 (NP_056287.1; SEQ ID NO: 24). Thus, in one embodiment, the invention includes a method of contacting a thermogenically competent cell or tissue with either WWTR1 or an activator of WWTR1, such that UCP1 expression occurs in the cell or tissue and thermogenesis is promoted.

ST6GALNAC3 has been identified herein as an activator of UCP1. ST6GALNAC3 is also known as ST6 N-acetylgalactosaminide alpha-2,6-sialyltransferase 3, STY, SIAT7C, PRO7177, and ST6GALNACIII. ST6GALNAC3 is a member of the sialyltransferase family. In one embodiment, ST6GALNAC3 is human ST6GALNAC3 (Gene ID: 256435). In one embodiment, the sequence of a human ST6GALNAC3 mRNA is set forth as GENBANK Accession GI:229892272 (NM_152996.2, isoform 1). In another embodiment, the sequence of a human ST6GALNAC3 mRNA is set forth as GENBANK Accession GI: GI:229892274 (NM_001160011.1, isoform 2). In one embodiment, the sequence of a human ST6GALNAC3 polypeptide sequence is set forth in GENBANK Accession No. GI:229892273 (NP_694541.2, isoform 1). In another embodiment, the sequence of a human ST6GALNAC3 protein is set forth as GENBANK Accession GI: GI:229892275 (NP_001153483.1, isoform 2). Thus, in one embodiment, the invention features a method of contacting a thermogenically competent cell or tissue with either ST6GALNAC3 or an activator of ST6GALNAC3, such that UCP1 expression occurs in the cell or tissue and thermogenesis is promoted.

S1PR3 has been identified herein as an activator of UCP1. S1PR3 is also known as sphingosine-1-phosphate receptor 3, EDG3, LPB3, S1P3, and EDG-3. S1PR3 is a receptor for the lysosphingolipid sphingosine 1-phosphate (S1P). In one embodiment, S1PR3 is human S1PR3 (Gene ID:1903). In one embodiment, the sequence of a human S1PR3 mRNA is set forth as GENBANK Accession GI: 385198082 (NM_005226.3). In one embodiment, the sequence of a human S1PR3 polypeptide sequence is set forth in GENBANK Accession No. GI:38788193 (NP_005217.2). Thus, in one embodiment, the invention includes a method of contacting a thermogenically competent cell or tissue with either S1PR3 or an activator of S1PR3, such that UCP1 expression occurs in the cell or tissue and thermogenesis is promoted.

SVIL has been identified herein as an activator of UCP1. SVIL is also known as supervillin. SVIL is similar to members of the gelsolin family of actin-binding proteins. In one embodiment, SVIL is human SVIL (Gene ID:6840). In one embodiment, the sequence of a human SVIL mRNA is set forth as GENBANK Accession Nos. NM_003174.3, GI:150417970 (isoform 1). In one embodiment, the sequence of a human SVIL polypeptide sequence is set forth in GENBANK Accession Nos. NP_003165.2, GI:150417971 (isoform 1). SVIL isoform 1 forms a high-affinity link between the actin cytoskeleton and the membrane and is among the first costameric proteins to assemble during myogenesis and it contributes to myogenic membrane structure and differentiation. In another embodiment, the sequence of a human SVIL mRNA is set forth as GENBANK Accession Nos. NM_021738.2, GI:150417972 (isoform 2). In another embodiment, the sequence of a human SVIL polypeptide sequence is set forth in GENBANK Accession Nos. NM_021738.2, GI:150417972 (isoform 2). SVIL isoform 2 may be involved in modulation of focal adhesions and/or play a role in cytokinesis through KIF14 interaction. In the polypeptide sequence of isoform 2, amino acids 276-669 and amino acids 750-781 in the canonical polypeptide sequence of isoform 1 are missing. In yet another embodiment, the sequence of a human SVIL mRNA is set forth as GENBANK Accession Nos. NM_001323599.1, GI:1021312263 (isoform 3). In one embodiment, the sequence of a human SVIL polypeptide sequence is set forth in GENBANK Accession Nos. NP_001310528.1, GI:1021312264 (isoform 3). In the polypeptide sequence of isoform 3, amino acids 276-302 in the canonical polypeptide sequence of isoform 1 are missing. In yet another embodiment, the sequence of a human SVIL mRNA is set forth as GENBANK Accession Nos. NM_001323600.1, GI:1021312179 (isoform 4). In one embodiment, the sequence of a human SVIL polypeptide sequence is set forth in GENBANK Accession Nos. NP_001310529.1, GI:1021312180 (isoform 4). In the polypeptide sequence of isoform 4, amino acids 750-781 in the canonical amino acid sequence of isoform 1 are missing. Thus, in one embodiment, the invention includes a method of contacting a thermogenically competent cell or tissue with either SVIL or an activator of SVIL, such that UCP1 expression occurs in the cell or tissue and thermogenesis is promoted.

C17orf60 has been identified herein as an activator of UCP1. C17orf60 is an immunoglobulin-like receptor which plays an inhibitory role in degranulation of mast cells. C17orf60 is also known as Mast Cell Immunoglobulin-Like Receptor 1 (MILR1), Mast Cell Antigen 32 (MCA32), and Allergin-1. In one embodiment, C17orf60 is human C17orf60 (Gene ID:284021). In one embodiment, the sequence of a human C17orf60 mRNA is set forth as GENBANK Accession GI: 146229332 (NM_001085423.1). In one embodiment, the sequence of a human C17orf60 polypeptide sequence is set forth in GENBANK Accession No. GI:146229333 (NP_001078892.1). Thus, in one embodiment, the invention includes a method of contacting a thermogenically competent cell or tissue with either C17orf60 or an activator of C17orf60, such that UCP1 expression occurs in the cell or tissue and thermogenesis is promoted.

MASP1 has been identified herein as an activator of UCP1. MASP1 is a serine protease which functions as a component of the lectin pathway of complement activation. MASP1 is also known as Mannan-Binding Lectin Serine Peptidase 1, Serine Protease 5, CRARF, and PRSS5. In one embodiment, MASP1 is human MASP1 (Gene ID:5648). In one embodiment, the sequence of a human MASP1 mRNA is set forth as GENBANK Accession GI: 294997266 (NM_001879.5). In one embodiment, the sequence of a human MASP1 polypeptide sequence is set forth in GENBANK Accession No. GI:21264357 (NP_001870.3). Thus, in one embodiment, the invention includes a method of contacting a thermogenically competent cell or tissue with either MASP1 or an activator of MASP1, such that UCP1 expression occurs in the cell or tissue and thermogenesis is promoted.

PXK has been identified herein as an activator of UCP1. PXK binds to and modulates brain Na,K-ATPase subunits ATP1B1 and ATP1B3, and may thereby participates in the regulation of electrical excitability and synaptic transmission. PXK is also known as PX domain containing serine/threonine kinase like and MONaKA. In one embodiment, PXK is human PXK (Gene ID: 54899). In one embodiment, the sequence of a human PXK mRNA is set forth as GENBANK Accession Nos. NM_017771.4, GI:574271714 (isoform 1). In this embodiment, the sequence of a human polypeptide sequence is set forth in GENBANK Accession Nos. NP_060241.2, GI:31543452 (isoform 1). In another embodiment, the sequence of a human PXK mRNA is set forth as GENBANK Accession Nos. NM_001289095.1, GI:574269522(isoform 2). In this embodiment, the sequence of a human PXK polypeptide sequence is set forth in GENBANK Accession Nos. NP_001276024 XP_005265308 (isoform 2). In yet another embodiment, the sequence of a human PXK mRNA is set forth as GENBANK Accession Nos. NM_001289096.1, GI:574269958 (isoform 3). In this embodiment, the sequence of a human PXK polypeptide sequence is set forth in GENBANK Accession Nos. NP_001276025.1, GI:574269959 (isoform 3). In other embodiments, the sequences of human PXK mRNA may include, for example, GENBANK Accession Nos. NM_001289098.1, GI:574273241 (isoform 4), GENBANK Accession Nos. NM_001289099.1, GI:574272532 (isoform 5), GENBANK Accession Nos. NM_001289100.1, GI:574271316 (isoform 6), or GENBANK Accession Nos. NM_001289101.1, GI:574272304 (isoform 7). Under these embodiments, the sequences of human PXK protein may include, for example, GENBANK Accession Nos. NP_001276027.1, GI:574273242 (isoform 4), GENBANK Accession Nos. NP_001276028.1, GI:574272533 (isoform 5), GENBANK Accession Nos. NP_001276029.1, GI:574271317 (isoform 6) or GENBANK Accession Nos. NP_001276030.1, GI:574272305 (isoform 7). Thus, in one embodiment, the invention includes a method of contacting a thermogenically competent cell or tissue with either PXK or an activator of PXK, such that UCP1 expression occurs in the cell or tissue and thermogenesis is promoted.

C10orf90 has been identified herein as an activator of UCP1. C10orf90 is a tumor suppressor that is required to sustain G2/M checkpoint after DNA damage and may mediate CDKN1A/p21 protein stability in a ubiquitin-independent manner. C10orf90 is also known as chromosome 10 open reading frame 90, FATS, and bA422P15.2. In one embodiment, C10orf90 is human C10orf90 (Gene ID: 118611). In one embodiment, the sequence of a human C10orf90 mRNA is set forth as GENBANK Accession Nos. NM_001004298.2, GI:52145311. In this embodiment, the sequence of a human C10orf90 polypeptide sequence is set forth in GENBANK Accession Nos. NP_001004298.2, GI:52145312. Thus, in one embodiment, the invention includes a method of contacting a thermogenically competent cell or tissue with either C10orf90 or an activator of C10orf90, such that UCP1 expression occurs in the cell or tissue and thermogenesis is promoted.

TBC1D19 has been identified herein as an activator of UCP1. TBC1D19 may act as a GTPase-activating protein for Rab family proteins. TBC1D19 is also known as TBC1 domain family member 19. In one embodiment, TBC1D19 is human TBC1D19 (Gene ID: 55296). In one embodiment, the sequence of a human TBC1D19 mRNA is set forth as GENBANK Accession Nos. NM_018317.3, GI:635574594 (isoform 1). In this embodiment, the sequence of a human TBC1D19 polypeptide sequence is set forth in GENBANK Accession Nos. NP_060787.2, GI:157388983 (isoform 1). In another embodiment, the sequence of a human TBC1D19 mRNA is set forth as GENBANK Accession Nos. NM_001292054.1, GI:635574577 (isoform 2). Under this embodiment, the sequence of a human TBC1D19 polypeptide sequence is set forth in GENBANK Accession Nos. NP_001278983.1, GI:635574578 (isoform 2). Thus, in one embodiment, the invention includes a method of contacting a thermogenically competent cell or tissue with either TBC1D19 or an activator of TBC1D19, such that UCP1 expression occurs in the cell or tissue and thermogenesis is promoted.

DNASE1L1 has been identified herein as an activator of UCP1. DNASE1L1 is a deoxyribonuclease protein that shows high sequence similarity to DNase I. DNASE1L1 is also known as deoxyribonuclease I-like 1, XIB, G4.8, DNL1L, and DNASEX. In one embodiment, DNASE1L1 is human DNASE1L1 (Gene ID: 1774). In one embodiment, the sequence of a human DNASE1L1 mRNA is set forth as GENBANK Accession Nos. NM_006730.3, GI:746816102 (variant 1). In this embodiment, the sequence of a human DNASE1L1 polypeptide sequence is set forth in GENBANK Accession Nos. NP_006721.1, GI:5803007 (variant 1). In other embodiments, the sequences of human DNASE1L1 mRNA may include, for example, GENBANK Accession Nos. NM_001009932.2, GI:746816107 (variant 2), GENBANK Accession Nos. NM_001009933.2, GI:746816108 (variant 3), GENBANK Accession Nos. NM_001009934.2, GI:746816109 (variant 4), or GENBANK Accession Nos. NM_001303620.1, GI:746816116 (variant 5). Under these embodiments, the sequences of human DNASE1L1 protein may include, for example, GENBANK Accession Nos. NP_001009932.1, GI:58430942 (variant 2), GENBANK Accession Nos. NP_001009933.1, GI:58430944 (variant 3), GENBANK Accession Nos. NP_001009934.1, GI:58430946 (variant 4) or GENBANK Accession Nos. NP_001290549.1, GI:746816117 (variant 5). Thus, in one embodiment, the invention includes a method of contacting a thermogenically competent cell or tissue with either DNASE1L1 or an activator of DNASE1L1, such that UCP1 expression occurs in the cell or tissue and thermogenesis is promoted.

GPCR5A has been identified herein as an activator of UCP1. GPCR5A is a member of the type 3 G protein-coupled receptor family. GPCR5A is also known as G protein-coupled receptor class C group 5 member A, RAI3, TIG1, RAIG1, GPCR5A, and PEIG-1. In one embodiment, GPCR5A is human GPCR5A (Gene ID: 9052). In one embodiment, the sequence of a human GPCR5A mRNA is set forth as GENBANK Accession Nos. NM_003979.3, GI:63252917. In this embodiment, the sequence of a human GPCR5A polypeptide sequence is set forth in GENBANK Accession Nos. NP_003970.1, GI:4506403. Thus, in one embodiment, the invention includes a method of contacting a thermogenically competent cell or tissue with either GPCR5A or an activator of GPCR5A, such that UCP1 expression occurs in the cell or tissue and thermogenesis is promoted.

ITGA10 has been identified herein as an activator of UCP1. ITGA10 is an integral transmembrane glycoprotein composed of non-covalently linked alpha and beta chains, which participate in cell adhesion (via collagen binding) as well as cell-surface mediated signaling. ITGA10 is also known as integrin subunit alpha 10, and PRO827. In one embodiment, ITGA10 is human ITGA10 (Gene ID: 118611). In one embodiment, the sequence of a human ITGA10 mRNA is set forth as GENBANK Accession Nos. NM_003637.4, GI:733216291 (isoform 1). In this embodiment, the sequence of a human ITGA10 polypeptide sequence is set forth in GENBANK Accession Nos. NP_003628.2, GI:38569398 (isoform 1). In another embodiment, the sequence of a human ITGA10 mRNA is set forth as GENBANK Accession Nos. NM_001303040.1, GI:733216271 (isoform 2). In this embodiment, the sequence of a human ITGA10 polypeptide sequence is set forth in GENBANK Accession Nos. NP_001289969.1, GI:733216272 (isoform 2). In yet another embodiment, the sequence of a human ITGA10 mRNA is set forth as GENBANK Accession Nos. NM_001303041.1, GI:733216350 (isoform 3). In this embodiment, the sequence of a human ITGA10 polypeptide sequence is set forth in GENBANK Accession Nos. NP_001289970.1, GI:733216351 (isoform 3). Thus, in one embodiment, the invention includes a method of contacting a thermogenically competent cell or tissue with either ITGA10 or an activator of ITGA10, such that UCP1 expression occurs in the cell or tissue and thermogenesis is promoted.

ETFDH has been identified herein as an activator of UCP1. ETFDH is a component of the electron-transfer system in mitochondria and is essential for electron transfer from a number of mitochondrial flavin-containing dehydrogenases to the main respiratory chain. ETFDH is also known as electron transfer flavoprotein dehydrogenase, MADD, and ETFQO. In one embodiment, ETFDH is human ETFDH (Gene ID: 2110). In one embodiment, the sequence of a human ETFDH mRNA is set forth as GENBANK Accession Nos. NM_004453.3, GI:528881079 (variant 1). In this embodiment, the sequence of a human ETFDH polypeptide sequence is set forth in GENBANK Accession Nos. NP_004444.2, GI:119703746 (variant 1). In another embodiment, the sequence of a human ETFDH mRNA is set forth as GENBANK Accession Nos. NM_001281737.1, GI:528881080 (variant 2). In this embodiment, the sequence of a human ETFDH polypeptide sequence is set forth in GENBANK Accession Nos. NP_001268666, GI:528881081 (variant 2). In yet another embodiment, the sequence of a human ETFDH mRNA is set forth as GENBANK Accession Nos. NM_001281738.1, GI:528881082 (variant 3). In this embodiment, the sequence of a human ETFDH polypeptide sequence is set forth in GENBANK Accession Nos. NP_001268667.1, GI:528881083 (variant 3). Thus, in one embodiment, the invention includes a method of contacting a thermogenically competent cell or tissue with either ETFDH or an activator of ETFDH, such that UCP1 expression occurs in the cell or tissue and thermogenesis is promoted.

MORN4 has been identified herein as an activator of UCP1. MORN4 is a protein that may be involved in axonal degeneration. MORN4 is also known as MORN repeat containing 4. In one embodiment, MORN4 is human MORN4 (Gene ID: 118812). In one embodiment, the sequence of a human MORN4 mRNA is set forth as GENBANK Accession Nos. NM_178832.3, GI:149999372 (variant 1). In this embodiment, the sequence of a human MORN4 polypeptide sequence is set forth in GENBANK Accession Nos. NP_849154.1, GI:30520314 (variant 1). In another embodiment, the sequence of a human MORN4 mRNA is set forth as GENBANK Accession Nos. NM_001098831.1, GI:149999375 (variant 2). In this embodiment, the sequence of a human MORN4 polypeptide sequence is set forth in GENBANK Accession Nos. NP_001092301.1, GI:149999376 (variant 2). Thus, in one embodiment, the invention includes a method of contacting a thermogenically competent cell or tissue with either MORN4 or an activator of MORN4, such that UCP1 expression occurs in the cell or tissue and thermogenesis is promoted.

MRPS6 has been identified herein as an activator of UCP1. MRPS6 is a member of the mammalian mitochondrial ribosomal proteins, which are encoded by nuclear genes and help in protein synthesis within the mitochondrion. MRPS6 is also known as mitochondrial ribosomal protein S6, S6mt, RPMS6, MRP-S6, and C21orf101. In one embodiment, MRPS6 is human MRPS6 (Gene ID: 64968). In one embodiment, the sequence of a human MRPS6 mRNA is set forth as GENBANK Accession Nos. NM_032476.3, GI:186928845. In this embodiment, the sequence of a human MRPS6 polypeptide sequence is set forth in GENBANK Accession Nos. NP_115865.1, GI:16554616. Thus, in one embodiment, the invention includes a method of contacting a thermogenically competent cell or tissue with either MRPS6 or an activator of MRPS6, such that UCP1 expression occurs in the cell or tissue and thermogenesis is promoted.

SETDB2 has been identified herein as an activator of UCP1. SETDB2 is a member of a family of proteins that contain a methyl-CpG-binding domain (MBD) and a SET domain and functions as a histone methyltransferase. SETDB2 is also known as SET domain bifurcated 2, CLLD8, CLLL8, KMT1F, and C13orf4. In one embodiment, SETDB2 is human SETDB2 (Gene ID: 83852). In one embodiment, the sequence of a human SETDB2 mRNA is set forth as GENBANK Accession Nos. NM_031915.2, GI:238624094 (isoform a). In this embodiment, the sequence of a human SETDB2 polypeptide sequence is set forth in GENBANK Accession Nos. NP_114121.2, GI:238624095 (isoform a). In another embodiment, the sequence of a human SETDB2 mRNA is set forth as GENBANK Accession Nos. NM_001160308.2, GI:1002623476 (isoform b). In this embodiment, the sequence of a human SETDB2 polypeptide sequence is set forth in GENBANK Accession Nos. NP_001153780.1, GI:238624099 (isoform b). In yet another embodiment, the sequence of a human SETDB2 mRNA is set forth as GENBANK Accession Nos. NM_001320699.1, GI:1002623479 (isoform c). In this embodiment, the sequence of a human SETDB2 polypeptide sequence is set forth in GENBANK Accession Nos. NP_001307628.1, GI:1002623480 (isoform c). Thus, in one embodiment, the invention includes a method of contacting a thermogenically competent cell or tissue with either SETDB2 or an activator of SETDB2, such that UCP1 expression occurs in the cell or tissue and thermogenesis is promoted.

WRB has been identified herein as an activator of UCP1. WRB is basic nuclear protein which serves as a receptor for ASNA1/TRC40-mediated insertion of tail-anchored (TA) proteins into the ER membrane. WRB is also known as tryptophan rich basic protein, CHD5 or GET1. In one embodiment, WRB is human WRB (Gene ID: 7485). In one embodiment, the sequence of a human WRB mRNA is set forth as GENBANK Accession Nos. NM_004627.4, GI:226246628 (isoform 1). In this embodiment, the sequence of a human WRB polypeptide sequence is set forth in GENBANK Accession Nos. NP_004618.2, GI:21536428 (isoform 1). In another embodiment, the sequence of a human WRB mRNA is set forth as GENBANK Accession Nos. NM_001146218.1, GI:226246629 (isoform 2). In this embodiment, the sequence of a human WRB polypeptide sequence is set forth in GENBANK Accession Nos. NP_001139690.1, GI:226246630 (isoform 2). Thus, in one embodiment, the invention includes a method of contacting a thermogenically competent cell or tissue with either WRB or an activator of WRB, such that UCP1 expression occurs in the cell or tissue and thermogenesis is promoted.

SYNRG has been identified herein as an activator of UCP1. SYNRG is thought to play a role in endocytosis and/or membrane trafficking at the trans-Golgi network (TGN). SYNRG is also known as synergin, gamma, SYNG, and AP1GBP1. In one embodiment, SYNRG is human SYNRG (Gene ID: 11276). In one embodiment, the sequence of a human SYNRG mRNA is set forth as GENBANK Accession Nos. NM_007247.5, GI:594140686 (isoform 1). In this embodiment, the sequence of a human SYNRG polypeptide sequence is set forth in GENBANK Accession Nos. NP_009178.3, GI:38569409 (isoform 1). In another embodiment, the sequence of a human SYNRG mRNA is set forth as GENBANK Accession Nos. NM_080550.4, GI:594140680 (isoform 2). In this embodiment, the sequence of a human SYNRG polypeptide sequence is set forth in GENBANK Accession Nos. NP_542117.3, GI:254587984 (isoform 2). In yet another embodiment, the sequence of a human SYNRG mRNA is set forth as GENBANK Accession Nos. NM_198882.2, GI:594140672 (isoform 3). In this embodiment, the sequence of a human SYNRG polypeptide sequence is set forth in GENBANK Accession Nos. NP_942583.1, GI:254587986 (isoform 3). In other embodiments, the sequences of human SYNRG mRNA may include, for example, GENBANK Accession Nos. NM_001163544.2, GI:594140690 (isoform 4), GENBANK Accession Nos. NM_001163545.2, GI:594140663 (isoform 5), GENBANK Accession Nos. NM_001163546.2, GI:594140632 (isoform 6), or GENBANK Accession Nos. NM_001163547.2, GI:594140691 (isoform 7). Under these embodiments, the sequences of human SYNRG protein may include, for example, GENBANK Accession Nos. NP_001157016.1, GI:254587988 (isoform 4), GENBANK Accession Nos. NP_001157017.1, GI:254587990 (isoform 5), GENBANK Accession Nos. NP_001157018.1, GI:254587992 (isoform 6) or GENBANK Accession Nos. NP_001157019.1, GI:254587994 (isoform 7). Thus, in one embodiment, the invention includes a method of contacting a thermogenically competent cell or tissue with either SYNRG or an activator of SYNRG, such that UCP1 expression occurs in the cell or tissue and thermogenesis is promoted.

ANP32A has been identified herein as an activator of UCP1. ANP32A is a protein that plays a role in E4F1-mediated transcriptional repression, including proliferation, differentiation, caspase-dependent and caspase-independent apoptosis, suppression of transformation (tumor suppressor), inhibition of protein phosphatase 2A, regulation of mRNA trafficking and stability in association with ELAVL1, and inhibition of acetyltransferases as part of the INHAT (inhibitor of histone acetyltransferases) complex. ANP32A is also known as acidic nuclear phosphoprotein 32 family member A, LANP, MAPM, PP32, HPPCn, PHAP1, PHAP1, I1PP2A, and C15orfl. In one embodiment, ANP32A is human ANP32A (Gene ID: 8125). In one embodiment, the sequence of a human ANP32A mRNA is set forth as GENBANK Accession Nos. NM_006305.3, GI:221219065. In this embodiment, the sequence of a human ANP32A polypeptide sequence is set forth in GENBANK Accession Nos. NP_006296.1, GI:5453880. Thus, in one embodiment, the invention includes a method of contacting a thermogenically competent cell or tissue with either ANP32A or an activator of ANP32A, such that UCP1 expression occurs in the cell or tissue and thermogenesis is promoted.

In some embodiments, UCP1 positive regulators are involved in calcium signaling pathways. Exemplary UCP1 positive regulators involved in calcium signaling pathways include, but are not limited to, EDNRB.

In other embodiments, UCP1 positive regulators are cell surface molecules.

Exemplary UCP1 positive regulators that are cell surface markers include, but are not limited to, S1PR3, GPRC5A and GPR56.

In yet another embodiment, UCP1 positive regulators are involved in the Hippo signaling pathway. Exemplary UCP1 positive regulators involved in Hippo signaling pathways include, but are not limited to, WWTR1. The Hippo pathway contains a network of proteins that controls organ/cell size through regulation of cell proliferation, apoptosis and differentiation. Expression of one of the key mediators of this pathway, WWTR1 (also known as TAZ), in preadipocytes is positively and significantly correlated with UCP1 levels in mature fat cells. TAZ is a PDZ-binding domain containing transcription factor, which interacts with the transcriptional coactivator YAP (Yes-associated protein) to regulate gene expression. Activities of YAP/TAZ are modulated by upstream kinases. For example, phosphorylation of YAP/TAZ by LAST1/2 primes YAP/TAZ for proteosomal degradation. Expression levels of several other members of this pathway were coordinately correlated with UCP1 levels by Ingenuity pathway analysis, as described herein. Other members of the Hippo pathway positively correlated with UCP1 levels include CRB1, PARD3, and SMAD2/3. Thus, an overall increase in the activity of the Hippo signaling pathway (e.g., by enhancing the activity of TAZ, CRB1, PARD3, and/or SMAD2/3) will lead to enhanced thermogenic capacity of mature brown/beige fat cells.

In one embodiment, the invention includes variants and isoforms of the UCP1 positive regulator amino acid or nucleotide sequences described herein.

One embodiment of the invention features a method of promoting thermogenic capacity in a cell or tissue by contacting a cell having thermogenic competency, such as a preadipocyte, with an activator of a UCP1 positive regulator, such that the cell is able to express UCP1 and promote thermogenesis. Examples of activators that may be used in the methods described herein include, but are not limited to, an agonist antibody, or antigen-binding fragment thereof, that binds the UCP1 positive regulator, or a polynucleotide associated with the CRISPR/Cas system which binds the UCP1 positive regulator and activates the transcription of the UCP1 positive regulator. Alternatively, the UCP1 positive regulator, either as a nucleic acid or protein, may be contacted with the thermogenically competent cell, e.g., a preadipocyte, in order to promote thermogenesis in the cell or tissue. In one embodiment, the UCP1 positive regulator is human PREX1, human CTTNBP2, human DMRTA1, or human ENDRB.

In one embodiment, thermogenesis is promoted by administering a UCP1 positive regulator to a subject or in vitro contacting a cell, e.g., a thermogenically competent cell, in order to increase UCP1 expression. Such methods may be performed either delivering a nucleic acid encoding the UCP1 positive regulator, or delivering the protein itself.

In one embodiment, a UCP1 positive regulator is contacted with a thermogenically competent cell or administered to a subject who would benefit from increased thermogenesis for therapeutic purposes, including the disorders described herein. In one embodiment, human PREX1 (SEQ ID NO: 10) is administered to a human subject in need thereof. In one embodiment, human CTTNBP2 (SEQ ID NO: 12) is administered to a human subject in need thereof. In one embodiment, human DMRTA1 (SEQ ID NO: 14) is administered to a human subject in need thereof. In one embodiment, human ENDRB (SEQ ID NO: 16) is administered to a human subject in need thereof.

RNA or DNA encoding the UCP1 positive regulator may be readily isolated, amplified, and/or sequenced using conventional procedures (e.g., by using oligonucleotide probes that are capable of binding specifically to the relevant genes, as described in, for example, Innis et al. in *PCR Protocols. A Guide to Methods and Applications*, Academic (1990), and Sanger et al., *Proc Natl Acad Sci USA* 74:5463 (1977)). Sequences of UCP1 positive regulators PREX1, CTTNBP2, DMRTA1, and ENDRB are provided herein. A nucleic acid molecule so amplified may be cloned into an appropriate vector and characterized by DNA sequence analysis. Furthermore, nucleotides corresponding to all or a portion of an isolated nucleic acid molecule for use in the methods of the invention can be prepared by standard synthetic techniques, e.g., using an automated DNA synthesizer.

In one embodiment, an isolated nucleic acid molecule for use in the methods of the invention comprises a nucleic acid molecule which has a nucleotide sequence complementary to the nucleotide sequence of a nucleic acid molecule encoding, a UCP1 positive regulator, for example, PREX1, CTTNBP2, DMRTA1, and ENDRB. A nucleic acid molecule which is complementary to a given nucleotide sequence is one which is sufficiently complementary to the given nucleotide sequence that it can hybridize to the given nucleotide sequence thereby forming a stable duplex.

The invention further encompasses nucleic acid molecules that differ, due to degeneracy of the genetic code, from the nucleotide sequence of nucleic acid molecules encoding a UCP1 positive regulator protein, e.g., PREX1, CTTNBP2, DMRTA1, and ENDRB, and thus encode the same protein. It will be appreciated by those skilled in the art that DNA sequence polymorphisms that lead to changes in the amino acid sequence can exist within a population. Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

Accordingly, in one embodiment a nucleic acid molecule suitable for use in the methods of the invention is at least about 40% identical, about 50%, 60%, 70%, 80%, 81%, 82%, 83%, 84%, 85%, 86%, 87%, 88%, 89%, 90%, 91%, 92%, 93%, 94%, 95%, 96%, 97%, 98%, or about 99% identical to the nucleotide sequence of a UCP1 positive regulator protein, e.g., PREX1 (SEQ ID NO: 9), CTTNBP2 (SEQ ID NO: 11), DMRTA1 (SEQ ID NO: 13), and ENDRB (SEQ ID NO: 15).

In addition to naturally occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species may be essential for activity and thus would not be likely targets for alteration.

A UCP1 positive regulator for use in the invention may be made according to methods know in the art. The recombinant vectors can comprise a nucleic acid encoding a UCP1 positive regulator in a form suitable for expression of the nucleic acid in a host cell. In some embodiments, this means that the recombinant vectors may include one or more regulatory sequences, selected on the basis of the host cells to be used for expression, which is operably linked to the nucleic acid sequence to be expressed (i.e., a recombinant expression vector). Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Methods in Enzymology: Gene Expression Technology vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide, or functional fragment thereof, in prokaryotic (e.g., E. coli) or eukaryotic cells (e.g., insect cells {using baculovirus expression vectors}, yeast cells or mammalian cells). Suitable host cells are discussed further in Goeddel, supra, and include, for example, E. coli cells, Bacillus cells, Saccharomyces cells, Pochia cells, NS0 cells, COS cells, Chinese hamster ovary (CHO) cells or myeloma cells. The RNA or DNA also may be modified, for example, by substituting bases to optimize for codon usage in a particular host or by covalently joining to the coding sequence of a heterologous polypeptide. Such an approach would be the basis for developing a subunit vaccine. Alternatively, the recombinant expression vector can be transcribed and translated in vitro.

Another aspect of the invention pertains to host cells into which a recombinant vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

A signal sequence can be used to facilitate secretion and isolation of UCP1 positive regulator proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to UCP1 positive regulator proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a nucleic acid molecule encoding a protein of interest, such as a UCP1 positive regulator, e.g., PREX1, CTTNBP2, DMRTA1, and ENDRB, or a functional segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a poly-histidine tag, a strep-tag, a FLAG-tag, a GST domain, etc.

Binary Regulators and Rheostat Regulators

In some embodiments, the UCP1 regulators, e.g., UCP1 positive and/or negative regulators, are binary regulators. Binary regulators act as binary on and off switches to determine cell fate, e.g., to suppress or enhance thermogenic capacity in a thermogenically competent cell. Some positive binary regulators are required for thermogenic differentiation, while some negative binary regulators need to be suppressed to allow UCP1 expression at any level.

In other embodiments, the UCP1 regulators, e.g., UCP1 positive and/or negative regulators, are rheostat regulators. Rheostat regulators act as genetic rheostats to suppress or enhance thermogenic capacity in a thermogenically competent cell incrementally as their expression level changed. Positive rheostat regulators support thermogenic differentiation of a thermogenically competent cell in proportion to their expression levels; while negative rheostat regulators suppress thermogenic differentiation of a thermogenically competent cell as their level of expression increases.

Accordingly, it may be desirable to modulate combinations of UCP1 regulators to influence thermogenic potential. For example, it is possible to activate multiple positive binary regulators, and/or inhibit multiple negative binary regulators. It is also possible to modulate multiple rheostat regulators to fine-tune thermogenic capacity.

In some embodiments, the invention features a method of promoting thermogenic capacity in a cell or tissue by contacting a cell having thermogenic competency, such as a preadipocyte, with a binary regulator of UCP1. In one embodiment, the invention comprises contacting the cell having thermogenic competency with one or more positive binary regulators. In another embodiment, the invention features a method of promoting thermogenic capacity in a cell or tissue by suppressing and/or depleting the expression of one or more negative binary regulators from the cell having thermogenic competency. Exemplary positive binary regulators of UCP1 include, but are not limited to, PREX1 and CTTNBP2. Exemplary negative binary regulators of UCP1 include, but are not limited to, ACTC1 and SSTR1. In one embodiment, the methods comprise contacting the cell having thermogenic competency with one or more positive binary regulators, e.g., PREX1 and/or CTTNBP2, or activators thereof, while also suppressing and/or depleting the expression of one or more negative binary regulators, e.g., ACTC1 and/or SSTR1. In an exemplary embodiment, a cell having thermogenic capacity is contacted with PREX1 and CTTNBP2, or activators thereof, and is contacted with inhibitors of ACTC1 and SSTR1, such that thermogenic capacity is promoted.

Thermogenic capacity can be further regulated by contacting the thermogenically competent cell with a rheostat regulator. Accordingly, in some embodiments, the foregoing methods further comprise contacting a cell having thermogenic competency with a rheostat regulator, e.g., one or more positive rheostat regulators, or activators thereof. In another embodiment, the foregoing methods further comprise suppressing and/or depleting the expression of one or more negative rheostat regulators from the cell having thermogenic competency. Exemplary positive rheostat regulators of UCP1 include, but are not limited to, DMRTA1 and EDNRB. Exemplary negative rheostat regulators of UCP1 include, but are not limited to, FAT1 and PTPRB. In one embodiment, the methods comprise contacting the cell having thermogenic competency with one or more positive rheostat regulators, e.g., DMRTA1 and/or EDNRB, and suppressing and/or depleting the expression of one or more negative rheostat regulators, e.g., FAT1 and/or PTPRB.

In some embodiments, the methods of the invention comprise contacting the cell having thermogenic competency with a binary regulator, e.g., one or more positive binary regulators, e.g., PREX1 and/or CTTNBP2, and/or a rheostat regulator, e.g., one or more positive rheostat regulators, e.g., DMRTA1 and/or EDNRB. In other embodiments, the methods of the invention comprise suppressing and/or depleting the expression of a binary regulator, e.g., one or more negative binary regulators, e.g., ACTC1 and/or SSTR1, and/or suppressing and/or depleting the expression of a rheostat regulator, e.g., one or more negative rheostat regulators, e.g., FAT1 and/or PTPRB. In yet another embodiment, the methods of the invention comprise contacting the cell having thermogenic competency with a binary regulator, e.g., one or more positive binary regulators, e.g., PREX1 and/or CTTNBP2, and/or a rheostat regulator, e.g., one or more positive rheostat regulators, e.g., DMRTA1 and/or EDNRB, and suppressing and/or depleting the expression of a binary regulator, e.g., one or more negative binary regulators, e.g., ACTC1 and/or SSTR1, and/or suppressing and/or depleting the expression of a rheostat regulator, e.g., one or more negative rheostat regulators, e.g., FAT1 and/or PTPRB.

B. Modulators of UCP1 Activators and Inhibitors

As described above, the invention includes, in some embodiments, modulation of UCP1 negative and/or positive regulators in order to increase the thermogenic activity of a cell or tissue. Examples of inhibitors and activators of UCP1 regulatory molecules that may be used in the methods and compositions described herein are provided below, and include, but are not limited to, inhibitory nucleic acids, nucleic acids (inhibitory or activating) relating to CRISPR technology, small molecule inhibitors or agonists, and agonist or antagonist antibodies. An inhibitory agent (i.e., inhibitor) or an activating agent (i.e., an activator) can be a nucleic acid, a polypeptide, an antibody, or a small molecule compound. In one example, the inhibitor or activator functions at a level of transcription, mRNA stability, translation, protein stability/degradation, protein modification, and protein binding.

Inhibitory Nucleic Acids

In one embodiment, the methods described herein include targeting UCP1 negative regulators using inhibitory nucleic acids. A nucleic acid inhibitor can encode a small interference RNA (e.g., an RNAi agent) that targets one or more of the above-mentioned genes, e.g. ACTC1, STR1 FAT1, or PTPRB, and inhibits its expression or activity. The term "RNAi agent" refers to an RNA, or analog thereof, having sufficient sequence complementarity to a target RNA to direct RNA interference. Examples also include a DNA that can be used to make the RNA.

RNA Interference:

RNA interference (RNAi) refers to a sequence-specific or selective process by which a target molecule (e.g., a target gene, protein or RNA) is down-regulated. Generally, an interfering RNA ("RNAi") is a double stranded short-interfering RNA (siRNA), short hairpin RNA (shRNA), or single-stranded micro-RNA (miRNA) that results in catalytic degradation of specific mRNAs, and also can be used to lower or inhibit gene expression. RNA interference (RNAi) is a process whereby double-stranded RNA (dsRNA) induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev., 12: 225-232 (2002); Sharp, Genes Dev., 15:485-490 (2001); Valencia-Sanchez et al. Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), by microRNA (miRNA), functional small-hairpin RNA (shRNA), or other dsRNAs which are expressed in vivo using DNA templates with RNA polymerase II or III promoters (Zeng et al., Mol. Cell 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002).)

siRNA Molecules: The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery.

In general, the methods described herein can use dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the invention includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004)).

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

siRNA Delivery:

Direct delivery of siRNA in saline or other excipients can silence target genes in tissues, such as the eye, lung, and central nervous system (Bitko et al., Nat. Med. 11:50-55 (2005); Shen et al., Gene Ther. 13:225-234 (2006); Thakker et al., Proc. Natl. Acad. Sci. U.S.A. (2004)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)).

Liposomes and nanoparticles can also be used to deliver siRNA into animals. Delivery methods using liposomes, e.g. stable nucleic acid-lipid particles (SNALPs), dioleoyl phosphatidylcholine (DOPC)-based delivery system, as well as lipoplexes, e.g. Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain 1:29 (2005); Zimmermann et al., Nature 441:111-114 (2006)). Conjugating siRNA to peptides, RNA aptamers, antibodies, or polymers, e.g. dynamic polyconjugates, cyclodextrin-based nanoparticles, atelocollagen, and chitosan, can improve siRNA stability and/or uptake. (Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007); Rozema et al., Proc. Natl. Acad. Sci. U.S.A. 104: 12982-12987 (2007); Song et al., Nat. Biotechnol. 23:709-

717 (2005); Soutschek (2004), supra; Wolfrum et al., Nat. Biotechnol. 25:1149-1157 (2007)).

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)).

Stable siRNA Expression:

Synthetic siRNAs can be delivered into cells, e.g., by direct delivery, cationic liposome transfection, and electroporation. However, these exogenous siRNA typically only show short term persistence of the silencing effect (4-5 days). Several strategies for expressing siRNA duplexes within cells from recombinant DNA constructs allow longer-term target gene suppression in cells, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

In another embodiment, siRNAs can be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, Cell 116:281-297 (2004); Valencia-Sanchez et al., Genes & Dev. 20:515-524 (2006)). One common feature of miRNAs is that they are excised from an approximately 70 nucleotide precursor RNA stem loop by Dicer, an RNase III enzyme, or a homolog thereof By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Uses of Engineered RNA Precursors to Induce RNAi:

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, the mRNA to be targeted by the siRNA generated from the engineered RNA precursor will be depleted from the cell or organism, leading to a decrease in the concentration of the protein encoded by that mRNA in the cell or organism.

Antisense:

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein relating to the identified UCP1 negative and positive regulators, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

The antisense nucleic acid molecules of the invention are typically administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In some embodiments, the antisense nucleic acid is a morpholino oligonucleotide (see, e.g., Heasman, Dev. Biol. 243:209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region, e.g., promoters and/or enhancers) to form triple helical structures that prevent transcription of the target gene in target cells. See generally, Helene, C. Anticancer Drug Des. 6:569-84 (1991); Helene, C. Ann. N.Y. Acad. Sci. 660:27-36 (1992); and Maher, Bioassays. 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

CRISPR Technology

In one embodiment, the inhibitory nucleic acid used to inhibit a UCP1 negative regulator is based on CRISPR technology. Alternatively, a nucleic acid which activates a UCP1 positive regulator based on CRISPR technology is also included in the methods of the invention.

The clustered, regularly interspaced, short palindromic repeat (CRISPR) technology is included in the invention as an approach for generating RNA-guided nuclease with customizable specificities for targeted genome editing. Genome editing mediated by these nucleases has been used to rapidly, easily and efficiently modify endogenous genes in a wide variety of biomedically important cell types and in organisms that have traditionally been challenging to manipulate genetically.

In general, the term "CRISPR system" refers collectively to transcripts and other/elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as Streptococcus pyogenes. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides (e.g., DNA or RNA of ACTC1, SSTR1, FAT1, or PTPRB). In some embodiments, a target sequence is located in the nucleus or cytoplasm of a cell.

In preferred embodiments of the invention, the CRISPR/Cas system is a type II CRISPR system and the Cas enzyme is Cas9, which catalyzes DNA cleavage. Enzymatic action by Cas9 derived from Streptococcus pyogenes or any closely related Cas9 generates double stranded breaks at target site sequences which hybridize to 20 nucleotides of the guide sequence and that have a protospacer-adjacent motif (PAM) sequence NGG following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archae, Mol. Cell 2010, Jan. 15; 37(1): 7.

The type II CRISPR locus from Streptococcus pyogenes SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

The expression of a target polynucleotide can be modified by allowing a CRISPR complex to bind to the polynucleotide, wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiment, binding of CRISPR complex to a target polynucleotide results in an increased expression of the target polynucleotide. In another embodiment, binding of CRISPR complex to a target polynucleotide results in a decreased expression of the target polynucleotide (e.g., DNA or RNA of ACTC1, SSTR1, FAT1, or PTPRB).

Antagonist and Agonist Antibodies

The invention further contemplates methods and compositions comprising either an antagonist antibody which inhibits a UCP1 negative regulator (and thereby induces expression of UCP1 and promotes thermogenesis) or an agonist antibody which activates a UCP1 positive regulator in a thermogenically competent cell. In one embodiment, the anti-UCP1 negative regulator antibody, or antigen binding portion thereof, (e.g., an ACTC1, anti-FAT1, anti-PTPRB, or an anti-SSTR1 antagonist antibody) increases UCP1 mRNA expression and/or UCP1 protein expression. In one embodiment, the antagonist anti-UCP1 negative regulator antibody, or antigen binding portion thereof. (e.g., anti-ACTC1, anti-FAT1, anti-PTPRB, or an anti-SSTR1 antagonist antibody) increases UCP1 mRNA expression and/or UCP1 protein expression. In another embodiment, the agonist anti-UCP1 positive regulator antibody, or antigen binding portion thereof. (e.g., anti-PREX1, anti-CTTNBP2, anti-DMRTA1, or an anti-ENDRB agonist antibody) increases UCP1 mRNA expression and/or UCP1 protein expression.

Agonist anti-UCP1 positive regulators and antagonist anti-UCP1 negative regulator antibodies, such as agonist anti-PREX1, anti-CTTNBP2, anti-DMRTA1, or an anti-ENDRB antibodies or antagonist anti-ACTC1, anti-FAT1, anti-PTPRB, or an anti-SSTR1 antibodies, may be identified, screened for (e.g., using phage display), or characterized for their physical/chemical properties and/or biological activities by various assays known in the art (see, for example, Antibodies: A Laboratory Manual. Second edition, Greenfield, ed. 2014). Assays, for example, described in the Examples may be used to identify antibodies having advantageous properties, such as the ability to increase energy expenditure in the absence of adipocyte differentiation. In one aspect, an anti-UCP1 negative or positive regulator antibody is tested for its antigen binding activity. e.g., by known methods such as ELISA, Western blot, etc.

Following identification of the antigen of the antibody e.g., ability to bind a UCP1 negative or positive regulator, the activity of the antibody may be tested. In one aspect, assays are provided for identifying anti-UCP1 positive regulators, e.g., PREX1. CTTNBP2, FAT1, or PTPRB, thereof having agonist activity. In one aspect, assays are provided for identifying anti-UCP1 negative regulators, e.g., ACTC1, FAT1, PTPRB, and SSTR1, thereof having antagonist activity. For example, biological activity may include the ability to activate signal transduction of particular pathways which can be measured, e.g., by determining levels of phospho-FRS2a, phospho-MEK, phospho-ERK/MAPK, phospho-STAT3 or using the GAL-Elk1-based luciferase assays described herein (see also, e.g., Wu et al. J. Biol. Chem. 5; 282(40):29069-72 (2007) and Wu et al. PLoS One 18; 6(3):e17868 (2011)).

Following screening and sequencing, antibodies may be produced using recombinant methods and compositions, e.g. as described in U.S. Pat. No. 4,816,567, incorporated by reference herein. An isolated nucleic acid encoding, for example, an anti-UCP1 negative regulator antibody is used to transform host cells for expression. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic. e.g. a Chinese Hamster Ovary (CHO) cell or lymphoid cell (e.g., Y0, NS0, Sp20 cell).

For recombinant production of an anti-UCP1 negative or positive regulator. e.g., ACTC1, FAT1. PTPRB, and SSTR1, antibody, a nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see. e.g., U.S. Pat. Nos. 5,648,237, 5,789,199, and 5,840,523. (See also Charlton, Methods in Molecular Biology, Vol. 248 (B. K. C. Lo, ed., Humana Press. Totowa. N.J., 2003). pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized." resulting in the production of an antibody with a partially or fully human glycosylation pattern. See Gerngross, Nat. Biotech. 22:1409-1414 (2004), and Li et al. Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described. e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR.sup.-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology. Vol. 248 (B. K. C. Lo, ed. Humana Press, Totowa. N.J.), pp. 255-268 (2003).

In one embodiment, the anti-UCP1 negative or positive regulator antibody, or antigen binding portion thereof, increases thermogenesis in a cell following treatment in vivo or in vitro with a thermogenically competent cell.

Test Compounds

In one embodiment, test compounds are identified through screening assays that act either an inhibitor of a UCP1 negative regulator, or act as an agonist to a UCP1 positive regulator. The test compounds can be, e.g., natural products or members of a combinatorial chemistry library.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library. These methods can also be used, for example, to screen a library of proteins or fragments thereof, e.g., proteins that are expressed in liver or pancreatic cells.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, Solid-Supported Combinatorial and Parallel Synthesis of Small-Molecular-Weight Compound Libraries, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, .theta.-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to a known phosphorylation or protein recognition site. For example, in one embodiment, a general library of small molecules is screened, e.g., using the methods described herein, to select a first test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate activity in a method described herein) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in treating disorders described herein. Thus, the invention also includes compounds identified as "hits" by a method described herein, and methods for their administration and use in the treatment, prevention, or delay of development or progression of a disease described herein.

Mimetics

Variants of a UCP1 positive regulator protein (e.g., PREX1, CTTNBP2, DMRTA1, and ENDRB) that function as agonists (mimetics) or variants of a UCP1 negative regulator (e.g., ACTC1, SSTR1, FAT1, and PTPRB) that function as antagonists can be identified by screening combinatorial libraries of mutants, e.g., truncation mutants, of the UCP1 positive regulator for agonist (in the case of UCP1 positive regulators where activity of the regulator is desired for increased UCP1 expression) or antagonist activity (in the case of UCP1 negative regulators where activity of the regulator is preferably inhibited such that UCP1 is expressed). In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

Thus, in a further embodiment, the methods of the invention also may be practiced using a mimetic of a UCP1 positive regulator (e.g., PREX1, CTTNBP2, DMRTA1, and ENDRB) or a UCP1 negative regulator (e.g., ACTC1, SSTR1, FAT1, and PTPRB).

C. Methods and Compositions Relating to Thermogenically Competent Cells

The present invention provides methods and compositions for selecting thermogenically competent cells, e.g., preadipocytes, from a plurality of cells. The present invention is based, at least in part, on the discovery that expression of certain cell surface markers, e.g., CD29 and/or ITGA10, and levels thereof, positively correlate with UCP1 expression and can be used to isolate precursor cells with thermogenic competency. Thus, the methods of the invention include, but are not limited to, contacting a plurality of cells with a binding protein for CD29 and/or ITGA10 (e.g., an anti-CD29 antibody, or antigen-binding portion thereof, or an anti-ITGA10 antibody, or antigen-binding portion thereof) in order to isolate and create a substantially homogenous or enriched population of cells having thermogenic competency.

In one embodiment of the invention, CD29 (also referred to as Integrin beta1, fibronectin receptor, beta polypeptide, FNRB, integrin VLA-4 Beta subunit) is used to identify, purify, enrich, or isolate cells that will be thermogenically competent. CD29 is a 130 kD single chain type I glycoprotein also known as integrin β1, VLA-β chain, or gpIIa. CD29 is broadly expressed on a majority of hematopoietic and non-hematopoietic cells, including leukocytes, platelets, fibroblasts, endothelial cells, epithelial cells, and mast cells. CD29 is a member of the integrin family. CD29 is non-covalently associated with integrin α1-α6 chains to form VLA-1 to VLA-6 molecules, respectively. Integrins, which include CD29, bind to several cell surface (e.g. VCAM-1, MadCAM-1) and extracellular matrix molecules. CD29 acts as a fibronectin receptor and is involved in a variety of cell-cell and cell-matrix interactions. In one embodiment, the sequence of human CD29 (ITGB1) mRNA can be found at, for example, GenBank Accession GI:182519230 (NM_002211.3; SEQ ID NO: 17), and the sequence of a human CD29 (ITGB1) polypeptide sequence can be found at, for example, GenBank Accession No. GI:19743813 (NP_002202.2; SEQ ID NO: 18).

Binding proteins useful for isolating or enriching thermogenically competent cells include anti-CD29 antibodies, or antigen-binding portions thereof. In one embodiment, the anti-CD29 antibody, or antigen-binding portion thereof, binds to the extracellular domain of CD29. Antibodies that bind to the extracellular domain of CD29 are known in the art. Exemplary anti-CD29 antibodies include, but are not limited to, antibody clone MAR4 (BD Pharmingen™), antibody clone HUTS-21 (BD Pharmingen™), antibody clone TS2/16 (Biolegend™), and antibody clone TS2/16 (eBioscience™).

In one embodiment, the binding protein for CD29 is an antibody, or antigen-binding portion thereof, that binds the same epitope as any of the foregoing antibodies that bind to the extracellular domain of CD29. In another embodiment, the binding protein for CD29 is an antibody, or antigen-binding portion thereof, that competes for binding to CD29 with any of the foregoing antibodies that bind to the extra-cellular domain of CD29. In yet another embodiment, the binding protein for CD29 is an antibody, or antigen-binding portion thereof, that has the same CDR sequence as any of the foregoing antibodies that bind to the extracellular domain of CD29. In another embodiment, the binding protein for CD29 is an antibody, or antigen-binding portion thereof, that has the same heavy chain and/or light chain variable region sequence as any of the foregoing antibodies that bind to the extracellular domain of CD29.

In one embodiment, the binding protein for CD29 is CD29 antibody clone TS2/16 (eBioscience, San Diego, Calif.). In another embodiment, the binding protein for CD29 is an antibody, or antigen-binding portion thereof, that binds the same epitope as CD29 antibody clone TS2/16. In a further embodiment, the binding protein for CD29 is an antibody, or antigen-binding portion thereof, that competes with CD29 antibody clone TS2/16 for binding to CD29. In yet another embodiment, the binding protein for CD29 is an antibody, or antigen-binding portion thereof, that has the same CDR sequence of CD29 antibody clone TS2/16. In another embodiment, the binding protein for CD29 is an antibody, or antigen-binding portion thereof, that has the same heavy chain and/or light chain variable region sequence as CD29 antibody clone TS2/16.

In one embodiment of the invention, ITGA10 (also referred to as Integrin alpha 10 and PR0827) is used to identify, purify, enrich, or isolate cells that will be thermogenically competent from a population having both thermogenically competent and incompetent cells. ITGA10 is a receptor for collagen, and belongs to the integrin alpha chain family. ITGA10 participates in cell adhesion as well as cell-surface mediated signalling. ITGA10 is expressed at high levels in chondrocytes, where it is transcriptionally regulated by AP-2 epsilon and Ets-1. In one embodiment, the sequence of human ITGA10 mRNA can be found at, for example, GenBank Accession GI:733216291 (NM_003637.4; SEQ ID NO: 19), and the sequence of human ITGA10 polypeptide sequence can be found at, for example, GenBank Accession No. GI:003628 (NP_003628.2; SEQ ID NO: 20).

Binding proteins useful for isolating or enriching thermogenically competent cells include anti-ITGA10 antibodies, or antigen-binding portions thereof. In one embodiment, the anti-ITGA10 antibody, or antigen-binding portion thereof, binds to the extracellular domain of ITGA10. Antibodies that bind to the extracellular domain of ITGA10 are known in the art. Exemplary anti-ITGA10 antibodies include, but are not limited to, antibody AB6030 (EMD Millipore™), antibody BOIP (Abnova Corporation), antibody orb335349 (Biorbyt), and antibody DCABH-200751 (Creative Dianostics).

In one embodiment, the binding protein for ITGA10 is an antibody, or antigen-binding portion thereof, that binds the same epitope as any of the foregoing antibodies that bind to the extracellular domain of ITGA10. In another embodiment, the binding protein for ITGA10 is an antibody, or antigen-binding portion thereof, that competes for binding to ITGA10 with any of the foregoing antibodies that bind to the extracellular domain of ITGA10. In yet another embodiment, the binding protein for ITGA10 is an antibody, or antigen-binding portion thereof, that has the same CDR sequence as any of the foregoing antibodies that bind to the extracellular domain of ITGA10. In another embodiment, the binding protein for ITGA10 is an antibody, or antigen-binding portion thereof, that has the same heavy chain and/or light chain variable region sequence as any of the foregoing antibodies that bind to the extracellular domain of ITGA10.

CD29 may be used alone or in combination with ITGA10 as a marker to identify cells that will be capable of burning energy.

In one aspect, the invention provides methods of selecting thermogenically competent cells, such as preadipocytes, from a plurality of cells or tissue (e.g., white adipose tissue) by contacting cells with a binding protein (e.g., an antibody or antigen binding portion thereof) that binds CD29 and/or ITGA10, and selecting cells bound by the binding protein, thereby selecting thermogenically competent preadipocytes. Cells may be selected using fluorescence activated cell sorting (FACS).

Contacting of the cell with a CD29 and/or ITGA10 binding protein may be done directly or indirectly and is generally done in vitro in order to collect the desired cells. Following the selection of thermogenically competent cells, the cells may be administered to a subject in need of an enriched plurality of thermogenically competent cells for, for example, treatment of obesity (described in more detail below with respect to therapeutic methods). In one embodiment, the enriched population of cells are brown preadipocytes.

In some embodiments of the invention, the cells are selected using fluorescence activated cell sorting (FACS). FACS, also known as flow cytometry, is a technique for counting and examining microscopic particles such as cells by suspending them in a stream of fluid and capturing the light that emerges from each cell as it passes through a laser beam. Cell surface molecules often referred to as "cluster of differentiation" (CD) molecules may be exploited in flow cytometry to characterize cell populations. For example, in fluorescence-activated cell sorting, an antibody (labeled with a fluorophore) is employed, which binds to a surface molecule (e.g., a CD molecule) present on and characteristic of the cell population in question. Thereafter, the fluorophore (attached to the antibody) is activated by a laser beam and the fluorescence signal detected by the flow cytometer. In this manner, fluorescently labeled antibodies can be used to detect and sort cells displaying a specific CD molecule (or set of CD molecules). Fluorophores for use with this or any other detection method by way of example and not of limitation, include fluorescein isothiocynate, allophycocyanin, peridinin chlorophyll protein, phycoerythrin, and cyanine 5, BB421 or any other fluorophore that may be covalently conjugated to an antibody.

As described in the Examples, FACS may be used to identify thermogenically competent cells, e.g., brown preadipocytes, wherein the measure of the cell according to FACS analysis indicates whether or not it will be thermogenically competent. Specifically, it has been discovered that a high level of CD29 or ITGA10 expression ($CD29^{high}$ or $ITGA10^{high}$) on the cell surface correlates with thermogenic competency (UCP1 expression when induced), whereas a low level ($CD29^{low}$ or $ITGA10^{low}$) indicates an inability or reduced ability of the cell to burn energy through thermogenesis. Thus, the enriched plurality may be based, in some embodiments, on the percentage of high or low cells within the population.

In one embodiment, the invention includes an enriched plurality of preadipocytes, e.g., brown preadipocytes, comprising at least about 20% CD29 high ($CD29^{high}$) cells and/or integrin alpha 10 high ($ITGA10^{high}$) cells. Alternatively, the enriched plurality of brown preadipocytes comprises at least about 25% CD29 high ($CD29^{high}$) cells and/or integrin alpha 10 high ($ITGA10^{high}$) cells; at least about 30% CD29 high ($CD29^{high}$) cells and/or integrin alpha 10 high ($ITGA10^{high}$) cells; at least about 35% CD29 high ($CD29^{high}$) cells and/or integrin alpha 10 high ($ITGA10^{high}$) cells; at least about 40% CD29 high ($CD29^{high}$) cells and/or integrin alpha 10 high ($ITGA10^{high}$) cells; at least about 45% CD29 high ($CD29^{high}$) cells and/or integrin alpha 10 high ($ITGA10^{high}$) cells; or 50% or higher CD29 high ($CD29^{high}$) cells and/or integrin alpha 10 high ($ITGA10^{high}$) cells.

In one embodiment, the invention includes an enriched plurality of brown preadipocytes comprising less than about 20% CD29 low ($CD29^{low}$) cells and/or integrin alpha 10 high ($ITGA10^{low}$) cells. Alternatively, the enriched plurality of brown preadipocytes comprises 15% or less $CD29^{low}$ cells and/or $ITGA10^{low}$ cells; 10% or less $CD29^{low}$ cells and/or $ITGA10^{low}$ cells; or 5% or less $CD29^{low}$ cells and/or $ITGA10^{low}$ cells.

The designation of a cell as being "high", "medium" or "low" refers to the level of CD29 or ITGA10 on the cell surface as determined according to flow cytometry (e.g., FACS), as compared to an unstained control (meaning no antibody applied in a flow cytometry assay).

The methods of the invention (including those described in Sections IIA to IIC above) provide, in certain embodiments, a therapeutic means to treat metabolic disorders that would benefit from increased energy consumption, e.g., diabetes or obesity, attained through increasing thermogenesis in cells or tissue of a subject.

Thus, in certain embodiments, the invention includes a method of treating a human subject having a disorder that would benefit from metabolic control by administering a therapeutically effective amount of an inhibitor of a UCP1 negative regulator to the human subject, such that the disorder is treated, where the UCP1 negative regulator is selected from the group consisting of human ACTC1, human SSTR1, human FAT1, and human PTPRB. In certain embodiments, the invention provides a method of decreasing the weight of a human subject by administering a therapeutically effective amount of an inhibitor of a UCP1 negative regulator to the human subject, such that the weight of the human subject is decreased, where the UCP1 negative regulator is selected from the group consisting of human ACTC1, human SSTR1, human FAT1, and human PTPRB. In one embodiment, the inhibitor of the UCP1 negative regulator is an inhibitory nucleic acid targeting the UCP1 negative regulator or an antagonist antibody, or antigen-binding fragment thereof, of the UCP1 negative regulator.

In other embodiments, the invention incudes a method of treating a human subject having a disorder that would benefit from metabolic control where the subject is administered a therapeutically effective amount of either an activator of a UCP1 positive regulator or a UCP1 positive regulator to the human subject, such that the disorder is treated, where the UCP1 positive regulator is selected from the group consisting of human PREX1, human CTTNBP2, human DMRTA1, and human ENDRB. In another embodiment, the invention features a method of decreasing the weight of a human subject by administering a therapeutically effective amount of either an activator of a UCP1 positive regulator or a UCP1 positive regulator to the human subject, such that the weight of the human subject is decreased, where the UCP1 positive regulator is selected from the group consisting of human PREX1, human CTTNBP2, human DMRTA1, and human ENDRB. In one embodiment, the activator of a UCP1 positive regulator is either an agonist antibody, or antigen-binding fragment thereof, that binds the UCP1 positive regulator, or a polynucleotide associated with the CRISPR/Cas system which binds the UCP1 positive regulator and activates the transcription of the UCP1 positive regulator.

In other embodiments, the invention includes a method of treating a metabolic disorder or obesity in a human subject where an enriched plurality of cells having thermogenic capacity (see, e.g., Section IIC above), is administered to the subject.

Thus, the invention includes methods of treating a variety of disorders, including disorders in which metabolic control would be advantageous and obesity. Examples of disorders that would benefit from metabolic control include, but are not limited to a disorder that would benefit from glucose control, a disorder that would benefit from weight control, a disorder that would benefit from cholesterol control, and a fatty acid metabolism disorder.

In one embodiment, the invention provides a method of treating a disorder that would benefit from glucose control comprising administering an inhibitor of a UCP1 negative regulator, an activator of a UCP1 positive regulator, a UCP1 positive regulator, and/or an enriched plurality of cells, to a subject in need thereof. Alternatively, cells contacted with an inhibitor of a UCP1 negative regulator, an activator of a UCP1 positive regulator, a UCP1 positive regulator, may be administered to a subject in need having a disorder that would benefit from glucose control. Examples of a disorder that would benefit from glucose control include, but are not limited to, insulin resistance, diabetes, hyperglycemia, and metabolic syndrome.

Diabetes is a disease which is marked by elevated levels of sugar (glucose) in the blood. Diabetes can be caused by too little insulin (a chemical produced by the pancreas to regulate blood sugar), resistance to insulin, or both. The methods and compositions of the invention may also be used to treat disorders associated with diabetes including, for example, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis.

Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDMM, juvenile onset diabetes, and diabetes—type I. Type 1 diabetes represents is the result of a progressive autoimmune destruction of the pancreatic β-cells with subsequent insulin deficiency.

The term "type 2 diabetes," refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes—type II.

The methods and compositions of the invention may be used to treat either type I or type II diabetes, by providing a means to control glucose levels in the subject in need thereof.

Diabetes can be diagnosed by the administration of a glucose tolerance test.

Clinically, diabetes is often divided into several basic categories. Primary examples of these categories include, autoimmune diabetes mellitus, non-insulin-dependent diabetes mellitus (type 1 NDDM), insulin-dependent diabetes mellitus (type 2 IDDM), non-autoimmune diabetes mellitus, non-insulin-dependent diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) $14^{th}$ ed., New York, McGraw-Hill).

In another embodiment, an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or UCP1 positive regulator such that UCP1 expression is induced) is administered in combination with a diabetic therapy and/or a HMG-CoA reductase inhibitor. Exemplary diabetic therapies are known in the art and include, for example, insulin sensitizers, such as biguanides (e.g., metformin) and thiazolidinediones (e.g., rosiglitazone, pioglitazone, troglitazone); secretagogues, such as the sulfonylureas (e.g., glyburide, glipizide, glimepiride, tolbutamide, acetohexamide, tolazamide, chlorpropamide, gliclazide, glycopyamide, gliquidone), the nonsulfonylurea secretagogues, e.g., meglitinide derivatives (e.g., repaglinide, nateglinide); the dipeptidyl peptidase IV inhibitors (e.g., sitagliptin, saxagliptin, linagliptin, vildagliptin, alogliptin, septagliptin); alpha-glucosidase inhibitors (e.g., acarbose, miglitol, voglibose); amylinomimetics (e.g., pramlintide acetate); incretin mimetics (e.g., exenatide, liraglutide, taspoglutide); insulin and its analogues (e.g., rapid acting, slow acting, and intermediate acting); bile acid sequestrants (e.g., colesevelam); and dopamine agonists (e.g., bromocriptine), alone or in combinations. Exemplary HMG-CoA reductase inhibitors include atorvastatin (Pfizer's Lipitor®/Tahor/Sortis/Torvast/

Cardyl), pravastatin (Bristol-Myers Squibb 's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis).

In one embodiment, the invention provides a method of treating a disorder that would benefit from weight control comprising administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to a subject in need thereof. Examples of a disorder that would benefit from weight control include, but are not limited to, liver disease, dyslipidemia, a glycemic control disorder, cardiovascular disease and obesity. Obesity refers to a condition in which the subject has an excess of body fat relative to lean body mass. In one embodiment, obesity refers to a condition in which an individual weighs at least about 20% or more over the maximum desirable for their height. When an adult is more than 100 pounds overweight, he or she is considered to be "morbidly obese." In another embodiment, obesity is defined as a BMI (body mass index) over 30 $kg/m^2$. Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea. Obesity can be treated with the methods and compositions of the invention alone or in combination with other metabolic disorders, including diabetes. In another embodiment, a disorder that would benefit from metabolic control may be a disorder associated with obesity, for example, high blood pressure, diabetes, hyperglycemia, heart disease, high cholesterol, cancer, infertility, back pain, skin infections, gastric ulcers, gallstones, sleep apnea and osteoarthritis.

In one embodiment, the invention provides a method of treating a disorder that would benefit from cholesterol control comprising administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to a subject in need thereof. A disorder that would benefit from cholesterol control may be, for example, heart disease.

In one embodiment, the invention provides a method of treating a fatty acid metabolism disorder comprising administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to a subject in need thereof. Fatty acid metabolism disorder is characterized by difficulty breaking down (metabolizing) fatty acids. Examples of fatty acid metabolism disorder include but are not limited to, medium chain acyl CoA dehydrogenase deficiency (MCADD), long chain acyl CoA dehydrogenase deficiency (LCHADD), and very long chain acyl CoA dehydrogenase deficiency (VLCHADD).

Another exemplary disorder that would benefit from metabolic control is metabolic syndrome. Accordingly, in one embodiment, the invention provides a method of treating or preventing metabolic syndrome in a subject, comprising administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to a subject in need thereof. Metabolic syndrome is a cluster of conditions that occur together in various combinations. These conditions include elevated blood pressure, high blood sugar level, excess body fat around the waist, and abnormal cholesterol levels. A combination of the foregoing conditions can increase the risk that a subject will develop heart disease, stroke, and diabetes. Metabolic syndrome is linked to insulin resistance, and subjects having metabolic syndrome frequently display insulin resistance as well. A subject can be diagnosed as having metabolic syndrome if the subject displays three or more traits selected from a large waist circumference (e.g., at least about 35 inches for women and at least about 40 inches for men); a high triglyceride level (e.g., a triglyceride level of at least about 150 mg/dL, e.g., at least about 1.7 mmol/L); reduced levels of HDL cholesterol (e.g., a HDL level of less than about 40 mg/dL (e.g., less than about 1.04 mmol/L) in men, or a HDL level of less than about 50 mg/dL (e.g., less than about 1.3 mmol/L) in women); increased blood pressure (e.g., blood pressure of at least about 130/85 mmHg); and elevated fasting blood sugar (e.g. a fasting blood sugar level of at least about 100 mg/dL (e.g., at least about 5.6 mmol/L). In some embodiments, traits associated with metabolic syndrome can also include receiving treatment for high triglyceride level, receiving treatment for low HDL level, receiving treatment for high blood pressure, and/or receiving treatment for high blood sugar. A subject at risk of developing metabolic syndrome can be identified by determining if the subject displays at least one of the foregoing traits, and/or by determining if the subject has insulin resistance. In one embodiment, a subject is at risk of developing metabolic syndrome can be identified by determining if the subject displays at least two of the foregoing traits, and/or by determining if the subject has insulin resistance.

In certain embodiments, the methods described herein are beneficial for increasing energy expenditure in preadipocytes (or other types of thermogenically competent cells) in order to achieve weight loss in a subject in need thereof (e.g., an obese subject), where the methods of the invention are used as a single therapy or in combination with other weight loss therapies, such as bariatric surgery. Thus, in one embodiment, the invention provides a method of achieving weight loss in a subject in need thereof, comprising administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to a subject, e.g., locally administering an antibody which activates a UCP1 positive regulator, prior to, during, or following bariatric surgery in the subject.

In one embodiment, the invention includes a method of treating a disorder that would benefit from metabolic control in a subject, comprising selecting a subject having or at risk for a disorder that would benefit from metabolic control, and administering an inhibitor of a UCP1 negative regulator, an activator of a UCP1 positive regulator, a UCP1 positive regulator, and/or an enriched plurality of cells (or a cell contacted with an inhibitor of a UCP1 negative regulator, an activator of a UCP1 positive regulator, and/or a UCP1 positive regulator such that UCP1 expression is induced) to the subject.

In one aspect, a selection step is performed wherein a subject having a disorder recited herein is selected prior to the administration of the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced). For example, in one embodiment, a subject having metabolic syndrome is selected. In another embodiment, a subject in need of weight loss is selected for treatment.

Typical modes of administration of the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) include parenteral (e.g., intravenous, subcutaneous, intraperitoneal, intramuscular) injection or oral administration. In one embodiment, the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) is administered by injection. In another embodiment, the injection is subcutaneous. In a particular embodiment, the injection is into adipose tissue of a human subject.

In one embodiment of the invention, the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) is administered locally to white adipose tissue. Such administration may be, for example, subcutaneous. Local administration provides for increases in energy consumption in particular locations within a subject's body that may benefit from such energy use. Thus, the invention provides a means of reducing localized fat deposits in areas having, brown, white, and/or beige fat. Such areas of a subject that may benefit from local delivery of an agent include thighs, hips, buttocks, abdomen, waist, upper arm, back, inner knee, chest area, cheeks, chin and neck, and calves and ankles. In one embodiment, locally delivery of the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) in order to increase energy consumption of the fatty tissue is performed in combination with liposuction.

In another embodiment, the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) is administered at a dose of about 0.5 mg/kg to about 300 mg/kg. In one embodiment, the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) is administered at a dose of about 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 100 mg/kg, 150 mg/kg, 200 mg/kg, 250 mg/kg, 300 mg/kg, 350 mg/kg, 400 mg/kg, 450 mg/kg or 500 mg/kg. Ranges within one or more of the preceding values, e.g., about 1 mg/kg to about 5 mg/kg, about 2 mg/kg to about 10 mg/kg, about 6 mg/kg to about 40 mg/kg, about 20 mg/kg to about 100 mg/kg, about 50 mg/kg to about 200 mg/kg, about 100 mg/kg to about 400 mg/kg or about 1 mg/kg to about 500 mg/kg are contemplated by the invention.

Viral vectors may be used to administer the nucleic acid encoding the inhibitor of a UCP1 negative regulator, the activator of a UCP1 positive regulator, and/or the UCP1 positive regulator, to the subject. One type of vector is a "plasmid", which refers to a circular double stranded DNA loop into which additional DNA segments can be ligated. Another type of vector is a viral vector, wherein additional DNA segments can be ligated into the viral genome (e.g., lentiviral vector). Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions. In one embodiment, the viral vector is a lentivirus expressing an the UCP1 regulator or a shRNA that is directly injected into the adipose tissue of the subject.

A drug delivery matrix may also be used to deliver the inhibitor of a UCP1 negative regulator, the activator of a UCP1 positive regulator, the UCP1 positive regulator, and/or the enriched plurality of cells (or a cell contacted with the inhibitor of a UCP1 negative regulator, the activator of a UCP1 positive regulator, and/or the UCP1 positive regulator such that UCP1 expression is induced) to the subject. For example, an activator of a UCP1 positive regulator, such as PREX1, CTTNBP2, DMRTA1, and/or ENDRB, is encapsulated into silk scaffolds as described by Jin H. J. et al. (Nature 424:1057-1061, 2003). The silk hydrogel is fashioned using silk fibroin derived from cocoons mixed with polyvinyl alcohol (Wang X. et al., *Biomaterials* 31:1025-1035, 2010). The silk scaffold is an ideal system for in vivo delivery due to its favorable properties, including controlled release of protein in active form and biocompatibility with minimal immunogenic response. In another embodiment, recombinant PREX1, CTTNBP2, DMRTA1, and/or ENDRB is loaded into the silk-hydrogel and the targeted release rate and duration are optimized. The prepared hydrogel may be implanted for example, through small incisions into adipose tissue of the subject.

In another aspect, the present invention provides ex vivo methods of treating a subject having a disorder that would benefit from metabolic control. The method comprises administering a thermogenically competent cell contacted with an inhibitor of a UCP1 negative regulator, an activator of a UCP1 positive regulator, and/or a UCP1 positive regulator (e.g., PREX1, CTTNBP2, DMRTA1, and/or ENDRB protein or a nucleic acid encoding PREX1, CTTNBP2, DMRTA1, and/or ENDRB to the subject), in which UCP1 expression is induced, wherein the thermogenically competent cell is administered to the subject, such that the disorder is treated.

Therapeutic formulations comprising an inhibitor of a UCP1 negative regulator, an activator of a positive regulator, or a UCP1 positive regulator of the present invention may be prepared for storage by mixing the protein or nucleic acid having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween™, Pluronics™ or polyethylene glycol (PEG).

The formulation herein may also contain more than one active compound as necessary for the particular indication being treated (e.g., a disease that would benefit from glucose control, a disease that would benefit from weight control, a disease that would benefit from appetite control), preferably those with complementary activities that do not adversely affect each other. Such molecules are suitably present in combination in amounts that are effective for the purpose intended. In one embodiment, the active compound is a diabetic therapy. In another embodiment, the active compound is an HMG-CoA reductase inhibitor.

The active ingredients may also be packaged in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration. In an alternative embodiment, one or more of the pharmaceutical compositions of the invention is supplied in liquid form in a hermetically sealed container indicating the quantity and concentration of the agent.

The active agent can be incorporated into a pharmaceutical composition suitable for parenteral administration, typically prepared as an injectable solution. The injectable solution can be composed of either a liquid or lyophilized dosage form in a flint or amber vial, ampule or pre-filled syringe. The liquid or lyophilized dosage may further comprise a buffer (e.g., L-histidine, sodium succinate, sodium citrate, sodium phosphate or potassium phosphate, sodium chloride), a cryoprotectant (e.g., sucrose trehalose or lactose, a bulking agent (e.g., mannitol), a stabilizer (e.g., L-Methionine, glycine, arginine), an adjuvant (hyaluronidase).

The compositions of this invention may be in a variety of forms. These include, for example, liquid, semi-solid and solid dosage forms, such as liquid solutions (e.g., injectable and infusible solutions), microemulsion, dispersions, liposomes or suspensions, tablets, pills, powders, liposomes and suppositories. The preferred form depends on the intended mode of administration and therapeutic application. Typical modes of administration include parenteral (e.g., intravenous, subcutaneous, intraperitoneal, intramuscular) injection or oral administration. In a preferred embodiment, the UCP1 regulator (or agonist or antagonist thereof) is administered by injection. In another embodiment, the injection is subcutaneous. In a particular embodiment, the administration is into adipose tissue Pharmaceutical compositions comprising an agent described herein may be formulated for administration to a particular tissue. For example, in certain embodiments, it may be desirable to administer the agent into adipose tissue, either in a diffuse fashion or targeted to a site (e.g., subcutaneous adipose tissue).

In another aspect, the invention provides pharmaceutical compositions that utilize cells in various methods for treatment of diseases that would benefit from glucose control, weight control and or appetite control. Certain embodiments encompass pharmaceutical compositions comprising live cells. The pharmaceutical composition may further comprise other active agents, such as anti-inflammatory agents, anti-apoptotic agents, antioxidants or growth factors.

In one embodiment, the methods described herein are done in a human. In a further embodiment, the methods described herein are not performed on a mouse or other non-human animal.

D. Predictive Methods and Compositions of Invention

Genes (or biomarkers) identified herein (see, e.g., biomarkers described in Table 4, ACTC1, FAT1, SSTR1, PTPRB, PREX1, CTTNBP2, DMRTA1, and ENDRB) may be used as a predictive means for determining whether a human subject may be at risk for or has a metabolic disorder based on a determined level of a UCP1 negative regulator and/or a UCP1 positive regulator. Thus, the invention may be used to determine whether a human subject has or is at risk of having a metabolic disorder or obesity.

The invention identifies certain biomarkers associated with metabolic disorders and obesity which may be used to determine whether a subject is at risk for developing such a disorder. Such predictive means benefit the overall health of the subject, as faster responses can be made to determine the appropriate therapy. The methods described herein also decrease the overall cost of the treatment process by more quickly eliminating ineffective therapies.

The term "known standard level" or "control level" refers to an accepted or pre-determined level (e.g., mRNA level or protein level) of the UCP1 positive or negative regulator (or, generally, marker) which is used to compare the UCP1 positive or negative regulator level derived from a sample of a patient. In one embodiment, the known standard level of the UCP1 positive and/or negative regulator is based on a subject or subjects having a metabolic disorder or obesity, and, therefore, represents the disease state. In another embodiment, the known standard level of the biomarker indicates an unaffected, i.e., non-disease, state of a subject who does not have obesity or a metabolic disorder. When compared to the known standard level of a certain biomarker, deviation from the known standard level generally indicates either an improvement or deterioration in the disease state. Alternatively, when compared to the known standard level of a certain biomarker, equivalence to the known standard level generally indicates confirmation of the disease activity, confirmation of a non-disease state, or, if the biomarker level of the patient is obtained following therapeutic treatment for the disease, failure of a therapy to improve a patient's disease state.

Generally, the invention includes comparing biomarker levels from a patient at risk of having obesity or a metabolic disorder, with a known standard level associated with disease activity, to determine whether the patient's biomarker level is increased, decreased, or the same, relative to the control. Thus, in determining the likelihood a patient will develop obesity or a metabolic disorder, biomarker levels may be pre-determined. In one embodiment, the invention includes a method for determining whether a human subject is at risk for developing a metabolic disorder or obesity, where a level of a marker described herein from a patient having obesity or a metabolic disorder is compared with a known standard level of the biomarker associated with the disease state to determine whether it corresponds to the disease state (predicting development or occurrence of the disease) or whether it is above or below (depending in the marker) the control, indicating no presence of disease.

In one embodiment, the method includes contacting a sample from a human subject comprising preadipocytes with a binding protein that binds CD29 and/or integrin alpha 10 (ITGA10), and determining the level of preadipocytes bound by the binding protein. The level of bound protein can then be used to determine whether the subject is at risk for having a metabolic disorder or obesity. For example, if the level of preadipocytes bound by the binding protein correlates with a known standard for a subject who does not have or is not at risk of having a metabolic disorder or obesity, then the subject does not have or is unlikely to develop the disorder. Alternatively, if the level of preadipocytes bound by the binding protein correlates with a known standard for a subject who has or is at risk of having a metabolic disorder or obesity, then the subject has or is at risk for developing the disorder.

In one embodiment, the invention provides a method of determining whether a human subject has or is at risk of having a metabolic disorder or obesity, said method comprising comparing a pre-determined level of a UCP1 negative regulator from a sample comprising preadipocytes from the subject, with a known standard level of the UCP1 negative regulator associated with the metabolic disorder or obesity; and assessing whether the subject's UCP1 negative regulator level is equal to or greater than the known standard level of the UCP1 negative regulator, wherein an equal or greater level of UCP1 negative regulator level from the subject relative to the known standard level indicates that the subject has or is at risk of having a metabolic disorder or obesity.

In a further embodiment, the invention provides a method of determining whether a human subject has or is at risk of having a metabolic disorder or obesity, said method comprising comparing a pre-determined level of a UCP1 positive regulator from a sample comprising preadipocytes from the subject, with a known standard level of the UCP1 positive regulator associated with a subject who is not obese or has a metabolic disorder; and assessing whether the subject's UCP1 negative regulator level is equal to or greater than the known standard level of the UCP1 negative regulator, wherein an equal or greater level of UCP1 positive regulator level from the subject relative to the known standard level indicates that the subject does not have or is not at risk of having a metabolic disorder or obesity.

The level of an mRNA encoding a marker described herein can be measured using methods known to those skilled in the art, e.g. Northern analysis. Gene expression of the marker can be detected at the RNA level. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., Nuc. Acids Res. 12:7035), Northern blotting and In Situ hybridization. Gene expression can also be detected by microarray analysis as described below.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample. The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, real time (RT-PCR) (also called QPCR) is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

The methods of the invention may be performed using protein-based assays to determine the level of the given marker. Examples of protein-based assays include immunohistochemical and/or Western analysis, quantitative blood based assays, e.g., serum ELISA, and quantitative urine based assays, e.g., urine ELISA. In one embodiment, an immunoassay is performed to provide a quantitative assessment of the given marker.

Proteins from samples can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

The amount of marker may be determined by detecting or quantifying the corresponding expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, and Western blotting.

The methods of the invention may be performed using protein-based assays to determine the level of the given biomarker. Examples of protein-based assays include immunohistochemical and/or Western analysis, quantitative blood based assays, e.g., serum ELISA, and quantitative urine based assays, e.g., urine ELISA. In one embodiment, an immunoassay is performed to provide a quantitative assessment of the given biomarker.

Proteins from patient samples can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

The amount of a UCP1 negative or positive regulator, CD29, and/or ITGA10 may be determined by detecting or quantifying the corresponding expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, and Western blotting.

In one embodiment the level of a UCP1 negative or positive regulator, CD29, and/or ITGA10 may be determined using an immunoassay. The use of antibodies directed to biomarkers described herein can be used to screen human biological samples, e.g., fluids, for the levels of the specific biomarker antigen, i.e., CP1 negative or positive regulator, CD29, and/or ITGA10. By way of illustration, human fluids, such as blood serum or urine, can be taken from a patient and assayed for a specific epitope, either as released antigen or membrane-bound on cells in the sample fluid, using anti-biomarker antibodies in standard RIAs or ELISAs, for example, known in the art. In immunoassays, the agent for detecting a UCP1 negative or positive regulator, CD29, and/or ITGA10 polypeptide may be an antibody capable of binding to the protein of the a UCP1 negative or positive regulator, CD29, and/or ITGA10. Antibodies can be polyclonal, or more preferably, monoclonal. An intact antibody, or a fragment thereof (e.g., Fab or F(ab')$_2$) can be used.

Competitive binding assays may be used to determine the level of the protein corresponding to the UCP1 negative or positive regulator, CD29, and/or ITGA10. One example of a competitive binding assay is an enzyme-linked immunosorbent sandwich assay (ELISA). ELISA can be used to detect the presence of a UCP1 negative or positive regulator, CD29, and/or ITGA10 in a sample. ELISA is a sensitive immunoassay that uses an enzyme linked to an antibody or antigen as a marker for the detection of a specific protein, especially an antigen or antibody. ELISA is an assay wherein bound antigen or antibody is detected by a linked enzyme that generally converts a colorless substrate into a colored product, or a product which can be detected. One of the most common types of ELISA is "sandwich ELISA." In one embodiment, the level of the a UCP1 negative or positive regulator, CD29, and/or ITGA10 is determined using an ELISA assay. In addition, a skilled artisan can readily adapt known protein/antibody detection methods for use in determining the amount of a marker of the present invention. Antibodies used in immunoassays known in the art and described herein to determine levels of biomarkers, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In a one embodiment, the antibody is labeled, e.g. a radio-labeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a UCP1 negative or positive regulator, CD29, and/or ITGA10.

In one embodiment of the invention, proteomic methods, e.g., mass spectrometry, are used for detecting and quantitating the UCP1 negative or positive regulator, CD29, and/or ITGA10. For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to detect and quantitate UCP1 negative or positive regulator, CD29, and/or ITGA10. Mass spectrometric methods are described in, for example, U.S. Pat. Nos. 5,622,824, 5,605,798 and 5,547,835, the entire contents of each of which are incorporated herein by reference.

In one embodiment, the level of an mRNA encoding said biomarker can be measured using methods known to those skilled in the art, e.g. Northern analysis. Gene expression of the biomarker can be detected at the RNA level. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting and In Situ hybridization. Gene expression can also be detected by microarray analysis as described below.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

Nuclease Protection Assays (including both ribonuclease protection assays and S1 nuclease assays) provide an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. NPAs allow the simultaneous detection of several RNA species.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification (TAS) methods have been described in the literature, for example, general reviews of these methods in Landegren, U. et al., Science 242:229-237 (1988) and Lewis, R., Genetic Engineering News 10:1, 54-55 (1990). PCR is a nucleic acid amplification method common in the art and described inter alia in U.S. Pat. Nos. 4,683,195 and 4,683,202. PCR can be used to amplify any known nucleic acid in a diagnostic context (Mok et al., 1994, Gynaecologic Oncology 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, Proc. Natl. Acad. Sci. USA 87:1874). Ligation amplification reaction or ligation amplification system uses DNA ligase and four oligonucleotides, two per target strand. This technique is described by Wu, D. Y. and Wallace, R. B., 1989, Genomics 4:560. In the Q.beta. Replicase technique, RNA replicase for the bacteriophage Q.beta., which replicates single-stranded RNA, is used to amplify the target DNA, as described by Lizardi et al., 1988, Bio/Technology 6:1197. Quantitative PCR (Q-PCR) is a technique which allows relative amounts of transcripts within a sample to be determined.

The contents of all references, patents and published patent applications cited throughout this application are incorporated herein by reference

Examples

In order to investigate the heterogeneous nature of the progenitor cell population in human BAT and WAT, the following examples describe the generation of clonal cell lines from human neck fat, whereby their adipogenic differentiation and metabolic functions in vitro and in vivo are characterized after transplantation. Using a UCP1 reporter system and gene expression profiling, the following examples also define unique sets of gene signatures in human preadipocytes that can be used to predict the thermogenic potential of mature adipocytes. Deletion of positive regulators in a brown fat progenitor clone severely diminished the thermogenic potential of mature brown adipocytes. These data highlight cellular heterogeneity in human BAT and WAT and provide novel gene targets that may prime preadipocytes for thermogenic differentiation and positive thermogenic capacity.

The following methods were used in the examples below unless otherwise specified.

Materials and Methods

Recombinant human BMP7 was kindly provided by Stryker Regenerative Medicine (Hopkinton, Mass.), recombinant human BMP8 was purchased from R&D Systems (Minneapolis, Minn.). Antibody sources are as follows: anti-UCP1 was from Abcam (Cambridge, Mass.) and AnaSpec (Fremont, Calif.); anti-α-tubulin was from Sigma-Aldrich (Dallas, Tex.); anti-CD29 was from eBioscience (San Diego, Calif.). All other chemicals were purchased from Sigma-Aldrich (Dallas, Tex.), unless otherwise specified.

This study followed the institutional guidelines of and was approved by the Human Studies Institutional Review Boards of Beth Israel Deaconess Medical Center and Joslin Diabetes Center. Details on procedures of human subject collection were described previously[19]. There were two independent human subject cohorts: for isolation and immortalization of fat progenitors, human neck fat from 4 subjects was analyzed; for gene expression verification, neck fat from 7 different people was studied. All subjects gave written informed consent before taking part in the study.

Isolation and Culture of Primary Human White and Brown Fat Progenitors.

Isolation of primary stromal-vascular fraction (SVF) from human neck fat was described previously (Cannon and Nedergaard, Physiol Rev, 84: 277-359, 2004). Briefly, freshly resected superficial fat (pooled subcutaneous and subplatysmal) and fat located in the deeper neck regions (pooled carotid sheath, longus colli and prevertebral) were collected, minced and digested using collagenase 1 (2 mg/mL in PBS with the addition of 3.5% BSA; Worthington Biochemical Corporation, Lakewood, N.J.), and the SVF was isolated. SVF cells were plated and grown in high glucose Dulbecco's modified Eagle's medium (DMEM/H) supplemented with 10% (v/v) fetal bovine serum (FBS) and 1% penicillin/streptomycin. For adipocyte differentiation, cells were grown to confluent for 6 days (day 6) and then exposed to adipogenic induction mixture in DMEM/H medium containing isobutylmethylxanthine (0.5 mM), dexamethasone (0.1 µM), human insulin (0.5 µM; Sigma-Aldrich, Dallas, Tex.), T3 (2 nM), indomethacin (30 µM), pantothenate (17 µM), biotin (33 µM) and 2% FBS for another 12 days (referred as day 18). Induction medium was changed every 3 days until collected.

Culture and Differentiation of Immortalized Human White and Brown Fat Progenitors.

Immortalized progenitor cells were plated and grown in DMEM/H medium supplemented with 10% FBS (day 0). For adipocyte differentiation, cell were grown for 6 days until reaching confluence (day 6), and then treated with the adipogenic induction medium as described above for 12 days (termed as day 18). To further stimulate thermogenic program, fully differentiated cells were incubated with 10 µM forskolin for 4 h. For BMPs and FGF21 pre-treatment, recombinant BMP7 (3.3 nM), BMP8 (3.3 nM), or FGF21 (50 nM) were added to undifferentiated cells in medium containing insulin (0.5 µM), T3 (2 nM) and 2% FBS for 6 days followed by adipogenic induction for 12 days. For BMPs and FGF21 post-treatment, fully differentiated adipocytes at day 18 were treated with recombinant BMP7 (3.3 nM), BMP8 (3.3 nM), or FGF21 (50 nM) in medium containing insulin (0.5 µM), T3 (2 nM) and 2% FBS for 2 days.

Oil Red O staining.

Cells were washed twice with PBS and fixed with 10% buffered formalin for 30 min at room temperature. Cells were then stained for 4 h at room temperature with a filtered Oil Red O solution (0.5% Oil Red O in isopropyl alcohol), washed twice with distilled water, and visualized.

Quantitative RT-PCR.

RNA extraction, cDNA synthesis, and quantitative real-time PCR (Q-RT-PCR) were performed as described before (Cypess, A. M., et al. Nat Med 19, 635-639, 2013; Tseng, Y. H., et al. Nature 454, 1000-1004, 2008). Q-RT-PCR assays were run in duplicates and quantified in the ABI Prism 7900 sequence-detection system using SYBR (Roche Applied Science, Indianapolis, Ind.). Relative mRNA expression was determined by the delta-$C_t$ method and the values were normalized to the expression of 18S ribosomal RNA (18s).

Western Blotting.

Protein detection by western blotting was performed as described before (Tseng, Y. H., et al. Nature 454, 1000-1004, 2008). Primary antibodies were incubated overnight at 4° C.: UCP1 (1:500, rabbit polyclonal; Abcam, Cambridge, Mass.) and α-tubulin (1:4,000, mouse monoclonal). HRP-coupled secondary antibodies (Cell Signaling Technologies, Beverly, Mass.) were used at 1:2,000 dilutions at room temperature for 2 h followed by detection using the ECL system.

Immunofluorescence Staining.

Cells were grown and differentiation on a chamber covered with a glass slide (Lab-Tek II chamber CC2 glass slide cover; Thermo Scientific, Waltham, Mass.). Fully differentiated cells were fixed in 4% paraformaldehyde for 10 min, washed three times with PBS. Cells were permeabilized with 0.1% Triton X-100 for 30 min and incubated with primary antibodies overnight at 4° C.: UCP1 (1:50, rabbit polyclonal; AnaSpec, Fremont, Calif.). After primary antibody incubation, cells were washed and incubated with appropriate secondary antibody (Alexa Fluor-488 (green); Invitrogen, Life Technologies, Carlsbad, Calif.) at a 1:200 dilution for 10 min in the dark. After secondary antibody incubation, cells were washed with distilled water for DAPI staining (0.1 µg/mL in water for 5 min in the dark), and mounted. Cells were kept in the dark after mounting and analyzed by a fluorescence microscope (Olympus BX60F-3; Olympus Corporation, Tokyo, Japan). Identical conditions and settings were used for picture acquisition and analysis. A threshold was set for each image to eliminate background and to create a binary mode image. For every sections and cells, images from three representative areas were analyzed.

Seahorse Bioenergetic Profiling.

To assess mitochondrial respiration, a Seahorse Extracellular Flux Analyzer (Seahorse Bioscience Inc., North Billerica, Mass.) was used to quantify oxygen consumption rates (OCR) of differentiated human white and brown adipocytes. Progenitor cells were seeded on 24-well format plates and allowed to adhere overnight. After 6 days, adipogenesis was induced as described above. After adipogenic induction for 12 days, OCR was analyzed. To measure OCR independent of oxidative phosphorylation, 0.5 µM oligomycin (EMD Chemicals Inc., Gibbstown, N.J.) was added to cells. Subsequently, 0.8 µM FCCP (carbonyl cyanide-p-trifluoromethoxyphenylhydrazone) and 1 µM respiratory chain inhibitors (rotenone) were added to measure maximal respiration and basal rates of nonmitochondrial respiration. For cAMP-induced respiration, fully differentiated adipocytes were incubated with 10 µM forskolin for 4 hours. For BMP7 pretreatment-induced respiration, recombinant BMP7 (3.3 nM) was added to the undifferentiated cells for 6 days and then adipogenic induction mixture medium was added to the confluent cells for 12 days, followed by measurement of cellular respiration. All data were average of four-time points with 10 wells per time point by quantified in bar plots, and error bars are standard error of the mean (s.e.m.). Statistical comparisons were done by Student's t-test.

Glucose Uptake Assay.

After serum starvation in DMEM/H medium containing 1% of BSA for 2-3 h, differentiated human white and brown adipocytes were washed with HEPES buffer. Then they were incubated with or without 100 nM insulin for 30 min in DMEM/H medium containing 1% of BSA. Glucose transport was determined by the addition of 2-deoxy-[$^3$H]glucose (0.1 mM, 0.5 µCi/mL; PerkinElmer Life and Analytical Science, Waltham, Mass.). After 5 min of incubation, the reaction was stopped by ice-cold PBS and cells were washed twice with ice-cold PBS. Cells were then lysed in 0.1% SDS, and glucose uptake was assessed in 4 mL of scintillant using Beckman LS6500 scintillation counter (Beckman Coulter, Indianapolis Ind.). Nonspecific 2-deoxy-[$^3$H]glucose uptake was measured in the presence of cytochalasin B (20 µM) and was subtracted from the total uptake to get specific glucose uptake. Results were expressed as the mean±s.e.m. of the indicated number of experiments. The protein content was determined by the Bradford method.

Fatty Acid Uptake and Fatty Acid Oxidation Assays.

Fatty acid uptake and oxidation were determined by measuring both $^{14}$C-labeled palmitic acid uptake and conversion of $^{14}$C-labeled palmitic acid into CO2. Briefly, the culture medium was removed, and cells were incubated with DMEM/H containing 4% fatty acid free BSA, 0.5 mM palmitic acid, and 0.2 µCi/mL [1-$^{14}$C]-palmitic acid (PerkinElmer Life and Analytical Science, Waltham, Mass.) for 1 h. The incubation medium was transferred to a vial containing 1 M acetic acid, capped quickly, and allowed to sit 1 h for CO2 gas to be released. $^{14}$CO2 released was absorbed by hyamine hydroxide, and activity was counted. Fatty acid oxidation was calculated from CO2 generated. To measure fatty acid uptake, cells were rinsed twice with PBS and lysed after incubation with [1-$^{14}$C]-palmitic acid. Lipids were extracted using a chloroform-methanol mixture (2:1), and $^{14}$C counts were determined in the organic phase. Fatty acid uptake was calculated as the total of $^{14}$C lipids in the cells and $^{14}$CO2 generated.

Generation of cells with a hUCP1 reporter.

Immortalized human fat progenitor cells were infected with a lentivirus containing the plasmid, pLV.ExBi.P/Puro-hUCP1promoter-Luc(firefly)-T2A-hrGFP that expresses luciferase and GFP driven by human UCP1 promoter. 4148 bp human UCP1 promoter was cloned from pLightSwitch_hUCP1-Prom (S723122; Switch Gear Genomics, Carlsbad, Calif.) and was then sub-cloned into a lentiviral plasmid to generate plasmid containing a UCP1 reporter (Cyagen Biosciences Inc., Santa Clara, Calif.). 293T cells (ATCC) were transfected with hUCP1promoter-Luc-T2A-GFP, pMD2.G and psPAX2 DNA using PolyJet DNA in vitro transfection reagent (SignaGen Laboratories, Rockville, Md.). Culture supernatants containing virus were collected every 24 hrs after infection and filtered through a 0.45 µm filter (Fisher, Scientific, Pittsburgh, Pa.). Immortalized human white and brown fat progenitors at 80% confluence were infected with viral supernatants in the presence of 4 µg/mL Polybrene every day until cells reached 90% confluence. Then cells were treated with 1 µg/mL puromycin in DMEM/H medium containing 10% FBS and antibiotics. Once drug selection was finished, the cells were maintained in culture medium with 0.2 µg/mL puromycin for 2 weeks.

Luciferase Reporter Assay.

In vitro luciferase assays were performed using luciferase assay kits (Promega, Madison, Wis.) according to the manufacturer's instructions. Remove culture medium from differentiated adipocytes and wash cells in PBS. Dispense an appropriate volume of 1× lysis reagent (Passive Lysis Buffer) into each culture well. Scrape attached cells from the wells, and transfer the cell lysates into white 96-well plate (Corning Inc., Tewksbury, Mass.) for detection of the bioluminescence signal using luminometer plate reader (BioTek Instruments, Inc., Winooski, Vt.). Use a reagent injector to dispense 100 µL of Luciferase assay buffer with substrate and 100 µL of Stop & Glo Reagent. And perform a 2-second pre-measurement delay, followed by a 10-second measurement period for each reporter assay. Luciferase activity data were normalized to protein content.

Time Lapse Imaging System.

Human immortalized cells with hUCP1-promoter-Luc/GFP were plated on a Hi-Q4 culture dish (Nikon, Tokyo, Japan) and cultured in a Nikon BioStation IM-Q (Nikon, Tokyo, Japan) which is a compact cell incubator and monitoring system that allows for live cell imaging. Cells were maintained in BioStation IM-Q at 37° C. in 5% CO2 environment. Adipogenesis was induced as described. Bright field and fluorescent images were obtained every hour over the course every three days between medium changes for a total of 18 days.

Cell Transplantations and IVIS Imaging System.

Human immortalized white and brown fat progenitors with hUCP1-promoter-Luc/GFP were grown in the presence and absence of 3.3 nM BMP7 for 6 days to reach confluence. Cells were washed, trypsinzed, and resuspended in growth medium with an equal amount of Matrigel Matrix (BD Biosciences, San Diego, Calif.). Then, 1.0×10$^7$ cells in 0.3 mL volume were injected into the thoracic/sternum region of 6-week-old male BALB/c athymic nude mice (n=2 mice for white fat progenitors transplantation group, n=3 mice for brown fat progenitors transplantation group; Harlan laboratories, Indianapolis, Ind.) using an 18-gauge needle, according to the methods described previously (Schulz, T. J., et al. Proc Natl Acad Sci USA 108, 143-148, 2011; Tseng, Y. H., et al. Nature 454, 1000-1004, 2008). No statistical method was used to predetermine sample size and experiments were not randomized. For an acquisition of the bioluminescence images, the mice were sedated with 2% isoflurane in 100% 02 in the chamber. D-Luciferin (PerkinElmer Life and Analytical Science, Waltham, Mass.) was diluted to 3 mg/100 µL in normal saline and 0.6 mg of D-Luciferin was administrated intraperitoneally into mice. An IVIS-Spectrum CT imaging system equipped with a CCD camera (Caliper, PerkinElmer Life and Analytical Science, Hopkinton, Mass.) was used for in vivo bioluminescence imaging. The luminescence intensity in regions of interest from each image was quantified to examine the viability of the implanted cells. Mice were scanned by IVIS each week after transplantation. After 6 weeks of transplantation, mice were sacrificed, and adipose tissue derived from implanted cells was excised and processed for Q-RT-PCR analysis. There was no blinding during animal experiments. The animal experiment was performed according to procedures approved by the Joslin Diabetes Center Institutional Animal Care and Use Committee (IACUC).

Generation of Immortalized Clonal Cell Lines.

To derive subclones of immortalized human white and brown progenitors with hUCP1-promoter-Luc/GFP reporter, limiting dilution of cells into 96-well plates was performed as previously described (Tchkonia, T., et al. *Diabetes* 55, 2571-2578, 2006). Briefly, cells were plated at 50 cells/96-well plate in DMEM/H containing 10% FBS. After 2 weeks, colonies were evident. Cells at approximately 80% confluence were trypsinized and further propagated in 48-well, then 12-well and finally 6-well plate. 152 clonal lines originated from neck superficial fat depot and 128 clonal lines from deep fat were selected for adipogenic potential after induction. The highly adipogenic clonal lines were selected for further analysis (67 clonal white fat progenitor lines; 90 clonal brown fat progenitor lines).

Nile Red Staining.

To detect intracellular lipid droplet in live cells, Nile Red staining was performed in differentiated adipocytes. Cells were washed twice in PBS and then incubated in PBS containing 3 µM Nile Red (Life Technologies, Carlsbad, Calif.) for 60 min at 37° C. To remove the Nile Red working solution from the cells, wash the cells with PBS. Monitor the fluorescence change at Ex/Em=552/636 nm with a fluorescence microscope or fluorescent plate reader (BioTek Instruments, Inc., Winooski, Vt.).

Microarray Analysis.

Analysis of gene expression using GeneChip® PrimeView (Affymetrix, Santa Clara, Calif.) was performed on 42 highly adipogenic clonal white and brown cell lines. RNA was isolated from clonal cell lines using Direct-zol RNA MiniPrep kit (Zymo Research, Irvine, Calif.) according to the manufacturer's instructions. The quality of total RNA was evaluated by A260/A280 ratio, which was within the value of 1.9 to 2.0 defined as high quality total RNA. Biotin-labeled cRNA was synthesized, purified and fragmented using GeneChip 3'IVT Express Kit (Affymetrix, Santa Clara, Calif.). Integrity and fragmented cRNA was assessed by running aliquots on the Agilent 2100 Bioanalyzer prior to proceeding further. The high quality cRNA meets the following criteria: the A260/A280 ratio should fall within the value of 1.9 to 2.0;

the 28S/18S RNA bands (from the gel) should be crisp and the intensity of the 28S band should be roughly twice the intensity of the 18S band. As one clone from hWAT-SVF had had poor cRNA quality, this clone was excluded from analysis. Array hybridization and scanning were performed by the Advanced Genomics and Genetics Core of Joslin Diabetes Center according to established methods. This data is being prepared for submission to the Gene Expression Omnibus (GEO). Microarray data were normalized using robust multi-array average (RMA) (Irizarry, R. A., et al. *Biostatistics* 4, 249-264, 2003), which placed it on a log-2 scale. The log transformation is particularly helpful for making gene expression data approximately normally distributed, so (although we did not explicitly test for normality) the normalized data for each probe set were correlated to $\log_2$ (UCP1) using Pearson correlation with a two-sided alternative (with function cor.test), which yielded correlation coefficients and P-values. P-values were adjusted for multiple testing using the False Discovery Rate (FDR)[48] with function p.adjust. The 50 probe sets from unique genes most strongly associated with $\log_2$ (UCP1) were plotted in a heat map along with $\log_2$ (UCP1) using the heatmap.2 function in the gplots package and color palettes from the RColorBrewer package. The probesets' values were centered to have mean zero and restricted to the interval [−2,2] to aid visualization, and a color bar representing UCP1 was added at top, where darker indicates higher UCP1. All microarray analyses were done in the R programming language (www.r-project.org).

Engineering Target Gene Knockout Cell Clones Using CRISPR/Cas9 System.

Cas9 vectors express the Cas9 nuclease and guide RNA (gRNA) were obtained from Horizon Discovery Group plc (Cambridge, United Kingdom). 5 gRNAs of each target gene were designed using Horizon's proprietary gUIDE-book software and cloned into a Case9 expressing plasmid on behalf of Horizon by DNA2.0. The plasmid carrying Cas9 and gRNA with GFP selection marker was introduced into cells by transfection using PolyJet DNA in vitro transfection reagent (SignaGen Laboratories, Rockville, Md.). Next day, the cells were replaced with fresh medium supplemented with 10% FBS, and re-seed when the cells became confluent. To derive subclones with plasmid insertion, limiting dilution of cells into 96-well plates was performed as previously described. Select and expand the clones with GFP signal, followed by extraction of total RNA for Q-RT-PCR using standard methods.

Cell Sorting.

CD29 positive progenitors were sorted by FACS, as previously described before (Schulz, T. J., et al. *Proc Natl Acad Sci USA* 108, 143-148, 2011). Briefly cells were trypsinized, centrifuged, and resuspended in HBSS (Invitrogen, Life Technologies, Carlsbad, Calif.) with 2% FBS. CD29 antibody (β1-integrin, 1:200, APC conjugate, clone TS2/16; eBioscience, San Diego, Calif.) incubation was performed for 20 min on ice in HBSS containing 2% FBS. For cell sorting, Cytomation Moflo (Cytomation Inc.) instrument was used. FACS data were collected using Summit software (Cytomation Inc.) and analyzed offline using FlowJo software (Tree Star, Inc., Macintosh version 8.1.1).

Statistics

All results were expressed as mean±s.e.m. All statistical analyses were performed using the programs Excel (Microsoft) and Statview (SAS Institute). Two-tailed Student's t-test was used to determine P values. Statistical significance was defined as P<0.05. Gene expression level in human WAT versus BAT was analyzed by using Wilcoxon matched-pairs signed-rank test. No statistical method was used to predetermine sample size. The experiments were not randomized. All experiments were not blinded.

Example 1. Characterization of Immortalized Human BAT and WAT Progenitors

Figure 1:
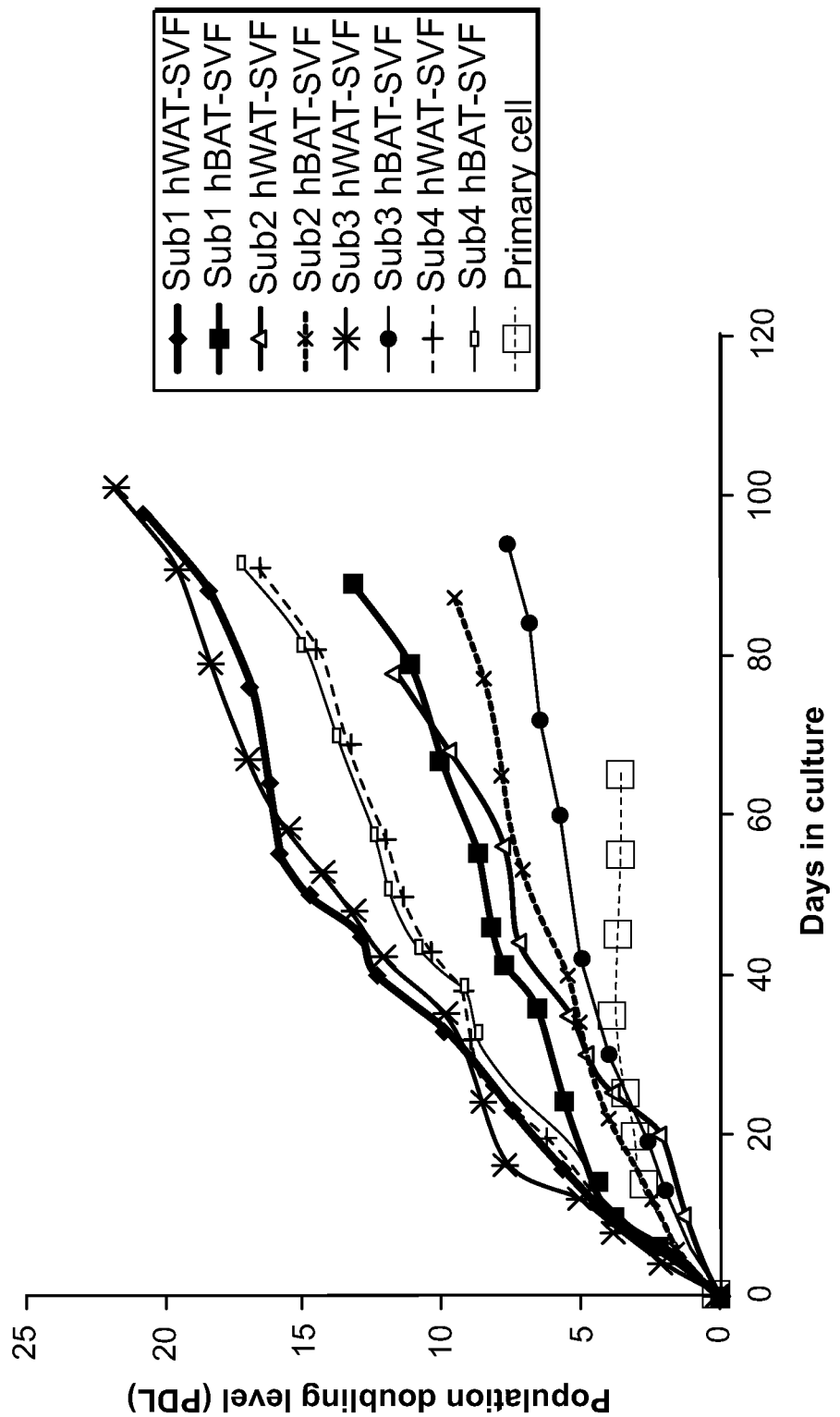
FIG. 1 depicts a comparison of population doubling levels (PDL) of immortalized hWAT-SVF and hBAT-SVF from 4 subjects and primary SVF. Primary and immortalized human SVF were grown in DMEM/H supplemented with 10% FBS and 1% penicillin/streptomycin. Population Doubling Level (PDL) was calculated with the following formula: $\Delta PDL=\log(nh/ni)/\log 2$, wherein ni is the initial number of cells, and nh is the final number of cells at each passage.

To define molecular and functional characteristics of specific adipose progenitors, human preadipocyte pooled cell populations derived from a total of four human subjects were generated by isolating cells from the stromal vascular fraction (SVF) of human neck fat and immortalizing them via stable expression of human telomere reverse transcriptase (hTert). Pairs of immortalized progenitors for human BAT (hBAT-SVF, isolated from deep neck fat) and human WAT (hWAT-SVF, isolated from superficial neck fat) of the same individuals were established from each of the four individuals for proper comparisons (Table 1). The immortalized cells were passaged in culture for more than 90 days and were followed for up to 20 population doublings (FIG. 1).

TABLE 1

Clinical characteristics of subjects whose neck fat were used for generation of immortalized human WAT and BAT progenitors

| Patient Code | Age (year) | Sex | BMI (kg/m$^2$) | hWAT[a] | hBAT[a] |
|---|---|---|---|---|---|
| Subject 1 | 58 | M | 28.0 | SQ[b] SP[c] | CS[d] LC[e] |
| Subject 2 | 54 | M | 25.1 | SQ SP | CS PV[f] |
| Subject 3 | 42 | M | 33.0 | SQ SP | CS PV |
| Subject 4 | 63 | M | 33.3 | SQ SP | CS LC PV |

Figure 2A:
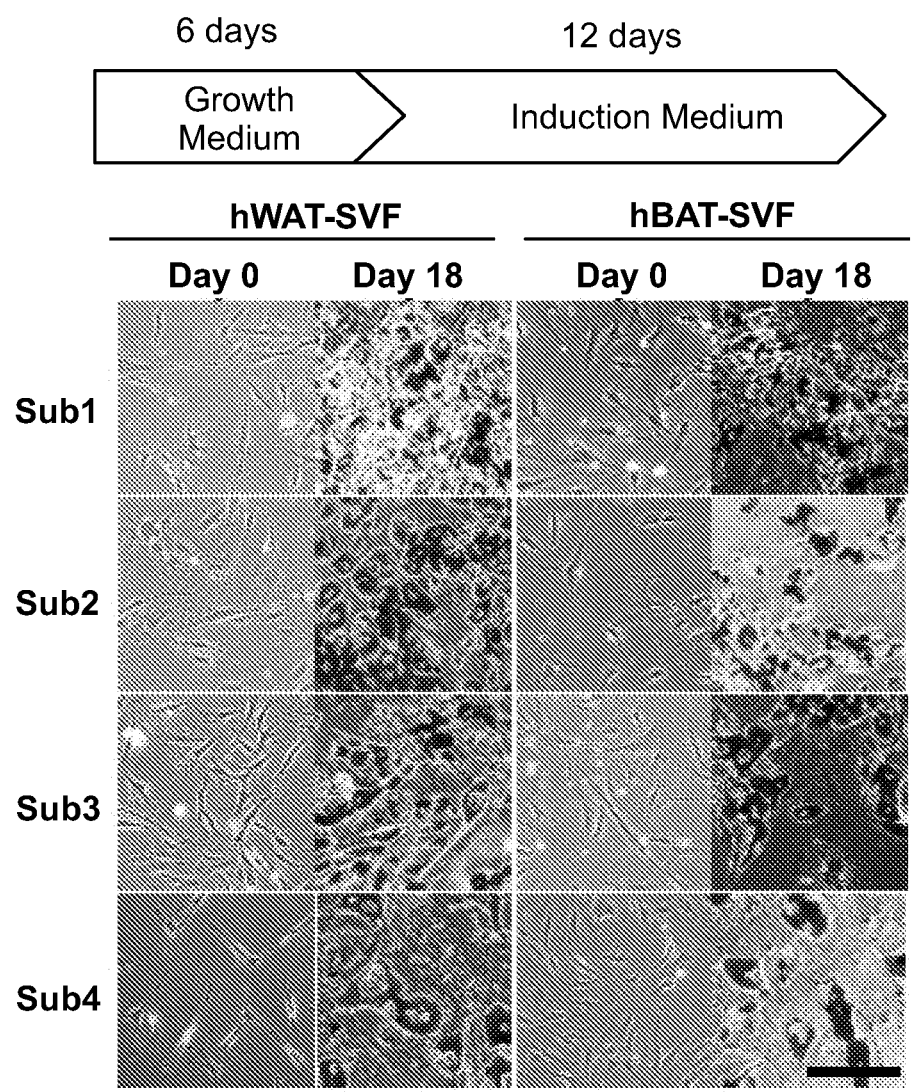
FIG. 2A-2H graphically depict generation and characterization of immortalized human brown and white fat progenitors. Cells from the stromal vascular fraction (SVF) of human neck fat were immortalized by stable expression of human telomere reverse transcriptase (hTert).
Figure 2B:
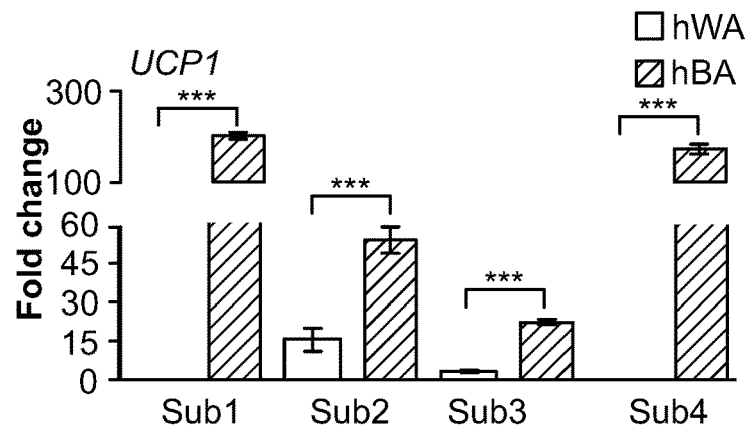
Figure 2C:
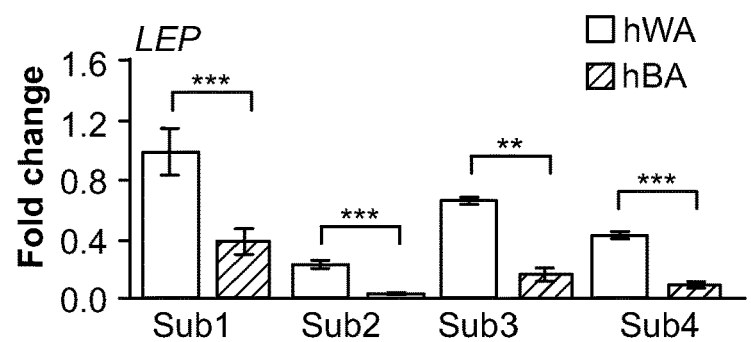
Figure 2D:
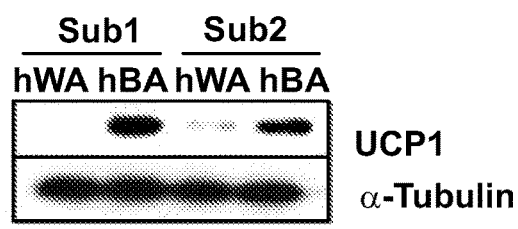
Figure 3:
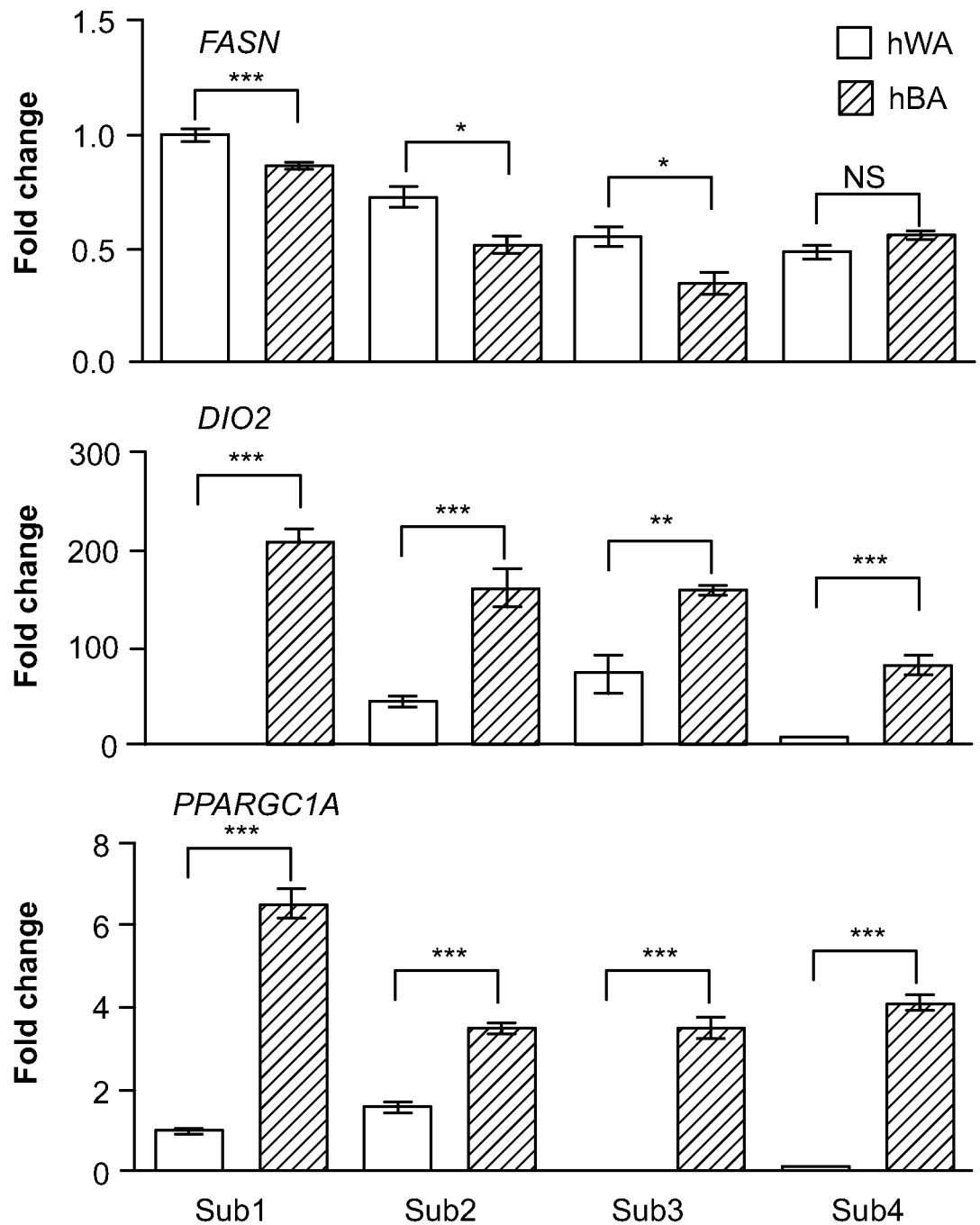
FIG. 3 depicts Q-RT-PCR analysis for FAS, DIO2 and PGC1α mRNA expression in differentiated human white fat (hWA) and brown fat (hBA) progenitors from 4 subjects. Data are presented as a fold change compared to Sub1 hWA (mean±s.e.m., n=3; two-tailed Student's t-test; N.S: not significant, *P<0.05, P<0.01, *P<0.001).
Figure 5:
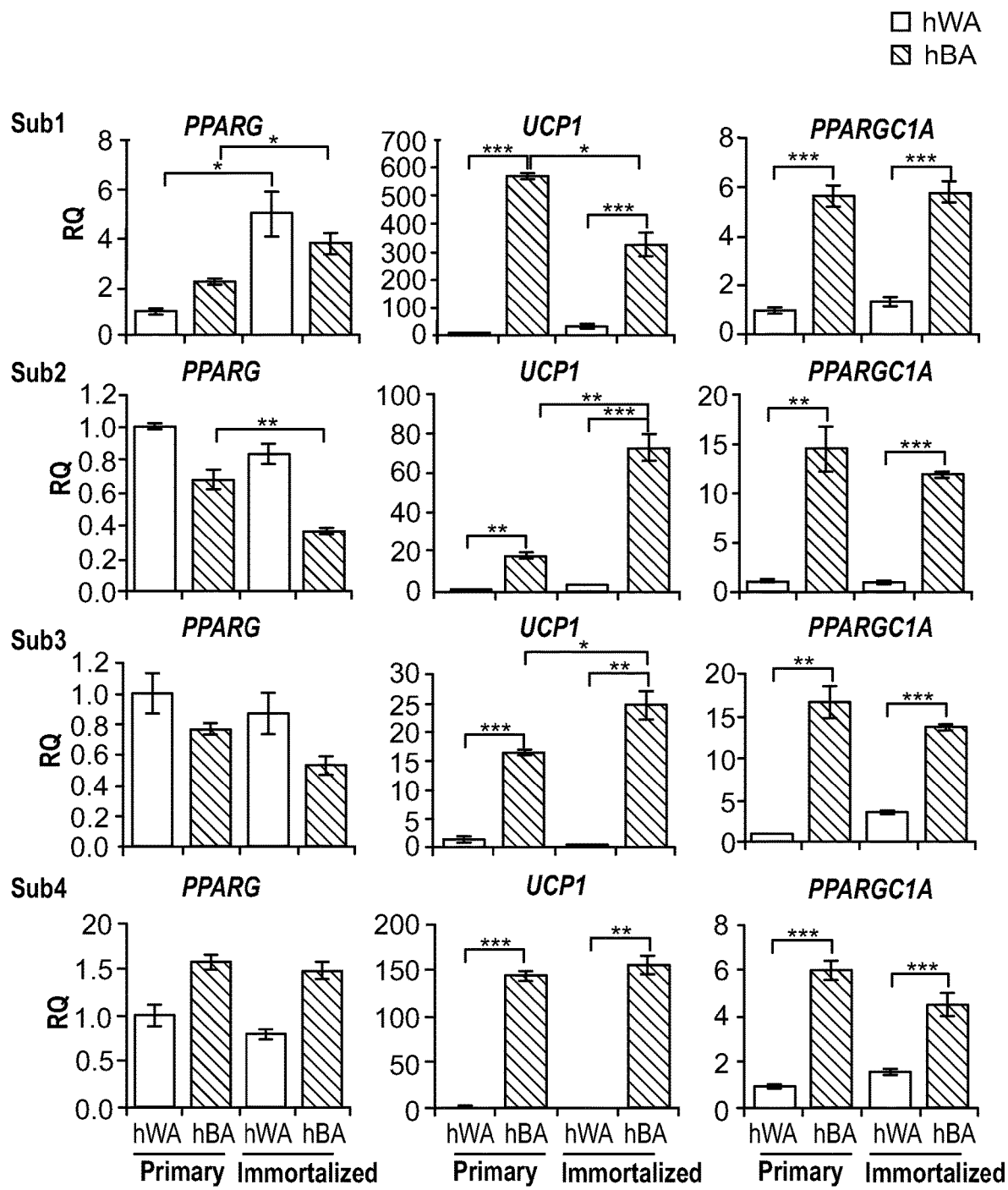
FIG. 5 depicts Q-RT-PCR analysis for selected markers. Specifically, RNA was isolated from differentiated primary and immortalized hWA and hBA from 4 subjects, and Q-RT-PCR analysis was performed for the adipocyte marker, PPARγ, and brown-fat-specific markers, UCP1 and PGC1a. Data are presented as a fold change compared to primary hWA in each subject (mean±s.e.m., n=3; two-tailed Student's t-test; *P<0.05, P<0.01, *P<0.001). A representative experiment from a total of three independent studies is shown.

[a]These two columns indicate the anatomical locations of neck fat tissues used for generation of adipose progenitors.
[b]Subcutaneous
[c]Subplatysmal
[d]Carotid sheath
[e]Longus colli
[f]Prevertebral After immortalization the cells from both WAT and BAT depots of the four human subjects maintained a fibroblast-like morphology and following induction with a standard adipogenic differentiation protocol all precursors became lipid-laden cells expressing a high level of the mature adipocyte marker fatty acid synthase (FAS) (FIG. 2A and FIG. 3). Notably, in differentiated hBAT-SVF cells (referred as human brown adipocytes, hBA), expression of the brown fat marker UCP1 was up to 200-fold higher than in differentiated hWAT-SVF cells (human white adipocytes, hWA) (FIG. 2B), and was accompanied by robust induction of UCP1 protein (FIG. 2D). A comparable pattern of expression was observed in other brown fat markers such as deiodinase 2 (DIO2) and peroxisome proliferator-activated receptor gamma coactivator (PGC)-1α (FIG. 3). LEPTIN, a marker of WAT, was selectively expressed in hWA compared to hBA in all subjects (FIG. 2C). Importantly, the immortalized cells retained differentiation characteristics of primary cells (FIG. 5).

Figure 2E:
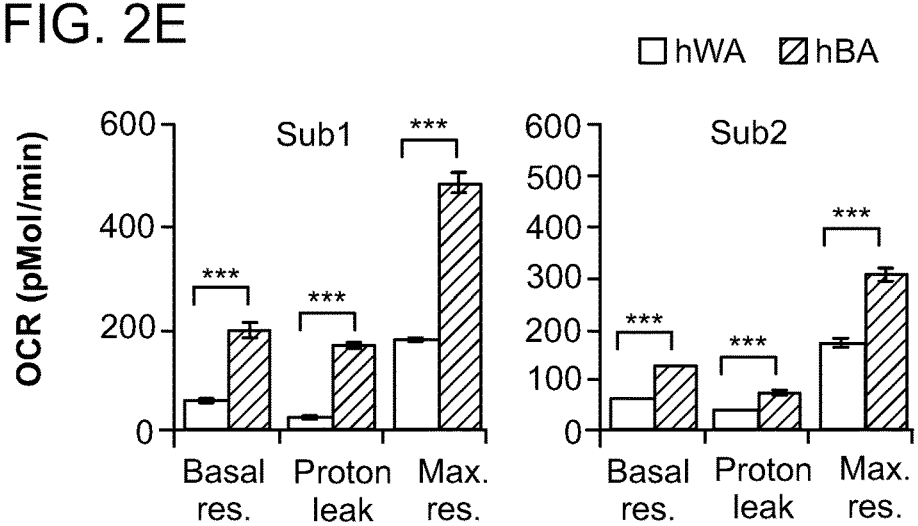
Figure 2F:
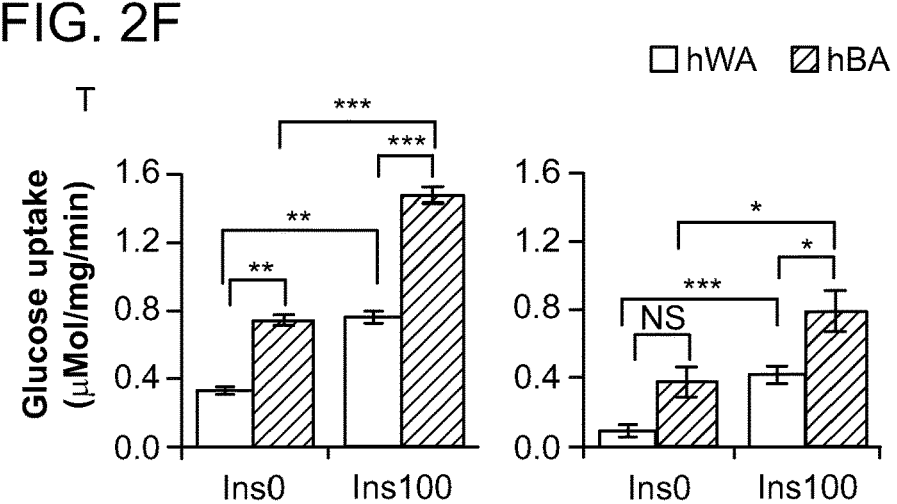
Figure 2G:
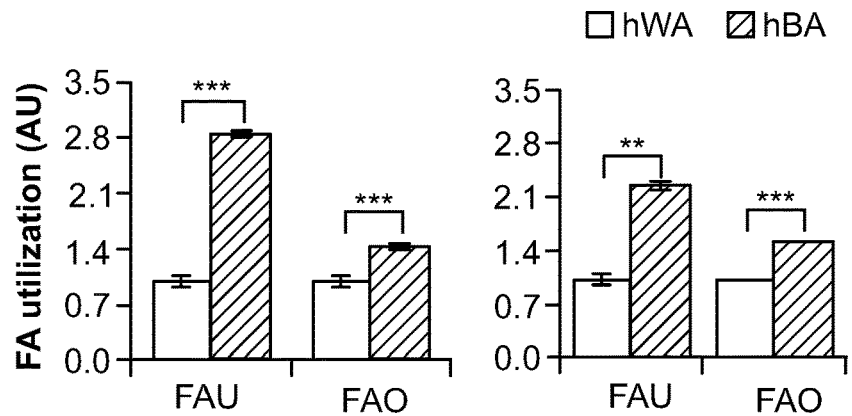
Figure 4A:
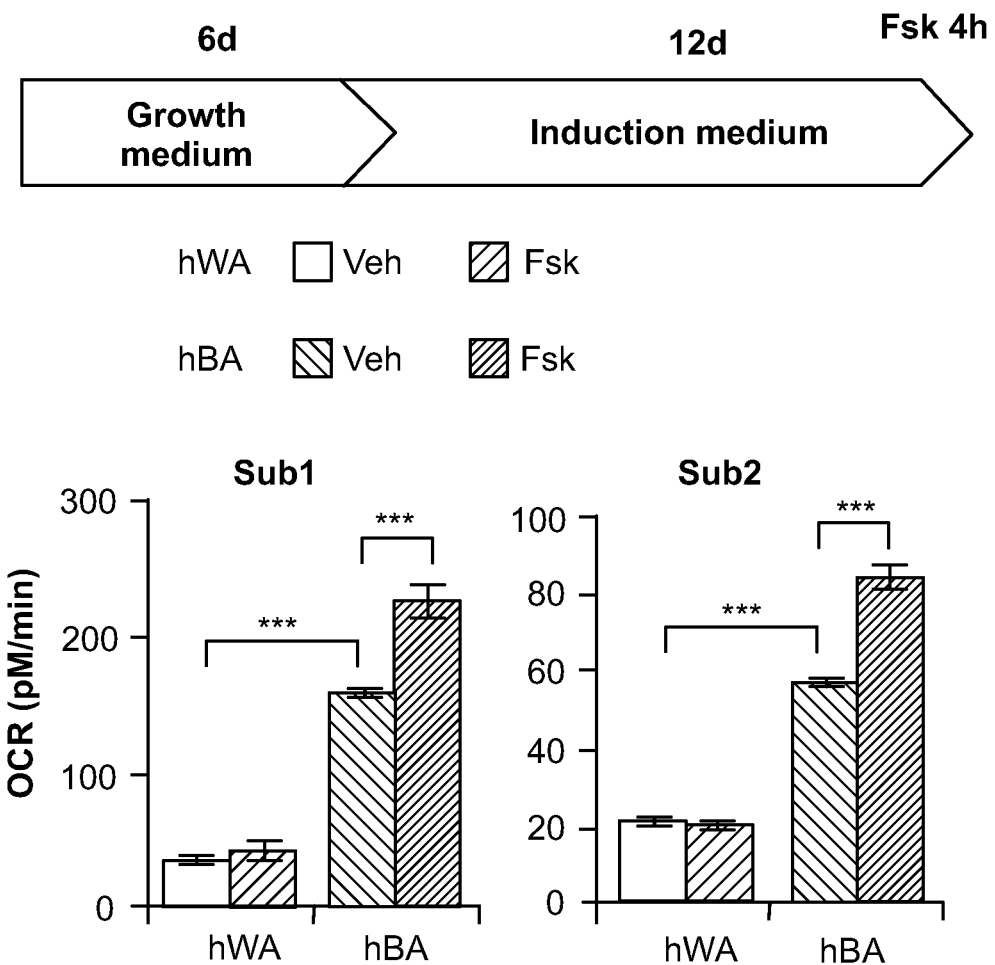
FIG. 4A depicts total cellular respiration rate (OCR) measured using the Seahorse extracellular flux analyzer in differentiated hWA and hBA from Sub1 and Sub2 that were treated for 4 h with 10 uM forskolin (Fsk). The same number of cells was used in the assay. Data are presented as mean±s.e.m. (n=10; two-tailed Student's t-test; *P<0.05, P<0.01, *P<0.001). A representative experiment from a total of three independent studies is shown.
Figure 4B:
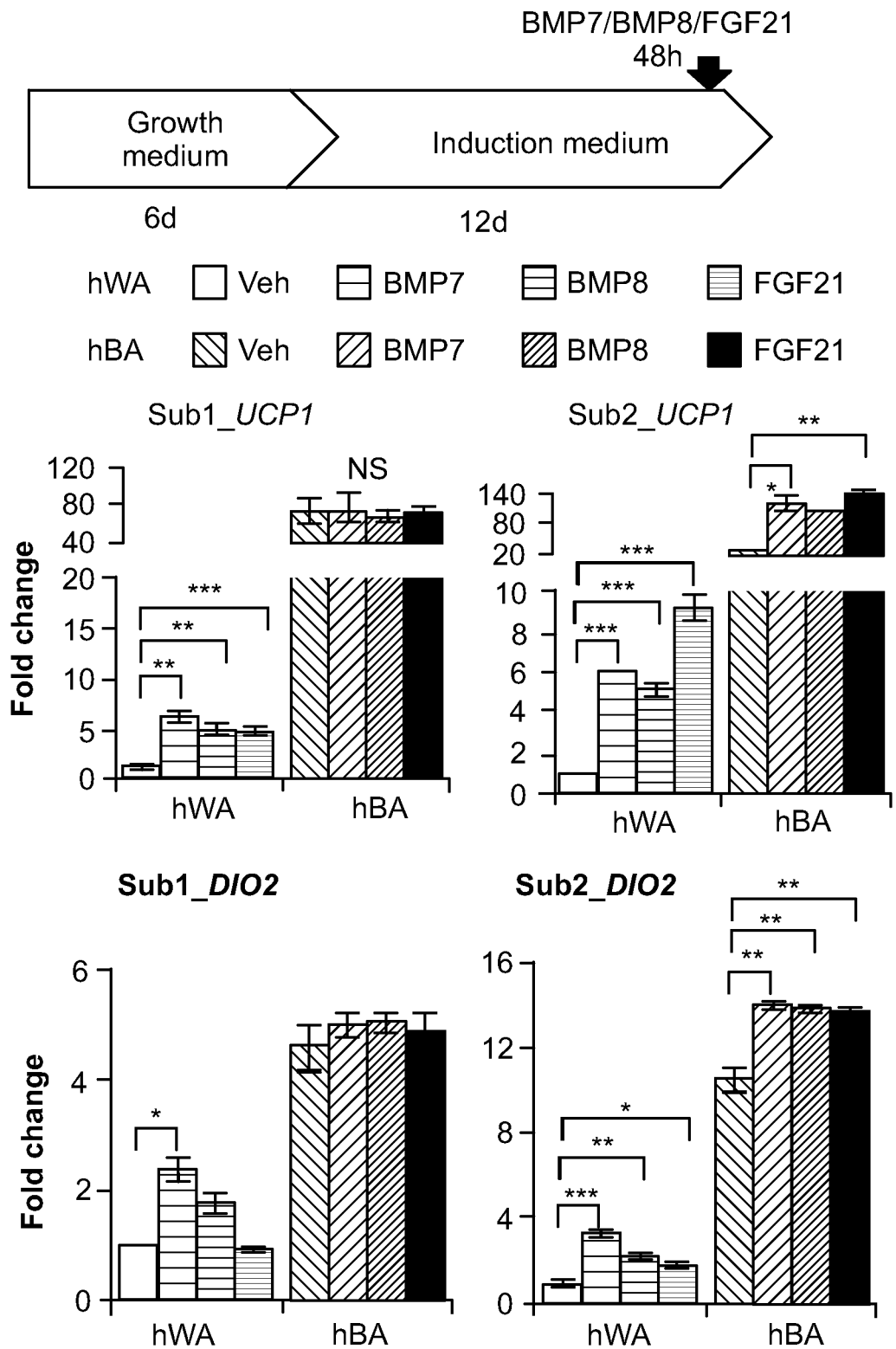
FIG. 4B depicts Q-RT-PCR analysis for UCP1 and DIO2 expression in differentiated hWA and hBA from Sub1 and Sub2 that were treated for 48 h with 3.3 nM BMP7, 3.3 nM BMP8 and 50 nM FGF21. Data are presented as a fold change compared to vehicle treatment of hWA in each subject (mean±s.e.m., n=3; two-tailed Student's t-test; *P<0.05, P<0.01, *P<0.001). A representative experiment from a total of three independent studies is shown. Data are represented in the same order as appeared in the legend.
Figure 4C:
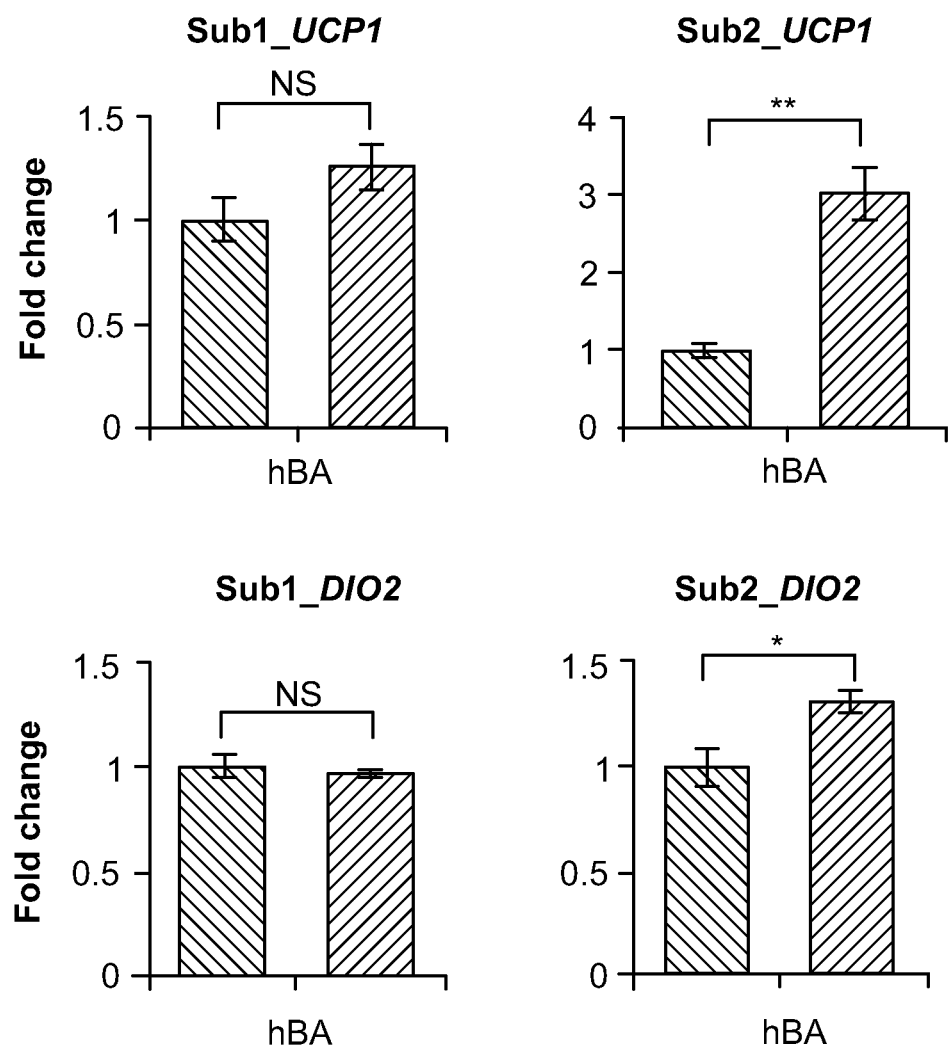
FIG. 4C depicts characterization of differentiated hBA treated with NE. Q-RT-PCR analysis for UCP1 and DIO2 expression in differentiated hBA from Sub1 and Sub2. Cells were treated for 4 h with 1 uM norepinephrine (NE). Data are presented as fold changes relative to vehicle control (mean±s.e.m., n=3; two-tailed Student's t-test; *P<0.05, P<0.01, *P<0.001). A representative experiment from a total of three independent studies is shown.

To determine whether the differentiated cells possessed metabolic capacity, cellular respiration and fuel utilization were evaluated in hBA and hWA of Subject 1 and 2. Consistent with changes in gene expression, the levels of basal and maximal respiration as well as proton leak in hBA were significantly higher compared with hWA (FIG. 2E). Glucose uptake in both the basal and insulin stimulated state was also notably higher in hBA than hWA as was both fatty acid uptake and oxidation rate (FIGS. 2F and 2G). In addition, differentiated brown, but not white, adipocytes were able to respond to forskolin, a chemical mimic of β-adrenergic stimulation, by increasing oxygen consumption rate (FIG. 4A). In addition, hBAs from subject 2 could respond to stimulations by norepinephrine and other browning agents by increasing the levels of UCP1 and DIO2 (FIGS. 4B and 4C), suggesting that the mature human brown adipocytes are responsive to both physiological and pharmacological adrenergic stimuli.

To determine whether human-derived progenitors can respond to browning agents, the aforementioned precursors from Subject 1 and 2 were treated with BMP7 for 6 days, followed by adipogenic induction (Schulz, T. J., et al. *Proc Natl Acad Sci USA* 108, 143-148, 2011; Tseng, Y. H., et al. *Nature* 454, 1000-1004, 2008). Pre-exposure to BMP7 of hWAT-SVF from both subjects and hBAT-SVF from Subject 2 led to increased UCP1 expression, enhanced mitochondrial activity and fuel utilization in mature adipocytes (FIG. 2H and FIGS. 6B-6F), suggesting a fraction of these progenitors are inducible. Pretreatment with BMP7 also augmented peroxisome proliferator-activated receptor gamma (PPARγ) expression in mature brown adipocytes from Subject 2 only. BMP8, another browning agent (Whittle, A. J., et al. *Cell* 149, 871-885, 2012). exerted similar effects (FIG. 6A).

hBAT-SVF cells and hBAs derived from subject 2, but not subject 1, consistently responded to browning agents, suggesting that the cells derived from subject 2 were more inducible, whereas cells derived from subject 1 may represent the classical brown fat cells, which possess a very high basal level of UCP1. The distinction of classical versus inducible hBAs between subjects 1 and 2 was further supported by the differential expression levels of the classical BAT marker ZIC1 (refs. 4, 30, 31) (FIG. 6G).

These data support previous characterization of the tissue from human neck BAT and WAT (Cypess, A. M., et al. *Nat Med* 19, 635-639, 2013) and demonstrate that the progenitor cell populations recapitulate adipogenic differentiation and thermogenic expression profiles in vitro. Further, inter-subject differences not only exist in whole adipose tissue as previously noted (Cypess, A. M., et al. *Nat Med* 19, 635-639, 2013), but also exist in adipose progenitors and their derivative adipocytes. Despite the inter-subject variations, human brown adipocytes clearly possess great metabolic capacity.

Example 2. Generation of a UCP1 Reporter System for Monitoring UCP1 Expression in Vitro and In Vivo To allow direct assessment of the thermogenic potential of differentiated cells, a transgenic reporter construct was introduced into the white and brown fat precursors to measure UCP1 gene expression by coupling a bicistronic luciferase/green fluorescent protein (GFP) reporter system to a 4.1-Kb human UCP1 promoter fragment (FIGS. 7A and 7B). In mature adipocytes which stably expressed the reporter construct, luciferase activity was strongly correlated with endogenous UCP1 gene expression and only detected in mature brown adipocytes not in undifferentiated cells (FIG. 7C). Differentiating cells were monitored using time-lapse microscopy and activation of the GFP reporter was detected as early as day 9 in differentiating BAT cells (FIG. 7D).

To determine if these cells were capable of differentiation in vivo, progenitor cells were transplanted into immune-deficient nude mice and in vivo bioluminescent imaging was used to measure UCP1 reporter activity (FIG. 7E). Luciferase activity was high in mice implanted with hBAT progenitors, and could be further induced by BMP7 pretreatment of progenitors. Conversely, mice receiving transplanted hWAT progenitors displayed almost no detectable luciferase activity. Consistent with luciferase activity, fat grafts from hBAT-SVF displayed at least 100-fold increase in UCP1 mRNA compared to hWAT-SVF-derived fat pads (FIG. 7F). These data demonstrate that the UCP1 reporter system accurately indicates differentiation into mature brown adipocytes and establish the utility of these reporter cells as human tissue models in semi-humanized mice.

The foregoing cells lines stably expressing a UCP1 reporter construct offer opportunities for high-throughput screenings aimed at identifying targets that enhance thermogenic differentiation or activate mature cells by measuring UCP1 reporter activity longitudinally. Further, the UCP1 reporter allows for the generation of human xenograft models wherein human BAT and WAT can be dynamically assayed for induction of UCP1 in vivo. The foregoing experiment using BMP7 pretreatment of hBAT preadipocytes demonstrates the exciting prospect of using mice with human-derived BAT and WAT to screen for novel activators of thermogenesis in an in vivo setting.

Example 3. Clonal Analysis of Human Brown and White Fat Progenitors

In order to study homogenous cell populations derived from human adipose precursor cells, a total of 280 clonal preadipocyte cell lines (152 hWAT-SVF clones and 128 hBAT-SVF clones) were isolated from the immortalized pool populations of all four subjects. Of these lines, 44% (67 out of 152) of hWAT-SVF and 70% (90 out of 128) of hBAT-SVF clones robustly differentiated into mature adipocytes (FIG. 8A and FIG. 9). To determine UCP1 induction in the differentiated state, luciferase reporter activity was measured in each clonal line after 18-days of adipogenic differentiation (FIG. 10). The data revealed that up to 96% of the hWAT-SVF clones were UCP1 negative, while more than 94% of the hBAT-SVF clones displayed differential levels of UCP1-luciferase activities (FIG. 8A).

Figure 2H:
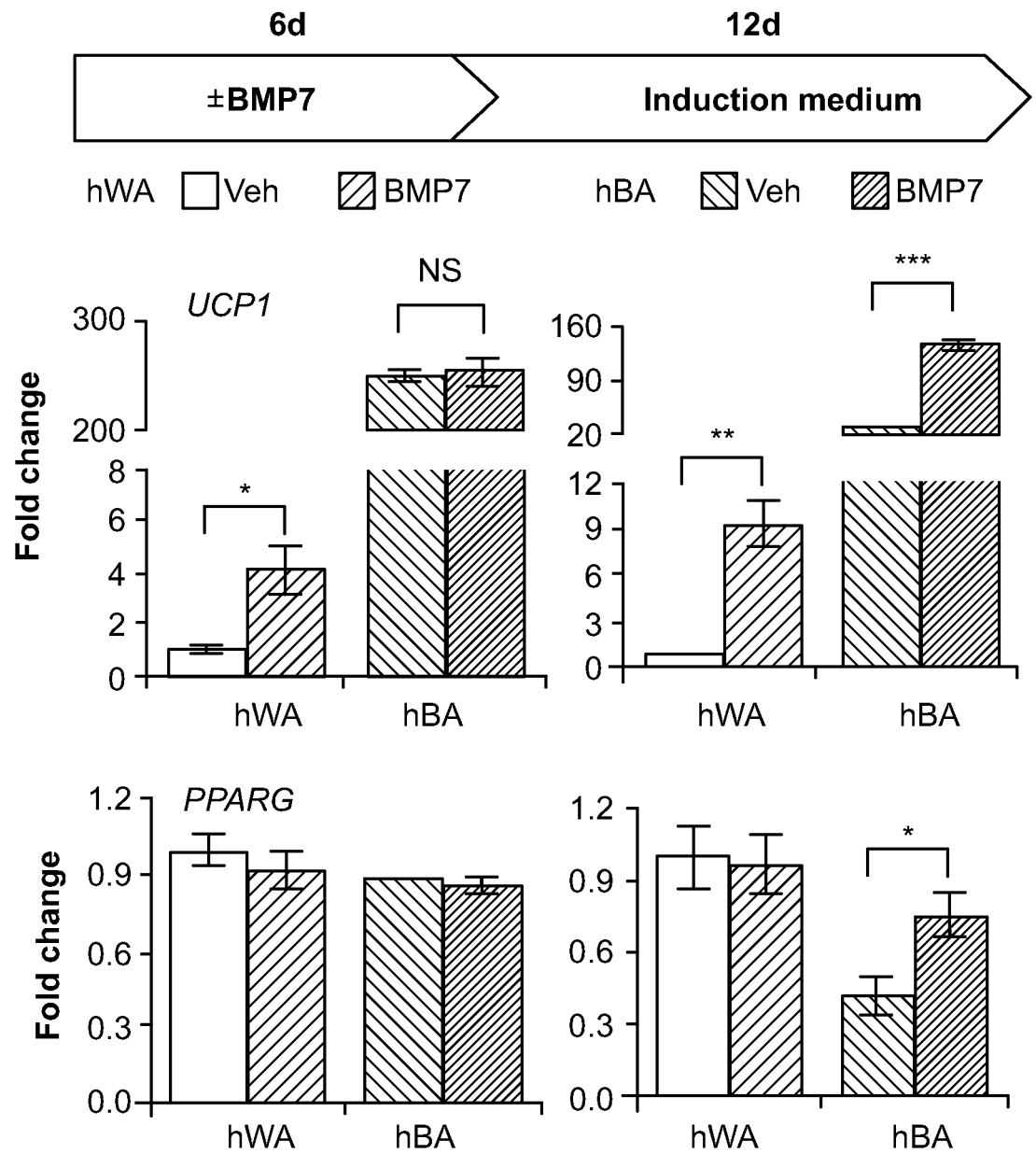

As shown in FIG. 2H, certain subpopulations of hWAT or hBAT precursors could respond to inductive signals, such as BMP7, to further increase their thermogenic capacity. To identify the precursor clones that could respond to stimulation, undifferentiated cells were pretreated with BMP7 and reporter expression in mature cells was determined. While only 1% of the highly adipogenic hWAT-SVF clones could respond to BMP7 pretreatment, a substantial number of hBAT-SVF clones (up to 37%) could be induced by BMP7 pretreatment (FIG. 8). Further analyzing the clones in terms of their human subject origins revealed that more than 60% of the hBAT-SVF clones from Subject 2 and Subject 3 could respond to BMP7 stimulation while the majority of the hBAT-SVF clones from Subject 1 and Subject 4 were not responsive to BMP7 pretreatment (Table 2).

TABLE 2

Distribution of human WAT-SVF and human BAT-SVF clones that displayed different UCP1 levels and differential responses to BMP7 pre-treatment in 4 human subjects hWAT-SVF Clones (n = 67)

| Patient Code | Total N | UCP1 (−)[a] | | UCP1 (+)[b] |
|---|---|---|---|---|
| | | BMP7 Respf (−)[c] | BMP7 Resp(+)[d] | BMP7 Resp(+) |
| Subject 1 | 32 | 32/32 | 0/32 | 0/32 |
| Subject 2 | 20 | 20/20 | 0/20 | 0/20 |
| Subject 3 | 12 | 11/12 | 0/12 | 1/12 |
| Subject 4 | 3 | 3/3 | 0/3 | 0/3 | hBAT-SVF Clones (n = 90)

| Patient Code | Total N | UCP1(−) | | UCP1(+) |
|---|---|---|---|---|
| | | BMP7 Resp(−) | BMP7 Resp(−) | BMP7 Resp(+) |
| Subject 1 | 41 | 2/41 | 29/41 (71%) | 10/41 |
| Subject 2 | 15 | 0/15 | 5/15 | 10/15 (67%) |
| Subject 3 | 15 | 3/15 | 3/15 | 9/15 (60%) |
| Subject 4 | 19 | 0/19 | 14/19 (74%) | 5/19 |

These data not only support the analysis of the pooled progenitor populations described above, but also suggest that the thermogenic features of mature adipocytes are regulated by the anatomical location of the tissue they originate from in addition to genetic influences of the individual human subjects. They also highlight the heterogeneity of the human adipose clones, even among cell lines isolated from a common subject and a common tissue.

Example 4. Prediction of Thermogenic Potential of Mature Adipocytes by Gene Expression Profiles in Adipose Progenitors To identify molecular markers of thermogenically competent cells, the UCP1 reporter system was utilized in each clonal cell line to select a set of clones from all four subjects that represented a wide range of luciferase activity after adipogenic differentiation for further analysis (FIG. 11A). These clones' gene expression in the preadipocyte state were assayed with micro arrays, and correlated with UCP1 expression in the differentiated state. After applying the stringent threshold of P<0.001, which is associated with a false discovery rate of 0.03, 581 genes that displayed significant positive correlation and 454 genes that displayed significant negative correlation were prioritized (FIG. 11B). Plotting the expression levels of a subset of these genes along with UCP1 illustrated the association between gene expression in the preadipocyte state and UCP1 expression in the differentiated state. Several previously identified brown and white fat markers are among the list of positive or negative predictors (Table 3).

TABLE 3

Correlation of expression of known adipose markers in human preadipocytes with UCP1-reporter levels in adipocytes.

| Gene Name | #Cor Coe | P-values | FDR | Reference |
|---|---|---|---|---|
| General preadipocyte marker | | | | |
| ZNF423 | 0.336 | 0.0317* | 0.23 | Gupta et al., Cell Metab. 2012 |
| PDGFRB | −0.282 | 0.0741 | 0.355 | Tang et al., Science 2008 |
| WAT marker | | | | |
| SLC7A10 (ASC-1) | −0.0694 | 0.666 | 0.893 | Ussar et al., Sci Transi Me. 2014 |
| HOXC8 | −0.398 | 0.00996* | 0.121 | Gesta et al., PNAS 2006; Timmons et al., PNAS 2007 |
| HOXC9 | −0.619 | 0.0000162* | 0.00254 | GesTa et al., PNAS 2006; Timmons et al., PNAS 2007 |
| Brown/Beige fat marker | | | | |
| PRDM16 | 0.578 | 0.0000748* | 0.0059 | Seale et al., Nature 2008 |
| EBF2 | 0.262 | 0.0974 | 0.408 | Rajakumari et al., Cell Metab 2013 |
| EBF3 | 0.364 | 0.0195* | 0.175 | Wu et al., Cell 2012 |
| FBXO31 | 0.381 | 0.014* | 0.145 | Wu et al., Cell 2012 |
| KCNK3 | −0.215 | 0.177 | 0.54 | Shinoda et al., Nat Med 2015 |
| MTUS1 | −0.432 | 0.0048* | 0.0781 | Shinoda et al., Mat Med 2015 |
| Beige fat marker | | | | |
| TBX15 | −0.395 | 0.0106* | 0.125 | Gesta et al., PNAS 2006; Timmons et |
| TMEM26 | 0.226 | 0.156 | 0.509 | Wu et al., Cell 2012 |

Cor. Coe. = Correlation Coefficient (see methods)
−indicates negative correlation
*indicates significance (P < 0.05)

Scatter plot analysis revealed two general categories of genes in preadipocytes that may regulate thermogenic program turned on during late stage of differentiation (FIG. 11C).

The first category of genes acted as binary on/off switches to determine cell fate. Positive regulators in this category are likely required for thermogenic differentiation, while negative regulators would be completely suppressed to allow UCP1 expression of any level. Representatives of this category included phosphatidylinositol-3,4,5-trisphosphate-dependent Rac exchange factor 1 (PREX1)(Welch, H. C., et al. *Cell* 108, 809-821, 2002), cortactin binding protein 2 (CTTNBP2) Cheung, J., et al. *Genomics* 78, 7-11, 2001), cardiac actin 1(ACTC1) (Zhang, S. X., et al. *J Biol Chem* 280, 19115-19126, 2005), and somatostatin receptor 1 (SSTR1)(Yamada, Y., et al. *Proc Natl Acad Sci USA* 89, 251-255, 1992).

The second category of genes acted as genetic rheostats to suppress or enhance thermogenic capacity incrementally as their expression level changed. Positive regulators in this category, such as doublesex and mab-3-related transcription factor-like family A1(DMRTA1) (Kikkawa, T., et al. *Genes Cells* 18, 636-649, 2013) and endothelin receptor type B (EDNRB) (Garciafigueroa, D. Y., et al. *Toxicol Sci* 134, 335-344, 2013) might support thermogenic differentiation in proportion to their expression levels; while negative regulators, such as FAT atypical cadherin 1 (FAT1) (Chen, T. Y., et al. *Drug Des Devel Ther* 7, 545-552, 2013) and protein tyrosine phosphatase, receptor type B (PTPRB) (Behjati, S., et al. *Nat Genet* 46, 376-379, 2014) might suppress thermogenic potential more as they are expressed more. Interestingly, most of these candidate genes have never been directly implicated in adipocyte differentiation or thermogenic regulation.

Thus, in sum, microarray analysis in adipose clones revealed two general classifications of genes that regulate thermogenic differentiation: 1) the binary on/off and 2) the continuous categories. These two categories of genes suggest a distinct commitment step in brown adipogenesis, followed by differentiation to a level that is concordant with certain genetic regulators that can act to support or repress differentiation after the commitment phase. Both categories of genes present interesting opportunities for human therapy. By activating on switches and deactivating off switches, activate pools of precursor cells could be activated to differentiate into brown adipocytes. This approach could be combined with a second strategy targeting the genes that act as genetic rheostats with the goal of fine-tuning regulators to increase UCP1 expression in mature adipocytes.

Example 5. Essential Role of PREX1 and EDNRB in Determining Thermogenic Competency To select promising candidate genes for further analyses, the following three criteria were applied to the analysis described in Example 4. First, the primary selection criterion was based on correlation coefficients, P values and FDR values (Table 4). Second, the top-ranking candidate genes were further verified by qRT-PCR assays in a set of ten independent single-cell clones derived from the same four subjects (but not included in the original microarray analysis) for positive or negative correlations between the expression levels of the selected candidate genes including PREX1, CTTNBP2, DMRTA1, EDNRB, ACTC1, SSTR1, FAT1 and PTPRB in the preadipocytes and UCP1 mRNA levels in mature adipocytes. Third, genes were also validated in seven pairs of the human neck BAT and WAT (FIG. 13).

TABLE 4

Correlation coefficients, P-values and FDR for top-ranking positively and negatively correlated candidate genes in human neck fat derived from 7 subjects.

| | # Cor. Coe. | P-Value | FDR | Gene Symbol |
|---|---|---|---|---|
| Positive Correlation | 0.691 | 5.71E-07 | 0.000421 | EDNRB |
| | 0.696 | 4.39E-07 | 0.000376 | ST6GALNAC3 |
| | 0.695 | 4.7E-07 | 0.000387 | CTTNBP2 |
| | 0.794 | 5.88E-10 | 5.51E-06 | PREX1 |
| | 0.732 | 5.33E-08 | 0.000106 | S1PR3 |
| | 0.723 | 9.36E-08 | 0.000144 | SVIL |
| | 0.727 | 7.25E-08 | 0.000128 | C17orf60 |
| | 0.72 | 1.13E-07 | 0.000156 | MASP1 |
| | 0.691 | 5.61E-07 | 0.00042 | PXK |
| | 0.702 | 3.09E-07 | 0.000288 | C10orf90 |
| | 0.728 | 6.97E-08 | 0.000128 | TBC1D19 |
| | 0.732 | 5.39E-08 | 0.000106 | DNASE1L1 |
| | 0.713 | 1.7E-07 | 0.0002 | GPRC5A |
| | 0.7 | 3.5E-07 | 0.00032 | ITGA10 |
| | 0.72 | 1.11E-07 | 0.000156 | ETFDH |
| | 0.695 | 4.5E-07 | 0.000376 | MORN4 |
| | 0.72 | 1.14E-07 | 0.000156 | MRPS6 |
| | 0.802 | 2.82E-10 | 4.64E-06 | SETDB2 |
| | 0.73 | 6.2 E-08 | 0.000118 | WRB |
| | 0.692 | 5.47E-07 | 0.00042 | SYNRG |
| | 0.705 | 2.64E-07 | 0.000269 | ANP32A |
| | 0.82 | 5.62E-11 | 2.78E-06 | DMRTA1 |
| | 0.685 | 7.77E-07 | 5.05E-04 | GPR56 |
| | 0.668 | 1.83E-06 | 8.09E-04 | WWTR1 |
| Negative Correlation | -0.721 | 1.05E-07 | 0.000156 | TEK |
| | -0.764 | 6.15E-09 | 3.15E-05 | CDH13 |
| | -0.692 | 5.38E-07 | 0.00042 | EPB41L3 |
| | -0.69 | 6.02E-07 | 0.000437 | KRTCAP2 |
| | -0.705 | 2.72E-07 | 0.000269 | NUCB2 |
| | -0.711 | 1.93E-07 | 0.000222 | SMYD2 |
| | -0.755 | 1.15E-08 | 4.61 E-05 | PSME4 |
| | -0.715 | 1.46E-07 | 0.000181 | TJP1 |
| | -0.741 | 2.98E-08 | 7.26E-05 | ZNF518B |
| | -0.753 | 1.31E-08 | 4.61E-05 | GRIK2 |
| | -0.696 | 4.45E-07 | 0.000376 | ANTXR1 |
| | -0.706 | 2.59E-07 | 0.000269 | SLC7A6 |
| | -0.795 | 5.36E-10 | 5.51E-06 | FAT1 |
| | -0.692 | 5.51E-07 | 0.00042 | THBS1 |
| | -0.741 | 3.09E-08 | 7.26E-05 | TOM1L1 |
| | -0.747 | 1.98E-08 | 6.13E-05 | CSRP2 |
| | -0.81 | 1.48E-10 | 3.65E-06 | STXBP6 |
| | -0.702 | 3.09E-07 | 0.000288 | ACTC1 |
| | -0.708 | 2.22E-07 | 0.000246 | SHROOM3 |
| | -0.749 | 1.81E-08 | 5.98E-05 | WNT2 |
| | -0.718 | 1.24E-07 | 0.000166 | HAPLN1 |
| | -0.737 | 3.87E-08 | 8.31E-05 | COL12A1 |
| | -0.746 | 2.2 E-08 | 6.39E-05 | NALCN |
| | -0.739 | 3.44E-08 | 7.72E-05 | PLCXD3 |
| | -0.776 | 2.49E-09 | 1 54E-05 | PTPRB |
| | -0.744 | 2.55E-08 | 6.64E-05 | SSTR1 |
| | -0.518 | 5.28E-04 | 2.04E-02 | CNTN3 |

To validate the roles of the identified biomarkers in thermogenic capacity, CRISPR-Cas9 was used to knock out the positive UCP1 regulators PREX1 and EDNRB in an hBAT-SVF clone (FIG. 12A). Compared to control cells, gene ablation had no effect on the differentiation of precursor cells into lipid-laden adipocytes that expressed normal levels of PPARG (FIG. 12B). Expression of the thermogenic markers UCP1, DIO2 and PPARGC1A, however, were markedly decreased in both knockout cell lines (FIG. 12B). Consequently, basal respiration, proton leak, and maximal respiration capacity were significantly reduced in PREX1-knockout cells compared to control cells (P=0.03835, 0.02884, and 0.00932, respectively) (FIGS. 14A-C). Similarly, EDNRB-knockout cells showed a significant reduction of maximal respiration (P=0.03351) and a trend of lower levels of basal respiration and proton leak compared to control cells.

To test the effects of a negative regulator on UCP1 expression, SSTR1 was knocked out in an hWAT-SVF clone (FIG. 12C). As was observed for the positive regulators, gene deletion had no effect on adipogenic differentiation, yet thermogenic gene expression remained repressed in white adipocytes (FIG. 12D).

These data demonstrated the predictive value of the genes that were identified with the microarray analysis. Indeed, using CRISPRs to knockout the positive UCP1 regulators PREX1 and EDNRB in brown preadipocytes, the high level of UCP1 in mature brown fat cells was almost completely abolished. However, ablation of the negative regulator SSTR1 in white fat precursors failed to turn on the thermogenic program. These findings suggest that these positive regulators play an important role in determining thermogenic competency in brown preadipocytes.

Example 6. Isolation of Thermogenically Competent Progenitors Using Specific Cell Surface Markers To identify surface markers that can be used to isolate precursors with thermogenic competency, genes encoding cell surface proteins that had expression patterns positively correlated with UCP1 reporter activity were focused on (FIGS. 11A-11D). Two members of the integrin family, integrin α10 (ITGA10) and integrin β31 (ITGB1, also known as CD29) exhibited significantly positive correlation with UCP1 level (FIGS. 15A and 15B). Integrins are heterodimeric trans-membrane receptors consisting of α and β subunits that mediate various biological functions, such as cell proliferation, differentiation, and migration (Takada. Y., et al. *Genome Biol* 8, 215, 2007; Margadant, C., et al. *Curr Opin Cell Biol* 23, 607-614, 2011).

Using fluorescence-activated-cell-sorting (FACS) with an antibody against CD29, subpopulations of cells from pooled hWAT-SVF and hBAT-SVF were separated based on the abundance of CD29 on the cell surface. Interestingly, hWAT-SVF contained 22.2% CD29$^{low}$, 68.5% CD29$^{med}$ and 9.3% CD29$^{high}$ cells, while hBAT-SVF had almost equal proportions of CD29$^{med}$ and CD29$^{high}$ cells (50.2% and 49.7%, respectively), and very few CD29$^{low}$ cells (0.01%) (FIG. 15C). The ability of CD29-positive SVF cells to differentiate into lipid-laden cells appeared to be positively correlated with CD29 levels (FIG. 15D). Importantly, CD29$^{high}$ hBAT-SVF cells could effectively differentiate into brown adipocytes which expressed the highest level of UCP1 among all the groups (FIGS. 15E and 15F). These data suggest the exciting potential of using an antibody against CD29 to prospectively isolate human adipose progenitors that can give rise to mature adipocytes with great thermogenic capability.

In this study, the utility of a CD29 antibody to prospectively isolate human preadipocytes with high thermogenic potential has been shown, suggesting the promising prospect of using this approach to profile the thermogenic potential of different patient populations. Human adipose tissue-derived mesenchymal stem cells highly express surface markers CD29[43]. Furthermore, compared with other surface marker-selected cells, such as CD71, CD73 and CD90, CD29 positive cells from adipose tissue have the highest adipogenic differentiation potential[44]. Our data also shows a similar result wherein CD29$^{low}$ cells from WAT-SVF accumulate fewer lipids than CD29$^{med}$ and CD29$^{high}$ cells. CD29 is involved in the formation of the transmembrane linkage between the extracellular matrix and the microfilaments which in turn control regulatory events that affect cell adhesion and cell shape during adipocyte differentiation[45,46]. Interestingly, the CD29$^{med}$ and CD29$^{high}$ BAT-SVF subpopulations reported here both display robust adipogenesis in cell culture, but a much higher UCP1 level in CD29$^{high}$ derived adipocytes. These results indicate that we have identified one subpopulation of hWAT-SVF and hBAT-SVF that may be significantly enriched for brown adipocyte precursor cells.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

We claim:

1. A method of promoting thermogenic capacity in a thermogenically competent cell, the method comprising contacting the thermogenically competent cell with either an activator of a uncoupling protein 1 (UCP1) positive regulator or a UCP1 positive regulator, such that thermogenic capacity is promoted, wherein the UCP1 positive regulator is selected from the group consisting of phosphatidylinositol-3,4,5-triphosphate-dependent Rac exchange factor 1 (PREX1), cortactin binding protein 2 (CTTNBP2), doublesex and mab-3-related transcription factor-like family A1 (DMRTA1) and endothelin receptor type B (EDNRB), or combinations thereof.

2. The method of claim 1, wherein the thermogenically competent cell is contacted with either
   a) an agonist antibody, or antigen-binding fragment thereof, that binds the UCP1 positive regulator;
   b) the UCP1 positive regulator;
   c) a nucleic acid molecule encoding the UCP1 positive regulator, or
   d) a polynucleotide associated with the CRISPR/Cas system which binds the UCP1 positive regulator and activates the transcription of the UCP1 positive regulator.

3. The method of claim 1, wherein the activator of a UCP1 positive regulator is either an agonist antibody, or antigen-binding fragment thereof, that binds the UCP1 positive regulator, or a polynucleotide associated with the CRISPR/Cas system which binds the UCP1 positive regulator and activates the transcription of the UCP1 positive regulator.

4. A method of treating a human subject having obesity, said method comprising administering a therapeutically effective amount of
   (1) an activator of a UCP1 positive regulator to the human subject, wherein the UCP1 positive regulator is selected from the group consisting of human PREX1, human CTTNBP2, human DMRTA1, and human EDNRB, or
   (2) a UCP1 positive regulator to the human subject, wherein the UCP1 positive regulator is selected from the group consisting of human PREX1, human CTTNBP2, human DMRTA1, and human EDNRB,
   such that the obesity is treated.

5. A method of decreasing the weight of a human subject, said method comprising administering a therapeutically effective amount of
   (1) an activator of a UCP1 positive regulator to the human subject, wherein the UCP1 positive regulator is selected from the group consisting of human PREX1, human CTTNBP2, human DMRTA1, and human EDNRB, or
   (2) a UCP1 positive regulator to the human subject, wherein the UCP1 positive regulator is selected from the group consisting of human PREX1, human CTTNBP2, human DMRTA1, and human EDNRB,
   such that the weight of the human subject is decreased.

* * * * *

SEQUENCE LISTING

```
<160> NUMBER OF SEQ ID NOS: 26

<210> SEQ ID NO 1
<211> LENGTH: 3693
<212> TYPE: DNA
<213> ORGANISM: Homo sapiens
<220> FEATURE:
<221> NAME/KEY: misc_feature
<222> LOCATION: (1)..(3693)
<223> OTHER INFORMATION: actin, alpha, cardiac muscle 1 (ACTC1), mRNA

<400> SEQUENCE: 1
tggctgatcc tctcccctgc ccttggctcc atgaatggcc tcggcagtcc tagcgggtgc      60
gaaggggacc aaataaggca aggtggcaga ccgggccccc caccectgcc cccggctgct     120 ccaactgacc ctgtccatca gcgttctata aagcggccct cctggagcca gccacccaga     180
gcccgctgcc gccggagccg agccgacccg ccccgccgac gaacccectg aagctgtgcc     240 aagatgtgtg acgacgagga gaccaccgcc ctggtgtgcg acaacggctc tgggctggtg     300
aaggccggct ttgcgggcga tgacgcgccc cgcgctgtct tcccgtccat cgtgggccgc     360
```

```
ccgcggcacc agggagttat ggtgggtatg ggtcagaagg actcctacgt aggtgatgaa      420
gcccagagca agagaggcat cctgaccctg aagtatccca tcgagcatgg tatcatcacc      480
aactgggacg acatggagaa gatctggcac cacaccttct acaatgagct ccgtgtggct      540
cccgaggagc accccaccct gctcacagag gcccgctga accccaaggc caaccgggag       600
aagatgactc agatcatgtt tgagaccttc aatgtccctg ccatgtacgt ggccatccag      660
gcagtgctat ccctgtatgc ttctggccgt accacaggca ttgttctgga ctctggggat      720
ggtgtaactc acaatgtccc catctatgag ggctacgctt gccccatgc catcatgcgt       780
ctggatctgg ctggtcggga cctcactgac tacctcatga agatcctcac tgagcgtggc      840
tactcctttg tcaccactgc tgaacgtgaa attgtccgtg acattaaaga aagctgtgc       900
tatgtcgccc tggattttga gaatgagatg gccacagctg cctcttcctc ctccctggag      960
aagagctatg aactgcctga tggccaagtc atcactattg caatgagcg cttccgctgt      1020
cctgagacac tcttccagcc ctccttcatt ggtatggaat ctgctggcat ccatgaaaca     1080
acttacaata gcatcatgaa gtgtgacatt gatatccgca aggacctgta tgccaacaat     1140
gtcttatctg gaggccacac tatgtaccct ggtattgctg atcgtatgca aaggaaaatc     1200
actgctctgg ctcctagcac catgaagatt aagattattg ctccccctga gcgtaaatac     1260
tctgtctgga ttgggggctc catcctggcc tctctgtcca ccttccagca atgtggatt      1320
agcaagcaag agtacgatga ggcaggccca tccattgtcc accgcaaatg cttctaagat     1380
gccttctctc tccatctacc ttccagtcag gatgacggta ttatgcttct ggagtcttc     1440
caaaccacct tccctcatct ttcatcaatc attgtacagt tgtttacac acgtgcaatt     1500
tgtttgtgct ctaatatttt attgctttat aaataaacca gaccaggact tgcaacctat     1560
aaaagcctct cgtttgtttt tggggtaggc gtggggtggg gcaggtgttt gctttgacac     1620
cctgagcatt gtcaaagttc agtaccacaa ggttcatcca gatgaattaa tatgacagtt     1680
agctgggagt tataatgcta acttttgatt tcatattttg agacagaatc atgaatatat     1740
ttcatacctg aaaagcagat taaggtttag ttccatataa gtaagaaatg aaattgaata     1800
agatagttct ctagaattag ttgctgcaga tgacactgaa gattatttta acatatgttc     1860
cagttgtttt tgtaaccttg cagaaaatac acatatattg ataatgagaa agtcaaagat     1920
tattttaaat gaattggctt aacttttcaa ttctttgaac tcttcaattt tcttcctggg     1980
ggctatgaaa gaaacatgaa ggttagctga cagttgggcc agccacatcc cattgcaaat     2040
accctctaaa catatcaaga ccattgtgtg tgtgcaaaac aaatgtgagg aagcaggagc     2100
caaacacttc tgcctgatca gtgactaact tgcgagacag aagccttcaa tctcttcgtt     2160
tctttgaaat cttgagatct tgggttgagt gaactgaagg ctgcgaggtc ctgagggagc     2220
aaggggaggc gagagccaca gtgtttgctt tgctctgtgc agagctctct gcaaagtatg     2280
gtgggaaggc tgctaggggc agcgttgaaa agaattgaat gtgttccatc ctcgaggagt     2340
tcacacacct acacataatc ccccagtgcg tgtggcctgg aggctttaag gagatgtatg     2400
tgggtctggg tcttagagaa tggtcaggaa ttagggaggt gagaagagca gagaggacat     2460
ctcagcagaa ggaagtgtgg cagaagccag gatacaagac atgggcagg ctggtaggtg      2520
ctgatgaatt ttagaaaatc cactgggaaa ggtagatttc aactagattg cagaagcctt     2580
acagattttt gttttcaaat taattgccag tgaactgtta gcattcacag aagtgtttga     2640
atagacttaa ttgaatttta ttgatgagga ttcaagacac agagattaag caactggtgc     2700
aatgttataa actttatttg tggaatgtgc tagacaggaa ctcagatttt ctgacaccta     2760
```

-continued

```
ctctgatggt gtctctaaaa taatctttct aactttatag tttatcaagg gtaaccccat    2820
tctatcacat gccttttgag aatttgggtt caatatttgg agtactctgg actcatcaga    2880
catctttaat aaattgtaat acattgccac tgtcattcaa ggtcctatgt gtgtcttttt    2940
gcctattcat accaaaaata tcttttgatc cctgactctg ggtcgggcat agtattaagg    3000 gcagggaca caaagatgta tgagagcaca ttttctgtga ataaaaagct cagagtttag     3060
agttctgtat gtagcatatt caaatggaag gccttctatg caataaaggc taaataatac    3120
atcaacttgg tggcatttta tttagataag gtgcaaacat tattgtacat atgccccccg    3180
cccccaccac cccattgtat cctatagcac agttgaactg gttaaaagc catgcatggg     3240 gaggtatgat ttcactagtt tttgtgtctc tttcttttcc tctgtacaat tgagtgcata    3300
aatattatga attgtatcct ctgaacacag tattaatgct ttaactgtag atgattggct    3360
ggggtatcac ctctggttct ttccatctgt gattagaaat ggagaggaca ttttattc      3420 tatgtaaaag tagaagcttt aagaatcagc ttctgatatt tatatcagaa gaggtaagca    3480
cccagattct tgttgaattc tgaggtcttc tcatctttgc ttgattatag ggtataaagt    3540
attagaacaa ttgaatctta aaaattgtgc ttaaggaagg tactaagaca aaaatgtttg    3600
cttaaggtaa tcttcatatg tatacaataa ctgagacatg gatagtgcct acgtctttgg    3660
ttaaagtgca ataaacaaag aactatataa att                                 3693
```

<210> SEQ ID NO 2
<211> LENGTH: 377
<212> TYPE: PRT
<213> ORGANISM: Homo sapiens
<220> FEATURE:
<221> NAME/KEY: misc_feature
<222> LOCATION: (1)..(377)
<223> OTHER INFORMATION: actin, alpha cardiac muscle 1 proprotein

<400> SEQUENCE: 2

```
Met Cys Asp Asp Glu Glu Thr Thr Ala Leu Val Cys Asp Asn Gly Ser
1               5                   10                  15

Gly Leu Val Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Thr Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
```

|     |     | 180 |     |     | 185 |     |     | 190 |     |     |     |
| --- | --- | --- | --- | --- | --- | --- | --- | --- | --- | --- | --- |
| Lys | Ile | Leu | Thr | Glu | Arg | Gly | Tyr | Ser | Phe | Val | Thr | Thr | Ala | Glu | Arg |
|     |     |     | 195 |     |     |     |     | 200 |     |     |     |     | 205 |     |     |

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
                260                 265                 270

Ser Ala Gly Ile His Glu Thr Thr Tyr Asn Ser Ile Met Lys Cys Asp
            275                 280                 285

Ile Asp Ile Arg Lys Asp Leu Tyr Ala Asn Asn Val Leu Ser Gly Gly
            290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
                340                 345                 350

Thr Phe Gln Gln Met Trp Ile Ser Lys Gln Glu Tyr Asp Glu Ala Gly
            355                 360                 365

Pro Ser Ile Val His Arg Lys Cys Phe
370                 375

<210> SEQ ID NO 3
<211> LENGTH: 4343
<212> TYPE: DNA
<213> ORGANISM: Homo sapiens
<220> FEATURE:
<221> NAME/KEY: misc_feature
<222> LOCATION: (1)..(4343)
<223> OTHER INFORMATION: somatostatin receptor 1 (SSTR1), mRNA

<400> SEQUENCE: 3

```
tggtcatcgc acggcggcag ctcctcacct ggatttagaa gagctggcgt ccccgcccgc      60
ccaagccttt aaactctcgt ctgccagaac ccgccaactc tccaggctta gggccagttt     120
ccgcgattct aagagtaatt gcgtgggcac ctgtgctggg gccaggcgca agaagggag      180
ttggtctgcg cgaagatcgt caacctgcta acagaccgca catgcacttt gcaccgacca     240
tctacgtctc agtctggagg ttgcgcactt tggctgctga cgcgctggtg gtgcctatta     300
atcatttacc agtccagagc cgcgccagtt aatggctgtg ccgtgcggtg ctcccacatc     360
ctggcctctc ctctccacgg tcgcctgtgc ccgggcaccc cggagctgca aactgcagag     420
cccaggcaac cgctgggctg tgcgccccgc cggcgccggt aggagccgcg ctccccgcag     480
cggttgcgct ctacccggag cgctgggcg gctgtgggct gcaggcaagc ggtcgggtgg      540
ggagggaggg cgcaggcggc gggtgcgcga ggagaaagcc ccagccctgg cagccccact     600
ggcccccctc agctgggatg ttccccaatg caccgcctc ctctccttcc tcctctccta      660
gccccagccc gggcagctgc ggcgaaggcg gcggcagcag gggccccggg gccggcgctg     720
cggacggcat ggaggagcca gggcgaaatg cgtcccagaa cgggaccttg agcgagggcc     780
agggcagcgc catcctgatc tctttcatct actccgtggt gtgcctggtg gggctgtgtg     840
ggaactctat ggtcatctac gtgatcctgc gctatgccaa gatgaagacg gccaccaaca     900
```

```
tctacatcct aaatctggcc attgctgatg agctgctcat gctcagcgtg cccttcctag    960
tcacctccac gttgttgcgc cactggccct tcggtgcgct gctctgccgc ctcgtgctca   1020
gcgtggacgc ggtcaacatg ttcaccagca tctactgtct gactgtgctc agcgtggacc   1080
gctacgtggc cgtggtgcat cccatcaagg cggcccgcta ccgccggccc accgtggcca   1140
aggtagtaaa cctgggcgtg tgggtgctat cgctgctcgt catcctgccc atcgtggtct   1200
tctctcgcac cgcggccaac agcgacggca cggtggcttg caacatgctc atgccagagc   1260
ccgctcaacg ctggctggtg ggcttcgtgt tgtacacatt tctcatgggc ttcctgctgc   1320
ccgtgggggc tatctgcctg tgctacgtgc tcatcattgc taagatgcgc atggtggccc   1380
tcaaggccgg ctggcagcag cgcaagcgct cggagcgcaa gatcacctta atggtgatga   1440
tggtggtgat ggtgtttgtc atctgctgga tgccttccta cgtggtgcag ctggtcaacg   1500
tgtttgctga gcaggacgac gccacggtga gtcagctgtc ggtcatcctc ggctatgcca   1560
acagctgcgc caaccccatc ctctatggct ttctctcaga caacttcaag cgctctttcc   1620
aacgcatcct atgcctcagc tggatggaca acgccgcgga ggagccggtt gactattacg   1680
ccaccgcgct caagagccgt gcctacagtg tggaagactt ccaacctgag aacctggagt   1740
ccggcggcgt cttccgtaat ggcacctgca cgtcccggat cacgacgctc tgagcccggg   1800
ccacgcaggg gctctgagcc cgggccacgc aggggccctg agccaaaaga ggggagaat    1860
gagaagggaa ggccgggtgc gaaagggacg gtatccaggg cgccagggtg ctgtcgggat   1920
aacgtgggc taggacactg acagcctttg atggaggaac ccaagaaagg cgcgcgacaa   1980
tggtagaagt gagagctttg cttataaact gggaaggctt tcaggctacc tttttctggg   2040
tctcccactt tctgttcctt cctccactgc gcttactcct ctgaccctcc ttctatttc    2100
cctaccctgc aacttctatc ctttcttccg caccgtcccg ccagtgcaga tcacgaactc   2160
attaacaact cattctgatc ctcagccccct ccagtcgtta tttctgtttg tttaagctga   2220
gccacggata ccgccacggg tttccctcgg cgttagtccc tagccgcgcg gggccgctgt   2280
ccaggttctg tctggtgccc ctactggagt cccgggaatg accgctctcc cttgcgcag    2340
ccctacctta aggaaagttg gacttgagaa agatctaagc agctggtctt ttctcctact   2400
cttgggtgaa ggtgcatctt tccctgccct ccctgtccc cctctcgccg cccgccgcc    2460
accaccactc tcactccacc cagagtagag ccaggtgctt agtaaaatag gtcccgcgct   2520
tcgaactcca ggctttctgg agttcccacc caagccctcc tttggagcaa agaaggagct   2580
gagaacaagc cgaatgagga gttttttataa gattgcgggg tcggagtgtg ggcgcgtaat   2640
aggaatcacc ctcctactgc gcgttttcaa agaccaagcg ctgggcgctc ccgggccgcg   2700
cgtctgcgtt aggcagggca gggtagtgca gggcacacct tccccggggt cggggttcg    2760
gggttcggtt gcagggctgc agcccgcctt ggctttctcc ctcacccaag tttccggagg   2820
agccgaccta aaagtaacaa tagataaggt ttcctgctcc agtgtatctc aaaagaccgg   2880
gcgccagggg cggggggacct agggcgacgt cttcagagtc cgccagtgtt ggcggtgtcg   2940
ccgcaacctg caggctcccg agtggggcct gcctggtctc tagagggttg ctgcctttca   3000
agcggtgcct aagaagttat tttcttgttt aacatatata tttattaatt tatttgtcgt   3060
gttggaaaat gtgtctctgc tttccttttc tctgcttgcc tagcccccag tcttttcttt   3120
gggaccctgg gggcgggcat ggaagtggaa gtagggggcaa gctcttgccc cactccctgg   3180
ccatctcaac gcctctcctc aatgctgggc cctcttatct catcctttcc tctagctttt   3240
```

```
ctattttttga ttgtgttgag tgaagtttgg agattttttca tacttttctt actatagtct    3300
cttgtttgtc ttattaggat aatacataaa tgataatgtg ggttatcctc ctctccatgc    3360
acagtggaaa gtcctgaact cctggctttc caggagacat atataggggga acatcaccct    3420 atatataatt tgagtgtata tatatttata tatatgatgt ggacatatgt atacttatct    3480
tgctccattg tcatgagtcc atgagtctaa gtatagccac tgatggtgac aggtgtgagt    3540
ctggctggaa cactttcagt ttcaggagtg caagcagcac tcaaacctgg agctgaggaa    3600
tctaattcag acagagactt taatcactgc tgaagatgcc cctgctccct ctgggttcca    3660
gcagaggtga ttcttacata tgatccagtt aacatcatca cttttttttga ggacattgaa    3720 agtgaaataa tttgtgtctg tgtttaatat taccaactac attggaagcc tgagcagggc    3780
gaggaccaat aattttaatt atttatattt cctgtattgc tttagtatgc tggcttgtac    3840
atagtaggca ctaaatacat gtttgttggt tgattgttta agccagagtg tattacaaca    3900
atctggagat actaaatctg gggttctcag gttcactcat tgacatgata tacaatggtt    3960
aaaatcacta ttgaaaaata cgttttgtgt atatttgctt caacaacttt gtgctttcct    4020
gaaagcagta accaagagtt aagatatccc taatgttttg cttaaactaa tgaacaaata    4080
tgctttgggt cataaatcag aaagtttaga tctgtccctt aataaaaata tatattacta    4140
ctcctttgga aaatagattt ttaatggtta agaactgtga aatttacaaa tcaaaatctt    4200
aatcattatc cttctaagag gatacaaatt tagtgctctt aacttgttac cattgtaata    4260
ttaactaaat aaacagatgt attatgctgt taaaaaaaaa aaaaaaaaaa aaaaaaaaa    4320 aaaaaaaaa aaaaaaaaaa aaa    4343
```

<210> SEQ ID NO 4
<211> LENGTH: 391
<212> TYPE: PRT
<213> ORGANISM: Homo sapiens
<220> FEATURE:
<221> NAME/KEY: misc_feature
<222> LOCATION: (1)..(391)
<223> OTHER INFORMATION: somatostatin receptor type 1

<400> SEQUENCE: 4

```
Met Phe Pro Asn Gly Thr Ala Ser Ser Pro Ser Ser Ser Pro Ser Pro
1               5                   10                  15

Ser Pro Gly Ser Cys Gly Glu Gly Gly Ser Arg Gly Pro Gly Ala
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160
```

```
His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390

<210> SEQ ID NO 5
<211> LENGTH: 14773
<212> TYPE: DNA
<213> ORGANISM: Homo sapiens
<220> FEATURE:
<221> NAME/KEY: misc_feature
<222> LOCATION: (1)..(14773)
<223> OTHER INFORMATION: FAT atypical cadherin 1 (FAT1), mRNA

<400> SEQUENCE: 5
ctgggcggcc gggcgcgggg agagggcgcg ggagcggctc gtgcggcagg taccatgcgg      60
acgcgcgagc ccggcgaggg ccccggcagg cccggtccct gctcggggtc gcgctgagac     120
ggcgggtgag ctccacgaga cgccgtcgc cacttcgggc caactttgcg attcccgaca     180
gttaagcaat ggggagacat ttggctttgc tcctgcttct gctccttctc ttccaacatt     240
ttggagacag tgatggcagc caacgacttg aacagactcc tctgcagttt acacacctcg     300
agtacaacgt caccgtgcag gagaactctg cagctaagac ttatgtgggg catcctgtca     360
agatgggtgt ttacattaca catccagcgt gggaagtaag gtacaaaatt gtttccggag     420
acagtgaaaa cctgttcaaa gctgaagagt acattctcgg agacttttgc tttctaagaa     480
taaggaccaa aggaggaaat acagctattc ttaatagaga agtgaaggat cactacacat     540
tgatagtgaa agcacttgaa aaaaatacta atgtggaggc gcgaacaaag gtcagggtgc     600
aggtgctgga tacaaatgac ttgagaccgt tattctcacc cacctcatac agcgtttctt     660
```

```
tacctgaaaa cacagctata aggaccagta tcgcaagagt cagcgccacg gatgcagaca    720
taggaaccaa cggggaattt tactacagtt ttaaagatcg aacagatatg tttgctattc    780
acccaaccag tggtgtgata gtgttaactg gtagacttga ttacctagag accaagctct    840
atgagatgga aatcctcgct gcggaccgtg gcatgaagtt gtatgggagc agtggcatca    900
gcagcatggc caagctaacg gtgcacatcg aacaggccaa tgaatgtgct ccggtgataa    960
cagcagtgac attgtcacca tcagaactgg cagggaccc agcatatgca attgtgacag    1020
tggatgactg cgatcagggt gccaatggtg acatagcatc tttaagcatc gtggcaggtg    1080
accttctcca gcagtttaga acagtgaggt cctttccagg gagtaaggag tataaagtca    1140
aagccatcgg tggcattgat tgggacagtc atcctttcgg ctacaatctc acactacagg    1200
ctaaagataa aggaactccg ccccagttct cttctgttaa agtcattcac gtgacttctc    1260
cacagttcaa agccgggcca gtcaagtttg aaaaggatgt ttacagagca gaaataagtg    1320
aatttgctcc tcccaacaca cctgtggtca tggtaaaggc cattcctgct tattcccatt    1380
tgaggtatgt ttttaaaagt acacctggaa aagctaaatt cagtttaaat tacaacactg    1440
gtctcatttc tattttagaa ccagttaaaa gacagcaggc agcccatttt gaacttgaag    1500
taacaacaag tgacagaaaa gcgtccacca aggtcttggt gaaagtctta ggtgcaaata    1560
gcaatccccc tgaatttacc cagacagcgt acaaagctgc ttttgatgag aacgtgccca    1620
ttggtactac tgtcatgagc ctgagtgccg tagaccctga tgagggtgag aacgggtacg    1680
tgacatacag tatcgcaaat ttaaatcatg tgccgtttgc gattgaccat ttcactggtg    1740
ccgtgagtac gtcagaaaac ctggactacg aactgatgcc tcgggtttat actctgagga    1800
ttcgtgcatc agactggggc ttgccgtacc gccgggaagt cgaagtcctt gctacaatta    1860
ctctcaataa cttgaatgac aacacacctt tgtttgagaa aataaattgt gaagggacaa    1920
ttcccagaga tctaggcgtg ggagagcaaa taaccactgt ttctgctatt gatgcagatg    1980
aacttcagtt ggtacagtat cagattgaag ctggaaatga actggatttc tttagtttaa    2040
accccaactc gggggtattg tcattaaagc gatcgctaat ggatggctta ggtgcaaagg    2100
tgtctttcca cagtctgaga atcacagcta cagatggaga aaattttgcc acaccattat    2160
atatcaacat aacagtggct gccagtcaca agctggtaaa cttgcagtgt gaagagactg    2220
gtgttgccaa aatgctggca gagaagctcc tgcaggcaaa taattacac aaccagggag    2280 aggtggagga tattttcttc gattctcact ctgtcaatgc tcacataccg cagtttagaa    2340
gcactcttcc gactggtatt caggtaaagg aaaaccagcc tgtgggttcc agtgtaattt    2400
tcatgaactc cactgacctt gacactggct tcaatggaaa actggtctat gctgtttctg    2460
gaggaaatga ggatagttgc ttcatgattg atatggaaac aggaatgctg aaaattttat    2520
ctcctcttga ccgtgaaaca acagacaaat acaccctgaa tattaccgtc tatgaccttg    2580 ggataccca gaaggctgcg tggcgtcttc tacatgtcgt ggttgtcgat gccaatgata    2640
atccacccga gttttacag gagagctatt ttgtggaagt gagtgaagac aaggaggtac    2700
atagtgaaat catccaggtt gaagccacag ataaagacct ggggcccaac ggacacgtga    2760
cgtactcaat tgttacagac acagacacat tttcaattga cagcgtgacg ggtgttgtta    2820
acatcgcacg ccctctggat cgagagctgc agcatgagca ctccttaaag attgaggcca    2880
gggaccaagc cagagaagag cctcagctgt tctccactgt cgttgtgaaa gtatcactag    2940
aagatgttaa tgacaacccca cctacatttta ttccacctaa ttatcgtgtg aaagtccgag    3000
```

-continued

```
aggatcttcc agaaggaacc gtcatcatgt ggttagaagc ccacgatcct gatttaggtc    3060
agtctggtca ggtgagatac agccttctgg accacggaga aggaaacttc gatgtggata    3120
aactcagtgg agcagttagg atcgtccagc agttggactt tgagaagaag caagtgtata    3180
atctcactgt gagggccaaa gacaagggaa agccagtttc tctgtcttct acttgctatg    3240
ttgaagttga ggtggttgat gtgaatgaga acctgcaccc accegtgttt ccagctttg     3300
tggaaaaggg gacagtgaaa gaagatgcac ctgttggttc attggtaatg acggtgtcgg    3360
ctcatgatga ggacgccaga agagatgggg agatccgata ctccattaga gatggctctg    3420
gcgttggtgt tttcaaaata ggtgaagaga caggtgtcat agagacgtca gatcgactgg    3480
accgtgaatc gacctcccat tattggctaa cagtctttgc aaccgatcag ggtgtcgtgc    3540
ctctttcatc gttcatagag atctacatag aggttgagga tgtcaatgac aatgcaccac    3600
agacatcaga gcctgtttat tacccagaaa tcatggaaaa ttctcctaaa gatgtatctg    3660
tggtccagat cgaggcattt gatccagatt cgagctctaa tgacaagctc atgtacaaaa    3720
ttacaagtgg aaatccacaa ggattctttt caatacatcc taaaacaggt ctcatcacaa    3780
ctacgtcaag gaagctagac cgagaacagc aagatgaaca catattagag gttactgtga    3840
cagacaatgg tagtccccc aaatcaacca ttgcaagagt cattgtgaaa atccttgatg     3900
aaaatgacaa caaacctcag tttctgcaaa agttctacaa aatcagactc cctgagcggg    3960
aaaagccaga ccgagaaaga aatgccgacg gggagccgct ctatcacgtc atagccaccg    4020
acaaggatga gggcccccaat gcagaaatct cctacagcat cgaagacggg aatgagcatg    4080
gcaaatttt catcgaaccg aaaactggag tggtttcgtc caagaggttt tcagcagctg     4140
gagaatatga tattctttca attaaggcag ttgacaatgg tcgccctcaa aagtcatcaa    4200
ccaccagact ccatattgaa tggatctcca agcccaaacc gtccctggag cccatttcat    4260
ttgaagaatc attttttacc tttactgtga tggaaagtga ccccgttgct cacatgattg    4320
gagtaatatc tgtggagcct cctggcatac ccctttggtt tgacatcact ggtggcaact    4380
acgacagtca cttcgatgtg gacaagggaa ctggaaccat cattgttgcc aaacctcttg    4440
atgcagaaca gaagtcaaac tacaacctca cagtcgaggc tacagatgga accaccacta    4500
tcctcactca ggtattcatc aaagtaatag acacaaatga ccatcgtcct cagttttcta    4560
catcaaagta tgaagttgtt attcctgaag atacagcgcc agaaacagaa attttgcaaa    4620
tcagtgctgt ggatcaggat gagaaaaaca aactaatcta cactctgcag agcagtagag    4680
atccactgag tctcaagaaa tttcgtcttg atcctgcaac cggctctctc tatacttctg    4740
agaaactgga tcatgaagct gttcaccagc acaccctcac ggtcatggta cgagatcaag    4800
atgtgcctgt aaaacgcaac tttgcaagga ttgtggtcaa tgtcagcgac acgaatgacc    4860
acgcccgtg gttcaccgct tcctcctaca aagggcgggt ttatgaatcg gcagccgttg     4920
gctcagttgt gttgcaggtg acggctctgg acaaggacaa agggaaaaat gctgaagtgc    4980
tgtactcgat cgagtcagga aatattggaa attcttttat gattgatcct gtcttgggct    5040
ctattaaaac tgccaaagaa ttagatcgaa gtaaccaagc ggagtatgat ttaatggtaa    5100
aagctacaga taagggcagt ccaccaatga gtgaaataac ttctgtgcgt atctttgtca    5160
caattgctga caacgcctct ccgaagttta catcaaaaga atattctgtt gaacttagtg    5220
aaactgtcag cattgggagt ttcgttggga tggttacagc ccatagtcaa tcatcagtgg    5280
tgtatgaaat aaaagatgga aatacaggtg atgcttttga tattaatcca cattctggaa    5340
ctatcatcac tcagaaagcc ctggactttg aaactttgcc catttacaca ttgataatac    5400
```

-continued

```
aaggaactaa catggctggt ttgtccacta atacaacggt tctagttcac ttgcaggatg    5460
agaatgacaa cgcgccagtt tttatgcagg cagaatatac aggactcatt agtgaatcag    5520
cctcaattaa cagcgtggtc ctaacagaca ggaatgtccc actggtgatt cgagcagctg    5580
atgctgataa agactcaaat gctttgcttg tatatcacat tgttgaacca tctgtacaca    5640
catattttgc tattgattct agcactggtg ctattcatac agtactaagt ctggactatg    5700
aagaaacaag tattttcac tttaccgtcc aagtgcatga catgggaacc ccacgtttat    5760
ttgctgagta tgcagcgaat gtaacagtac atgtaattga cattaatgac tgcccccctg    5820
tgtttgccaa gccattatat gaagcatctc ttttgttacc aacatacaaa ggagtaaaag    5880
tcatcacagt aaatgctaca gatgctgatt caagtgcatt ctcacagttg atttactcca    5940
tcaccgaagg caacatcggg gagaagtttt ctatggacta caagactggt gctctcactg    6000
tccaaaacac aactcagtta agaagccgct acgagctaac cgttagagct tccgatggca    6060
gatttgccgg ccttacctct gtcaaaatta atgtgaaaga agcaaagaa agtcacctaa    6120 agtttaccca ggatgtctac tctgcggtag tgaaagagaa ttccaccgag gccgaaacat    6180
tagctgtcat tactgctatt gggaatccaa tcaatgagcc tttgtttat cacatcctca    6240 acccagatcg cagatttaaa ataagccgca cttcaggagt tctgtcaacc actggcacgc    6300
ccttcgatcg tgagcagcag gaggcgtttg atgtggttgt agaagtgaca gaggaacata    6360
agccttctgc agtggcccac gttgtcgtga aggtcattgt agaagaccaa aatgataatg    6420
cgccggtgtt tgtcaacctt ccctactacg ccgttgttaa agtggacact gaggtgggcc    6480
atgtcattcg ctatgtcact gctgtagaca gagacagtgg cagaaacggg gaagtgcatt    6540
actacctcaa ggaacatcat gaacactttc aaattggacc cttgggtgaa atttcactga    6600
aaaagcaatt tgagcttgac accttaaata agaatatct tgttacagtg gttgcaaaag    6660
atggagggaa cccggccttt tcagcggaag ttatcgttcc gatcactgtc atgaataaag    6720
ccatgcctgt gtttgaaaaa ccttctctaca gtgcagagat tgcagagagc atccaggtgc    6780
acagccctgt ggtccacgtg caggctaaca gcccggaagg cctgaaagtg ttctacagca    6840
tcacagacgg agacccttc agccagttca ctattaactt caatactgga gttatcaatg    6900
tcatagctcc tctggacttt gaggcccacc cggcatataa gctgagcata cgcgcaactg    6960
actccttgac gggcgctcat gctgaagtat ttgtggacat catagtagac gacatcaatg    7020
ataaccctcc tgtgtttgct cagcagtctt atgcggtgac cctgtctgag gcatctgtaa    7080
ttggaacgtc tgttgttcaa gttagagcca ccgattctga ttcagaacca atagaggaa    7140 tctcatacca gatgtttggg aatcacagca agagtcatga tcattttcat gtagacagca    7200
gcactggcct catctcacta ctcagaaccc tggattacga gcagtcccgg cagcacacga    7260
tttttgtgag gcagttgat ggtggtatgc ccacgctgag cagtgatgtg attgtcacgg    7320
tggacgttac cgacctcaat gataatccac cactctttga acaacagatt tatgaagcca    7380
gaattagcga gcacgccct catgggcatt tcgtgacctg tgtaaaagcc tatgatgcag    7440
acagttcaga catagacaag ttgcagtatt ccattctgtc tggcaatgat cataaacatt    7500
ttgtcattga cagtgcaaca gggattatca ccctctcaaa cctgcaccgg cacgccctga    7560
agccatttta cagtcttaac ctgtcagtgt ctgatggagt ttttagaagt tccacccagg    7620
ttcatgtaac tgtaattgga ggcaatttgc acagtcctgc tttccttcag aacgaatatg    7680
aagtggaact agctgaaaac gctcccctac atacccctggt gatggaggtg aaaactacgg    7740
```

```
atgggattc tggtatttat ggtcacgtta cttaccatat tgtaaatgac tttgccaaag     7800
acagatttta cataaatgag agaggacaga tatttacttt ggaaaaactt gatcgagaaa     7860
ccccggcgga gaaagtgatc tcagtccgtt taatggctaa ggatgctgga ggaaaagttg     7920
ctttctgcac cgtgaatgtc atccttacag atgacaatga caatgcacca caatttcgag     7980
caaccaaata cgaagtgaat atcgggtcca gtgctgctaa agggacttca gtcgttaaag     8040
ttcttgcaag tgatgccgat gagggctcca atgccgacat cacctatgcc attgaagcag     8100
actctgaaag tgtaaaagag aatttggaaa ttaacaaact gtccggcgta atcactacaa     8160
aggagagcct cattggcttg gaaaatgaat tcttcacttt ctttgttaga gctgtggata     8220
atgggtctcc atcaaaagaa tctgttgttc ttgtctatgt taaaatcctt ccaccggaaa     8280
tgcagcttcc aaaattttca gaaccttcct ataccttcac agtgtcagag acgtgccta    8340 ttggaacaga gatagatctc atccgagcag aacatagtgg gactgttctt tacagcctgg     8400
tcaaagggaa tactccagaa agcaataggg atgagtcctt tgtgattgac agacagagcg     8460
ggagactgaa gttggagaag agtcttgatc atgagacaac taagtggtat cagttttcca     8520
tactggccag gtgcactcaa gatgaccatg agatggtggc ttctgtagat gttagtatcc     8580
aagtgaaaga tgcaaatgac aacagcccgg tctttgaatc tagtccatat gaggcattca     8640
ttgttgaaaa cctgccaggg ggaagtagag taattcagat cagggcatct gatgctgact     8700
caggaaccaa cggccaagtt atgtatagcc tggatcagtc acaaagtgtg gaagtcattg     8760
aatcctttgc cattaacatg gaaacaggct ggattacaac tttaaaggaa cttgaccatg     8820
aaaagagaga caattaccag attaaagtgg ttgcatcaga tcatggtgaa aagatccagc     8880
tatcctccac agccattgtg gatgttaccg tcaccgatgt caacgatagt ccaccacgat     8940
tcacggccga gatctataaa gggactgtga gtgaggatga ccccaaggtt ggggtgattg     9000
ccatcttaag taccacggat gctgattctg aagagatcaa cagacaagtt acatatttca     9060
taacaggagg ggatccttta ggacagtttg ccgttgaaac tatacagaat gaatggaagg     9120
tatatgtgaa gaaacctcta gacagggaaa aagggacaa ttaccttctt actatcacgg     9180
caactgatgg caccttctca tcaaaagcga tagttgaagt gaaagttctg gatgcaaatg     9240
acaacagtcc agtttgtgaa aagactttat attcagacac tattcctgaa gacgtccttc     9300
ctggaaaatt gatcatgcag atctctgcta cagacgcaga catccgctct aacgctgaaa     9360
ttacttacac gttattgggt tcaggtgcag aaaaattcaa actaaatcca gacacaggtg     9420
aactgaaaac gtcaaccccc cttgatcgtg aggagcaagc tgtttatcat cttctcgtca     9480
gggccacaga tggaggagga agattctgcc aagccagtat tgtgctcacg ctagaagatg     9540
tgaacgataa cgccccgaa ttctctgccg atccttatgc catcaccgtg tttgaaaaca     9600
cagagccggg aacgctgctg acaagagtgc aggccacaga tgccgacgca ggattaaatc     9660
ggaagatttt atactcactg attgactctg ctgatgggca gttctccatt aacgaattat     9720
ctggaattat tcagttagaa aaacctttgg acagagaact ccaggcagta tacaccctct     9780
ctttgaaagc tgtggatcaa ggcttgccaa ggaggctgac tgccactggc actgtgattg     9840
tatcagttct tgacataaat gacaaccccc ctgtgtttga gtaccgtgaa tatggtgcca     9900
ccgtgtctga ggacattctt gttggaactg aagttcttca agtgtatgca gcaagtcggg     9960
atattgaagc aaatgcagaa atcacctact caataataag tggaaatgaa catgggaaat    10020
tcagcataga ttctaaaaca ggggccgtat ttatcattga gaatctggat tatgagagct    10080
ctcatgagta ttacctaaca gtagaggcca ctgatggagg cacgccttca ctgagcgacg    10140
```

```
ttgccactgt gaacgttaat gtaacagata tcaacgataa taccoctgtg ttcagccaag   10200 acacctacac gacagtcatc agtgaagatg ccgttcttga gcagtctgtc atcacggtta   10260
tggccgatga tgccgatgga ccttccaaca gccacatcca ctactcaatt atagatggca   10320
accaaggaag ctcgttcaca attgaccccg tcaggggaga agtcaaagtg accaaacttc   10380
tcgaccgaga aacgatttca ggttacacgc tcacggttca agcttctgat aatggcagtc   10440
cacccagagt caacacgacg accgtgaaca tcgatgtgtc cgatgtcaat gacaacgcgc   10500
ccgtcttctc caggggaaac tacagtgtca ttatccagga aaataagcca gtgggcttca   10560
gcgtgctgca gctggtagta acagatgagg attcttccca taacggtcca cccttcttct   10620
ttactattgt aactggaaat gatgagaagg cttttgaagt taacccgcaa ggagtcctcc   10680
tgacatcatc tgccatcaag aggaaggaga aagatcatta cttactgcag gtgaaggtgg   10740
cagataatgg aaagcctcag ttgtcatctt tgacatacat tgacattagg gtaattgagg   10800
agagcatcta tccgcctgcg attttgcccc tggagatttt catcacctct tctggagaag   10860
aatactcagg tggcgtcatt gggaagatcc atgccacaga ccaggacgtg tatgatactc   10920
taacctacag tctcgaccct cagatggaca acctgttctc tgtttccagc acaggggggca   10980 agctgatagc acacaaaaag ctagacatag gcaataccct tctcaatgtc agcgtaacag   11040
atgggaagtt cacgacggtg gccgacatca cagtgcatat cagacaagtc acacaggaga   11100
tgttgaacca caccatcgcg atccgctttg ccaacctcac tccggaagaa ttcgttggtg   11160
actactggcg caacttccag cgagctttac ggaacatcct gggtgtgagg aggaacgaca   11220
tacagattgt tagtttgcag tcctctgaac ctcacccaca tctggacgtc ttacttttttg   11280 tagagaaacc aggtagtgct cagatctcaa caaaacaact tctgcacaag attaactctt   11340
ccgtgactga cattgaggaa atcattggag ttaggatact gaatgtattc cagaaactct   11400
gcgcgggact ggactgcccc tggaagttct gcgatgaaaa ggtgtctgtg atgaaagtg   11460 tgatgtcaac acacagcaca gccagactga gttttgtgac tccccgccac cacagggcag   11520
cggtgtgtct ctgcaaagag ggaaggtgcc cacctgtcca ccatggctgt gaagatgatc   11580
cgtgccctga gggatccgaa tgtgtgtctg atccctggga ggagaaacac acctgtgtct   11640
gtcccagcgg caggtttggt cagtgcccag ggagttcatc tatgacactg actggaaaca   11700
gctacgtgaa ataccgtctg acggaaaatg aaaacaaatt agagatgaaa ctgaccatga   11760
ggctcagaac atattccacg catgcggttg tcatgtatgc tcgaggaact gactatagca   11820
tcttggagat tcatcatgga aggctgcagt acaagtttga ctgtggaagt ggccctggaa   11880
ttgtctctgt tcagagcatt caggtcaatg atgggcagtg gcacgcagtg gccctggaag   11940
tgaatggaaa ctatgctcgc ttggttctag accaagttca tactgcatcg ggcacagccc   12000
cagggactct gaaaacccctg aacctggata actatgtgtt ttttggtggc cacatccgtc   12060
agcagggaac aaggcatgga agaagtcctc aagttggtaa tggtttcagg ggttgtatgg   12120 actccatttta ttttgaatggg caggagctcc ctttaaacag caaacccaga agctatgcac   12180
acatcgaaga gtcggtggat gtatctccag gctgcttcct gacggccacg gaagactgcg   12240
ccagcaaccc ttgccagaat ggaggcgttt gcaatccgtc acctgctgga ggttattact   12300
gcaaatgcag tgccttgtac atagggaccc actgtgagat aagcgtcaat ccgtgttcct   12360
ccaagccatg cctctatggg ggcacgtgtg ttgtcgacaa cggaggcttt gtttgccagt   12420
gtagaggatt atatactggt cagaggtgtc agcttagtcc atactgcaaa gatgaaccct   12480
```

```
gtaagaatgg cggaacatgc tttgacagtt tggatggcgc cgtttgtcag tgtgattcgg    12540
gttttagggg agaaaggtgt cagagtgata tcgacgagtg ctctggaaac ccttgcctgc    12600
acggggccct ctgtgagaac acgcacggct cctatcactg caactgcagc cacgagtaca    12660
ggggacgtca ctgcgaggat gctgcgccca accagtatgt gtccacgccg tggaacattg    12720
ggttggcgga aggaattgga atcgttgtgt ttgttgcagg gatattttta ctggtggtgg    12780
tgtttgttct ctgccgtaag atgattagtc ggaaaaagaa gcatcaggct gaacctaaag    12840
acaagcacct gggacccgct acggctttct tgcaaagacc gtattttgat tccaagctaa    12900
ataagaacat ttactcagac ataccacccc aggtgcctgt ccggcctatt tcctacaccc    12960
cgagtattcc aagtgactca agaaacaatc tggaccgaaa ttccttcgaa ggatctgcta    13020
tcccagagca tcccgaattc agcactttta accccgagtc tgtgcacggg caccgaaaag    13080
cagtggcggt ctgcagcgtg gcgccaaacc tgcctccccc accccttca aactccccctt    13140
ctgacagcga ctccatccag aagcctagct gggactttga ctatgacaca aaagtggtgg    13200
atcttgatcc ctgtctttcc aagaagcctc tagaggaaaa gccttcccag ccatacagtg    13260
cccgggaaag cctgtctgaa gtgcagtctc tgagctcctt ccagtccgaa tcgtgcgatg    13320
acaatgggta tcactgggat acatcagatt ggatgccaag cgttcctctg ccggacatac    13380
aagagttccc caactatgag gtgattgatg agcagacacc cctgtactca gcagatccaa    13440
acgccatcga tacggactat taccctggag gctacgacat cgaaagtgat ttcctccac    13500
ccccagaaga cttccccgca gctgatgagc taccaccgtt accgcccgaa ttcagcaatc    13560
agtttgaatc catccaccct cctagagaca tgcctgccgc gggtagcttg ggttcttcat    13620
caagaaaccg gcagaggttc aacttgaatc agtatttgcc caattttat ccctcgata    13680
tgtctgaacc tcaaacaaaa ggcactggtg agaatagtac ttgtagagaa ccccatgccc    13740
cttacccgcc agggtatcaa agacacttcg aggcgcccgc tgtcgagagc atgcccatgt    13800
ctgtgtacgc ctccaccgcc tcctgctctg acgtgtcagc ctgctgcgaa gtggagtccg    13860
aggtcatgat gagtgactat gagagcgggg acgacggcca cttcgaagag gtgacgatcc    13920
cgccccctgga ttcccagcag cacacggaag tctgactctc aactcccccc aaagtgcctg    13980
actttagtga acctagaggt gatgtgagta atccgcgctg ttctttgcag cagtgcttcc    14040
aagcttttttt tggtgagccg aatgggcatg gctgcgctgg atcctgcgcc tctggacgtg    14100
ctagccattt ccagtgtccc aactactgtc atcgtgaggt tttcatcggc tgtgccattt    14160
cccaacgtct tttgggattt acatctgtct gtgttaaaat aatcaaacga aaaatcagtc    14220
ctgtgttgtc agcatgattc atgtatttat atagatttga ttattttaat tttcctgtct    14280
cttttttttg taaattttat gtacagattt gattttcat agttttaact agatttccaa    14340
gatattttgt gcatttgttt caactgaatt ttggtggtgt cagtgccatt atctagcacc    14400
ctgatttttt ttttttttact ataaccaggg tttcattctg tcttttttcca ctgaagtgtg    14460
acatttgtt agtacatttc agtgtagtca ttcatttcta gctgtacata ggatgaagga    14520
gagatcagat acatgaacat gtcttacatg ggttgctgta tttagaatta taaacatttt    14580
tcattattgg aaagtgtaac ggggaccttc tgcatacctg tttagaacca aaaccaccat    14640
gacacagttt ttatagtgtc tgtatatttg tgatgcaatg gtcttgtaaa ggtttttaat    14700
gaaaactacc attagccagt ctttcttact gacaataaat tattaataaa atacttgagc    14760
tttaaaaaaa aaa                                                       14773
```

```
<210> SEQ ID NO 6
<211> LENGTH: 4588
<212> TYPE: PRT
<213> ORGANISM: Homo sapiens
<220> FEATURE:
<221> NAME/KEY: misc_feature
<222> LOCATION: (1)..(4588)
<223> OTHER INFORMATION: protocadherin Fat 1 precursor

<400> SEQUENCE: 6
```

| | | | | | | | | | | | | | | |
|---|---|---|---|---|---|---|---|---|---|---|---|---|---|---|
| Met | Gly | Arg | His | Leu | Ala | Leu | Leu | Leu | Leu | Leu | Leu | Leu | Phe | Gln |
| 1 | | | | 5 | | | | | 10 | | | | | 15 |
| His | Phe | Gly | Asp | Ser | Asp | Gly | Ser | Gln | Arg | Leu | Glu | Gln | Thr | Pro | Leu |
| | | | 20 | | | | | 25 | | | | | 30 | | |
| Gln | Phe | Thr | His | Leu | Glu | Tyr | Asn | Val | Thr | Val | Gln | Glu | Asn | Ser | Ala |
| | | | 35 | | | | | 40 | | | | | 45 | | |
| Ala | Lys | Thr | Tyr | Val | Gly | His | Pro | Val | Lys | Met | Gly | Val | Tyr | Ile | Thr |
| | 50 | | | | | 55 | | | | | 60 | | | | |
| His | Pro | Ala | Trp | Glu | Val | Arg | Tyr | Lys | Ile | Val | Ser | Gly | Asp | Ser | Glu |
| 65 | | | | | 70 | | | | | 75 | | | | | 80 |
| Asn | Leu | Phe | Lys | Ala | Glu | Glu | Tyr | Ile | Leu | Gly | Asp | Phe | Cys | Phe | Leu |
| | | | | 85 | | | | | 90 | | | | | 95 | |
| Arg | Ile | Arg | Thr | Lys | Gly | Gly | Asn | Thr | Ala | Ile | Leu | Asn | Arg | Glu | Val |
| | | | 100 | | | | | 105 | | | | | 110 | | |
| Lys | Asp | His | Tyr | Thr | Leu | Ile | Val | Lys | Ala | Leu | Glu | Lys | Asn | Thr | Asn |
| | | | 115 | | | | | 120 | | | | | 125 | | |
| Val | Glu | Ala | Arg | Thr | Lys | Val | Arg | Val | Gln | Val | Leu | Asp | Thr | Asn | Asp |
| | 130 | | | | | 135 | | | | | 140 | | | | |
| Leu | Arg | Pro | Leu | Phe | Ser | Pro | Thr | Ser | Tyr | Ser | Val | Ser | Leu | Pro | Glu |
| 145 | | | | | 150 | | | | | 155 | | | | | 160 |
| Asn | Thr | Ala | Ile | Arg | Thr | Ser | Ile | Ala | Arg | Val | Ser | Ala | Thr | Asp | Ala |
| | | | | 165 | | | | | 170 | | | | | 175 | |
| Asp | Ile | Gly | Thr | Asn | Gly | Glu | Phe | Tyr | Tyr | Ser | Phe | Lys | Asp | Arg | Thr |
| | | | 180 | | | | | 185 | | | | | 190 | | |
| Asp | Met | Phe | Ala | Ile | His | Pro | Thr | Ser | Gly | Val | Ile | Val | Leu | Thr | Gly |
| | | | 195 | | | | | 200 | | | | | 205 | | |
| Arg | Leu | Asp | Tyr | Leu | Glu | Thr | Lys | Leu | Tyr | Glu | Met | Glu | Ile | Leu | Ala |
| | 210 | | | | | 215 | | | | | 220 | | | | |
| Ala | Asp | Arg | Gly | Met | Lys | Leu | Tyr | Gly | Ser | Ser | Gly | Ile | Ser | Ser | Met |
| 225 | | | | | 230 | | | | | 235 | | | | | 240 |
| Ala | Lys | Leu | Thr | Val | His | Ile | Glu | Gln | Ala | Asn | Glu | Cys | Ala | Pro | Val |
| | | | | 245 | | | | | 250 | | | | | 255 | |
| Ile | Thr | Ala | Val | Thr | Leu | Ser | Pro | Ser | Glu | Leu | Asp | Arg | Asp | Pro | Ala |
| | | | 260 | | | | | 265 | | | | | 270 | | |
| Tyr | Ala | Ile | Val | Thr | Val | Asp | Asp | Cys | Asp | Gln | Gly | Ala | Asn | Gly | Asp |
| | | | 275 | | | | | 280 | | | | | 285 | | |
| Ile | Ala | Ser | Leu | Ser | Ile | Val | Ala | Gly | Asp | Leu | Leu | Gln | Gln | Phe | Arg |
| | 290 | | | | | 295 | | | | | 300 | | | | |
| Thr | Val | Arg | Ser | Phe | Pro | Gly | Ser | Lys | Glu | Tyr | Lys | Val | Lys | Ala | Ile |
| 305 | | | | | 310 | | | | | 315 | | | | | 320 |
| Gly | Gly | Ile | Asp | Trp | Asp | Ser | His | Pro | Phe | Gly | Tyr | Asn | Leu | Thr | Leu |
| | | | | 325 | | | | | 330 | | | | | 335 | |
| Gln | Ala | Lys | Asp | Lys | Gly | Thr | Pro | Pro | Gln | Phe | Ser | Ser | Val | Lys | Val |
| | | | 340 | | | | | 345 | | | | | 350 | | |
| Ile | His | Val | Thr | Ser | Pro | Gln | Phe | Lys | Ala | Gly | Pro | Val | Lys | Phe | Glu |
| | | | 355 | | | | | 360 | | | | | 365 | | |

```
Lys Asp Val Tyr Arg Ala Glu Ile Ser Glu Phe Ala Pro Pro Asn Thr
    370                 375                 380

Pro Val Val Met Val Lys Ala Ile Pro Ala Tyr Ser His Leu Arg Tyr
385                 390                 395                 400

Val Phe Lys Ser Thr Pro Gly Lys Ala Lys Phe Ser Leu Asn Tyr Asn
                405                 410                 415

Thr Gly Leu Ile Ser Ile Leu Glu Pro Val Lys Arg Gln Gln Ala Ala
                420                 425                 430

His Phe Glu Leu Glu Val Thr Thr Ser Asp Arg Lys Ala Ser Thr Lys
                435                 440                 445

Val Leu Val Lys Val Leu Gly Ala Asn Ser Asn Pro Pro Glu Phe Thr
    450                 455                 460

Gln Thr Ala Tyr Lys Ala Ala Phe Asp Glu Asn Val Pro Ile Gly Thr
465                 470                 475                 480

Thr Val Met Ser Leu Ser Ala Val Asp Pro Asp Glu Gly Glu Asn Gly
                485                 490                 495

Tyr Val Thr Tyr Ser Ile Ala Asn Leu Asn His Val Pro Phe Ala Ile
                500                 505                 510

Asp His Phe Thr Gly Ala Val Ser Thr Ser Glu Asn Leu Asp Tyr Glu
    515                 520                 525

Leu Met Pro Arg Val Tyr Thr Leu Arg Ile Arg Ala Ser Asp Trp Gly
    530                 535                 540

Leu Pro Tyr Arg Arg Glu Val Glu Val Leu Ala Thr Ile Thr Leu Asn
545                 550                 555                 560

Asn Leu Asn Asp Asn Thr Pro Leu Phe Glu Lys Ile Asn Cys Glu Gly
                565                 570                 575

Thr Ile Pro Arg Asp Leu Gly Val Gly Glu Gln Ile Thr Thr Val Ser
                580                 585                 590

Ala Ile Asp Ala Asp Glu Leu Gln Leu Val Gln Tyr Gln Ile Glu Ala
    595                 600                 605

Gly Asn Glu Leu Asp Phe Phe Ser Leu Asn Pro Asn Ser Gly Val Leu
    610                 615                 620

Ser Leu Lys Arg Ser Leu Met Asp Gly Leu Gly Ala Lys Val Ser Phe
625                 630                 635                 640

His Ser Leu Arg Ile Thr Ala Thr Asp Gly Glu Asn Phe Ala Thr Pro
                645                 650                 655

Leu Tyr Ile Asn Ile Thr Val Ala Ala Ser His Lys Leu Val Asn Leu
                660                 665                 670

Gln Cys Glu Glu Thr Gly Val Ala Lys Met Leu Ala Glu Lys Leu Leu
    675                 680                 685

Gln Ala Asn Lys Leu His Asn Gln Gly Glu Val Glu Asp Ile Phe Phe
    690                 695                 700

Asp Ser His Ser Val Asn Ala His Ile Pro Gln Phe Arg Ser Thr Leu
705                 710                 715                 720

Pro Thr Gly Ile Gln Val Lys Glu Asn Gln Pro Val Gly Ser Ser Val
                725                 730                 735

Ile Phe Met Asn Ser Thr Asp Leu Asp Thr Gly Phe Asn Gly Lys Leu
                740                 745                 750

Val Tyr Ala Val Ser Gly Gly Asn Glu Asp Ser Cys Phe Met Ile Asp
    755                 760                 765

Met Glu Thr Gly Met Leu Lys Ile Leu Ser Pro Leu Asp Arg Glu Thr
    770                 775                 780
```

```
Thr Asp Lys Tyr Thr Leu Asn Ile Thr Val Tyr Asp Leu Gly Ile Pro
785                 790                 795                 800

Gln Lys Ala Ala Trp Arg Leu Leu His Val Val Val Asp Ala Asn
            805                 810                 815

Asp Asn Pro Pro Glu Phe Leu Gln Glu Ser Tyr Phe Val Glu Val Ser
                820                 825                 830

Glu Asp Lys Glu Val His Ser Glu Ile Ile Gln Val Glu Ala Thr Asp
            835                 840                 845

Lys Asp Leu Gly Pro Asn Gly His Val Thr Tyr Ser Ile Val Thr Asp
            850                 855                 860

Thr Asp Thr Phe Ser Ile Asp Ser Val Thr Gly Val Val Asn Ile Ala
865                 870                 875                 880

Arg Pro Leu Asp Arg Glu Leu Gln His Glu His Ser Leu Lys Ile Glu
                885                 890                 895

Ala Arg Asp Gln Ala Arg Glu Glu Pro Gln Leu Phe Ser Thr Val Val
            900                 905                 910

Val Lys Val Ser Leu Glu Asp Val Asn Asp Asn Pro Pro Thr Phe Ile
            915                 920                 925

Pro Pro Asn Tyr Arg Val Lys Val Arg Glu Asp Leu Pro Glu Gly Thr
        930                 935                 940

Val Ile Met Trp Leu Glu Ala His Asp Pro Asp Leu Gly Gln Ser Gly
945                 950                 955                 960

Gln Val Arg Tyr Ser Leu Leu Asp His Gly Glu Gly Asn Phe Asp Val
                965                 970                 975

Asp Lys Leu Ser Gly Ala Val Arg Ile Val Gln Gln Leu Asp Phe Glu
            980                 985                 990

Lys Lys Gln Val Tyr Asn Leu Thr Val Arg Ala Lys Asp Lys Gly Lys
        995                 1000                1005

Pro Val Ser Leu Ser Ser Thr Cys Tyr Val Glu Val Glu Val Val
    1010                1015                1020

Asp Val Asn Glu Asn Leu His Pro Pro Val Phe Ser Ser Phe Val
    1025                1030                1035

Glu Lys Gly Thr Val Lys Glu Asp Ala Pro Val Gly Ser Leu Val
    1040                1045                1050

Met Thr Val Ser Ala His Asp Glu Asp Ala Arg Arg Asp Gly Glu
    1055                1060                1065

Ile Arg Tyr Ser Ile Arg Asp Gly Ser Gly Val Gly Val Phe Lys
    1070                1075                1080

Ile Gly Glu Glu Thr Gly Val Ile Glu Thr Ser Asp Arg Leu Asp
    1085                1090                1095

Arg Glu Ser Thr Ser His Tyr Trp Leu Thr Val Phe Ala Thr Asp
    1100                1105                1110

Gln Gly Val Val Pro Leu Ser Ser Phe Ile Glu Ile Tyr Ile Glu
    1115                1120                1125

Val Glu Asp Val Asn Asp Asn Ala Pro Gln Thr Ser Glu Pro Val
    1130                1135                1140

Tyr Tyr Pro Glu Ile Met Glu Asn Ser Pro Lys Asp Val Ser Val
    1145                1150                1155

Val Gln Ile Glu Ala Phe Asp Pro Asp Ser Ser Asn Asp Lys
    1160                1165                1170

Leu Met Tyr Lys Ile Thr Ser Gly Asn Pro Gln Gly Phe Phe Ser
    1175                1180                1185

Ile His Pro Lys Thr Gly Leu Ile Thr Thr Thr Ser Arg Lys Leu
```

-continued

```
            1190                1195                1200

Asp Arg Glu Gln Gln Asp Glu His Ile Leu Glu Val Thr Val Thr
        1205                1210                1215

Asp Asn Gly Ser Pro Pro Lys Ser Thr Ile Ala Arg Val Ile Val
        1220                1225                1230

Lys Ile Leu Asp Glu Asn Asp Asn Lys Pro Gln Phe Leu Gln Lys
        1235                1240                1245

Phe Tyr Lys Ile Arg Leu Pro Glu Arg Glu Lys Pro Asp Arg Glu
        1250                1255                1260

Arg Asn Ala Arg Arg Glu Pro Leu Tyr His Val Ile Ala Thr Asp
        1265                1270                1275

Lys Asp Glu Gly Pro Asn Ala Glu Ile Ser Tyr Ser Ile Glu Asp
        1280                1285                1290

Gly Asn Glu His Gly Lys Phe Phe Ile Glu Pro Lys Thr Gly Val
        1295                1300                1305

Val Ser Ser Lys Arg Phe Ser Ala Ala Gly Glu Tyr Asp Ile Leu
        1310                1315                1320

Ser Ile Lys Ala Val Asp Asn Gly Arg Pro Gln Lys Ser Ser Thr
        1325                1330                1335

Thr Arg Leu His Ile Glu Trp Ile Ser Lys Pro Lys Pro Ser Leu
        1340                1345                1350

Glu Pro Ile Ser Phe Glu Glu Ser Phe Phe Thr Phe Thr Val Met
        1355                1360                1365

Glu Ser Asp Pro Val Ala His Met Ile Gly Val Ile Ser Val Glu
        1370                1375                1380

Pro Pro Gly Ile Pro Leu Trp Phe Asp Ile Thr Gly Gly Asn Tyr
        1385                1390                1395

Asp Ser His Phe Asp Val Asp Lys Gly Thr Gly Thr Ile Ile Val
        1400                1405                1410

Ala Lys Pro Leu Asp Ala Glu Gln Lys Ser Asn Tyr Asn Leu Thr
        1415                1420                1425

Val Glu Ala Thr Asp Gly Thr Thr Thr Ile Leu Thr Gln Val Phe
        1430                1435                1440

Ile Lys Val Ile Asp Thr Asn Asp His Arg Pro Gln Phe Ser Thr
        1445                1450                1455

Ser Lys Tyr Glu Val Val Ile Pro Glu Asp Thr Ala Pro Glu Thr
        1460                1465                1470

Glu Ile Leu Gln Ile Ser Ala Val Asp Gln Asp Glu Lys Asn Lys
        1475                1480                1485

Leu Ile Tyr Thr Leu Gln Ser Ser Arg Asp Pro Leu Ser Leu Lys
        1490                1495                1500

Lys Phe Arg Leu Asp Pro Ala Thr Gly Ser Leu Tyr Thr Ser Glu
        1505                1510                1515

Lys Leu Asp His Glu Ala Val His Gln His Thr Leu Thr Val Met
        1520                1525                1530

Val Arg Asp Gln Asp Val Pro Val Lys Arg Asn Phe Ala Arg Ile
        1535                1540                1545

Val Val Asn Val Ser Asp Thr Asn Asp His Ala Pro Trp Phe Thr
        1550                1555                1560

Ala Ser Ser Tyr Lys Gly Arg Val Tyr Glu Ser Ala Ala Val Gly
        1565                1570                1575

Ser Val Val Leu Gln Val Thr Ala Leu Asp Lys Asp Lys Gly Lys
        1580                1585                1590
```

```
Asn Ala Glu Val Leu Tyr Ser Ile Glu Ser Gly Asn Ile Gly Asn
1595                1600                1605

Ser Phe Met Ile Asp Pro Val Leu Gly Ser Ile Lys Thr Ala Lys
1610                1615                1620

Glu Leu Asp Arg Ser Asn Gln Ala Glu Tyr Asp Leu Met Val Lys
1625                1630                1635

Ala Thr Asp Lys Gly Ser Pro Pro Met Ser Glu Ile Thr Ser Val
1640                1645                1650

Arg Ile Phe Val Thr Ile Ala Asp Asn Ala Ser Pro Lys Phe Thr
1655                1660                1665

Ser Lys Glu Tyr Ser Val Glu Leu Ser Glu Thr Val Ser Ile Gly
1670                1675                1680

Ser Phe Val Gly Met Val Thr Ala His Ser Gln Ser Ser Val Val
1685                1690                1695

Tyr Glu Ile Lys Asp Gly Asn Thr Gly Asp Ala Phe Asp Ile Asn
1700                1705                1710

Pro His Ser Gly Thr Ile Ile Thr Gln Lys Ala Leu Asp Phe Glu
1715                1720                1725

Thr Leu Pro Ile Tyr Thr Leu Ile Ile Gln Gly Thr Asn Met Ala
1730                1735                1740

Gly Leu Ser Thr Asn Thr Thr Val Leu Val His Leu Gln Asp Glu
1745                1750                1755

Asn Asp Asn Ala Pro Val Phe Met Gln Ala Glu Tyr Thr Gly Leu
1760                1765                1770

Ile Ser Glu Ser Ala Ser Ile Asn Ser Val Val Leu Thr Asp Arg
1775                1780                1785

Asn Val Pro Leu Val Ile Arg Ala Ala Asp Ala Asp Lys Asp Ser
1790                1795                1800

Asn Ala Leu Leu Val Tyr His Ile Val Glu Pro Ser Val His Thr
1805                1810                1815

Tyr Phe Ala Ile Asp Ser Ser Thr Gly Ala Ile His Thr Val Leu
1820                1825                1830

Ser Leu Asp Tyr Glu Glu Thr Ser Ile Phe His Phe Thr Val Gln
1835                1840                1845

Val His Asp Met Gly Thr Pro Arg Leu Phe Ala Glu Tyr Ala Ala
1850                1855                1860

Asn Val Thr Val His Val Ile Asp Ile Asn Asp Cys Pro Pro Val
1865                1870                1875

Phe Ala Lys Pro Leu Tyr Glu Ala Ser Leu Leu Leu Pro Thr Tyr
1880                1885                1890

Lys Gly Val Lys Val Ile Thr Val Asn Ala Thr Asp Ala Asp Ser
1895                1900                1905

Ser Ala Phe Ser Gln Leu Ile Tyr Ser Ile Thr Glu Gly Asn Ile
1910                1915                1920

Gly Glu Lys Phe Ser Met Asp Tyr Lys Thr Gly Ala Leu Thr Val
1925                1930                1935

Gln Asn Thr Thr Gln Leu Arg Ser Arg Tyr Glu Leu Thr Val Arg
1940                1945                1950

Ala Ser Asp Gly Arg Phe Ala Gly Leu Thr Ser Val Lys Ile Asn
1955                1960                1965

Val Lys Glu Ser Lys Glu Ser His Leu Lys Phe Thr Gln Asp Val
1970                1975                1980
```

```
Tyr Ser Ala Val Val Lys Glu Asn Ser Thr Glu Ala Glu Thr Leu
    1985                1990                1995

Ala Val Ile Thr Ala Ile Gly Asn Pro Ile Asn Glu Pro Leu Phe
    2000                2005                2010

Tyr His Ile Leu Asn Pro Asp Arg Arg Phe Lys Ile Ser Arg Thr
    2015                2020                2025

Ser Gly Val Leu Ser Thr Thr Gly Thr Pro Phe Asp Arg Glu Gln
    2030                2035                2040

Gln Glu Ala Phe Asp Val Val Val Glu Val Thr Glu Glu His Lys
    2045                2050                2055

Pro Ser Ala Val Ala His Val Val Val Lys Val Ile Val Glu Asp
    2060                2065                2070

Gln Asn Asp Asn Ala Pro Val Phe Val Asn Leu Pro Tyr Tyr Ala
    2075                2080                2085

Val Val Lys Val Asp Thr Glu Val Gly His Val Ile Arg Tyr Val
    2090                2095                2100

Thr Ala Val Asp Arg Asp Ser Gly Arg Asn Gly Glu Val His Tyr
    2105                2110                2115

Tyr Leu Lys Glu His His Glu His Phe Gln Ile Gly Pro Leu Gly
    2120                2125                2130

Glu Ile Ser Leu Lys Lys Gln Phe Glu Leu Asp Thr Leu Asn Lys
    2135                2140                2145

Glu Tyr Leu Val Thr Val Val Ala Lys Asp Gly Gly Asn Pro Ala
    2150                2155                2160

Phe Ser Ala Glu Val Ile Val Pro Ile Thr Val Met Asn Lys Ala
    2165                2170                2175

Met Pro Val Phe Glu Lys Pro Phe Tyr Ser Ala Glu Ile Ala Glu
    2180                2185                2190

Ser Ile Gln Val His Ser Pro Val Val His Val Gln Ala Asn Ser
    2195                2200                2205

Pro Glu Gly Leu Lys Val Phe Tyr Ser Ile Thr Asp Gly Asp Pro
    2210                2215                2220

Phe Ser Gln Phe Thr Ile Asn Phe Asn Thr Gly Val Ile Asn Val
    2225                2230                2235

Ile Ala Pro Leu Asp Phe Glu Ala His Pro Ala Tyr Lys Leu Ser
    2240                2245                2250

Ile Arg Ala Thr Asp Ser Leu Thr Gly Ala His Ala Glu Val Phe
    2255                2260                2265

Val Asp Ile Ile Val Asp Asp Ile Asn Asp Asn Pro Pro Val Phe
    2270                2275                2280

Ala Gln Gln Ser Tyr Ala Val Thr Leu Ser Glu Ala Ser Val Ile
    2285                2290                2295

Gly Thr Ser Val Val Gln Val Arg Ala Thr Asp Ser Asp Ser Glu
    2300                2305                2310

Pro Asn Arg Gly Ile Ser Tyr Gln Met Phe Gly Asn His Ser Lys
    2315                2320                2325

Ser His Asp His Phe His Val Asp Ser Ser Thr Gly Leu Ile Ser
    2330                2335                2340

Leu Leu Arg Thr Leu Asp Tyr Glu Gln Ser Arg Gln His Thr Ile
    2345                2350                2355

Phe Val Arg Ala Val Asp Gly Gly Met Pro Thr Leu Ser Ser Asp
    2360                2365                2370

Val Ile Val Thr Val Asp Val Thr Asp Leu Asn Asp Asn Pro Pro
```

```
                    2375                2380                2385
Leu  Phe  Glu  Gln  Gln  Ile  Tyr  Glu  Ala  Arg  Ile  Ser  Glu  His  Ala
     2390                2395                2400

Pro  His  Gly  His  Phe  Val  Thr  Cys  Val  Lys  Ala  Tyr  Asp  Ala  Asp
     2405                2410                2415

Ser  Ser  Asp  Ile  Asp  Lys  Leu  Gln  Tyr  Ser  Ile  Leu  Ser  Gly  Asn
     2420                2425                2430

Asp  His  Lys  His  Phe  Val  Ile  Asp  Ser  Ala  Thr  Gly  Ile  Ile  Thr
     2435                2440                2445

Leu  Ser  Asn  Leu  His  Arg  His  Ala  Leu  Lys  Pro  Phe  Tyr  Ser  Leu
     2450                2455                2460

Asn  Leu  Ser  Val  Ser  Asp  Gly  Val  Phe  Arg  Ser  Ser  Thr  Gln  Val
     2465                2470                2475

His  Val  Thr  Val  Ile  Gly  Gly  Asn  Leu  His  Ser  Pro  Ala  Phe  Leu
     2480                2485                2490

Gln  Asn  Glu  Tyr  Glu  Val  Glu  Leu  Ala  Glu  Asn  Ala  Pro  Leu  His
     2495                2500                2505

Thr  Leu  Val  Met  Glu  Val  Lys  Thr  Thr  Asp  Gly  Asp  Ser  Gly  Ile
     2510                2515                2520

Tyr  Gly  His  Val  Thr  Tyr  His  Ile  Val  Asn  Asp  Phe  Ala  Lys  Asp
     2525                2530                2535

Arg  Phe  Tyr  Ile  Asn  Glu  Arg  Gly  Gln  Ile  Phe  Thr  Leu  Glu  Lys
     2540                2545                2550

Leu  Asp  Arg  Glu  Thr  Pro  Ala  Glu  Lys  Val  Ile  Ser  Val  Arg  Leu
     2555                2560                2565

Met  Ala  Lys  Asp  Ala  Gly  Gly  Lys  Val  Ala  Phe  Cys  Thr  Val  Asn
     2570                2575                2580

Val  Ile  Leu  Thr  Asp  Asp  Asn  Asp  Asn  Ala  Pro  Gln  Phe  Arg  Ala
     2585                2590                2595

Thr  Lys  Tyr  Glu  Val  Asn  Ile  Gly  Ser  Ser  Ala  Ala  Lys  Gly  Thr
     2600                2605                2610

Ser  Val  Val  Lys  Val  Leu  Ala  Ser  Asp  Ala  Asp  Glu  Gly  Ser  Asn
     2615                2620                2625

Ala  Asp  Ile  Thr  Tyr  Ala  Ile  Glu  Ala  Asp  Ser  Glu  Ser  Val  Lys
     2630                2635                2640

Glu  Asn  Leu  Glu  Ile  Asn  Lys  Leu  Ser  Gly  Val  Ile  Thr  Thr  Lys
     2645                2650                2655

Glu  Ser  Leu  Ile  Gly  Leu  Glu  Asn  Glu  Phe  Phe  Thr  Phe  Phe  Val
     2660                2665                2670

Arg  Ala  Val  Asp  Asn  Gly  Ser  Pro  Ser  Lys  Glu  Ser  Val  Val  Leu
     2675                2680                2685

Val  Tyr  Val  Lys  Ile  Leu  Pro  Pro  Glu  Met  Gln  Leu  Pro  Lys  Phe
     2690                2695                2700

Ser  Glu  Pro  Phe  Tyr  Thr  Phe  Thr  Val  Ser  Glu  Asp  Val  Pro  Ile
     2705                2710                2715

Gly  Thr  Glu  Ile  Asp  Leu  Ile  Arg  Ala  Glu  His  Ser  Gly  Thr  Val
     2720                2725                2730

Leu  Tyr  Ser  Leu  Val  Lys  Gly  Asn  Thr  Pro  Glu  Ser  Asn  Arg  Asp
     2735                2740                2745

Glu  Ser  Phe  Val  Ile  Asp  Arg  Gln  Ser  Gly  Arg  Leu  Lys  Leu  Glu
     2750                2755                2760

Lys  Ser  Leu  Asp  His  Glu  Thr  Thr  Lys  Trp  Tyr  Gln  Phe  Ser  Ile
     2765                2770                2775
```

```
Leu Ala Arg Cys Thr Gln Asp Asp His Glu Met Val Ala Ser Val
    2780            2785                2790

Asp Val Ser Ile Gln Val Lys Asp Ala Asn Asp Asn Ser Pro Val
    2795            2800                2805

Phe Glu Ser Ser Pro Tyr Glu Ala Phe Ile Val Glu Asn Leu Pro
    2810            2815                2820

Gly Gly Ser Arg Val Ile Gln Ile Arg Ala Ser Asp Ala Asp Ser
    2825            2830                2835

Gly Thr Asn Gly Gln Val Met Tyr Ser Leu Asp Gln Ser Gln Ser
    2840            2845                2850

Val Glu Val Ile Glu Ser Phe Ala Ile Asn Met Glu Thr Gly Trp
    2855            2860                2865

Ile Thr Thr Leu Lys Glu Leu Asp His Glu Lys Arg Asp Asn Tyr
    2870            2875                2880

Gln Ile Lys Val Val Ala Ser Asp His Gly Glu Lys Ile Gln Leu
    2885            2890                2895

Ser Ser Thr Ala Ile Val Asp Val Thr Val Thr Asp Val Asn Asp
    2900            2905                2910

Ser Pro Pro Arg Phe Thr Ala Glu Ile Tyr Lys Gly Thr Val Ser
    2915            2920                2925

Glu Asp Asp Pro Gln Gly Gly Val Ile Ala Ile Leu Ser Thr Thr
    2930            2935                2940

Asp Ala Asp Ser Glu Glu Ile Asn Arg Gln Val Thr Tyr Phe Ile
    2945            2950                2955

Thr Gly Gly Asp Pro Leu Gly Gln Phe Ala Val Glu Thr Ile Gln
    2960            2965                2970

Asn Glu Trp Lys Val Tyr Val Lys Lys Pro Leu Asp Arg Glu Lys
    2975            2980                2985

Arg Asp Asn Tyr Leu Leu Thr Ile Thr Ala Thr Asp Gly Thr Phe
    2990            2995                3000

Ser Ser Lys Ala Ile Val Glu Val Lys Val Leu Asp Ala Asn Asp
    3005            3010                3015

Asn Ser Pro Val Cys Glu Lys Thr Leu Tyr Ser Asp Thr Ile Pro
    3020            3025                3030

Glu Asp Val Leu Pro Gly Lys Leu Ile Met Gln Ile Ser Ala Thr
    3035            3040                3045

Asp Ala Asp Ile Arg Ser Asn Ala Glu Ile Thr Tyr Thr Leu Leu
    3050            3055                3060

Gly Ser Gly Ala Glu Lys Phe Lys Leu Asn Pro Asp Thr Gly Glu
    3065            3070                3075

Leu Lys Thr Ser Thr Pro Leu Asp Arg Glu Glu Gln Ala Val Tyr
    3080            3085                3090

His Leu Leu Val Arg Ala Thr Asp Gly Gly Gly Arg Phe Cys Gln
    3095            3100                3105

Ala Ser Ile Val Leu Thr Leu Glu Asp Val Asn Asp Asn Ala Pro
    3110            3115                3120

Glu Phe Ser Ala Asp Pro Tyr Ala Ile Thr Val Phe Glu Asn Thr
    3125            3130                3135

Glu Pro Gly Thr Leu Leu Thr Arg Val Gln Ala Thr Asp Ala Asp
    3140            3145                3150

Ala Gly Leu Asn Arg Lys Ile Leu Tyr Ser Leu Ile Asp Ser Ala
    3155            3160                3165
```

```
Asp Gly Gln Phe Ser Ile Asn Glu Leu Ser Gly Ile Ile Gln Leu
3170             3175                 3180

Glu Lys Pro Leu Asp Arg Glu Leu Gln Ala Val Tyr Thr Leu Ser
3185             3190                 3195

Leu Lys Ala Val Asp Gln Gly Leu Pro Arg Arg Leu Thr Ala Thr
3200             3205                 3210

Gly Thr Val Ile Val Ser Val Leu Asp Ile Asn Asp Asn Pro Pro
3215             3220                 3225

Val Phe Glu Tyr Arg Glu Tyr Gly Ala Thr Val Ser Glu Asp Ile
3230             3235                 3240

Leu Val Gly Thr Glu Val Leu Gln Val Tyr Ala Ala Ser Arg Asp
3245             3250                 3255

Ile Glu Ala Asn Ala Glu Ile Thr Tyr Ser Ile Ile Ser Gly Asn
3260             3265                 3270

Glu His Gly Lys Phe Ser Ile Asp Ser Lys Thr Gly Ala Val Phe
3275             3280                 3285

Ile Ile Glu Asn Leu Asp Tyr Glu Ser Ser His Glu Tyr Tyr Leu
3290             3295                 3300

Thr Val Glu Ala Thr Asp Gly Gly Thr Pro Ser Leu Ser Asp Val
3305             3310                 3315

Ala Thr Val Asn Val Asn Val Thr Asp Ile Asn Asp Asn Thr Pro
3320             3325                 3330

Val Phe Ser Gln Asp Thr Tyr Thr Thr Val Ile Ser Glu Asp Ala
3335             3340                 3345

Val Leu Glu Gln Ser Val Ile Thr Val Met Ala Asp Asp Ala Asp
3350             3355                 3360

Gly Pro Ser Asn Ser His Ile His Tyr Ser Ile Ile Asp Gly Asn
3365             3370                 3375

Gln Gly Ser Ser Phe Thr Ile Asp Pro Val Arg Gly Glu Val Lys
3380             3385                 3390

Val Thr Lys Leu Leu Asp Arg Glu Thr Ile Ser Gly Tyr Thr Leu
3395             3400                 3405

Thr Val Gln Ala Ser Asp Asn Gly Ser Pro Pro Arg Val Asn Thr
3410             3415                 3420

Thr Thr Val Asn Ile Asp Val Ser Asp Val Asn Asp Asn Ala Pro
3425             3430                 3435

Val Phe Ser Arg Gly Asn Tyr Ser Val Ile Ile Gln Glu Asn Lys
3440             3445                 3450

Pro Val Gly Phe Ser Val Leu Gln Leu Val Val Thr Asp Glu Asp
3455             3460                 3465

Ser Ser His Asn Gly Pro Pro Phe Phe Phe Thr Ile Val Thr Gly
3470             3475                 3480

Asn Asp Glu Lys Ala Phe Glu Val Asn Pro Gln Gly Val Leu Leu
3485             3490                 3495

Thr Ser Ser Ala Ile Lys Arg Lys Glu Lys Asp His Tyr Leu Leu
3500             3505                 3510

Gln Val Lys Val Ala Asp Asn Gly Lys Pro Gln Leu Ser Ser Leu
3515             3520                 3525

Thr Tyr Ile Asp Ile Arg Val Ile Glu Glu Ser Ile Tyr Pro Pro
3530             3535                 3540

Ala Ile Leu Pro Leu Glu Ile Phe Ile Thr Ser Ser Gly Glu Glu
3545             3550                 3555

Tyr Ser Gly Gly Val Ile Gly Lys Ile His Ala Thr Asp Gln Asp
```

```
                 3560                3565                3570

Val Tyr Asp Thr Leu Thr Tyr Ser Leu Asp Pro Gln Met Asp Asn
    3575                3580                3585

Leu Phe Ser Val Ser Ser Thr Gly Gly Lys Leu Ile Ala His Lys
    3590                3595                3600

Lys Leu Asp Ile Gly Gln Tyr Leu Leu Asn Val Ser Val Thr Asp
    3605                3610                3615

Gly Lys Phe Thr Thr Val Ala Asp Ile Thr Val His Ile Arg Gln
    3620                3625                3630

Val Thr Gln Glu Met Leu Asn His Thr Ile Ala Ile Arg Phe Ala
    3635                3640                3645

Asn Leu Thr Pro Glu Glu Phe Val Gly Asp Tyr Trp Arg Asn Phe
    3650                3655                3660

Gln Arg Ala Leu Arg Asn Ile Leu Gly Val Arg Arg Asn Asp Ile
    3665                3670                3675

Gln Ile Val Ser Leu Gln Ser Ser Glu Pro His Pro His Leu Asp
    3680                3685                3690

Val Leu Leu Phe Val Glu Lys Pro Gly Ser Ala Gln Ile Ser Thr
    3695                3700                3705

Lys Gln Leu Leu His Lys Ile Asn Ser Ser Val Thr Asp Ile Glu
    3710                3715                3720

Glu Ile Ile Gly Val Arg Ile Leu Asn Val Phe Gln Lys Leu Cys
    3725                3730                3735

Ala Gly Leu Asp Cys Pro Trp Lys Phe Cys Asp Glu Lys Val Ser
    3740                3745                3750

Val Asp Glu Ser Val Met Ser Thr His Ser Thr Ala Arg Leu Ser
    3755                3760                3765

Phe Val Thr Pro Arg His His Arg Ala Ala Val Cys Leu Cys Lys
    3770                3775                3780

Glu Gly Arg Cys Pro Pro Val His His Gly Cys Glu Asp Asp Pro
    3785                3790                3795

Cys Pro Glu Gly Ser Glu Cys Val Ser Asp Pro Trp Glu Glu Lys
    3800                3805                3810

His Thr Cys Val Cys Pro Ser Gly Arg Phe Gly Gln Cys Pro Gly
    3815                3820                3825

Ser Ser Ser Met Thr Leu Thr Gly Asn Ser Tyr Val Lys Tyr Arg
    3830                3835                3840

Leu Thr Glu Asn Glu Asn Lys Leu Glu Met Lys Leu Thr Met Arg
    3845                3850                3855

Leu Arg Thr Tyr Ser Thr His Ala Val Val Met Tyr Ala Arg Gly
    3860                3865                3870

Thr Asp Tyr Ser Ile Leu Glu Ile His His Gly Arg Leu Gln Tyr
    3875                3880                3885

Lys Phe Asp Cys Gly Ser Gly Pro Gly Ile Val Ser Val Gln Ser
    3890                3895                3900

Ile Gln Val Asn Asp Gly Gln Trp His Ala Val Ala Leu Glu Val
    3905                3910                3915

Asn Gly Asn Tyr Ala Arg Leu Val Leu Asp Gln Val His Thr Ala
    3920                3925                3930

Ser Gly Thr Ala Pro Gly Thr Leu Lys Thr Leu Asn Leu Asp Asn
    3935                3940                3945

Tyr Val Phe Phe Gly Gly His Ile Arg Gln Gln Gly Thr Arg His
    3950                3955                3960
```

Gly Arg Ser Pro Gln Val Gly Asn Gly Phe Arg Gly Cys Met Asp
    3965            3970            3975

Ser Ile Tyr Leu Asn Gly Gln Glu Leu Pro Leu Asn Ser Lys Pro
    3980            3985            3990

Arg Ser Tyr Ala His Ile Glu Glu Ser Val Asp Val Ser Pro Gly
    3995            4000            4005

Cys Phe Leu Thr Ala Thr Glu Asp Cys Ala Ser Asn Pro Cys Gln
    4010            4015            4020

Asn Gly Gly Val Cys Asn Pro Ser Pro Ala Gly Gly Tyr Tyr Cys
    4025            4030            4035

Lys Cys Ser Ala Leu Tyr Ile Gly Thr His Cys Glu Ile Ser Val
    4040            4045            4050

Asn Pro Cys Ser Ser Lys Pro Cys Leu Tyr Gly Gly Thr Cys Val
    4055            4060            4065

Val Asp Asn Gly Gly Phe Val Cys Gln Cys Arg Gly Leu Tyr Thr
    4070            4075            4080

Gly Gln Arg Cys Gln Leu Ser Pro Tyr Cys Lys Asp Glu Pro Cys
    4085            4090            4095

Lys Asn Gly Gly Thr Cys Phe Asp Ser Leu Asp Gly Ala Val Cys
    4100            4105            4110

Gln Cys Asp Ser Gly Phe Arg Gly Glu Arg Cys Gln Ser Asp Ile
    4115            4120            4125

Asp Glu Cys Ser Gly Asn Pro Cys Leu His Gly Ala Leu Cys Glu
    4130            4135            4140

Asn Thr His Gly Ser Tyr His Cys Asn Cys Ser His Glu Tyr Arg
    4145            4150            4155

Gly Arg His Cys Glu Asp Ala Ala Pro Asn Gln Tyr Val Ser Thr
    4160            4165            4170

Pro Trp Asn Ile Gly Leu Ala Glu Gly Ile Gly Ile Val Val Phe
    4175            4180            4185

Val Ala Gly Ile Phe Leu Leu Val Val Val Phe Val Leu Cys Arg
    4190            4195            4200

Lys Met Ile Ser Arg Lys Lys Lys His Gln Ala Glu Pro Lys Asp
    4205            4210            4215

Lys His Leu Gly Pro Ala Thr Ala Phe Leu Gln Arg Pro Tyr Phe
    4220            4225            4230

Asp Ser Lys Leu Asn Lys Asn Ile Tyr Ser Asp Ile Pro Pro Gln
    4235            4240            4245

Val Pro Val Arg Pro Ile Ser Tyr Thr Pro Ser Ile Pro Ser Asp
    4250            4255            4260

Ser Arg Asn Asn Leu Asp Arg Asn Ser Phe Glu Gly Ser Ala Ile
    4265            4270            4275

Pro Glu His Pro Glu Phe Ser Thr Phe Asn Pro Glu Ser Val His
    4280            4285            4290

Gly His Arg Lys Ala Val Ala Val Cys Ser Val Ala Pro Asn Leu
    4295            4300            4305

Pro Pro Pro Pro Pro Ser Asn Ser Pro Ser Asp Ser Asp Ser Ile
    4310            4315            4320

Gln Lys Pro Ser Trp Asp Phe Asp Tyr Asp Thr Lys Val Val Asp
    4325            4330            4335

Leu Asp Pro Cys Leu Ser Lys Lys Pro Leu Glu Glu Lys Pro Ser
    4340            4345            4350

Gln Pro Tyr Ser Ala Arg Glu Ser Leu Ser Glu Val Gln Ser Leu
    4355                4360                4365

Ser Ser Phe Gln Ser Glu Ser Cys Asp Asp Asn Gly Tyr His Trp
    4370                4375                4380

Asp Thr Ser Asp Trp Met Pro Ser Val Pro Leu Pro Asp Ile Gln
    4385                4390                4395

Glu Phe Pro Asn Tyr Glu Val Ile Asp Glu Gln Thr Pro Leu Tyr
    4400                4405                4410

Ser Ala Asp Pro Asn Ala Ile Asp Thr Asp Tyr Tyr Pro Gly Gly
    4415                4420                4425

Tyr Asp Ile Glu Ser Asp Phe Pro Pro Pro Glu Asp Phe Pro
    4430                4435                4440

Ala Ala Asp Glu Leu Pro Pro Leu Pro Pro Glu Phe Ser Asn Gln
    4445                4450                4455

Phe Glu Ser Ile His Pro Pro Arg Asp Met Pro Ala Ala Gly Ser
    4460                4465                4470

Leu Gly Ser Ser Ser Arg Asn Arg Gln Arg Phe Asn Leu Asn Gln
    4475                4480                4485

Tyr Leu Pro Asn Phe Tyr Pro Leu Asp Met Ser Glu Pro Gln Thr
    4490                4495                4500

Lys Gly Thr Gly Glu Asn Ser Thr Cys Arg Glu Pro His Ala Pro
    4505                4510                4515

Tyr Pro Pro Gly Tyr Gln Arg His Phe Glu Ala Pro Ala Val Glu
    4520                4525                4530

Ser Met Pro Met Ser Val Tyr Ala Ser Thr Ala Ser Cys Ser Asp
    4535                4540                4545

Val Ser Ala Cys Cys Glu Val Glu Ser Glu Val Met Met Ser Asp
    4550                4555                4560

Tyr Glu Ser Gly Asp Asp Gly His Phe Glu Glu Val Thr Ile Pro
    4565                4570                4575

Pro Leu Asp Ser Gln Gln His Thr Glu Val
    4580                4585

<210> SEQ ID NO 7
<211> LENGTH: 11332
<212> TYPE: DNA
<213> ORGANISM: Homo sapiens
<220> FEATURE:
<221> NAME/KEY: misc_feature
<222> LOCATION: (1)..(11332)
<223> OTHER INFORMATION: protein tyrosine phosphatase, receptor type, B
      (PTPRB), transcript variant 1, mRNA

<400> SEQUENCE: 7
tttttttttt cccccaagcga agcatgaaca gttgctaagt ggaaaatgga ggctgaattt      60
tacatggtga ttcttacctg cttgatcttc aggaactcag aagggtttca gattgtccat     120
gtccagaaac aacagtgtct tttcaaaaat gagaaagtgg tcgtgggctc atgcaacagg     180
accatccaga accagcagtg gatgtggact gaggatgaaa agctccttca tgttaaatct     240
gcactgtgct tggccatctc caactcttcc cgcggcccct cccgctcagc catcttggac     300
cgctgttccc aggcaccccg atggacctgc tatgatcagg aaggcttcct tgaggtggaa     360
aatgcctctc tctttctcca gaaacaaggc tccagagtag tggtcaagaa ggccaggaaa     420
tacctccata gctggatgaa aatagatgtc aacaaggagg gaaaactggt caatgaaagc     480
ctctgtttac aaaaagctgg cctgggagca gaagtttcgg tgaggagcac tagaaacacg     540

```
gctccacccc agattctcac tacctttaat gcagttccag atggcctggt attccttatt    600
aggaatacca cagaggcctt catcagaaat gctgcagaaa actacagcca aaacagcagc    660
gagaggcagc atcccaatct gcacatgact ggaattacag acacatcatg ggttttgtcg    720
actactcagc ccttctccag caccactgaa gagactggac tggcggagcc agagagatgt    780
aacttcaccc tggcggagtc caaggcctcc agccattctg tgtctatcca gtggagaatt    840
ttgggctcac cctgtaactt tagcctcatc tatagcagtg acaccctggg ggccgcgttg    900
tgccctacct ttcggataga caacaccaca tacggatgta accttcaaga tttacaagca    960
ggaaccatct ataacttcag gattatttct ctggatgaag agaacagtg ggtcttgcaa     1020 acagatcctt tacctcctgc taggtttgga gtcagtaaag agaagacgac ttcaaccagc    1080
ttgcatgttt ggtggactcc ttcttccgga aaagtcacct catatgaggt gcaattattt    1140
gatgaaaata accaaaagat acaggggtt caaattcaag aaagtacttc atggaatgaa     1200 tacactttt tcaatctcac tgctggtagt aaatacaata ttgccatcac agctgtttct     1260
ggaggaaaac gttctttttc agtttatacc aatggatcaa cagtgccatc tccagtgaaa    1320
gatattggta tttccacaaa agccaattct ctcctgattt cctggtccca tggttctggg    1380
aatgtggaac gataccggct gatgctaatg gataaaggga tcctagttca tggcggtgtt    1440
gtggacaaac atgctacttc ctatgctttt cacgggctga cccctggcta cctctacaac    1500
ctcactgtta tgactgaggc tgcagggctg caaaactaca ggtggaaact agtcaggaca    1560
gcccccatgg aagtctcaaa tctgaaggtg acaaatgatg gcagtttgac ctctctaaaa    1620
gtcaaatggc aaagacctcc tggaaatgtg gattcttaca atatcaccct gtctcacaaa    1680
gggaccatca aggaatccag agtattagca ccttggatta ctgaaactca ctttaaagag    1740
ttagtccccg gtcgacttta tcaagttact gtcagctgtg tctctggtga actgtctgct    1800
cagaagatgg cagtgggcag aacatttcca gacaaagttg caaacctgga ggcaaacaat    1860
aatggcagga tgaggtctct tgtagtgagc tggtcgcccc ctgctggaga ctgggagcag    1920
tatcggatcc tactcttcaa tgattctgtg gtgctgctca acatcactgt gggaaaggaa    1980
gaaacacagt atgtcatgga tgacacgggg ctcgtaccgg aagacagta tgaggtggaa     2040 gtcattgttg agagtggaaa tttgaagaat tctgagcgtt gccaaggcag acagtccc     2100 ctggctgtcc tccagcttcg tgtcaaacat gccaatgaaa cctcactgag tatcatgtgg    2160
cagacccctg tagcagaatg ggagaaatac atcatttccc tagctgacag agacctctta    2220
ctgatccaca agtcactctc caaagatgcc aaagaattca cttttactga cctggtgcct    2280
ggacgaaaat acatggctac agtcaccagt attagtggag acttaaaaaa ttcctcttca    2340
gtaaaaggaa gaacagtgcc tgcccaagtg actgacttgc atgtggccaa ccaaggaatg    2400
accagtagtc tgtttactaa ctggacccag gcacaaggag acgtagaatt ttaccaagtc    2460
ttactgatcc atgaaaatgt ggtcattaaa aatgaaagca tctccagtga accagcaga    2520 tacagcttcc actctctcaa gtccggcagc ctgtactccg tggtggtaac aacagtgagt    2580
ggagggatct cttcccgaca agtggttgtg gagggaagaa cagtcccttc cagtgtgagt    2640
ggagtaacgg tgaacaattc cggtcgtaat gactacctca gcgtttcctg gctgctggcg    2700
cccggagatg tggataacta tgaggtaaca ttgtctcatg acggcaaggt ggttcagtcc    2760
cttgtcattg ccaagtctgt cagagaatgt tccttcagct ccctcacccc aggccgcctc    2820
tacaccgtga ccataactac aaggagtggc aagtatgaaa atcactcctt cagccaagag    2880
cggacagtgc ctgacaaagt ccagggagtc agtgttagca actcagccag gagtgactat    2940
```

```
ttaagggtat cctgggtgca tgccactgga gactttgatc actatgaagt caccattaaa   3000
aacaaaaaca acttcattca aactaaaagc attcccaagt cagaaaacga atgtgtattt   3060
gttcagctag tccctggacg gttgtacagt gtcactgtta ctacaaaaag tggacaatat   3120
gaagccaatg aacaagggaa tgggagaaca attccagagc ctgttaagga tctaacattg   3180
cgcaacagga gcactgagga cttgcatgtg acttggtcag gagctaatgg ggatgtcgac   3240
caatatgaga tccagctgct cttcaatgac atgaaagtat ttcctccttt tcaccttgta   3300
aataccgcaa ccgagtatcg atttacttcc ctaacaccag gccgccaata caaaattctt   3360
gtcttgacga ttagcgggga tgtacagcag tcagccttca ttgagggctt cacagttcct   3420
agtgctgtca aaaatattca catttctccc aatggagcaa cagatagcct gacggtgaac   3480
tggactcctg gtgggggaga cgttgattcc tacacggtgt cggcattcag gcacagtcaa   3540
aaggttgact ctcagactat tcccaagcac gtctttgagc acacgttcca cagactggag   3600
gccggggagc agtaccagat catgattgcc tcagtcagcg ggtccctgaa gaatcagata   3660
aatgtggttg gcggacagt tccagcatct gtccaaggag taattgcaga caatgcatac   3720
agcagttatt ccttaatagt aagttggcaa aaagctgctg gtgtggcaga agatatgat   3780 atcctgcttc taactgaaaa tggaatcctt ctgcgcaaca catcagagcc agccaccact   3840
aagcaacaca aatttgaaga tctaacacca ggcaagaaat acaagataca gatcctaact   3900
gtcagtggag gcctctttag caaggaagcc cagactgaag gccgaacagt cccagcagct   3960
gtcaccgacc tgaggatcac agagaactcc accaggcacc tgtccttccg ctggaccgcc   4020 tcagagggg agctcagctg gtacaacatc tttttgtaca cccagatgg gaatctccag   4080 gagagagctc aagttgaccc actagtccag agcttctctt tccagaactt gctacaaggc   4140
agaatgtaca agatggtgat tgtaactcac agtggggagc tgtctaatga gtctttcata   4200
tttggtagaa cagtcccagc ctctgtgagt catctcaggg ggtccaatcg gaacacgaca   4260
gacagccttt ggttcaactg gagtccagcc tctggggact ttgactttta tgagctgatt   4320
ctctataatc ccaatggcac aaagaaggaa aactggaaag acaaggacct gacggagtgg   4380
cggtttcaag gccttgttcc tggaaggaag tacgtgctgt gggtggtaac tcacagtgga   4440
gatctcagca ataaagtcac agcggagagc agaacagctc caagtcctcc cagtcttatg   4500
tcatttgctg acattgcaaa cacatccttg gccatcacgt ggaaagggcc cccagactgg   4560
acagactaca cgactttga gctgcagtgg ttgcccagag atgcacttac tgtcttcaac   4620
ccctacaaca acagaaaatc agaaggacgc attgtgtatg gtcttcgtcc agggagatcc   4680
tatcaattca acgtcaagac tgtcagtggt gattcctgga aaacttacag caaaccaatt   4740
tttggatctg tgaggacaaa gcctgacaag atacaaaacc tgcattgccg gcctcagaac   4800
tccacggcca ttgcctgttc ttggatccct cctgattctg actttgatgg ttatagtatt   4860
gaatgccgga aaatgacac ccaagaagtt gagtttccca gaaagctgga gaagaaaaa   4920 tctctgctca acatcatgat gctagtgccc cataagaggt acctggtgtc catcaaagtg   4980
cagtcggccg gcatgaccag cgaggtggtt gaagacagca ctatcacaat gatagaccgc   5040
ccccctcctc caccccaca cattcgtgtg aatgaaaagg atgtgctaat tagcaagtct   5100
tccatcaact ttactgtcaa ctgcagctgg ttcagcgaca ccaatggagc tgtgaaatac   5160
ttcacagtgg tggtgagaga ggctgatggc agtgatgagc tgaagccaga acagcagcac   5220
cctctccctt cctacctgga gtacaggcac aatgcctcca ttcgggtgta tcagactaat   5280
```

```
tattttgcca gcaaatgtgc cgaaaatcct aacagcaact ccaagagttt taacattaag    5340
cttggagcag agatggagag cctaggtgga aaatgcgatc ccactcagca aaaattctgt    5400
gatggaccac tgaagccaca cactgcctac agaatcagca ttcgagcttt tacacagctc    5460
tttgatgagg acctgaagga attcacaaag ccactctatt cagacacatt tttttcttta    5520
cccatcacta ctgaatcaga gcccttgttt ggagctattg aaggtgtgag tgctggtctg    5580
tttttaattg gcatgctagt ggctgttgtt gccttattga tctgcagaca gaaagtgagc    5640
catggtcgag aaagaccctc tgcccgtctg agcattcgta gggatcgacc attatctgtc    5700
cacttaaacc tgggccagaa aggtaaccgg aaaacttctt gtccaataaa aataaatcag    5760
tttgaagggc atttcatgaa gctacaggct gactccaact accttctatc caaggaatac    5820
gaggagttaa aagacgtggg ccgaaaccag tcatgtgaca ttgcactctt gccggagaat    5880
agagggaaaa atcgatacaa caatatattg ccctatgatg ccacgcgagt gaagctctcc    5940
aatgtagatg atgatccttg ctctgactac atcaatgcca gctacatccc tggcaacaac    6000
ttcagaagag aatacattgt cactcaggga ccgcttcctg gcaccaagga tgacttctgg    6060
aaaatggtgt gggaacaaaa cgttcacaac atcgtcatgg tgacccagtg tgttgagaag    6120
ggccgagtaa agtgtgacca ttactggcca gcggaccagg attccctcta ctatgggac     6180
ctcatcctgc agatgctctc agagtccgtc ctgcctgagt ggaccatccg ggagtttaag    6240
atatgcggtg aggaacagct tgatgcacac agactcatcc gccactttca ctatacggtg    6300
tggccagacc atggagtccc agaaaccacc cagtctctga tccagtttgt gagaactgtc    6360
agggactaca tcaacagaag cccgggtgct gggcccactg tggtgcactg cagtgctggt    6420
gtgggtagga ctggaaccct tattgcattg gaccgaatcc tccagcagtt agactccaaa    6480
gactctgtgg acatttatgg agcagtgcac gacctaagac ttcacagggt tcacatggtc    6540
cagactgagt gtcagtatgt ctacctacat cagtgtgtaa gagatgtcct cagagcaaga    6600
aagctacgga gtgaacaaga aaacccctig tttccaatct atgaaaatgt gaatccagag    6660
tatcacagag atccagtcta ttcaaggcat tgagaatgta cctgaagagc tcctggataa    6720
aaattattca ctgtgtgatt tgttttttaaa aacttgcttc atgccctaca gaggtgccag    6780
ctatttctgt tgatactatg tataatttat taatctggag aatgtttaaa attttatata    6840
atttaaaggt aacagatatt attgtacata gttgtatttt gtagtttctt ctgtaaaatat   6900
gtattttca taatgtttaa tattaagctt tatataatac tattttccca cactaaagtg    6960
ttcatgactt gttctacata aaactaattc aacctgtatg acaggactac tggtaaaatg    7020
catatggagg tggtggcaga gacaatcctt caggccatgt tttctacctg ttttgatatt    7080
cactggacag gaaaaagggc agggctagag agagcaaata ctatggctag atttgctgca    7140
ttgctgtccc atgaatctcg agagccaaca gacatgtcct aacttgctat taggacaaat    7200
gtgacagtca aaaaaaggat tagagggagg gagaaaaaag aattaagcag taccaaagct    7260
gaactagatg cttgtgtctg aactagttgc tctctctctc ctttctcctt ccagggattc    7320
aagccaaagt ggtcagctca gggatcatgt aacttgcagt gcaagcccag gatggtagga    7380
tgcagggttg agggttctga tagagaatga ttccaaacag aagtgatgaa ttcctttgt     7440
taataagatg ccagctatac ccagactgga aacataacat gcaaagcact atctacagtg    7500
attagagatc ctttcattgc attcatggtg tggagtgtga acatccacac ccatactgta    7560
atgtatttat acacactagt ttctgtctca tttttcagtgg tctccattcc tagaaaagtc    7620
acaattatcc attcctactt gatttcccat taaaagaata ttatggtagc agattgtgcc    7680
```

```
cctcattaaa aggcttaatg ccaacatttt catagaaatg actacaaaca tcatatatag    7740
taaatttaaa aacaatagca aaaacaaaaa cagtggtctt cagtaaaatt ttcaaaactt    7800
cttttagtaa atcaatgaag tcaaaatgtc aagtaatcac ccaaagttgc atttaataac    7860
aaaaggcact acatactgta ccaagtttat cttcaatatt tgtgccttac ttactttgac    7920
tataacaaat tccaatgagt cagaaagtat ttccttcatc aaggtccagt tccgacagca    7980
ttcctgggaa aaatttgaaa ggagtttgta cggaatcttc atagatacct gagaagatga    8040
gctggagatg tttgcctttt tcacactaca aattttctg taataaactt gggaattaga    8100
ggtcaagttt gttgatggca tagcttcctt tgcataaaga gtatatttct tttcaaagta    8160
tatatttttg taacctacca taaagtccgt aagtgaatac aacgaatgta attgacataa    8220
taattgaaaa tcattgacta tacctaaaat agttctttat aattaaataa ctctacaccc    8280
aatctggaaa tttttccaag gttatttgaa gtttacaaaa atgtgaagca taatcataag    8340
cttcaaagat tcacagtttc attgtgctca atgctcttgt gaaatgacag tcttaagctc    8400
tgattctgta tcaaggaact aagtgaatct tctggaaatg aaaaggaaca acatatgtgt    8460
aagtgcagta gatgtaccac cagcgagaaa atagaggtca gagatctaca acgtgtggca    8520
tccattagaa atcacctttc ctacattgaa aagaaaaaag agaaaaagca gaattttaca    8580
ctaatgttgc ttgatgcaaa gcacattaat gcttggaagg atacattcat tttcgacttt    8640
tcattcactc agaaaacttc tagtaagtat ctgcaacctg ctaggcactg ttccagaatc    8700
tacacatttc tactcacata aagagaatcc tcataaagtt aggattgttg ttactacctt    8760
caattgagct taaaagacag cctcatcaag ggaatgggat aactgagcca gtctaggaca    8820
gtggtcacct tccacaggcc acacactgga aagtgctaat gctactttaa tagcaaacct    8880
ctggatctag gagagagagc aattaattgc acaaaccagg agttaaaacc ataaaaaaaa    8940
cctatgcatc tgtaatagta aataacactc acgtactctg gcaacatcta gggtagtatc    9000
agaattatgt aaatggacat gacagggaaa aatcgtaggt ttttttagtc taatccaacc    9060
caggaaatgt ttattcctac cctacaccta atttttaaacc ttcttagcaa caaatatttc    9120
actattcgct cctactcctg ggaagactaa atatataatt gacttattta ttaaatttag    9180
gagaaaaaaa aagttttcct tgacattcag ctctattgga tttatttcca tttaattgca    9240
tcatgtgtta tgtcttggta aacactccat ttcctgtctt ggtgggcatc ctgtctgtgt    9300
acctgtgcag tacactttaa tcatcaagac ttcaaagtgc ttttgagcta tcaaatcttg    9360
ggagagtccc atctagcatc ttaataatta tttttccaag ttcgttataa ttaactcctt    9420
taacctcatc tcattaaatc aattttgtat tgtcattctg ttgttctctg gaaagcagcc    9480
aattgttcag ctcttgaatc agaattttca aagactcacc tctcttacct gggcttgcac    9540
atatttgtcc taagtaattc tctatcccctt aaacctctga gtccctctgt tttattactt    9600
gccccactcc tcctacttga atatgttgt tttcccagtt gaatgtgatt tttatctact    9660
gttcatatta tcttttatac ccatgagtat aatttcatag tcctttcagg ttccacatca    9720
tcaaagagat gaccataatt tcactttttt ttgaaatgaa gtcttgctct gttgcccagg    9780
ctggagtgca gtggcacaat ctcagctcac tacaacctcc gcctcccagg ttcaagcgat    9840
tctgccttag cctcccaagt agctggaatt acaggtgcct gccaccatgt ctggctaatt    9900
tttgtgtttt tagtagagat ggggtttcac catgttggcc aggctggtct tgaactcgtg    9960
accttaggtg atccacccac ctcaacctcc caaagtgcta ggattacaag agtgagccac   10020
```

```
cgcacctggc caattcactt ttaaatacta aaaggcacac agcacacaga catttttcggg    10080 gcagttttct ttgggagggt ctttgataaa ttttgtaatc acctctcgga agaaagccca    10140
aaatgacatg tgaaaataat attaaaccat ttaccagatg tccagcaata taaaaataga    10200
cctcacatgc taccttcac atgctgattc tcttgccttg ctgtttaagg atccagtttc     10260
ttatgttaaa cattttcctt accttttgca ataatattat tggccatata ctaaattctc    10320
attcacttag ctttctaaga attctttgag gttggaatcc tgaaatcata aagctaccag    10380
atctgcacaa cagcagtggt agtatctgag cccaaactct gagacgctct agagttttag    10440
tttacaaaca tgagccagac caaacctgac ctggtgaaaa tcataggta ataaactgct      10500 tgtatatgat agcagttcaa gggctttctg ggttccattt cactgaggaa atgaaaatat    10560
aactgattag ccaagacaga gtggcaataa ggaataactg atcctcctcc aagttgcagt    10620
gagcaagccc tcaagcctac ctcattcctg aagagttgaa ggagaaaatg ccgtgctaat    10680
tttctgccct gctatttta acctgaaatt tagaattaca tcaggtattc aaagaatgtt    10740
ccctatcaaa ggaaaatctg taaacgatga ctgcaaaaag caagtgaaat gatgcaaaga    10800
gaaaatattt gcaaaacaga atctaaccag acatcatcat gaagataaaa tggcatctct    10860
tctgtgtggc ctgggtgtgc ttggacaatc ctgtcacacg tttctattag acatgttgc     10920 cctttttgagg attcactcta tgttggccag atggtttaac tgattaaaca attgaatcaa    10980
tttattttgc tttttgaatt gaccagatat ttaactaaat gtactgggtt tggcatttta    11040
gacacactgc cttagattct tgtagtgcat gatgactttg aaaatgtttg gccatttag     11100 ttaaaatgca gggtaacatt tgatgcagcc atgataacag gaaaaatctg ttctgttcta    11160
aaaatgtttc tagcaataga agtatttctg gctaagagaa tactcttgac ttgtagggag    11220
gctccctcgg aataaatgta tgcaacacaa ataaggcatt ttatttttta aaagattgtc    11280
tatataagat acacttatta aataaagaaa ttgttggtga atgctctgaa aa            11332

<210> SEQ ID NO 8
<211> LENGTH: 2215
<212> TYPE: PRT
<213> ORGANISM: Homo sapiens
<220> FEATURE:
<221> NAME/KEY: misc_feature
<222> LOCATION: (1)..(2215)
<223> OTHER INFORMATION: receptor-type tyrosine-protein phosphatase beta
      isoform a

<400> SEQUENCE: 8

Met Glu Ala Glu Phe Tyr Met Val Ile Leu Thr Cys Leu Ile Phe Arg
1               5                   10                  15

Asn Ser Glu Gly Phe Gln Ile Val His Val Gln Lys Gln Gln Cys Leu
            20                  25                  30

Phe Lys Asn Glu Lys Val Val Val Gly Ser Cys Asn Arg Thr Ile Gln
        35                  40                  45

Asn Gln Gln Trp Met Trp Thr Glu Asp Glu Lys Leu Leu His Val Lys
    50                  55                  60

Ser Ala Leu Cys Leu Ala Ile Ser Asn Ser Ser Arg Gly Pro Ser Arg
65                  70                  75                  80

Ser Ala Ile Leu Asp Arg Cys Ser Gln Ala Pro Arg Trp Thr Cys Tyr
                85                  90                  95

Asp Gln Glu Gly Phe Leu Glu Val Glu Asn Ala Ser Leu Phe Leu Gln
            100                 105                 110

Lys Gln Gly Ser Arg Val Val Val Lys Lys Ala Arg Lys Tyr Leu His
```

```
              115                 120                 125
Ser Trp Met Lys Ile Asp Val Asn Lys Glu Gly Lys Leu Val Asn Glu
130                 135                 140

Ser Leu Cys Leu Gln Lys Ala Gly Leu Gly Ala Glu Val Ser Val Arg
145                 150                 155                 160

Ser Thr Arg Asn Thr Ala Pro Pro Gln Ile Leu Thr Thr Phe Asn Ala
                165                 170                 175

Val Pro Asp Gly Leu Val Phe Leu Ile Arg Asn Thr Thr Glu Ala Phe
            180                 185                 190

Ile Arg Asn Ala Ala Glu Asn Tyr Ser Gln Asn Ser Ser Glu Arg Gln
        195                 200                 205

His Pro Asn Leu His Met Thr Gly Ile Thr Asp Thr Ser Trp Val Leu
    210                 215                 220

Ser Thr Thr Gln Pro Phe Ser Ser Thr Thr Glu Glu Thr Gly Leu Ala
225                 230                 235                 240

Glu Pro Glu Arg Cys Asn Phe Thr Leu Ala Glu Ser Lys Ala Ser Ser
                245                 250                 255

His Ser Val Ser Ile Gln Trp Arg Ile Leu Gly Ser Pro Cys Asn Phe
            260                 265                 270

Ser Leu Ile Tyr Ser Ser Asp Thr Leu Gly Ala Ala Leu Cys Pro Thr
        275                 280                 285

Phe Arg Ile Asp Asn Thr Thr Tyr Gly Cys Asn Leu Gln Asp Leu Gln
    290                 295                 300

Ala Gly Thr Ile Tyr Asn Phe Arg Ile Ile Ser Leu Asp Glu Glu Arg
305                 310                 315                 320

Thr Val Val Leu Gln Thr Asp Pro Leu Pro Pro Ala Arg Phe Gly Val
                325                 330                 335

Ser Lys Glu Lys Thr Thr Ser Thr Ser Leu His Val Trp Trp Thr Pro
            340                 345                 350

Ser Ser Gly Lys Val Thr Ser Tyr Glu Val Gln Leu Phe Asp Glu Asn
        355                 360                 365

Asn Gln Lys Ile Gln Gly Val Gln Ile Gln Glu Ser Thr Ser Trp Asn
    370                 375                 380

Glu Tyr Thr Phe Phe Asn Leu Thr Ala Gly Ser Lys Tyr Asn Ile Ala
385                 390                 395                 400

Ile Thr Ala Val Ser Gly Gly Lys Arg Ser Phe Ser Val Tyr Thr Asn
                405                 410                 415

Gly Ser Thr Val Pro Ser Pro Val Lys Asp Ile Gly Ile Ser Thr Lys
            420                 425                 430

Ala Asn Ser Leu Leu Ile Ser Trp Ser His Gly Ser Gly Asn Val Glu
        435                 440                 445

Arg Tyr Arg Leu Met Leu Met Asp Lys Gly Ile Leu Val His Gly Gly
    450                 455                 460

Val Val Asp Lys His Ala Thr Ser Tyr Ala Phe His Gly Leu Thr Pro
465                 470                 475                 480

Gly Tyr Leu Tyr Asn Leu Thr Val Met Thr Glu Ala Ala Gly Leu Gln
                485                 490                 495

Asn Tyr Arg Trp Lys Leu Val Arg Thr Ala Pro Met Glu Val Ser Asn
            500                 505                 510

Leu Lys Val Thr Asn Asp Gly Ser Leu Thr Ser Leu Lys Val Lys Trp
        515                 520                 525

Gln Arg Pro Pro Gly Asn Val Asp Ser Tyr Asn Ile Thr Leu Ser His
    530                 535                 540
```

```
Lys Gly Thr Ile Lys Glu Ser Arg Val Leu Ala Pro Trp Ile Thr Glu
545                 550                 555                 560

Thr His Phe Lys Glu Leu Val Pro Gly Arg Leu Tyr Gln Val Thr Val
                565                 570                 575

Ser Cys Val Ser Gly Glu Leu Ser Ala Gln Lys Met Ala Val Gly Arg
            580                 585                 590

Thr Phe Pro Asp Lys Val Ala Asn Leu Glu Ala Asn Asn Asn Gly Arg
            595                 600                 605

Met Arg Ser Leu Val Val Ser Trp Ser Pro Ala Gly Asp Trp Glu
610                 615                 620

Gln Tyr Arg Ile Leu Leu Phe Asn Asp Ser Val Val Leu Leu Asn Ile
625                 630                 635                 640

Thr Val Gly Lys Glu Glu Thr Gln Tyr Val Met Asp Asp Thr Gly Leu
                645                 650                 655

Val Pro Gly Arg Gln Tyr Glu Val Glu Val Ile Val Glu Ser Gly Asn
            660                 665                 670

Leu Lys Asn Ser Glu Arg Cys Gln Gly Arg Thr Val Pro Leu Ala Val
        675                 680                 685

Leu Gln Leu Arg Val Lys His Ala Asn Glu Thr Ser Leu Ser Ile Met
690                 695                 700

Trp Gln Thr Pro Val Ala Glu Trp Glu Lys Tyr Ile Ile Ser Leu Ala
705                 710                 715                 720

Asp Arg Asp Leu Leu Leu Ile His Lys Ser Leu Ser Lys Asp Ala Lys
                725                 730                 735

Glu Phe Thr Phe Thr Asp Leu Val Pro Gly Arg Lys Tyr Met Ala Thr
            740                 745                 750

Val Thr Ser Ile Ser Gly Asp Leu Lys Asn Ser Ser Ser Val Lys Gly
        755                 760                 765

Arg Thr Val Pro Ala Gln Val Thr Asp Leu His Val Ala Asn Gln Gly
    770                 775                 780

Met Thr Ser Ser Leu Phe Thr Asn Trp Thr Gln Ala Gln Gly Asp Val
785                 790                 795                 800

Glu Phe Tyr Gln Val Leu Leu Ile His Glu Asn Val Val Ile Lys Asn
                805                 810                 815

Glu Ser Ile Ser Ser Glu Thr Ser Arg Tyr Ser Phe His Ser Leu Lys
            820                 825                 830

Ser Gly Ser Leu Tyr Ser Val Val Thr Thr Val Ser Gly Gly Ile
        835                 840                 845

Ser Ser Arg Gln Val Val Glu Gly Arg Thr Val Pro Ser Ser Val
850                 855                 860

Ser Gly Val Thr Val Asn Asn Ser Gly Arg Asn Asp Tyr Leu Ser Val
865                 870                 875                 880

Ser Trp Leu Leu Ala Pro Gly Asp Val Asp Asn Tyr Glu Val Thr Leu
                885                 890                 895

Ser His Asp Gly Lys Val Val Gln Ser Leu Val Ile Ala Lys Ser Val
            900                 905                 910

Arg Glu Cys Ser Phe Ser Ser Leu Thr Pro Gly Arg Leu Tyr Thr Val
        915                 920                 925

Thr Ile Thr Thr Arg Ser Gly Lys Tyr Glu Asn His Ser Phe Ser Gln
    930                 935                 940

Glu Arg Thr Val Pro Asp Lys Val Gln Gly Val Ser Val Ser Asn Ser
945                 950                 955                 960
```

```
Ala Arg Ser Asp Tyr Leu Arg Val Ser Trp Val His Ala Thr Gly Asp
            965                 970                 975

Phe Asp His Tyr Glu Val Thr Ile Lys Asn Lys Asn Phe Ile Gln
        980                 985                 990

Thr Lys Ser Ile Pro Lys Ser Glu Asn Glu Cys Val Phe Val Gln Leu
        995                 1000                1005

Val Pro Gly Arg Leu Tyr Ser Val Thr Val Thr Lys Ser Gly
    1010                1015                1020

Gln Tyr Glu Ala Asn Glu Gln Gly Asn Gly Arg Thr Ile Pro Glu
    1025                1030                1035

Pro Val Lys Asp Leu Thr Leu Arg Asn Arg Ser Thr Glu Asp Leu
    1040                1045                1050

His Val Thr Trp Ser Gly Ala Asn Gly Asp Val Asp Gln Tyr Glu
    1055                1060                1065

Ile Gln Leu Leu Phe Asn Asp Met Lys Val Phe Pro Pro Phe His
    1070                1075                1080

Leu Val Asn Thr Ala Thr Glu Tyr Arg Phe Thr Ser Leu Thr Pro
    1085                1090                1095

Gly Arg Gln Tyr Lys Ile Leu Val Leu Thr Ile Ser Gly Asp Val
    1100                1105                1110

Gln Gln Ser Ala Phe Ile Glu Gly Phe Thr Val Pro Ser Ala Val
    1115                1120                1125

Lys Asn Ile His Ile Ser Pro Asn Gly Ala Thr Asp Ser Leu Thr
    1130                1135                1140

Val Asn Trp Thr Pro Gly Gly Gly Asp Val Asp Ser Tyr Thr Val
    1145                1150                1155

Ser Ala Phe Arg His Ser Gln Lys Val Asp Ser Gln Thr Ile Pro
    1160                1165                1170

Lys His Val Phe Glu His Thr Phe His Arg Leu Glu Ala Gly Glu
    1175                1180                1185

Gln Tyr Gln Ile Met Ile Ala Ser Val Ser Gly Ser Leu Lys Asn
    1190                1195                1200

Gln Ile Asn Val Val Gly Arg Thr Val Pro Ala Ser Val Gln Gly
    1205                1210                1215

Val Ile Ala Asp Asn Ala Tyr Ser Ser Tyr Ser Leu Ile Val Ser
    1220                1225                1230

Trp Gln Lys Ala Ala Gly Val Ala Glu Arg Tyr Asp Ile Leu Leu
    1235                1240                1245

Leu Thr Glu Asn Gly Ile Leu Leu Arg Asn Thr Ser Glu Pro Ala
    1250                1255                1260

Thr Thr Lys Gln His Lys Phe Glu Asp Leu Thr Pro Gly Lys Lys
    1265                1270                1275

Tyr Lys Ile Gln Ile Leu Thr Val Ser Gly Gly Leu Phe Ser Lys
    1280                1285                1290

Glu Ala Gln Thr Glu Gly Arg Thr Val Pro Ala Ala Val Thr Asp
    1295                1300                1305

Leu Arg Ile Thr Glu Asn Ser Thr Arg His Leu Ser Phe Arg Trp
    1310                1315                1320

Thr Ala Ser Glu Gly Glu Leu Ser Trp Tyr Asn Ile Phe Leu Tyr
    1325                1330                1335

Asn Pro Asp Gly Asn Leu Gln Glu Arg Ala Gln Val Asp Pro Leu
    1340                1345                1350

Val Gln Ser Phe Ser Phe Gln Asn Leu Leu Gln Gly Arg Met Tyr
```

-continued

```
            1355                1360                1365
Lys Met Val Ile Val Thr His Ser Gly Glu Leu Ser Asn Glu Ser
        1370                1375                1380
Phe Ile Phe Gly Arg Thr Val Pro Ala Ser Val Ser His Leu Arg
        1385                1390                1395
Gly Ser Asn Arg Asn Thr Thr Asp Ser Leu Trp Phe Asn Trp Ser
        1400                1405                1410
Pro Ala Ser Gly Asp Phe Asp Phe Tyr Glu Leu Ile Leu Tyr Asn
        1415                1420                1425
Pro Asn Gly Thr Lys Lys Glu Asn Trp Lys Asp Lys Asp Leu Thr
        1430                1435                1440
Glu Trp Arg Phe Gln Gly Leu Val Pro Gly Arg Lys Tyr Val Leu
        1445                1450                1455
Trp Val Val Thr His Ser Gly Asp Leu Ser Asn Lys Val Thr Ala
        1460                1465                1470
Glu Ser Arg Thr Ala Pro Ser Pro Pro Ser Leu Met Ser Phe Ala
        1475                1480                1485
Asp Ile Ala Asn Thr Ser Leu Ala Ile Thr Trp Lys Gly Pro Pro
        1490                1495                1500
Asp Trp Thr Asp Tyr Asn Asp Phe Glu Leu Gln Trp Leu Pro Arg
        1505                1510                1515
Asp Ala Leu Thr Val Phe Asn Pro Tyr Asn Asn Arg Lys Ser Glu
        1520                1525                1530
Gly Arg Ile Val Tyr Gly Leu Arg Pro Gly Arg Ser Tyr Gln Phe
        1535                1540                1545
Asn Val Lys Thr Val Ser Gly Asp Ser Trp Lys Thr Tyr Ser Lys
        1550                1555                1560
Pro Ile Phe Gly Ser Val Arg Thr Lys Pro Asp Lys Ile Gln Asn
        1565                1570                1575
Leu His Cys Arg Pro Gln Asn Ser Thr Ala Ile Ala Cys Ser Trp
        1580                1585                1590
Ile Pro Pro Asp Ser Asp Phe Asp Gly Tyr Ser Ile Glu Cys Arg
        1595                1600                1605
Lys Met Asp Thr Gln Glu Val Glu Phe Ser Arg Lys Leu Glu Lys
        1610                1615                1620
Glu Lys Ser Leu Leu Asn Ile Met Met Leu Val Pro His Lys Arg
        1625                1630                1635
Tyr Leu Val Ser Ile Lys Val Gln Ser Ala Gly Met Thr Ser Glu
        1640                1645                1650
Val Val Glu Asp Ser Thr Ile Thr Met Ile Asp Arg Pro Pro Pro
        1655                1660                1665
Pro Pro Pro His Ile Arg Val Asn Glu Lys Asp Val Leu Ile Ser
        1670                1675                1680
Lys Ser Ser Ile Asn Phe Thr Val Asn Cys Ser Trp Phe Ser Asp
        1685                1690                1695
Thr Asn Gly Ala Val Lys Tyr Phe Thr Val Val Arg Glu Ala
        1700                1705                1710
Asp Gly Ser Asp Glu Leu Lys Pro Glu Gln Gln His Pro Leu Pro
        1715                1720                1725
Ser Tyr Leu Glu Tyr Arg His Asn Ala Ser Ile Arg Val Tyr Gln
        1730                1735                1740
Thr Asn Tyr Phe Ala Ser Lys Cys Ala Glu Asn Pro Asn Ser Asn
        1745                1750                1755
```

-continued

```
Ser Lys Ser Phe Asn Ile Lys Leu Gly Ala Glu Met Glu Ser Leu
    1760            1765            1770

Gly Gly Lys Cys Asp Pro Thr Gln Gln Lys Phe Cys Asp Gly Pro
    1775            1780            1785

Leu Lys Pro His Thr Ala Tyr Arg Ile Ser Ile Arg Ala Phe Thr
    1790            1795            1800

Gln Leu Phe Asp Glu Asp Leu Lys Glu Phe Thr Lys Pro Leu Tyr
    1805            1810            1815

Ser Asp Thr Phe Phe Ser Leu Pro Ile Thr Thr Glu Ser Glu Pro
    1820            1825            1830

Leu Phe Gly Ala Ile Glu Gly Val Ser Ala Gly Leu Phe Leu Ile
    1835            1840            1845

Gly Met Leu Val Ala Val Val Ala Leu Leu Ile Cys Arg Gln Lys
    1850            1855            1860

Val Ser His Gly Arg Glu Arg Pro Ser Ala Arg Leu Ser Ile Arg
    1865            1870            1875

Arg Asp Arg Pro Leu Ser Val His Leu Asn Leu Gly Gln Lys Gly
    1880            1885            1890

Asn Arg Lys Thr Ser Cys Pro Ile Lys Ile Asn Gln Phe Glu Gly
    1895            1900            1905

His Phe Met Lys Leu Gln Ala Asp Ser Asn Tyr Leu Leu Ser Lys
    1910            1915            1920

Glu Tyr Glu Glu Leu Lys Asp Val Gly Arg Asn Gln Ser Cys Asp
    1925            1930            1935

Ile Ala Leu Leu Pro Glu Asn Arg Gly Lys Asn Arg Tyr Asn Asn
    1940            1945            1950

Ile Leu Pro Tyr Asp Ala Thr Arg Val Lys Leu Ser Asn Val Asp
    1955            1960            1965

Asp Asp Pro Cys Ser Asp Tyr Ile Asn Ala Ser Tyr Ile Pro Gly
    1970            1975            1980

Asn Asn Phe Arg Arg Glu Tyr Ile Val Thr Gln Gly Pro Leu Pro
    1985            1990            1995

Gly Thr Lys Asp Asp Phe Trp Lys Met Val Trp Glu Gln Asn Val
    2000            2005            2010

His Asn Ile Val Met Val Thr Gln Cys Val Glu Lys Gly Arg Val
    2015            2020            2025

Lys Cys Asp His Tyr Trp Pro Ala Asp Gln Asp Ser Leu Tyr Tyr
    2030            2035            2040

Gly Asp Leu Ile Leu Gln Met Leu Ser Glu Ser Val Leu Pro Glu
    2045            2050            2055

Trp Thr Ile Arg Glu Phe Lys Ile Cys Gly Glu Glu Gln Leu Asp
    2060            2065            2070

Ala His Arg Leu Ile Arg His Phe His Tyr Thr Val Trp Pro Asp
    2075            2080            2085

His Gly Val Pro Glu Thr Thr Gln Ser Leu Ile Gln Phe Val Arg
    2090            2095            2100

Thr Val Arg Asp Tyr Ile Asn Arg Ser Pro Gly Ala Gly Pro Thr
    2105            2110            2115

Val Val His Cys Ser Ala Gly Val Gly Arg Thr Gly Thr Phe Ile
    2120            2125            2130

Ala Leu Asp Arg Ile Leu Gln Gln Leu Asp Ser Lys Asp Ser Val
    2135            2140            2145
```

```
Asp Ile Tyr Gly Ala Val His Asp Leu Arg Leu His Arg Val His
    2150                2155                2160

Met Val Gln Thr Glu Cys Gln Tyr Val Tyr Leu His Gln Cys Val
    2165                2170                2175

Arg Asp Val Leu Arg Ala Arg Lys Leu Arg Ser Glu Gln Glu Asn
    2180                2185                2190

Pro Leu Phe Pro Ile Tyr Glu Asn Val Asn Pro Glu Tyr His Arg
    2195                2200                2205

Asp Pro Val Tyr Ser Arg His
    2210                2215

<210> SEQ ID NO 9
<211> LENGTH: 6633
<212> TYPE: DNA
<213> ORGANISM: Homo sapiens
<220> FEATURE:
<221> NAME/KEY: misc_feature
<222> LOCATION: (1)..(6633)
<223> OTHER INFORMATION: phosphatidylinositol-3,4,5-trisphosphate-
      dependent Rac exchange factor 1 (PREX1), mRNA

<400> SEQUENCE: 9
```

| | | | | | |
|---|---|---|---|---|---|
| cggcgccgcg | cggccgcgct | agaatggagg | cgcccagcgg | cagcgagccc | ggcggcgacg | 60 |
| gggccgggga | ctgcgcccac | ccggaccccc | gggcccctgg | cgccgcggcg | cccagctccg | 120 |
| gccccggccc | gtgcgcggcc | gcccgggagt | ccgagcgcca | gctgcgcctc | cgcctctgcg | 180 |
| tcctcaacga | gatcttgggc | accgagaggg | actacgtggg | caccttgcgc | ttcttgcagt | 240 |
| cggcattcct | gcatcgcatc | cggcagaacg | tggccgactc | agtggagaag | ggcctcacgg | 300 |
| aggagaatgt | caaggtcctg | ttctcgaaca | tcgaagacat | cctggaagtt | cataaggatt | 360 |
| tcttggccgc | cttggagtat | tgtttacacc | cggagccgca | gtctcagcat | gaacttggga | 420 |
| atgttttctt | aaaattcaag | gacaagttct | gcgtgtacga | ggagtattgc | agcaaccatg | 480 |
| agaaagccct | gaggctgctg | gtggagctga | acaagatccc | taccgtgcgc | gccttccttt | 540 |
| tgagctgcat | gcttctggga | ggccggaaga | ccacggacat | ccctttggaa | ggctacctgt | 600 |
| tgtctccgat | ccagaggatc | tgcaagtacc | cgctcctcct | taaggagctg | gccaagagga | 660 |
| ctcccggcaa | gcacccagac | caccccgcgg | tccagagtgc | cctgcaggcc | atgaagaccg | 720 |
| tttgctccaa | catcaatgag | accaagcggc | agatggagaa | gctggaagcc | ctggagcagc | 780 |
| tgcagtccca | catcgaaggc | tgggagggtt | ccaacctcac | agacatctgc | actcagctcc | 840 |
| tcctgcaagg | gactttgtta | agatctctg | cgggcaacat | ccaggaaagg | gccttcttcc | 900 |
| tcttcgacaa | ccttctcgtc | tactgcaagc | ggaaatccag | ggtcaccggg | agcaagaagt | 960 |
| ccaccaagag | gaccaaatcc | atcaacggct | ccctctacat | cttcagggt | cgaatcaaca | 1020 |
| ctgaagtcat | ggaggtggag | aatgtggaag | atgggacagc | ggattaccat | agcaacggct | 1080 |
| ataccgtcac | caacggctgg | aagatccaca | cacggccaa | gaataagtgg | tttgtctgca | 1140 |
| tggccaagac | ggcagaggag | aagcagaagt | ggctggatgc | catcatccgc | gagcgggagc | 1200 |
| agcgcgagag | cctgaagctg | ggcatggagc | gtgatgccta | cgtcatgatt | gcggagaagg | 1260 |
| gggagaagct | gtaccacatg | atgatgaaca | agaaggtgaa | cctcatcaag | gaccgccgga | 1320 |
| gaaagctgag | cactgtcccc | aagtgctttc | ttggcaatga | gttcgttgcc | tggctcctag | 1380 |
| aaattggtga | atcagcaag | acggaagaag | gagtcaactt | gggccaagcc | ctgttggaga | 1440 |
| atggcatcat | ccaccatgtt | tccgacaagc | accagttcaa | gaatgagcag | gtgatgtatc | 1500 |
| gcttccgcta | cgacgatggc | acctacaagg | cccgaagtga | gctggaggac | atcatgtcca | 1560 |

```
agggtgtgag gctttactgc cgtcttcaca gcctctacac cccggtgatc aaagaccgtg    1620
attaccacct gaagacctac aagtcagtgc ttcccgggag caagctggtg gactggctgc    1680
tggctcaggg agactgccag actcgggagg aggcagtggc gctcggcgtg ggtctgtgca    1740
acaatggctt catgcaccac gtgctggaga gagcgagtt cagggatgag tcccagtact    1800
tccgctttca tgctgacgag gagatggagg ggaccagcag caagaacaaa cagcttcgca    1860
acgacttcaa gctggtggag aacattctgg ccaagcgcct gctgatcctg ccccaggagg    1920
aggactatgg ctttgacatc gaggagaaga acaaggctgt ggtggtgaag tccgtccaga    1980 gggctcgct ggctgaggtg gctggcctgc aggtggggag gaagatctac tccatcaatg    2040
aggacctggt gttcctgcgg ccgttttcag aggtggagtc catcctcaac cagtccttct    2100
gctcccgccg ccctctgcgc ctcctggtgg ccacgaaggc caaagagatc atcaaaatcc    2160
ccgaccagcc ggacacactg tgcttccaga ttcgtggagc tgccccaccg tacgtctatg    2220
ctgtggggag aggctctgag gccatggctg cagggctctg tgctggtcag tgcattctga    2280
aggtcaatgg cagcaacgtg atgaacgatg gtgcccctga ggtcctggag cacttccagg    2340
cattccggag tcggcgcgaa gaggccctgg gcctgtacca gtggatctac cacacccatg    2400
aggatgccca ggaagcacga gccagtcagg aggcctccac tgaggacccc agtggcgagc    2460
aggcccagga ggaagaccag gctgattcag ccttcccact gctgtccctg ggtccccggc    2520
tgagcctgtg tgaggacagc cccatggtca ccctgactgt ggacaacgtg cacctggaac    2580
acggcgtggt gtatgagtat gtgagcacgg caggcgtcag gtgccatgtg ctggagaaga    2640
tcgtggagcc ccgcggctgc ttcggcctca ccgccaagat cctcgaggcc tttgctgcca    2700 atgacacgcgt cttcgtggag aactgcaggc ggctcatggc cctgagcagc gccatcgtga    2760
ccatgcccca ctttgagttc cgcaacatct gtgacaccaa gctggagagc attggccaga    2820
ggattgcctg ctaccaggag tttgcagccc aactgaagag cagggtcagc ccacccttca    2880
aacaagcccc cctggagccc cacccgctgt gtggcctgga cttctgcccc accaattgcc    2940
acatcaacct catggaagtg tcctaccccca agaccacccc ctcagtgggc aggtccttca    3000
gcatccgctt tggacgcaaa ccctccctca tcggccttga cccggagcaa ggccacctga    3060
accccatgtc gtacacccag cactgcatca ccaccatggc tgctccctcc tggaagtgct    3120
tgcctgctgc agagggtgat ccccaaggcc agggtctcca tgatggcagc ttcgggccag    3180
ccagtgggac ccttggtcag gaagaccggg gcctcagctt cctactcaag caggaggacc    3240
gtgagatcca ggatgcctac ctgcagctct tcaccaagct ggatgtggcc ctgaaggaga    3300
tgaagcaata tgtcacccag atcaacaggc tgctgtccac catcacagag cccacctcgg    3360
gtgggtcctg cgacgcatcc ttggctgagg aggcctcctc cctgccctg gtcagtgaag    3420 agagcgagat ggacaggagt gaccatgggg gcatcaagaa ggtgtgcttc aaggtggccg    3480
aggaggacca ggaggactca ggccacgaca ccatgagtta tcgcgactcc tacagcgagt    3540
gtaacagcaa tcgagactcg gtcctgtcct acaccagcgt gagaagtaac agctcctact    3600
tgggcagcga cgagatgggg tctggagatg agctgccctg tgacatgcgg atcccatctg    3660
acaagcagga caagcttcat ggctgcctgg agcacctctt taaccaggtg gactccatca    3720
atgctctcct caaggggcca gtcatgagcc gggctttcga agagaccaag catttcccta    3780
tgaaccacag cttacaagag tttaaacaga aagaagagtg tacaatccgt ggccggagcc    3840
tgatccagat tagcatccag gaggaccccct ggaacctccc caactccatc aagaccctgg    3900
```

```
tggacaacat tcagagatat gtggaagatg ggaagaacca gctgctcctg gccttgctga    3960
agtgcacaga cacggagctg cagctgcgca gagacgcgat cttctgccag gccctggtgg    4020
ccgccgtgtg caccttctcc gagcagctgc tggcggccct gggctaccgc tacaacaaca    4080
atggcgagta cgaggagagc agccgcgacg ccagccgcaa gtggctggag caggtggcgg    4140
ccacgggcgt cctgctgcac tgccagtccc tgctctcgcc agccacagtg aaggaggaac    4200
ggaccatgct ggaggacatc tggggtgacgc tgtcagagct ggacaatgtc accttctcct    4260
ttaagcagct ggacgagaac tatgtggcca acaccaacgt cttctaccac attgagggca    4320
gccggcaggc gctgaaggtc atcttctacc tcgacagcta ccacttctcc aagctgccct    4380
cccgcctgga gggtggggcc agcctgaggc tgcacacagc gctgttcacg aaagtgctgg    4440
agaacgtgga ggggctgcct ctccaggca gccaggccgc ggaggatttg cagcaggaca    4500
tcaacgcgca gtccctggag aaagttcagc agtattaccg caaactcagg gcattttacc    4560
tggagcggtc taacctgccc acggatgcca gcaccacggc ggtaaagata gaccagctga    4620
tccgccccat caatgccctg gatgagctct gccgcctcat gaagtccttt gtccacccaa    4680
agcctggtgc tgctgggagt gtgggcgccg cctcatccc catctcctcg gagctctgct    4740
accgcctggg ggcctgccag atggtcatgt gtggcacagg catgcagagg agcaccctga    4800
gcgtgtccct ggagcaggcg gccatcttgg cacggagcca cgggttgctg cccaagtgca    4860
tcatgcaggc cacggacatc atgcggaagc agggcccaag ggtggagatt ctggccaaaa    4920
acctgcgagt caaggaccag atgcccagg gtgctccgcg cctctaccgc ctctgccagc    4980
cgccggtgga tggggacctc tgaacaccca aatgccccac gctgggccgc ggcctctgga    5040
gctgggattt gggaggacac agcaggcagc gctggccttc tccagggatg cccaaggct    5100
tccgcagccg cccgttccgg gacctgccca gcgtcctccc tgcctccttc cgggacaagc    5160
ctggccaccc tcgctgtgat gacgagctgg ctgattggcc ctgggccggc ccattcttca    5220
cacgcctgcc agaagctgga ggggtgctgg agacccatag agctgatggg agcagctggt    5280
gcctggcctt cggctcctgc gtccccagaa cccaagggaa cgtcatggag gccacatggg    5340
gccaccggc tccctcggga tggctccgcc tgcactttg aaaccccggt ttccttcaac    5400
gtccacattc caggtgacca cacgtgtctc ctcctcctca tcttagcttc caggttcacc    5460
ctaaccctgt actaacctgc ttggtggact tggaaaagac ttggctctgt cgggaaagga    5520
gagacggggc ctccatcacg cctgttacca gaggatcccc gagagccaca ccagctctgg    5580
acatcaccgc ccctggaact ggggccacca gccctgggca cgagatttgc tctgactttta   5640
tttatatggc atgaaatctc tggtttatt tgggatttt tgttgttggt gttgtcaaag    5700
tttgtttttt ctaaagttgt gtgattatat atttgacatt ttacatttca aagaaaggta    5760
tgttgtctaa caggggacca acagaaggta gtattgacaa ctgttcctgc ttctactaaa    5820
aaaaaaagag cacaaagaa aaactaaatt attgaaaaat taaaaaatgt cattgtttcc    5880
tgtttgttaa tattagggtt gtaaggtgtc gttttgaggt atcgactgtg attccttccc    5940
ccacccctcca ttctccagcg gttggccggt gttagaactc gctctctttg agtgactggc    6000
tacaagggcc tgagaggtgg ccagccaggg ttggagctgg aggggatgga gccccacctg    6060
aggtgccgtg tcacacgggt tagagggtca ctgggaaaca ccgggcggtg gcttctgtga    6120
tttattttct tgatggtaac ttctcagagc agggcgattg gacatcacc agccagagca    6180
caggaagcca ccctgcctgc tggggaggag ggacccacac aagcccccctc ggcagtttgt    6240
cccccccagct tcggtatgcc ttcagggaaa ggtcacagct ggggaggaag cgggggggacg    6300
```

```
cctgtcaccc ctggcaggtg gtgagttcag gtgggggctc cctgctgccc ccaggcctgg    6360
gagcttgaag ccctcccggc atctggcatc cgagcctccc gccctccagg gtgcgcttcc    6420
ctctcttgcc gcagcataca cgagggcagg cagtggcctt gtcactgtat cttgcatcag    6480
agacaaagga ggacccgctt tagccctgct gcgggaaatg ggggagggcc cagggccagc    6540
gcattgtgca ctggtttact ttaaaatgta cagattcttc tcgttaaatt cttgatagat    6600
tttttattat tattaaaagt cagtttataa tac                                 6633
```

<210> SEQ ID NO 10
<211> LENGTH: 1659
<212> TYPE: PRT
<213> ORGANISM: Homo sapiens
<220> FEATURE:
<221> NAME/KEY: misc_feature
<222> LOCATION: (1)..(1659)
<223> OTHER INFORMATION: phosphatidylinositol 3,4,5-trisphosphate-
      dependent Rac exchanger 1 protein

<400> SEQUENCE: 10

```
Met Glu Ala Pro Ser Gly Ser Glu Pro Gly Gly Asp Gly Ala Gly Asp
1               5                   10                  15

Cys Ala His Pro Asp Pro Arg Ala Pro Gly Ala Ala Ala Pro Ser Ser
                20                  25                  30

Gly Pro Gly Pro Cys Ala Ala Ala Arg Glu Ser Glu Arg Gln Leu Arg
            35                  40                  45

Leu Arg Leu Cys Val Leu Asn Glu Ile Leu Gly Thr Glu Arg Asp Tyr
        50                  55                  60

Val Gly Thr Leu Arg Phe Leu Gln Ser Ala Phe Leu His Arg Ile Arg
65                  70                  75                  80

Gln Asn Val Ala Asp Ser Val Glu Lys Gly Leu Thr Glu Glu Asn Val
                85                  90                  95

Lys Val Leu Phe Ser Asn Ile Glu Asp Ile Leu Glu Val His Lys Asp
            100                 105                 110

Phe Leu Ala Ala Leu Glu Tyr Cys Leu His Pro Glu Pro Gln Ser Gln
        115                 120                 125

His Glu Leu Gly Asn Val Phe Leu Lys Phe Lys Asp Lys Phe Cys Val
    130                 135                 140

Tyr Glu Glu Tyr Cys Ser Asn His Glu Lys Ala Leu Arg Leu Leu Val
145                 150                 155                 160

Glu Leu Asn Lys Ile Pro Thr Val Arg Ala Phe Leu Leu Ser Cys Met
                165                 170                 175

Leu Leu Gly Gly Arg Lys Thr Thr Asp Ile Pro Leu Glu Gly Tyr Leu
            180                 185                 190

Leu Ser Pro Ile Gln Arg Ile Cys Lys Tyr Pro Leu Leu Leu Lys Glu
        195                 200                 205

Leu Ala Lys Arg Thr Pro Gly Lys His Pro Asp His Pro Ala Val Gln
    210                 215                 220

Ser Ala Leu Gln Ala Met Lys Thr Val Cys Ser Asn Ile Asn Glu Thr
225                 230                 235                 240

Lys Arg Gln Met Glu Lys Leu Glu Ala Leu Glu Gln Leu Gln Ser His
                245                 250                 255

Ile Glu Gly Trp Glu Gly Ser Asn Leu Thr Asp Ile Cys Thr Gln Leu
            260                 265                 270

Leu Leu Gln Gly Thr Leu Leu Lys Ile Ser Ala Gly Asn Ile Gln Glu
        275                 280                 285
```

-continued

Arg Ala Phe Phe Leu Phe Asp Asn Leu Leu Val Tyr Cys Lys Arg Lys
290                 295                 300

Ser Arg Val Thr Gly Ser Lys Lys Ser Thr Lys Arg Thr Lys Ser Ile
305                 310                 315                 320

Asn Gly Ser Leu Tyr Ile Phe Arg Gly Arg Ile Asn Thr Glu Val Met
                325                 330                 335

Glu Val Glu Asn Val Glu Asp Gly Thr Ala Asp Tyr His Ser Asn Gly
                340                 345                 350

Tyr Thr Val Thr Asn Gly Trp Lys Ile His Asn Thr Ala Lys Asn Lys
                355                 360                 365

Trp Phe Val Cys Met Ala Lys Thr Ala Glu Glu Lys Gln Lys Trp Leu
370                 375                 380

Asp Ala Ile Ile Arg Glu Arg Glu Gln Arg Glu Ser Leu Lys Leu Gly
385                 390                 395                 400

Met Glu Arg Asp Ala Tyr Val Met Ile Ala Glu Lys Gly Glu Lys Leu
                405                 410                 415

Tyr His Met Met Met Asn Lys Lys Val Asn Leu Ile Lys Asp Arg Arg
                420                 425                 430

Arg Lys Leu Ser Thr Val Pro Lys Cys Phe Leu Gly Asn Glu Phe Val
                435                 440                 445

Ala Trp Leu Leu Glu Ile Gly Glu Ile Ser Lys Thr Glu Glu Gly Val
450                 455                 460

Asn Leu Gly Gln Ala Leu Leu Glu Asn Gly Ile Ile His His Val Ser
465                 470                 475                 480

Asp Lys His Gln Phe Lys Asn Glu Gln Val Met Tyr Arg Phe Arg Tyr
                485                 490                 495

Asp Asp Gly Thr Tyr Lys Ala Arg Ser Glu Leu Glu Asp Ile Met Ser
                500                 505                 510

Lys Gly Val Arg Leu Tyr Cys Arg Leu His Ser Leu Tyr Thr Pro Val
                515                 520                 525

Ile Lys Asp Arg Asp Tyr His Leu Lys Thr Tyr Lys Ser Val Leu Pro
530                 535                 540

Gly Ser Lys Leu Val Asp Trp Leu Leu Ala Gln Gly Asp Cys Gln Thr
545                 550                 555                 560

Arg Glu Glu Ala Val Ala Leu Gly Val Gly Leu Cys Asn Asn Gly Phe
                565                 570                 575

Met His His Val Leu Glu Lys Ser Glu Phe Arg Asp Glu Ser Gln Tyr
                580                 585                 590

Phe Arg Phe His Ala Asp Glu Glu Met Glu Gly Thr Ser Ser Lys Asn
                595                 600                 605

Lys Gln Leu Arg Asn Asp Phe Lys Leu Val Glu Asn Ile Leu Ala Lys
610                 615                 620

Arg Leu Leu Ile Leu Pro Gln Glu Glu Asp Tyr Gly Phe Asp Ile Glu
625                 630                 635                 640

Glu Lys Asn Lys Ala Val Val Val Lys Ser Val Gln Arg Gly Ser Leu
                645                 650                 655

Ala Glu Val Ala Gly Leu Gln Val Gly Arg Lys Ile Tyr Ser Ile Asn
                660                 665                 670

Glu Asp Leu Val Phe Leu Arg Pro Phe Ser Glu Val Glu Ser Ile Leu
                675                 680                 685

Asn Gln Ser Phe Cys Ser Arg Arg Pro Leu Arg Leu Leu Val Ala Thr
690                 695                 700

```
Lys Ala Lys Glu Ile Ile Lys Ile Pro Asp Gln Pro Asp Thr Leu Cys
705                 710                 715                 720

Phe Gln Ile Arg Gly Ala Ala Pro Pro Tyr Val Tyr Ala Val Gly Arg
            725                 730                 735

Gly Ser Glu Ala Met Ala Ala Gly Leu Cys Ala Gly Gln Cys Ile Leu
            740                 745                 750

Lys Val Asn Gly Ser Asn Val Met Asn Asp Gly Ala Pro Glu Val Leu
            755                 760                 765

Glu His Phe Gln Ala Phe Arg Ser Arg Glu Gln Ala Leu Gly Leu
770                 775                 780

Tyr Gln Trp Ile Tyr His Thr His Glu Asp Ala Gln Glu Ala Arg Ala
785                 790                 795                 800

Ser Gln Glu Ala Ser Thr Glu Asp Pro Ser Gly Glu Gln Ala Gln Glu
            805                 810                 815

Glu Asp Gln Ala Asp Ser Ala Phe Pro Leu Leu Ser Leu Gly Pro Arg
            820                 825                 830

Leu Ser Leu Cys Glu Asp Ser Pro Met Val Thr Leu Thr Val Asp Asn
            835                 840                 845

Val His Leu Glu His Gly Val Val Tyr Glu Tyr Val Ser Thr Ala Gly
            850                 855                 860

Val Arg Cys His Val Leu Glu Lys Ile Val Glu Pro Arg Gly Cys Phe
865                 870                 875                 880

Gly Leu Thr Ala Lys Ile Leu Glu Ala Phe Ala Ala Asn Asp Ser Val
            885                 890                 895

Phe Val Glu Asn Cys Arg Arg Leu Met Ala Leu Ser Ser Ala Ile Val
            900                 905                 910

Thr Met Pro His Phe Glu Phe Arg Asn Ile Cys Asp Thr Lys Leu Glu
            915                 920                 925

Ser Ile Gly Gln Arg Ile Ala Cys Tyr Gln Glu Phe Ala Ala Gln Leu
            930                 935                 940

Lys Ser Arg Val Ser Pro Pro Phe Lys Gln Ala Pro Leu Glu Pro His
945                 950                 955                 960

Pro Leu Cys Gly Leu Asp Phe Cys Pro Thr Asn Cys His Ile Asn Leu
            965                 970                 975

Met Glu Val Ser Tyr Pro Lys Thr Thr Pro Ser Val Gly Arg Ser Phe
            980                 985                 990

Ser Ile Arg Phe Gly Arg Lys Pro Ser Leu Ile Gly Leu Asp Pro Glu
            995                 1000                1005

Gln Gly His Leu Asn Pro Met Ser Tyr Thr Gln His Cys Ile Thr
            1010                1015                1020

Thr Met Ala Ala Pro Ser Trp Lys Cys Leu Pro Ala Ala Glu Gly
            1025                1030                1035

Asp Pro Gln Gly Gln Gly Leu His Asp Gly Ser Phe Gly Pro Ala
            1040                1045                1050

Ser Gly Thr Leu Gly Gln Glu Asp Arg Gly Leu Ser Phe Leu Leu
            1055                1060                1065

Lys Gln Glu Asp Arg Glu Ile Gln Asp Ala Tyr Leu Gln Leu Phe
            1070                1075                1080

Thr Lys Leu Asp Val Ala Leu Lys Glu Met Lys Gln Tyr Val Thr
            1085                1090                1095

Gln Ile Asn Arg Leu Leu Ser Thr Ile Thr Glu Pro Thr Ser Gly
            1100                1105                1110

Gly Ser Cys Asp Ala Ser Leu Ala Glu Glu Ala Ser Ser Leu Pro
```

```
            1115                1120                1125

Leu Val Ser Glu Ser Glu Met Asp Arg Ser His Gly Gly
    1130                1135                1140

Ile Lys Lys Val Cys Phe Lys Val Ala Glu Glu Gln Glu Asp
    1145                1150                1155

Ser Gly His Asp Thr Met Ser Tyr Arg Asp Ser Tyr Ser Glu Cys
    1160                1165                1170

Asn Ser Asn Arg Asp Ser Val Leu Ser Tyr Thr Ser Val Arg Ser
    1175                1180                1185

Asn Ser Ser Tyr Leu Gly Ser Asp Glu Met Gly Ser Gly Asp Glu
    1190                1195                1200

Leu Pro Cys Asp Met Arg Ile Pro Ser Asp Lys Gln Asp Lys Leu
    1205                1210                1215

His Gly Cys Leu Glu His Leu Phe Asn Gln Val Asp Ser Ile Asn
    1220                1225                1230

Ala Leu Leu Lys Gly Pro Val Met Ser Arg Ala Phe Glu Glu Thr
    1235                1240                1245

Lys His Phe Pro Met Asn His Ser Leu Gln Glu Phe Lys Gln Lys
    1250                1255                1260

Glu Glu Cys Thr Ile Arg Gly Arg Ser Leu Ile Gln Ile Ser Ile
    1265                1270                1275

Gln Glu Asp Pro Trp Asn Leu Pro Asn Ser Ile Lys Thr Leu Val
    1280                1285                1290

Asp Asn Ile Gln Arg Tyr Val Glu Asp Gly Lys Asn Gln Leu Leu
    1295                1300                1305

Leu Ala Leu Leu Lys Cys Thr Asp Thr Glu Leu Gln Leu Arg Arg
    1310                1315                1320

Asp Ala Ile Phe Cys Gln Ala Leu Val Ala Ala Val Cys Thr Phe
    1325                1330                1335

Ser Glu Gln Leu Leu Ala Ala Leu Gly Tyr Arg Tyr Asn Asn Asn
    1340                1345                1350

Gly Glu Tyr Glu Glu Ser Ser Arg Asp Ala Ser Arg Lys Trp Leu
    1355                1360                1365

Glu Gln Val Ala Ala Thr Gly Val Leu Leu His Cys Gln Ser Leu
    1370                1375                1380

Leu Ser Pro Ala Thr Val Lys Glu Glu Arg Thr Met Leu Glu Asp
    1385                1390                1395

Ile Trp Val Thr Leu Ser Glu Leu Asp Asn Val Thr Phe Ser Phe
    1400                1405                1410

Lys Gln Leu Asp Glu Asn Tyr Val Ala Asn Thr Asn Val Phe Tyr
    1415                1420                1425

His Ile Glu Gly Ser Arg Gln Ala Leu Lys Val Ile Phe Tyr Leu
    1430                1435                1440

Asp Ser Tyr His Phe Ser Lys Leu Pro Ser Arg Leu Glu Gly Gly
    1445                1450                1455

Ala Ser Leu Arg Leu His Thr Ala Leu Phe Thr Lys Val Leu Glu
    1460                1465                1470

Asn Val Glu Gly Leu Pro Ser Pro Gly Ser Gln Ala Ala Glu Asp
    1475                1480                1485

Leu Gln Gln Asp Ile Asn Ala Gln Ser Leu Glu Lys Val Gln Gln
    1490                1495                1500

Tyr Tyr Arg Lys Leu Arg Ala Phe Tyr Leu Glu Arg Ser Asn Leu
    1505                1510                1515
```

```
Pro Thr Asp Ala Ser Thr Thr Ala Val Lys Ile Asp Gln Leu Ile
    1520                1525                1530

Arg Pro Ile Asn Ala Leu Asp Glu Leu Cys Arg Leu Met Lys Ser
    1535                1540                1545

Phe Val His Pro Lys Pro Gly Ala Ala Gly Ser Val Gly Ala Gly
    1550                1555                1560

Leu Ile Pro Ile Ser Ser Glu Leu Cys Tyr Arg Leu Gly Ala Cys
    1565                1570                1575

Gln Met Val Met Cys Gly Thr Gly Met Gln Arg Ser Thr Leu Ser
    1580                1585                1590

Val Ser Leu Glu Gln Ala Ala Ile Leu Ala Arg Ser His Gly Leu
    1595                1600                1605

Leu Pro Lys Cys Ile Met Gln Ala Thr Asp Ile Met Arg Lys Gln
    1610                1615                1620

Gly Pro Arg Val Glu Ile Leu Ala Lys Asn Leu Arg Val Lys Asp
    1625                1630                1635

Gln Met Pro Gln Gly Ala Pro Arg Leu Tyr Arg Leu Cys Gln Pro
    1640                1645                1650

Pro Val Asp Gly Asp Leu
    1655

<210> SEQ ID NO 11
<211> LENGTH: 5980
<212> TYPE: DNA
<213> ORGANISM: Homo sapiens
<220> FEATURE:
<221> NAME/KEY: misc_feature
<222> LOCATION: (1)..(5980)
<223> OTHER INFORMATION: cortactin binding protein 2 (CTTNBP2), mRNA

<400> SEQUENCE: 11
ggacagcagc gggttaagtg ccgcccgcgc ggagacggct gagtccggag ccgcggctcc      60
gagctcgcat tcggatccgc tagagcagga agatggcgac ggacggcgcg agctgcgagc    120
ccgacttgtc ccgggccccg gaggacgcgg cggggccgc gcggaggcg gcgaaaaaag      180 agtttgatgt ggatactctc agtaaatccg agctgcggat gctcctcagc gtgatggaag    240
gggagctgga ggccagagac cttgtcatcg aggccctgcg ggctcgcagg aaggaggtat    300
ttatccagga acgtatggga agattaatc aaatgaccc gttcctggca ctccagagag      360
actatgaagc aggtgctggt gacaagagaa gaagccagt ttgtaccaac cccctctcca     420
tccttgaagc agtcatggcc cactgcaaga aaatgcaaga aaggatgtcc gcacagctgg    480
ctgctgctga gagcagacaa aagaagctgg aaatggagaa gcttcagcta caagcccttg    540
agcaagagca caagaagctg gctgcccgcc ttgaggaaga gcgtggcaag aacaagcagg    600
tggtcctgat gctggtcaaa gagtgcaagc agctctcagg caaagtcata gaggaggccc    660
agaagctcga agacgtaatg gccaaactgg aagaggaaaa gaaaaagacg aatgaattag    720
aagaggaact ctccgctgag aaacgaagaa gcacagaaat ggaagctcag atggaaaaac    780
aactctctga gtttgacact gagcgggaac agcttcgtgc caagctgaac cgggaagaag    840
cacacaccac tgacctcaaa gaggagatag acaagatgag gaaaatgatt gagcaactga    900
aaaggggaag tgacagcaaa ccaagcctct ctcttccacg aagacaaaaa gataggcgtt    960
tggtttccat atctgtggga acagaaggaa ctgtgacaag gtctgttgca tgccagacag   1020
acctagtgac agaaaatgct gaccacatga aaaagttgcc tttaaccatg cctgtaaaac   1080
```

```
cttccacagg gagtcccta gtttctgcaa atgcaaaagg gagcgtgtgc accagtgcca    1140
ccatggccag accaggtatt gacaggcagg cttcctatgg tgacttgatt ggcgcttctg    1200
tacccgcttt cccacctcca agtgcaaaca aaattgagga aaatggacca agcactggct    1260
caacaccaga tccaaccagt agcacacccc cacttcccag taacgctgcc cctcccaccg    1320
ctcaaacacc aggcatagct cctcagaact cgcaagctcc acctatgcac agtttacatt    1380
caccatgtgc caacacctct ttgcatccag gtctaaaccc acgaatccaa gcagctagat    1440
ttagatttca gggcaatgct aacgacccag accaaaatgg aaatactacc caaagtcctc    1500
cgtcaagaga tgtctcgcct acaagtcgtg acaacctagt ggccaaacaa ctagctcgga    1560
atactgtgac ccaagcactg tcaagattta caagccctca agcaggtgct ccctcaaggc    1620
ctggagtgcc cccaacaggg gatgttggca cccaccctcc agttggtcgg accagtttaa    1680
agactcatgg tgtagcacga gttgacagag gaaatcctcc tcctatccct ccaaaaaagc    1740
cagggctctc ccaaactcct tctccaccac accccaact caaggttatt atagacagca    1800
gcagggcctc gaacacaggg gccaaagttg ataacaaaac tgtggcttcg actccttcca    1860
gtttgccaca agggaacagg gtgatcaatg aggagaacct tcctaagtca tcctcccctc    1920
agctgccacc aaaaccatcc atagatttaa ctgtggcacc tgcaggctgt gccgtttcag    1980
ccctggccac gtctcaggtg ggtgcctggc ctgctgcaac cccggactg aaccaacctg    2040 catgttcaga cagttccctt gtcattccta ccaccattgc cttttgctct tccataaacc    2100
ccgttagtgc ctcatcctgt agaccaggtg cctcagacag cctcctggta acagcatcag    2160
gctggtcacc ctccctaacc cctttgctaa tgagtggtgg tcctgccccc ctggctggca    2220
ggcccaccct tcttcagcaa gctgctgccc agggaaatgt cactttatta tcaatgctgc    2280
ttaatgaaga aggactggac attaattact cctgtgaaga tggccattct gccttgtatt    2340
ctgctgctaa gaatggacat acagactgtg tgagattgct gctgagtgca gaagcccaag    2400
tcaatgctgc tgataaaaat ggcttccaca ccttgtgtgc tgcagctgct cagggacatt    2460
tcgagtgtgt agaattatta atttcatatg atgctaacat taatcatgct gctgatggag    2520
gacagacacc tctatacctg gcctgtaaaa atggaaataa agaatgtatt aaactcttgt    2580
tggaagctgg aaccaatcga agtgtaaaaa ccacagatgg ctggacacca gttcacgcag    2640
ctgtggacac tggtaatgtg gacagcctca agcttcttat gtaccataga ataccagctc    2700
atggaaattc tttcaatgag gaggagtccg agtcaagtgt ctttgacttg gatggaggag    2760
aagagagtcc tgaaggcata tccaagcctg ttgttcctgc agacctcatt aaccacgcca    2820
acagagaagg ctggactgct gcccacattg ctgcttccaa aggttttaag aactgcctag    2880
aaatcttgtg taggcacgga gggcttgagc cagaaaggag agacaagtgc aatcggactg    2940
tgcatgatgt tgccactgat gactgcaagc atttgctgga aatctgaat gctcttaaaa    3000 tacccttaag gatttcagtg ggtgagattg aaccaagcaa ctatggttct gatgacttgg    3060
aatgtgaaaa cacaatatgt gctttaaata tccgcaaaca gacatcatgg gatgattttt    3120
caaaagcagt gagtcaagct ctgacaaatc atttccaggc aatctcttct gatggatggt    3180
ggagtctgga agacgtgact tgcaataaca ccactgattc caacatcggc ctcagtgcaa    3240
gaagcatacg atccatcacg ctaggaaatg tgccgtggtc agtgggtcag agcttcgcgc    3300
agtccccgtg ggactttatg aggaagaata aggcagagca catcactgtg cttttgtcag    3360
gtcctcaaga aggctgtctc agtagtgtga cttatgcctc catgatccct tccagatga    3420 tgcagaacta cctcaggctg gttgagcaat atcataatgt cattttccac ggcccagaag    3480
```

```
gaagcttgca agactacata gtacatcagc ttgcactctg cctgaagcac agacaaatgg   3540
ctgcaggatt ctcctgtgaa atagtgagag ctgaagtaga tgctggtttt tccaaggaac   3600
agctactaga cctgttcatt agtagcgctt gtctgatccc agtgaaacaa tctcccagta   3660
agaagaaaat catcatcatt ttagaaaatt tagaaaaatc ttcactgtcg gagttattga   3720 gggactttt ggcacctctt gaaaatcgca gcactgaaag cccctgcact ttccaaaaag   3780
gaaatggact gtccgaatgt tattactttc atgagaactg ctttctgatg gaaccatcg    3840 ccaaggcctg tctccagggc tccgacttgc tggtgcagca gcatttccgc tgggtgcagc   3900
tgcggtggga tggcgagccc atgcaaggac tgctgcagag gttcttacga aggaaagttg   3960
tgaataagtt caaaggtcag gcgccctccc cctgcgatcc tgtgtgcaag attgtcgact   4020
gggctctgtc cgtctggcgt cagcttaact cctgcctggc ccgcttgggc cacctgaag    4080 cacttcttgg accaaaatat ttcctgtctt gtcctgtagt tcctgggcat gcccaagtga   4140
cagtgaagtg gatgtctaag ctgtggaatg cgtcatcgc acccagagtt caagaagcaa    4200
tattgtcaag agcctctgtg aaaagacaac ctggctttgg gcagacaact gctaaaagac   4260
accctagcca aggacagcag gctgtggtca aagctgctct cagcatcttg ctaaataaag   4320
ctgtactgca tggctgtccc ctccccagag cagagctaga ccagcataca gctgatttca   4380
aaggaggaag tttcccttta tccatagttt ccagttataa cacttgtaac aagaagaaag   4440
gagagagtgg tgcctggaga aggtgaaca ccagtcctcg caggaagtct ggccgcttct     4500
ctttacccac ctggaataag ccagacctaa gcactgaagg tatgaaaaat aagactatat   4560
cacagctgaa ttgtaacagg aatgcttctc tgtcaaaaca aaagtcttta gagaatgatc   4620
tatcactgac gttgaatttg gatcagagac tctctctggg ttcagatgac gaagcagatc   4680
ttgtcaagga acttcagagc atgtgctcca gcaagtctga gtctgatatc agcaagattg   4740
ctgattccag ggatgattta aggatgtttg atagttctgg aaacaaccct gtactttcag   4800
caactattaa taatctgaga atgccagtgt cacaaaagga ggtcagtcct ctcagcagcc   4860
atcaaactac tgaatgcagc aacagtaaat caaagactga gttgggtgtt tcaagagtta   4920
aatcttttct tcctgttcct agaagtaaag tcacccagtg ttcccagaac accaaaagaa   4980
gcagcagcag cagtaataca aggcaaatag aaatcaacaa caactcaaaa gaagtgaatt   5040
ggaacttaca caaaaatgaa cacctagaaa aacctaacaa ataggcctgc ctacaatatt   5100
ctcattatta acttcctcta tttcacacag aaaccaagga caacaagata caaatacctt   5160
taaattgata aaatgttttc actgtaatat aaattatgag tgcgggacca ctattcaatt   5220
tttttttgta aagaatgtat ttataaccaa catttgttg cttttttttt taattctgta    5280
ggattgaact tcaataccag gaagttatgc caacttttca agtagtttta aatagaaaa    5340 attgtaatag ttttaatcaa gatgttcagg ggtattaaaa cagaactgtg tactgtatat   5400
ctgtatatat gtatatatgt atgtatattt aaggaagtcc agaaatcata ctgcatacat   5460
gctacaaaaa agtagcaaaa aagtacaaag ttggcttaga taacttgtac cattttaaat   5520
ggagatcata attttatgtt cacttgatgg ggaatgacta gaatggggca ataacaaatc   5580
atttctaaac agttattttc cattaaaagc catattaagt attttgcttg ttaaattcta    5640
gttttatgtt ttaaatctct tagtggttac attgccattt ggtagcatca tgtatatatt    5700
tatgcttata agtttgcatt atgactcctg taaaatatga aattataatg caataaaagt    5760
gttatctttc ttacaaaagt tttgtaccta agtggatata gataactgca taaatgaata   5820
```

-continued

```
aattcagaat taactccttc aatatttcta gtagcacaac tgataatatt gatattttct    5880
acaaatgtta cttctaaaat tacagacaaa attacttaca caattcagtt aagatgcttt    5940
gacactgaat aaaatattga tttcatgaaa aaaaaaaaaa                          5980
```

<210> SEQ ID NO 12
<211> LENGTH: 1663
<212> TYPE: PRT
<213> ORGANISM: Homo sapiens
<220> FEATURE:
<221> NAME/KEY: misc_feature
<222> LOCATION: (1)..(1663)
<223> OTHER INFORMATION: cortactin-binding protein 2

<400> SEQUENCE: 12

```
Met Ala Thr Asp Gly Ala Ser Cys Glu Pro Asp Leu Ser Arg Ala Pro
1               5                   10                  15

Glu Asp Ala Ala Gly Ala Ala Ala Glu Ala Ala Lys Lys Glu Phe Asp
            20                  25                  30

Val Asp Thr Leu Ser Lys Ser Glu Leu Arg Met Leu Leu Ser Val Met
        35                  40                  45

Glu Gly Glu Leu Glu Ala Arg Asp Leu Val Ile Glu Ala Leu Arg Ala
    50                  55                  60

Arg Arg Lys Glu Val Phe Ile Gln Glu Arg Tyr Gly Arg Phe Asn Leu
65                  70                  75                  80

Asn Asp Pro Phe Leu Ala Leu Gln Arg Asp Tyr Glu Ala Gly Ala Gly
                85                  90                  95

Asp Lys Glu Lys Lys Pro Val Cys Thr Asn Pro Leu Ser Ile Leu Glu
            100                 105                 110

Ala Val Met Ala His Cys Lys Lys Met Gln Glu Arg Met Ser Ala Gln
        115                 120                 125

Leu Ala Ala Ala Glu Ser Arg Gln Lys Lys Leu Glu Met Glu Lys Leu
    130                 135                 140

Gln Leu Gln Ala Leu Glu Gln Glu His Lys Lys Leu Ala Ala Arg Leu
145                 150                 155                 160

Glu Glu Glu Arg Gly Lys Asn Lys Gln Val Val Leu Met Leu Val Lys
                165                 170                 175

Glu Cys Lys Gln Leu Ser Gly Lys Val Ile Glu Glu Ala Gln Lys Leu
            180                 185                 190

Glu Asp Val Met Ala Lys Leu Glu Glu Lys Lys Thr Asn Glu
        195                 200                 205

Leu Glu Glu Glu Leu Ser Ala Glu Lys Arg Arg Ser Thr Glu Met Glu
    210                 215                 220

Ala Gln Met Glu Lys Gln Leu Ser Glu Phe Asp Thr Glu Arg Glu Gln
225                 230                 235                 240

Leu Arg Ala Lys Leu Asn Arg Glu Glu Ala His Thr Thr Asp Leu Lys
                245                 250                 255

Glu Glu Ile Asp Lys Met Arg Lys Met Ile Glu Gln Leu Lys Arg Gly
            260                 265                 270

Ser Asp Ser Lys Pro Ser Leu Ser Leu Pro Arg Lys Thr Lys Asp Arg
        275                 280                 285

Arg Leu Val Ser Ile Ser Val Gly Thr Glu Gly Thr Val Thr Arg Ser
    290                 295                 300

Val Ala Cys Gln Thr Asp Leu Val Thr Glu Asn Ala Asp His Met Lys
305                 310                 315                 320

Lys Leu Pro Leu Thr Met Pro Val Lys Pro Ser Thr Gly Ser Pro Leu
```

```
                325                 330                 335
Val Ser Ala Asn Ala Lys Gly Ser Val Cys Thr Ser Ala Thr Met Ala
            340                 345                 350

Arg Pro Gly Ile Asp Arg Gln Ala Ser Tyr Gly Asp Leu Ile Gly Ala
        355                 360                 365

Ser Val Pro Ala Phe Pro Pro Ser Ala Asn Lys Ile Glu Glu Asn
    370                 375                 380

Gly Pro Ser Thr Gly Ser Thr Pro Asp Pro Thr Ser Ser Thr Pro Pro
385                 390                 395                 400

Leu Pro Ser Asn Ala Ala Pro Pro Thr Ala Gln Thr Pro Gly Ile Ala
                405                 410                 415

Pro Gln Asn Ser Gln Ala Pro Met His Ser Leu His Ser Pro Cys
            420                 425                 430

Ala Asn Thr Ser Leu His Pro Gly Leu Asn Pro Arg Ile Gln Ala Ala
                435                 440                 445

Arg Phe Arg Phe Gln Gly Asn Ala Asn Asp Pro Asp Gln Asn Gly Asn
    450                 455                 460

Thr Thr Gln Ser Pro Pro Ser Arg Asp Val Ser Pro Thr Ser Arg Asp
465                 470                 475                 480

Asn Leu Val Ala Lys Gln Leu Ala Arg Asn Thr Val Thr Gln Ala Leu
                485                 490                 495

Ser Arg Phe Thr Ser Pro Gln Ala Gly Ala Pro Ser Arg Pro Gly Val
            500                 505                 510

Pro Pro Thr Gly Asp Val Gly Thr His Pro Pro Val Gly Arg Thr Ser
        515                 520                 525

Leu Lys Thr His Gly Val Ala Arg Val Asp Arg Gly Asn Pro Pro
    530                 535                 540

Ile Pro Pro Lys Lys Pro Gly Leu Ser Gln Thr Pro Ser Pro Pro His
545                 550                 555                 560

Pro Gln Leu Lys Val Ile Ile Asp Ser Ser Arg Ala Ser Asn Thr Gly
                565                 570                 575

Ala Lys Val Asp Asn Lys Thr Val Ala Ser Thr Pro Ser Ser Leu Pro
            580                 585                 590

Gln Gly Asn Arg Val Ile Asn Glu Glu Asn Leu Pro Lys Ser Ser Ser
        595                 600                 605

Pro Gln Leu Pro Pro Lys Pro Ser Ile Asp Leu Thr Val Ala Pro Ala
    610                 615                 620

Gly Cys Ala Val Ser Ala Leu Ala Thr Ser Gln Val Gly Ala Trp Pro
625                 630                 635                 640

Ala Ala Thr Pro Gly Leu Asn Gln Pro Ala Cys Ser Asp Ser Ser Leu
                645                 650                 655

Val Ile Pro Thr Thr Ile Ala Phe Cys Ser Ser Ile Asn Pro Val Ser
            660                 665                 670

Ala Ser Ser Cys Arg Pro Gly Ala Ser Asp Ser Leu Leu Val Thr Ala
        675                 680                 685

Ser Gly Trp Ser Pro Ser Leu Thr Pro Leu Leu Met Ser Gly Gly Pro
    690                 695                 700

Ala Pro Leu Ala Gly Arg Pro Thr Leu Leu Gln Gln Ala Ala Gln
705                 710                 715                 720

Gly Asn Val Thr Leu Leu Ser Met Leu Leu Asn Glu Glu Gly Leu Asp
                725                 730                 735

Ile Asn Tyr Ser Cys Glu Asp Gly His Ser Ala Leu Tyr Ser Ala Ala
            740                 745                 750
```

```
Lys Asn Gly His Thr Asp Cys Val Arg Leu Leu Ser Ala Glu Ala
            755                 760                 765

Gln Val Asn Ala Ala Asp Lys Asn Gly Phe Thr Pro Leu Cys Ala Ala
770                 775                 780

Ala Ala Gln Gly His Phe Glu Cys Val Glu Leu Leu Ile Ser Tyr Asp
785                 790                 795                 800

Ala Asn Ile Asn His Ala Ala Asp Gly Gly Gln Thr Pro Leu Tyr Leu
            805                 810                 815

Ala Cys Lys Asn Gly Asn Lys Glu Cys Ile Lys Leu Leu Glu Ala
            820                 825                 830

Gly Thr Asn Arg Ser Val Lys Thr Thr Asp Gly Trp Thr Pro Val His
            835                 840                 845

Ala Ala Val Asp Thr Gly Asn Val Asp Ser Leu Lys Leu Leu Met Tyr
850                 855                 860

His Arg Ile Pro Ala His Gly Asn Ser Phe Asn Glu Glu Ser Glu
865                 870                 875                 880

Ser Ser Val Phe Asp Leu Asp Gly Gly Glu Ser Pro Glu Gly Ile
                885                 890                 895

Ser Lys Pro Val Val Pro Ala Asp Leu Ile Asn His Ala Asn Arg Glu
            900                 905                 910

Gly Trp Thr Ala Ala His Ile Ala Ala Ser Lys Gly Phe Lys Asn Cys
            915                 920                 925

Leu Glu Ile Leu Cys Arg His Gly Gly Leu Glu Pro Glu Arg Arg Asp
            930                 935                 940

Lys Cys Asn Arg Thr Val His Asp Val Ala Thr Asp Asp Cys Lys His
945                 950                 955                 960

Leu Leu Glu Asn Leu Asn Ala Leu Lys Ile Pro Leu Arg Ile Ser Val
            965                 970                 975

Gly Glu Ile Glu Pro Ser Asn Tyr Gly Ser Asp Asp Leu Glu Cys Glu
            980                 985                 990

Asn Thr Ile Cys Ala Leu Asn Ile Arg Lys Gln Thr Ser Trp Asp Asp
            995                 1000                1005

Phe Ser Lys Ala Val Ser Gln Ala Leu Thr Asn His Phe Gln Ala
        1010                1015                1020

Ile Ser Ser Asp Gly Trp Trp Ser Leu Glu Asp Val Thr Cys Asn
        1025                1030                1035

Asn Thr Thr Asp Ser Asn Ile Gly Leu Ser Ala Arg Ser Ile Arg
        1040                1045                1050

Ser Ile Thr Leu Gly Asn Val Pro Trp Ser Val Gly Gln Ser Phe
        1055                1060                1065

Ala Gln Ser Pro Trp Asp Phe Met Arg Lys Asn Lys Ala Glu His
        1070                1075                1080

Ile Thr Val Leu Leu Ser Gly Pro Gln Glu Gly Cys Leu Ser Ser
        1085                1090                1095

Val Thr Tyr Ala Ser Met Ile Pro Leu Gln Met Met Gln Asn Tyr
        1100                1105                1110

Leu Arg Leu Val Glu Gln Tyr His Asn Val Ile Phe His Gly Pro
        1115                1120                1125

Glu Gly Ser Leu Gln Asp Tyr Ile Val His Gln Leu Ala Leu Cys
        1130                1135                1140

Leu Lys His Arg Gln Met Ala Ala Gly Phe Ser Cys Glu Ile Val
        1145                1150                1155
```

```
Arg Ala Glu Val Asp Ala Gly Phe Ser Lys Glu Gln Leu Leu Asp
    1160            1165            1170

Leu Phe Ile Ser Ser Ala Cys Leu Ile Pro Val Lys Gln Ser Pro
    1175            1180            1185

Ser Lys Lys Lys Ile Ile Ile Ile Leu Glu Asn Leu Glu Lys Ser
    1190            1195            1200

Ser Leu Ser Glu Leu Leu Arg Asp Phe Leu Ala Pro Leu Glu Asn
    1205            1210            1215

Arg Ser Thr Glu Ser Pro Cys Thr Phe Gln Lys Gly Asn Gly Leu
    1220            1225            1230

Ser Glu Cys Tyr Tyr Phe His Glu Asn Cys Phe Leu Met Gly Thr
    1235            1240            1245

Ile Ala Lys Ala Cys Leu Gln Gly Ser Asp Leu Leu Val Gln Gln
    1250            1255            1260

His Phe Arg Trp Val Gln Leu Arg Trp Asp Gly Glu Pro Met Gln
    1265            1270            1275

Gly Leu Leu Gln Arg Phe Leu Arg Arg Lys Val Val Asn Lys Phe
    1280            1285            1290

Lys Gly Gln Ala Pro Ser Pro Cys Asp Pro Val Cys Lys Ile Val
    1295            1300            1305

Asp Trp Ala Leu Ser Val Trp Arg Gln Leu Asn Ser Cys Leu Ala
    1310            1315            1320

Arg Leu Gly Thr Pro Glu Ala Leu Leu Gly Pro Lys Tyr Phe Leu
    1325            1330            1335

Ser Cys Pro Val Val Pro Gly His Ala Gln Val Thr Val Lys Trp
    1340            1345            1350

Met Ser Lys Leu Trp Asn Gly Val Ile Ala Pro Arg Val Gln Glu
    1355            1360            1365

Ala Ile Leu Ser Arg Ala Ser Val Lys Arg Gln Pro Gly Phe Gly
    1370            1375            1380

Gln Thr Thr Ala Lys Arg His Pro Ser Gln Gly Gln Gln Ala Val
    1385            1390            1395

Val Lys Ala Ala Leu Ser Ile Leu Leu Asn Lys Ala Val Leu His
    1400            1405            1410

Gly Cys Pro Leu Pro Arg Ala Glu Leu Asp Gln His Thr Ala Asp
    1415            1420            1425

Phe Lys Gly Gly Ser Phe Pro Leu Ser Ile Val Ser Ser Tyr Asn
    1430            1435            1440

Thr Cys Asn Lys Lys Gly Glu Ser Gly Ala Trp Arg Lys Val
    1445            1450            1455

Asn Thr Ser Pro Arg Arg Lys Ser Gly Arg Phe Ser Leu Pro Thr
    1460            1465            1470

Trp Asn Lys Pro Asp Leu Ser Thr Glu Gly Met Lys Asn Lys Thr
    1475            1480            1485

Ile Ser Gln Leu Asn Cys Asn Arg Asn Ala Ser Leu Ser Lys Gln
    1490            1495            1500

Lys Ser Leu Glu Asn Asp Leu Ser Leu Thr Leu Asn Leu Asp Gln
    1505            1510            1515

Arg Leu Ser Leu Gly Ser Asp Asp Glu Ala Asp Leu Val Lys Glu
    1520            1525            1530

Leu Gln Ser Met Cys Ser Ser Lys Ser Glu Ser Asp Ile Ser Lys
    1535            1540            1545

Ile Ala Asp Ser Arg Asp Asp Leu Arg Met Phe Asp Ser Ser Gly
```

|   |   |   |   |   |   |   |   |   |   |
|---|---|---|---|---|---|---|---|---|---|
|   | 1550 |   |   | 1555 |   |   | 1560 |   |   |
| Asn | Asn | Pro | Val | Leu | Ser | Ala | Thr | Ile | Asn | Asn | Leu | Arg | Met | Pro |
|   | 1565 |   |   | 1570 |   |   |   | 1575 |   |
| Val | Ser | Gln | Lys | Glu | Val | Ser | Pro | Leu | Ser | Ser | His | Gln | Thr | Thr |
|   | 1580 |   |   |   | 1585 |   |   | 1590 |   |
| Glu | Cys | Ser | Asn | Ser | Lys | Ser | Lys | Thr | Glu | Leu | Gly | Val | Ser | Arg |
|   | 1595 |   |   |   | 1600 |   |   | 1605 |   |
| Val | Lys | Ser | Phe | Leu | Pro | Val | Pro | Arg | Ser | Lys | Val | Thr | Gln | Cys |
|   | 1610 |   |   |   | 1615 |   |   | 1620 |   |
| Ser | Gln | Asn | Thr | Lys | Arg | Ser | Ser | Ser | Ser | Asn | Thr | Arg | Gln |
|   | 1625 |   |   |   | 1630 |   |   | 1635 |   |
| Ile | Glu | Ile | Asn | Asn | Asn | Ser | Lys | Glu | Val | Asn | Trp | Asn | Leu | His |
|   | 1640 |   |   |   | 1645 |   |   | 1650 |   |
| Lys | Asn | Glu | His | Leu | Glu | Lys | Pro | Asn | Lys |
|   | 1655 |   |   |   | 1660 |   |

<210> SEQ ID NO 13
<211> LENGTH: 2302
<212> TYPE: DNA
<213> ORGANISM: Homo sapiens
<220> FEATURE:
<221> NAME/KEY: misc_feature
<222> LOCATION: (1)..(2302)
<223> OTHER INFORMATION: DMRT-like family A1 (DMRTA1), mRNA

<400> SEQUENCE: 13

```
ctctgccagg ctcacgggac agctgcacct ctcagcgtct ccagctccag gacgcggtcg      60
tcccaactcc ttccgagtgg aaagagtgta aaacttttgt ccgtgcgcgg gtggagctca     120
gtaggaccac ggcgcgtcct gccccggctt ccccagcctc ccagcagggt tagctgcggt     180
cagcgcactt tccacttggg actcccggcc agaaatttct cgggaatgga gcggtcacag     240
tgtggcagca gagaccgagg cgttagcggc cgacctcact tggcccctgg gctagtggtg     300
gctgccccctc cgcccccgtc cccggcgttg ccggtaccat cggggatgca ggttccccca     360
gcgttcctgc ggccgcccag cctctttctg cgagcagcgg ccgcggccgc cgccgccgct     420
gccgccacct cgggaagcgg aggctgcccg ccggctcccg ggctggagag cggggtaggc     480
gcggtgggct gcggctaccc gcggacgccc aagtgcgccc gctgtcgtaa ccatggtgtg     540
gtgtcagcgc tcaagggcca caagcgcttc tgccgctggc gggactgcgc gtgtgccaag     600
tgcaccctga tcgccgagcg ccagcgcgtc atggccgccc aggtggcgct gcgcaggcag     660
caggcgcagg aggagagcga agcccggggg ctacagaggc tcctgtgctc ggggctctcc     720
tggccccccg gtggtcgggc atccgggggc ggcggcagag ccgagaatcc acagtccacg     780
ggcggccctg cggcggggc tgcgctggga ctgggtgcct tgagacaggc cagtggttcc     840
gcgacccccg ctttcgaagt tttccagcaa gattatcctg aggaaaaaca agaacaaaaa     900
gagagtaaat gtgagtcatg ccagaatgga caagaagaac tgatctccaa atcccatcag     960
ctttacctag gatcatcttc taggtctaat ggtgtcattg ggaaacaaag tatcgggtca    1020
tctatttcag aatactccaa caagcctgat agtatcctgt ctcctcatcc tggagagcaa    1080
tcaggaggtg aagagagtcc caggtcctta tcatcctctg atctggaatc aggaaatgaa    1140
agtgaatggg tcaaagactt gactgcgacc aaggcaagcc ttccgacagt gtcctcaaga    1200
ccaagagatc ctcttgatat ccttactaag atttttccccaa attacaggcg cagccggcta    1260
gaaggcattc tacggttctg caaggggat gtggtccaag ccattgaaca ggttttaaat    1320
```

```
ggcaaagaac acaagccaga caacaggaac ctagcaaact cagaagaact ggaaaacaca    1380
gcctttcaga gagcttcaag ttttagtctt gctggaattg gttttggaac tctaggtaat    1440
aaatcagctt tctctcctct tcaaactact tctgcttctt atggaggtga ttcaagtctc    1500
tacggcgtaa atcctagagt aggtatcagt ccattaaggc tggcatattc ttctgcagga    1560
agagggttat ctggttttat gtcaccctac ctaacacctg ggttagtacc aaccttacct    1620
tttcggccag ctttggatta tgccttttca gggatgatta gagattcttc ctacctttcc    1680
agtaaagact caataacttg tggcagactg tacttcagac caaatcagga caatccgtaa    1740
tgtatatgcc cattctctct ttctggagtt tttccagcat acaatacatg cacgtgcaca    1800
cacatacaca cacatccatt aatatacttc agtaagtatg tgagtggatt atgaggtctt    1860
aaaatgctgg gttttttttt tttcaagcaa tataataggt cttagatctg aaaactcttc    1920
attaggattt atcaagtgaa agaagtaaat ctgaacatta tatgtgcctt gaataaagct    1980
atttcaggaa atatttaatg aattttctcc ctaaattatc atttgtaaac atttttattt    2040
taaaactagt ttttatttta ttgaaaagtg gaattttag tgataaaata catttgtaag    2100
tgtaaagcaa tacagcataa tagaatagaa tataaaccga aaggaagaac tgaacaatta    2160
aggcaattct aaataattac catttcaaaa ctgtttcttc tattcctggt tcataggaaa    2220 gaaaaagtt attcaaagta ttttttaaagc atttgatttg cagatgggtg attcgtaata    2280
aataaaacat ttgagcattt tg                                             2302
```

<210> SEQ ID NO 14
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: doublesex- and mab-3-related transcription
      factor A1

<400> SEQUENCE: 14

```
Met Glu Arg Ser Gln Cys Gly Ser Arg Asp Arg Gly Val Ser Gly Arg
1               5                   10                  15

Pro His Leu Ala Pro Gly Leu Val Val Ala Ala Pro Pro Pro Pro Ser
                20                  25                  30

Pro Ala Leu Pro Val Pro Ser Gly Met Gln Val Pro Pro Ala Phe Leu
            35                  40                  45

Arg Pro Pro Ser Leu Phe Leu Arg Ala Ala Ala Ala Ala Ala Ala Ala
        50                  55                  60

Ala Ala Ala Thr Ser Gly Ser Gly Gly Cys Pro Pro Ala Pro Gly Leu
65                  70                  75                  80

Glu Ser Gly Val Gly Ala Val Gly Cys Gly Tyr Pro Arg Thr Pro Lys
                85                  90                  95

Cys Ala Arg Cys Arg Asn His Gly Val Val Ser Ala Leu Lys Gly His
                100                 105                 110

Lys Arg Phe Cys Arg Trp Arg Asp Cys Ala Cys Ala Lys Cys Thr Leu
            115                 120                 125

Ile Ala Glu Arg Gln Arg Val Met Ala Ala Gln Val Ala Leu Arg Arg
        130                 135                 140

Gln Gln Ala Gln Glu Glu Ser Glu Ala Arg Gly Leu Gln Arg Leu Leu
145                 150                 155                 160

Cys Ser Gly Leu Ser Trp Pro Pro Gly Gly Arg Ala Ser Gly Gly Gly
                165                 170                 175
```

Gly Arg Ala Glu Asn Pro Gln Ser Thr Gly Pro Ala Ala Gly Ala
            180                 185                 190

Ala Leu Gly Leu Gly Ala Leu Arg Gln Ala Ser Gly Ser Ala Thr Pro
        195                 200                 205

Ala Phe Glu Val Phe Gln Gln Asp Tyr Pro Glu Glu Lys Gln Glu Gln
210                 215                 220

Lys Glu Ser Lys Cys Glu Ser Cys Gln Asn Gly Gln Glu Glu Leu Ile
225                 230                 235                 240

Ser Lys Ser His Gln Leu Tyr Leu Gly Ser Ser Arg Ser Asn Gly
                245                 250                 255

Val Ile Gly Lys Gln Ser Ile Gly Ser Ser Ile Ser Glu Tyr Ser Asn
            260                 265                 270

Lys Pro Asp Ser Ile Leu Ser Pro His Pro Gly Glu Gln Ser Gly Gly
        275                 280                 285

Glu Glu Ser Pro Arg Ser Leu Ser Ser Asp Leu Glu Ser Gly Asn
    290                 295                 300

Glu Ser Glu Trp Val Lys Asp Leu Thr Ala Thr Lys Ala Ser Leu Pro
305                 310                 315                 320

Thr Val Ser Ser Arg Pro Arg Asp Pro Leu Asp Ile Leu Thr Lys Ile
                325                 330                 335

Phe Pro Asn Tyr Arg Arg Ser Arg Leu Glu Gly Ile Leu Arg Phe Cys
            340                 345                 350

Lys Gly Asp Val Val Gln Ala Ile Glu Gln Val Leu Asn Gly Lys Glu
        355                 360                 365

His Lys Pro Asp Asn Arg Asn Leu Ala Asn Ser Glu Glu Leu Glu Asn
    370                 375                 380

Thr Ala Phe Gln Arg Ala Ser Ser Phe Ser Leu Ala Gly Ile Gly Phe
385                 390                 395                 400

Gly Thr Leu Gly Asn Lys Ser Ala Phe Ser Pro Leu Gln Thr Thr Ser
                405                 410                 415

Ala Ser Tyr Gly Gly Asp Ser Ser Leu Tyr Gly Val Asn Pro Arg Val
            420                 425                 430

Gly Ile Ser Pro Leu Arg Leu Ala Tyr Ser Ser Ala Gly Arg Gly Leu
        435                 440                 445

Ser Gly Phe Met Ser Pro Tyr Leu Thr Pro Gly Leu Val Pro Thr Leu
    450                 455                 460

Pro Phe Arg Pro Ala Leu Asp Tyr Ala Phe Ser Gly Met Ile Arg Asp
465                 470                 475                 480

Ser Ser Tyr Leu Ser Ser Lys Asp Ser Ile Thr Cys Gly Arg Leu Tyr
                485                 490                 495

Phe Arg Pro Asn Gln Asp Asn Pro
            500

<210> SEQ ID NO 15
<211> LENGTH: 4296
<212> TYPE: DNA
<213> ORGANISM: Homo sapiens
<220> FEATURE:
<221> NAME/KEY: misc_feature
<222> LOCATION: (1)..(4296)
<223> OTHER INFORMATION: endothelin receptor type B (EDNRB), transcript
      variant 1, mRNA

<400> SEQUENCE: 15
acattccggt gggggactct ggccagcccg agcaacgtgg atcctgagag cactcccagg        60

```
taggcatttg ccccggtggg acgccttgcc agagcagtgt gtggcaggcc cccgtggagg    120
atcaacacag tggctgaaca ctgggaagga actggtactt ggagtctgga catctgaaac    180
ttggctctga aactgcggag cggccaccgg acgccttctg gagcaggtag cagcatgcag    240
ccgcctccaa gtctgtgcgg acgcgccctg gttgcgctgg ttcttgcctg cggcctgtcg    300
cggatctggg gagaggagag aggcttcccg cctgacaggg ccactccgct tttgcaaacc    360
gcagagataa tgacgccacc cactaagacc ttatgggcca agggttccaa cgccagtctg    420
gcgcggtcgt tggcacctgc ggaggtgcct aaaggagaca ggacggcagg atctccgcca    480
cgcaccatct cccctccccc gtgccaagga cccatcgaga tcaaggagac tttcaaatac    540
atcaacacgg ttgtgtcctg ccttgtgttc gtgctgggga tcatcgggaa ctccacactt    600
ctgagaatta tctacaagaa caagtgcatg cgaaacggtc ccaatatctt gatcgccagc    660
ttggctctgg agacctgct gcacatcgtc attgacatcc ctatcaatgt ctacaagctg    720
ctggcagagg actggccatt tggagctgag atgtgtaagc tggtgccttt catacagaaa    780
gcctccgtgg gaatcactgt gctgagtcta tgtgctctga gtattgacag atatcgagct    840
gttgcttctt ggagtagaat taaaggaatt ggggttccaa aatggacagc agtagaaatt    900
gttttgattt gggtggtctc tgtggttctg gctgtccctg aagccatagg ttttgatata    960
attacgatgg actacaaagg aagttatctg cgaatctgct tgcttcatcc cgttcagaag    1020
acagctttca tgcagtttta caagacagca aaagattggt ggctattcag tttctatttc    1080
tgcttgccat tggccatcac tgcatttttt tatacactaa tgacctgtga aatgttgaga    1140
aagaaaagtg gcatgcagat tgctttaaat gatcacctaa agcagagacg ggaagtggcc    1200
aaaaccgtct tttgcctggt ccttgtcttt gccctctgct ggcttcccct tcacctcagc    1260
aggattctga agctcactct ttataatcag aatgatccca atagatgtga acttttgagc    1320
tttctgttgg tattggacta tattggtatc aacatggctt cactgaattc ctgcattaac    1380
ccaattgctc tgtatttggt gagcaaaaga ttcaaaaact gctttaagtc atgcttatgc    1440
tgctggtgcc agtcatttga agaaaaacag tccttggagg aaaagcagtc gtgcttaaag    1500
ttcaaagcta atgatcacgg atatgacaac ttccgttcca gtaataaata cagctcatct    1560
tgaaagaaga actattcact gtatttcatt ttctttatat tggaccgaag tcattaaaac    1620
aaaatgaaac atttgccaaa acaaaacaaa aaactatgta tttgcacagc acactattaa    1680
aatattaagt gtaattattt taacactcac agctacatat gacattttat gagctgttta    1740
cggcatggaa agaaaatcag tgggaattaa gaaagcctcg tcgtgaaagc acttaatttt    1800
ttacagttag cacttcaaca tagctcttaa caacttccag gatattcaca caacacttag    1860
gcttaaaaat gagctcactc agaatttcta ttctttctaa aaagagattt atttttaaat    1920
caatgggact ctgatataaa ggaagaataa gtcactgtaa aacagaactt ttaaatgaag    1980
cttaaattac tcaatttaaa attttaaaat cctttaaaac aacttttcaa ttaatattat    2040
cacactatta tcagattgta attagatgca aatgagagag cagtttagtt gttgcatttt    2100
tcggacactg gaaacattta aatgatcagg agggagtaac agaaagagca aggctgtttt    2160
tgaaaatcat tacactttca ctagaagccc aaacctcagc attctgcaat atgtaaccaa    2220
catgtcacaa acaagcagca tgtaacagac tggcacatgt gccagctgaa tttaaaatat    2280 aatacttttta aaagaaaat tattacatcc tttacattca gttaagatca aacctcacaa    2340
agagaaatag aatgtttgaa aggctatccc aaaagacttt tttgaatctg tcattcacat    2400
accctgtgaa gacaatacta tctacaattt tttcaggatt attaaaatct tcttctttca    2460
```

-continued

```
ctatcgtagc ttaaactctg tttggttttg tcatctgtaa atacttacct acatacactg   2520
catgtagatg attaaatgag ggcaggccct gtgctcatag ctttacgatg gagagatgcc   2580
agtgacctca taataaagac tgtgaactgc ctggtgcagt gtccacatga caaaggggca   2640
ggtagcaccc tctctcaccc atgctgtggt taaaatggtt tctagcatat gtataatgct   2700
atagttaaaa tactattttt caaaatcata cagattagta catttaacag ctacctgtaa   2760
agcttattac taattttgt attatttttg taaatagcca atagaaaagt ttgcttgaca    2820
tggtgctttt ctttcatcta gaggcaaaac tgcttttga gaccgtaaga acctcttagc    2880
tttgtgcgtt cctgcctaat ttttatatct tctaagcaaa gtgccttagg atagcttggg   2940
atgagatgtg tgtgaaagta tgtacaagag aaaacggaag agagaggaaa tgaggtgggg   3000
ttggaggaaa cccatgggga cagattccca ttcttagcct aacgttcgtc attgcctcgt   3060
cacatcaatg caaaaggtcc tgattttgtt ccagcaaaac acagtgcaat gttctcagag   3120
tgactttcga aataaattgg gcccaagagc tttaactcgg tcttaaaata tgcccaaatt   3180
tttactttgt ttttctttta ataggctggg ccacatgttg gaaataagct agtaatgttg   3240
ttttctgtca atattgaatg tgatggtaca gtaaaccaaa acccaacaat gtggccagaa   3300
agaaagagca ataataatta attcacacac catatggatt ctatttataa atcacccaca   3360
aacttgttct ttaattcat cccaatcact ttttcagagg cctgttatca tagaagtcat    3420
tttagactct caattttaaa ttaattttga atcactaata ttttcacagt ttattaatat   3480 attaatttc tatttaaatt ttagattatt tttattacca tgtactgaat tttacatcc     3540 tgataccctt tccttctcca tgtcagtatc atgttctcta attatcttgc caaattttga   3600
aactacacac aaaaagcata cttgcattat ttataataaa attgcattca gtggcttttt   3660 aaaaaatgt ttgattcaaa actttaacat actgataagt aagaaacaat tataatttct    3720
ttacatactc aaaaccaaga tagaaaaagg tgctatcgtt caacttcaaa acatgtttcc   3780
tagtattaag gactttaata tagcaacaga caaaattatt gttaacatgg atgttacagc   3840
tcaaaagatt tataaaagat tttaacctat tttctcccctt attatccact gctaatgtgg   3900
atgtatgttc aaacacccttt tagtattgat agcttacata tggccaaagg aatacagttt   3960
atagcaaaac atgggtatgc tgtagctaac tttataaaag tgtaatataa caatgtaaaa   4020
aattatatat ctgggaggat ttttggttg cctaaagtgg ctatagttac tgatttttta    4080
ttatgtaagc aaaaccaata aaaatttaag tttttttaac aactaccttta ttttcactg   4140 tacagacact aattcattaa atactaattg attgtttaaa agaaatataa atgtgacaag   4200
tggacattat ttatgttaaa tatacaatta tcaagcaagt atgaagttat tcaattaaaa   4260
tgccacattt ctggtctctg ggaaaaaaaa aaaaaa                             4296
```

<210> SEQ ID NO 16
<211> LENGTH: 442
<212> TYPE: PRT
<213> ORGANISM: Homo sapiens
<220> FEATURE:
<221> NAME/KEY: misc_feature
<222> LOCATION: (1)..(442)
<223> OTHER INFORMATION: endothelin B receptor isoform 1 precursor
<400> SEQUENCE: 16

```
Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
```

```
            20                  25                  30
Pro Asp Arg Ala Thr Pro Leu Leu Gln Thr Ala Glu Ile Met Thr Pro
            35                  40                  45
Pro Thr Lys Thr Leu Trp Pro Lys Gly Ser Asn Ala Ser Leu Ala Arg
 50                  55                  60
Ser Leu Ala Pro Ala Glu Val Pro Lys Gly Asp Arg Thr Ala Gly Ser
 65                  70                  75                  80
Pro Pro Arg Thr Ile Ser Pro Pro Cys Gln Gly Pro Ile Glu Ile
                 85                  90                  95
Lys Glu Thr Phe Lys Tyr Ile Asn Thr Val Val Ser Cys Leu Val Phe
                100                 105                 110
Val Leu Gly Ile Ile Gly Asn Ser Thr Leu Leu Arg Ile Ile Tyr Lys
                115                 120                 125
Asn Lys Cys Met Arg Asn Gly Pro Asn Ile Leu Ile Ala Ser Leu Ala
                130                 135                 140
Leu Gly Asp Leu Leu His Ile Val Ile Asp Ile Pro Ile Asn Val Tyr
145                 150                 155                 160
Lys Leu Leu Ala Glu Asp Trp Pro Phe Gly Ala Glu Met Cys Lys Leu
                165                 170                 175
Val Pro Phe Ile Gln Lys Ala Ser Val Gly Ile Thr Val Leu Ser Leu
                180                 185                 190
Cys Ala Leu Ser Ile Asp Arg Tyr Arg Ala Val Ala Ser Trp Ser Arg
                195                 200                 205
Ile Lys Gly Ile Gly Val Pro Lys Trp Thr Ala Val Glu Ile Val Leu
                210                 215                 220
Ile Trp Val Val Ser Val Val Leu Ala Val Pro Glu Ala Ile Gly Phe
225                 230                 235                 240
Asp Ile Ile Thr Met Asp Tyr Lys Gly Ser Tyr Leu Arg Ile Cys Leu
                245                 250                 255
Leu His Pro Val Gln Lys Thr Ala Phe Met Gln Phe Tyr Lys Thr Ala
                260                 265                 270
Lys Asp Trp Trp Leu Phe Ser Phe Tyr Phe Cys Leu Pro Leu Ala Ile
                275                 280                 285
Thr Ala Phe Phe Tyr Thr Leu Met Thr Cys Glu Met Leu Arg Lys Lys
                290                 295                 300
Ser Gly Met Gln Ile Ala Leu Asn Asp His Leu Lys Gln Arg Arg Glu
305                 310                 315                 320
Val Ala Lys Thr Val Phe Cys Leu Val Leu Val Phe Ala Leu Cys Trp
                325                 330                 335
Leu Pro Leu His Leu Ser Arg Ile Leu Lys Leu Thr Leu Tyr Asn Gln
                340                 345                 350
Asn Asp Pro Asn Arg Cys Glu Leu Leu Ser Phe Leu Leu Val Leu Asp
                355                 360                 365
Tyr Ile Gly Ile Asn Met Ala Ser Leu Asn Ser Cys Ile Asn Pro Ile
                370                 375                 380
Ala Leu Tyr Leu Val Ser Lys Arg Phe Lys Asn Cys Phe Lys Ser Cys
385                 390                 395                 400
Leu Cys Cys Trp Cys Gln Ser Phe Glu Glu Lys Gln Ser Leu Glu Glu
                405                 410                 415
Lys Gln Ser Cys Leu Lys Phe Lys Ala Asn Asp His Gly Tyr Asp Asn
                420                 425                 430
Phe Arg Ser Ser Asn Lys Tyr Ser Ser
                435                 440
```

<210> SEQ ID NO 17
<211> LENGTH: 3879
<212> TYPE: DNA
<213> ORGANISM: Homo sapiens
<220> FEATURE:
<221> NAME/KEY: misc_feature
<222> LOCATION: (1)..(3879)
<223> OTHER INFORMATION: integrin, beta 1 (fibronectin receptor, beta polypeptide, antigen CD29 includes MDF2, MSK12) (ITGB1), transcript variant 1A, mRNA

<400> SEQUENCE: 17

| | | | | | |
|---|---|---|---|---|---|
| atcagacgcg | cagaggaggc | ggggccgcgg | ctggtttcct | gccgggggc | ggctctgggc | 60 |
| cgccgagtcc | cctcctcccg | cccctgagga | ggaggagccg | ccgccaccg | ccgcgcccga | 120 |
| cacccgggag | gccccgccag | cccgcgggag | aggcccagcg | ggagtcgcgg | aacagcaggc | 180 |
| ccgagcccac | cgcgccgggc | cccggacgcc | gcgcggaaaa | gatgaattta | caaccaattt | 240 |
| tctggattgg | actgatcagt | tcagtttgct | gtgtgtttgc | tcaaacagat | gaaaatagat | 300 |
| gtttaaaagc | aaatgccaaa | tcatgtggag | aatgtataca | agcagggcca | aattgtgggt | 360 |
| ggtgcacaaa | ttcaacattt | ttacaggaag | gaatgcctac | ttctgcacga | tgtgatgatt | 420 |
| tagaagcctt | aaaaaagaag | ggttgccctc | cagatgacat | agaaaatccc | agaggctcca | 480 |
| aagatataaa | gaaaaataaa | aatgtaacca | accgtagcaa | aggaacagca | gagaagctca | 540 |
| agccagagga | tattactcag | atccaaccac | agcagttggt | tttgcgatta | agatcagggg | 600 |
| agccacagac | atttacatta | aaattcaaga | gagctgaaga | ctatcccatt | gacctctact | 660 |
| accttatgga | cctgtcttac | tcaatgaaag | acgatttgga | gaatgtaaaa | agtcttggaa | 720 |
| cagatctgat | gaatgaaatg | aggaggatta | cttcggactt | cagaattgga | tttggctcat | 780 |
| ttgtggaaaa | gactgtgatg | ccttacatta | gcacaacacc | agctaagctc | aggaacccctt | 840 |
| gcacaagtga | acagaactgc | accagcccat | ttagctacaa | aaatgtgctc | agtcttacta | 900 |
| ataaaggaga | agtatttaat | gaacttgttg | gaaaacagcg | catatctgga | aatttggatt | 960 |
| ctccagaagg | tggttttcgat | gccatcatgc | aagttgcagt | ttgtggatca | ctgattggct | 1020 |
| ggaggaatgt | tacacggctg | ctggtgtttt | ccacagatgc | cgggtttcac | tttgctggag | 1080 |
| atgggaaact | tggtggcatt | gttttaccaa | atgatggaca | atgtcacctg | gaaaataata | 1140 |
| tgtacacaat | gagccattat | tatgattatc | cttctattgc | tcaccttgtc | cagaaactga | 1200 |
| gtgaaaataa | tattcagaca | attttttgcag | ttactgaaga | atttcagcct | gtttacaagg | 1260 |
| agctgaaaaa | cttgatccct | aagtcagcag | taggaacatt | atctgcaaat | tctagcaatg | 1320 |
| taattcagtt | gatcattgat | gcatacaatt | ccctttcctc | agaagtcatt | ttggaaaacg | 1380 |
| gcaaattgtc | agaaggcgta | acaataagtt | acaaatctta | ctgcaagaac | ggggtgaatg | 1440 |
| gaacagggga | aaatggaaga | aaatgttcca | atatttccat | tggagatgag | gttcaatttg | 1500 |
| aaattagcat | aacttcaaat | aagtgtccaa | aaaaggattc | tgacagcttt | aaaattaggc | 1560 |
| ctctgggctt | tacggaggaa | gtagaggtta | ttcttcagta | catctgtgaa | tgtgaatgcc | 1620 |
| aaagcgaagg | catccctgaa | agtcccaagt | gtcatgaagg | aaatgggaca | tttgagtgtg | 1680 |
| gcgcgtgcag | gtgcaatgaa | gggcgtgttg | gtagacattg | taatgcagc | acagatgaag | 1740 |
| ttaacagtga | agacatggat | gcttactgca | ggaaagaaaa | cagttcagaa | atctgcagta | 1800 |
| acaatggaga | gtgcgtctgc | ggacagtgtg | tttgtaggaa | gagggataat | acaaatgaaa | 1860 |
| tttattctgg | caaattctgc | gagtgtgata | atttcaactg | tgatagatcc | aatggcttaa | 1920 |

|  |  |  |  |  |
|---|---|---|---|---|
| tttgtggagg | aaatggtgtt | tgcaagtgtc | gtgtgtgtga | gtgcaacccc | aactacactg | 1980 |
| gcagtgcatg | tgactgttct | ttggatacta | gtacttgtga | agccagcaac | ggacagatct | 2040 |
| gcaatggccg | gggcatctgc | gagtgtggtg | tctgtaagtg | tacagatccg | aagtttcaag | 2100 |
| ggcaaacgtg | tgagatgtgt | cagacctgcc | ttggtgtctg | tgctgagcat | aaagaatgtg | 2160 |
| ttcagtgcag | agccttcaat | aaaggagaaa | agaaagacac | atgcacacag | gaatgttcct | 2220 |
| attttaacat | taccaaggta | gaaagtcggg | acaaattacc | ccagccggtc | caacctgatc | 2280 |
| ctgtgtccca | ttgtaaggag | aaggatgttg | acgactgttg | gttctatttt | acgtattcag | 2340 |
| tgaatgggaa | caacgaggtc | atggttcatg | ttgtggagaa | tccagagtgt | cccactggtc | 2400 |
| cagacatcat | tccaattgta | gctggtgtgg | ttgctggaat | tgttcttatt | ggccttgcat | 2460 |
| tactgctgat | atggaagctt | ttaatgataa | ttcatgacag | aagggagttt | gctaaatttg | 2520 |
| aaaaggagaa | aatgaatgcc | aaatgggaca | cgggtgaaaa | tcctatttat | aagagtgccg | 2580 |
| taacaactgt | ggtcaatccg | aagtatgagg | gaaaatgagt | actgcccgtg | caaatcccac | 2640 |
| aacactgaat | gcaaagtagc | aatttccata | gtcacagtta | ggtagcttta | gggcaatatt | 2700 |
| gccatggttt | tactcatgtg | caggttttga | aaatgtacaa | tatgtataat | ttttaaaatg | 2760 |
| ttttattatt | ttgaaaataa | tgttgtaatt | catgccaggg | actgacaaaa | gacttgagac | 2820 |
| aggatggtta | ctcttgtcag | ctaaggtcac | attgtgcctt | tttgaccttt | tcttcctgga | 2880 |
| ctattgaaat | caagcttatt | ggattaagtg | atatttctat | agcgattgaa | agggcaatag | 2940 |
| ttaaagtaat | gagcatgatg | agagtttctg | ttaatcatgt | attaaaactg | atttttagct | 3000 |
| ttacaaatat | gtcagtttgc | agttatgcag | aatccaaagt | aaatgtcctg | ctagctagtt | 3060 |
| aaggattgtt | ttaaatctgt | tattttgcta | tttgcctgtt | agacatgact | gatgacatat | 3120 |
| ctgaaagaca | agtatgttga | gagttgctgg | tgtaaaatac | gtttgaaata | gttgatctac | 3180 |
| aaaggccatg | ggaaaaattc | agagagttag | gaaggaaaaa | ccaatagctt | taaaacctgt | 3240 |
| gtgccatttt | aagagttact | taatgtttgg | taacttttat | gccttcactt | tacaaattca | 3300 |
| agccttagat | aaaagaaccg | agcaattttc | tgctaaaaag | tccttgattt | agcactattt | 3360 |
| acatacaggc | catactttac | aaagtatttg | ctgaatgggg | accttttgag | ttgaatttat | 3420 |
| tttattattt | ttattttgtt | taatgtctgg | tgctttctgt | cacctcttct | aatcttttaa | 3480 |
| tgtatttgtt | tgcaattttg | gggtaagact | tttttatga | gtactttttc | tttgaagttt | 3540 |
| tagcggtcaa | tttgccttt | taatgaacat | gtgaagttat | actgtggcta | tgcaacagct | 3600 |
| ctcacctacg | cgagtcttac | tttgagttag | tgccataaca | gaccactgta | tgtttacttc | 3660 |
| tcaccatttg | agttgcccat | cttgtttcac | actagtcaca | ttcttgtttt | aagtgccttt | 3720 |
| agttttaaca | gttcactttt | tacagtgcta | tttactgaag | ttatttatta | aatatgccta | 3780 |
| aaatacttaa | atcggatgtc | ttgactctga | tgtatttat | caggttgtgt | gcatgaaatt | 3840 |
| tttatagatt | aaagaagttg | aggaaaagca | aaaaaaaa |  |  | 3879 |

<210> SEQ ID NO 18
<211> LENGTH: 798
<212> TYPE: PRT
<213> ORGANISM: Homo sapiens
<220> FEATURE:
<221> NAME/KEY: misc_feature
<222> LOCATION: (1)..(798)
<223> OTHER INFORMATION: integrin beta-1 isoform 1A precursor

<400> SEQUENCE: 18

Met Asn Leu Gln Pro Ile Phe Trp Ile Gly Leu Ile Ser Ser Val Cys

-continued

```
  1               5                    10                   15
Cys Val Phe Ala Gln Thr Asp Glu Asn Arg Cys Leu Lys Ala Asn Ala
                 20                  25                  30

Lys Ser Cys Gly Glu Cys Ile Gln Ala Gly Pro Asn Cys Gly Trp Cys
                 35                  40                  45

Thr Asn Ser Thr Phe Leu Gln Glu Gly Met Pro Thr Ser Ala Arg Cys
                 50                  55                  60

Asp Asp Leu Glu Ala Leu Lys Lys Gly Cys Pro Pro Asp Ile
 65              70                  75                  80

Glu Asn Pro Arg Gly Ser Lys Asp Ile Lys Lys Asn Lys Asn Val Thr
                 85                  90                  95

Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
                115                 120                 125

Gln Thr Phe Thr Leu Lys Phe Lys Arg Ala Glu Asp Tyr Pro Ile Asp
                130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
                195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
                290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
                370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430
```

```
Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
        530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
        610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
        690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
770                 775                 780

Ser Ala Val Thr Thr Val Val Asn Pro Lys Tyr Glu Gly Lys
785                 790                 795

<210> SEQ ID NO 19
<211> LENGTH: 5288
<212> TYPE: DNA
<213> ORGANISM: Homo sapiens
<220> FEATURE:
<221> NAME/KEY: misc_feature
<222> LOCATION: (1)..(5288)
<223> OTHER INFORMATION: integrin, alpha 10 (ITGA10), transcript variant
```

1, mRNA

<400> SEQUENCE: 19

```
gttttccttg gtctggggct ccccacagtt ccccaccatc actcctccca ttccttccaa       60
ctttatttt agctgccatt ggggggggc aggatgggag ggaaagtgaa gaaaacagaa         120
aaggagaggg acagaggcca gaggacttct catactggac agaaaccgat caggcatgga      180
actcccttc gtcactcacc tgttcttgcc cctggtgttc ctgacaggtc tctgctcccc       240
ctttaacctg gatgaacatc acccacgcct attcccaggg ccaccagaag ctgaatttgg      300
atacagtgtc ttacaacatg ttggggtgg acagcgatgg atgctggtgg gcgcccctg        360
ggatgggcct tcaggcgacc ggaggggga cgtttatcgc tgccctgtag ggggggccca       420
caatgcccca tgtgccaagg ccacttagg tgactaccaa ctgggaaatt catctcatcc       480
tgctgtgaat atgcacctgg ggatgtctct gttagagaca gatggtgatg ggggattcat     540
ggcctgtgcc cctctctggt ctcgtgcttg tggcagctct gtcttcagtt ctgggatatg     600
tgcccgtgtg gatgcttcat tccagcctca gggaagcctg gcacccactg cccaacgctg     660
cccaacatac atggatgttg tcattgtctt ggatggctcc aacagcatct accctggtc      720
tgaagttcag accttcctac gaagactggt agggaaactg tttattgacc agaacagat     780
acaggtggga ctggtacagt atggggagag ccctgtacat gagtggtccc tgggagattt   840
ccgaacgaag gaagaagtgg tgagagcagc aaagaacctc agtcggcggg agggacgaga    900
aacaaagact gcccaagcaa taatggtggc ctgcacagaa gggttcagtc agtcccatgg   960
gggccgaccc gaggctgcca ggctactggt ggttgtcact gatggagagt cccatgatgg    1020
agaggagctt cctgcagcac taaaggcctg tgaggctgga agagtgacac gctatgggat    1080
tgcagtcctt ggtcactacc tccggcggca gcgagatccc agctctttcc tgagagaaat    1140
tagaactatt gccagtgatc cagatgagcg attcttcttc aatgtcacag atgaggctgc   1200
tctgactgac attgtggatg cactaggaga tcggattttt ggccttgaag ggtcccatgc   1260
agaaaacgaa agctcctttg ggctggaaat gtctcagatt ggtttctcca ctcatcggct   1320
aaaggatggg attctttttg gatggtggg ggcctatgac tggggaggct ctgtgctatg    1380
gcttgaagga ggccaccgcc ttttccccc acgaatggca ctggaagacg agttcccccc   1440
tgcattgcag aaccatgcag cctacctggg ttactctgtt tcttccatgc ttttgcgggg   1500
tggacgccgc ctgttctct ctggggctcc tcgatttaga catcgaggaa aagtcatcgc   1560
cttccagctt aagaaagatg gggctgtgag ggttgcccag agcctccagg gggagcagat   1620
tggttcatac tttggcagtg agctctgccc attggataca gatagggatg gaacaactga   1680
tgtcttactt gtggctgccc ccatgttcct gggaccccag aacaaggaaa caggacgtgt    1740
ttatgtgtat ctggtaggcc agcagtcctt gctgaccctc caaggaacac ttcagccaga   1800
acccccccag gatgctcggt ttggcttttgc catgggagct cttcctgatc tgaaccaaga   1860
tggttttgct gatgtggctg tggggcgcc tctggaagat gggcaccagg gagcactgta   1920
cctgtaccat ggaacccaga gtggagtcag gccccatcct gcccagagga ttgctgctgc   1980
ctccatgcca catgccctca gctactttgg ccgaagtgtg gatggtcggc tagatctgga   2040
tggagatgat ctggtcgatg tggctgtggg tgcccagggg gcagccatcc tgctcagctc   2100
ccggcccatt gtccatctga ccccatcact ggaggtgacc ccacaggcca tcagtgtggt   2160
tcagagggac tgtaggcggc gaggccaaga ggcagtctgt ctgactgcag cccttttgctt    2220
ccaagtgacc tcccgtactc ctggtcgctg ggatcaccaa ttctacatga ggttcaccgc    2280
```

```
atcactggat gaatggactg ctggggcacg tgcagcattt gatggctctg gccagaggtt    2340
gtcccctcgg aggctccggc tcagtgtggg aatgtcact tgtgagcagc tacacttcca    2400
tgtgctggat acatcagatt acctccggcc agtggccttg actgtgacct ttgccttgga    2460
caatactaca aagccagggc ctgtgctgaa tgagggctca cccacctcta tacaaaagct    2520
ggtccccttc tcaaaggatt gtggccctga caatgaatgt gtcacagacc tggtgcttca    2580
agtgaatatg gacatcagag gctccaggaa ggccccattt gtggttcgag gtggccggcg    2640
gaaagtgctg gtatctacaa ctctggagaa cagaaaggaa aatgcttaca atacgagcct    2700
gagtctcatc ttctctagaa acctccacct ggccagtctc actcctcaga gagagagccc    2760
aataaaggtg aatgtgccg ccccttctgc tcatgcccgg ctctgcagtg tggggcatcc    2820
tgtcttccag actggagcca aggtgacctt tctgctagag tttgagttta gctgctcctc    2880
tctcctgagc caggtcttcg tgaagctgac tgccagcagt gacagcctgg agagaaatgg    2940
gacccttcaa gataacacag cccagacctc agcctacatc caatatgagc cccacctcct    3000
gttctctagt gagtctaccc tgcaccgcta tgaggttcac ccatatggga ccctcccagt    3060
gggtcctggc ccagaattca aaaccactct cagggttcag aacctaggct gctatgtggt    3120
cagtggcctc atcatctcag ccctccttcc agctgtggcc catggggca attacttcct    3180 atcactgtct caagtcatca ctaacaatgc aagctgcata gtgcagaacc tgactgaacc    3240
cccaggccca cctgtgcatc cagaggagct tcaacacaca aacagactga atgggagcaa    3300
tactcagtgt caggtggtga ggtgccacct tgggcagctg gcaaagggga ctgaggtctc    3360
tgttggacta ttgaggctgg ttcacaatga attttccga agagccaagt tcaagtccct    3420
gacggtggtc agcaccttg agctgggaac cgaagagggc agtgtcctac agctgactga    3480
agcctcccgt tggagtgaga gcctcttgga ggtggttcag acccggccta tcctcatctc    3540
cctgtggatc ctcataggca gtgtcctggg agggttgctc ctgcttgctc tccttgtctt    3600
ctgcctgtgg aagcttggct tctttgccca taagaaaatc cctgaggaag aaaaaagaga    3660
agagaagttg gagcaatgaa tgtagaataa gggtctagaa agtcctccct ggcagcttct    3720
tcaagagact tgcataaaag cagaggtttg ggggctcaga tgggacaaga agccgcctct    3780
ggactatctc cccagaccag cagcctgact tgacttttga gtcctaggga tgctgctggc    3840
tagagatgag gctttacctc agacaagaag agctggcacc aaaactagcc atgctcccac    3900
cctctgcttc cctcctcctc gtgatcctgg ttccatagcc aacactgggg cttttgtttg    3960 gggtccttt atccccagga atcaataatt ttttgccta ggtgcctgac tccttttcaga    4020 ttccctcttt atcttccctc acagtttgga aaggatgagg gttatcttcc tcgattcttc    4080
caccctctca ctttcctgcc tgttccccac tccacaggag ggagctgacg ttggcttgaa    4140
aggagtaaag tcaacatctg ctgctttcct gtggactctg gtgattcata gagccggatg    4200
gggagagtca acaggaaaaa aggagggagg aggaaaagcc acaagagaca ttctgtacaa    4260
ttccaaggaa cagagaagcc tttagacagg caactgccat ccccctgaa acctgagacc    4320 tgtagtgcac tcgaccgccc tcaggtgttg gtgaaacaga gctgccccca ggctcgctgg    4380
gcataggctt cctgattcca agcctttct gggagcaaag ccagggcctg gtgcctgatt    4440
ttctgaagcc aggagccctc aggtggctgg agctggaata gcaggagga ctgggtgtac    4500 ctaggcagta ttttctctac ttctctcaag tcttatactc actcttgagc cctccttggg    4560
gcctgcttag aaagcagaca ggagagagag tactgctact tgatgatggg aaatgctttc    4620
```

```
actttaccag ctttgggaag cagcagcccc atgggatcta aaagtgtgga gtctgcatta   4680
agaaacctac atgggtggca tggggctctg gggagcaagc ccttacttgc tcagcactgg   4740
ttatgtagca caaatagctc ctaggaaaat gtttctgggg caaccctaga accctggtca   4800
tattttgcag ggtttctctg gtggaatcag tttgccagcc cttgcttgat gcttactgga   4860
aatctccagg ttaatttcta tctctgatcc ctccccaacc cactccatat ttgggtcatg   4920
gacagtaaag gcagttggat tctcatagac aactgggtaa cttatatttc tttgtaatca   4980
agacttgaga tatcgaagtc agttattggt ctccagagtg cagctctggg agccttttga   5040
agaatcagca ctcattaaga gctgagaaga gagaagacct gattgggtgg ttgactagca   5100
gtcacagaac ctgtcctccc aggctgttcc tgaggcctga ccacagtatt tattttggca   5160
tgtctctggc cttctgcaga ggcccaccct catgggcatt gtctctgttt cccagtgggg   5220
tggacagtat atcagatggt cagaacaaat aaagttcagt gtcaaatgaa aaaaaaaaaa   5280
aaaaaaaa                                                             5288
```

<210> SEQ ID NO 20
<211> LENGTH: 1167
<212> TYPE: PRT
<213> ORGANISM: Homo sapiens
<220> FEATURE:
<221> NAME/KEY: misc_feature
<222> LOCATION: (1)..(1167)
<223> OTHER INFORMATION: integrin alpha-10 isoform 1 precursor

<400> SEQUENCE: 20

```
Met Glu Leu Pro Phe Val Thr His Leu Phe Leu Pro Leu Val Phe Leu
1               5                   10                  15

Thr Gly Leu Cys Ser Pro Phe Asn Leu Asp Glu His His Pro Arg Leu
            20                  25                  30

Phe Pro Gly Pro Pro Glu Ala Glu Phe Gly Tyr Ser Val Leu Gln His
        35                  40                  45

Val Gly Gly Gly Gln Arg Trp Met Leu Val Gly Ala Pro Trp Asp Gly
    50                  55                  60

Pro Ser Gly Asp Arg Arg Gly Asp Val Tyr Arg Cys Pro Val Gly Gly
65                  70                  75                  80

Ala His Asn Ala Pro Cys Ala Lys Gly His Leu Gly Asp Tyr Gln Leu
                85                  90                  95

Gly Asn Ser Ser His Pro Ala Val Asn Met His Leu Gly Met Ser Leu
            100                 105                 110

Leu Glu Thr Asp Gly Asp Gly Gly Phe Met Ala Cys Ala Pro Leu Trp
        115                 120                 125

Ser Arg Ala Cys Gly Ser Ser Val Phe Ser Ser Gly Ile Cys Ala Arg
    130                 135                 140

Val Asp Ala Ser Phe Gln Pro Gln Gly Ser Leu Ala Pro Thr Ala Gln
145                 150                 155                 160

Arg Cys Pro Thr Tyr Met Asp Val Val Ile Val Leu Asp Gly Ser Asn
                165                 170                 175

Ser Ile Tyr Pro Trp Ser Glu Val Gln Thr Phe Leu Arg Arg Leu Val
            180                 185                 190

Gly Lys Leu Phe Ile Asp Pro Glu Gln Ile Gln Val Gly Leu Val Gln
        195                 200                 205

Tyr Gly Glu Ser Pro Val His Glu Trp Ser Leu Gly Asp Phe Arg Thr
    210                 215                 220

Lys Glu Glu Val Val Arg Ala Ala Lys Asn Leu Ser Arg Arg Glu Gly
```

```
            225                 230                 235                 240
Arg Glu Thr Lys Thr Ala Gln Ala Ile Met Val Ala Cys Thr Glu Gly
                245                 250                 255

Phe Ser Gln Ser His Gly Gly Arg Pro Glu Ala Arg Leu Leu Val
        260                 265                 270

Val Val Thr Asp Gly Glu Ser His Asp Gly Glu Leu Pro Ala Ala
            275                 280                 285

Leu Lys Ala Cys Glu Ala Gly Arg Val Thr Arg Tyr Gly Ile Ala Val
        290                 295                 300

Leu Gly His Tyr Leu Arg Arg Gln Arg Asp Pro Ser Ser Phe Leu Arg
305                 310                 315                 320

Glu Ile Arg Thr Ile Ala Ser Asp Pro Asp Glu Arg Phe Phe Phe Asn
                325                 330                 335

Val Thr Asp Glu Ala Ala Leu Thr Asp Ile Val Asp Ala Leu Gly Asp
            340                 345                 350

Arg Ile Phe Gly Leu Glu Gly Ser His Ala Glu Asn Glu Ser Ser Phe
        355                 360                 365

Gly Leu Glu Met Ser Gln Ile Gly Phe Ser Thr His Arg Leu Lys Asp
    370                 375                 380

Gly Ile Leu Phe Gly Met Val Gly Ala Tyr Asp Trp Gly Gly Ser Val
385                 390                 395                 400

Leu Trp Leu Glu Gly Gly His Arg Leu Phe Pro Pro Arg Met Ala Leu
                405                 410                 415

Glu Asp Glu Phe Pro Pro Ala Leu Gln Asn His Ala Ala Tyr Leu Gly
            420                 425                 430

Tyr Ser Val Ser Ser Met Leu Leu Arg Gly Gly Arg Leu Phe Leu
        435                 440                 445

Ser Gly Ala Pro Arg Phe Arg His Arg Gly Lys Val Ile Ala Phe Gln
    450                 455                 460

Leu Lys Lys Asp Gly Ala Val Arg Val Ala Gln Ser Leu Gln Gly Glu
465                 470                 475                 480

Gln Ile Gly Ser Tyr Phe Gly Ser Glu Leu Cys Pro Leu Asp Thr Asp
                485                 490                 495

Arg Asp Gly Thr Thr Asp Val Leu Leu Val Ala Ala Pro Met Phe Leu
            500                 505                 510

Gly Pro Gln Asn Lys Glu Thr Gly Arg Val Tyr Val Tyr Leu Val Gly
        515                 520                 525

Gln Gln Ser Leu Leu Thr Leu Gln Gly Thr Leu Gln Pro Glu Pro Pro
    530                 535                 540

Gln Asp Ala Arg Phe Gly Phe Ala Met Gly Ala Leu Pro Asp Leu Asn
545                 550                 555                 560

Gln Asp Gly Phe Ala Asp Val Ala Val Gly Ala Pro Leu Glu Asp Gly
                565                 570                 575

His Gln Gly Ala Leu Tyr Leu Tyr His Gly Thr Gln Ser Gly Val Arg
            580                 585                 590

Pro His Pro Ala Gln Arg Ile Ala Ala Ala Ser Met Pro His Ala Leu
        595                 600                 605

Ser Tyr Phe Gly Arg Ser Val Asp Gly Arg Leu Asp Leu Asp Gly Asp
    610                 615                 620

Asp Leu Val Asp Val Ala Val Gly Ala Gln Gly Ala Ala Ile Leu Leu
625                 630                 635                 640

Ser Ser Arg Pro Ile Val His Leu Thr Pro Ser Leu Glu Val Thr Pro
                645                 650                 655
```

```
Gln Ala Ile Ser Val Val Gln Arg Asp Cys Arg Arg Gly Gln Glu
            660                 665                 670

Ala Val Cys Leu Thr Ala Ala Leu Cys Phe Gln Val Thr Ser Arg Thr
            675                 680                 685

Pro Gly Arg Trp Asp His Gln Phe Tyr Met Arg Phe Thr Ala Ser Leu
            690                 695                 700

Asp Glu Trp Thr Ala Gly Ala Arg Ala Ala Phe Asp Gly Ser Gly Gln
705                 710                 715                 720

Arg Leu Ser Pro Arg Arg Leu Arg Leu Ser Val Gly Asn Val Thr Cys
                725                 730                 735

Glu Gln Leu His Phe His Val Leu Asp Thr Ser Asp Tyr Leu Arg Pro
            740                 745                 750

Val Ala Leu Thr Val Thr Phe Ala Leu Asp Asn Thr Thr Lys Pro Gly
            755                 760                 765

Pro Val Leu Asn Glu Gly Ser Pro Thr Ser Ile Gln Lys Leu Val Pro
            770                 775                 780

Phe Ser Lys Asp Cys Gly Pro Asp Asn Glu Cys Val Thr Asp Leu Val
785                 790                 795                 800

Leu Gln Val Asn Met Asp Ile Arg Gly Ser Arg Lys Ala Pro Phe Val
                805                 810                 815

Val Arg Gly Gly Arg Arg Lys Val Leu Val Ser Thr Thr Leu Glu Asn
            820                 825                 830

Arg Lys Glu Asn Ala Tyr Asn Thr Ser Leu Ser Leu Ile Phe Ser Arg
            835                 840                 845

Asn Leu His Leu Ala Ser Leu Thr Pro Gln Arg Glu Ser Pro Ile Lys
            850                 855                 860

Val Glu Cys Ala Ala Pro Ser Ala His Ala Arg Leu Cys Ser Val Gly
865                 870                 875                 880

His Pro Val Phe Gln Thr Gly Ala Lys Val Thr Phe Leu Leu Glu Phe
                885                 890                 895

Glu Phe Ser Cys Ser Ser Leu Ser Gln Val Phe Val Lys Leu Thr
            900                 905                 910

Ala Ser Ser Asp Ser Leu Glu Arg Asn Gly Thr Leu Gln Asp Asn Thr
            915                 920                 925

Ala Gln Thr Ser Ala Tyr Ile Gln Tyr Glu Pro His Leu Leu Phe Ser
            930                 935                 940

Ser Glu Ser Thr Leu His Arg Tyr Glu Val His Pro Tyr Gly Thr Leu
945                 950                 955                 960

Pro Val Gly Pro Gly Pro Glu Phe Lys Thr Thr Leu Arg Val Gln Asn
                965                 970                 975

Leu Gly Cys Tyr Val Val Ser Gly Leu Ile Ile Ser Ala Leu Leu Pro
            980                 985                 990

Ala Val Ala His Gly Gly Asn Tyr  Phe Leu Ser Leu Ser  Gln Val Ile
            995                 1000                1005

Thr Asn  Asn Ala Ser Cys Ile  Val Gln Asn Leu Thr  Glu Pro Pro
     1010                1015                1020

Gly Pro  Pro Val His Pro Glu  Leu Gln His Thr  Asn Arg Leu
     1025                1030                1035

Asn Gly  Ser Asn Thr Gln Cys  Gln Val Val Arg Cys  His Leu Gly
     1040                1045                1050

Gln Leu  Ala Lys Gly Thr Glu  Val Ser Val Gly Leu  Leu Arg Leu
     1055                1060                1065
```

```
Val His Asn Glu Phe Phe Arg Arg Ala Lys Phe Lys Ser Leu Thr
    1070                1075                1080

Val Val Ser Thr Phe Glu Leu Gly Thr Glu Glu Gly Ser Val Leu
    1085                1090                1095

Gln Leu Thr Glu Ala Ser Arg Trp Ser Glu Ser Leu Leu Glu Val
    1100                1105                1110

Val Gln Thr Arg Pro Ile Leu Ile Ser Leu Trp Ile Leu Ile Gly
    1115                1120                1125

Ser Val Leu Gly Gly Leu Leu Leu Leu Ala Leu Leu Val Phe Cys
    1130                1135                1140

Leu Trp Lys Leu Gly Phe Phe Ala His Lys Lys Ile Pro Glu Glu
    1145                1150                1155

Glu Lys Arg Glu Glu Lys Leu Glu Gln
    1160                1165

<210> SEQ ID NO 21
<211> LENGTH: 3831
<212> TYPE: DNA
<213> ORGANISM: Homo sapiens
<220> FEATURE:
<221> NAME/KEY: misc_feature
<222> LOCATION: (1)..(3831)
<223> OTHER INFORMATION: G protein-coupled receptor G1 (ADGRG1),
      transcript variant 1, mRNA

<400> SEQUENCE: 21
agacaggcgg agcctcacct ggggctgccc gccagcccag acaagctcag actgggtgcc      60
tgtggccctg ggaggaggtg aaggggagg agcaggccac acaggcacag gccggtgagg     120
gacctgccca gacctggagg gtctcgctct gtcacacagg ctggagtgca gtggtgtgat     180
cttggctcat cgtaacctcc acctcccggg ttcaagtgat tctcatgcct cagcctcccg     240
agtagctggg attacaggtg gtgacttcca agagtgactc cgtcggagga aaatgactcc     300
ccagtcgctc ctgcagacga cactgttcct gctgagtctg ctcttcctgg tccaaggtgc     360
ccacggcagg ggccacaggg aagactttcg cttctgcagc cagcggaacc agacacacag     420
gagcagcctc cactacaaac ccacaccaga cctgcgcatc tccatcgaga actccgaaga     480
ggccctcaca gtccatgccc cttttccctg cagcccaccct gcttcccgat ccttccctga     540
ccccaggggc ctctaccact tctgcctcta ctggaaccga catgctggga gattacatct     600
tctctatggc aagcgtgact tcttgctgag tgacaaagcc tctagcctcc tctgcttcca     660
gcaccaggag gagagcctgg ctcagggccc ccgctgttta gccacttctg tcacctcctg     720
gtggagccct cagaacatca gcctgcccag tgccgccagc ttcaccttct ccttccacag     780
tcctccccac acggccgctc acaatgcctc ggtggacatg tgcgagctca aagggacct      840 ccagctgctc agccagttcc tgaagcatcc ccagaaggcc tcaaggaggc cctcggctgc     900
ccccgccagc cagcagttgc agagcctgga gtcgaaactg acctctgtga gattcatggg     960
ggacatggtg tccttcgagg aggaccggat caacgccacg gtgtggaagc tccagcccac    1020
agccggcctc caggacctgc acatccactc ccggcaggag gaggagcaga gcgagatcat    1080
ggagtactcg gtgctgctgc ctcgaacact cttccagagg acgaaaggcc ggagcgggga    1140
ggctgagaag agactcctcc tggtggactt cagcagccaa gccctgttcc aggacaagaa    1200
ttccagccaa gtcctgggtg agaaggtctc ggggattgtg gtacagaaca ccaaagtagc    1260
caacctcacg gagcccgtgg tgctcacttt ccagcaccag ctacagccga agaatgtgac    1320
tctgcaatgt gtgttctggg ttgaagaccc cacattgagc agcccggggc attggagcag    1380
```

-continued

```
tgctgggtgt gagaccgtca ggagagaaac ccaaacatcc tgcttctgca accacttgac   1440
ctactttgca gtgctgatgg tctcctcggt ggaggtggac gccgtgcaca agcactacct   1500
gagcctcctc tcctacgtgg gctgtgtcgt ctctgccctg gcctgccttg tcaccattgc   1560
cgcctacctc tgctccaggg tgcccctgcc gtgcaggagg aaacctcggg actacaccat   1620
caaggtgcac atgaacctgc tgctggccgt cttcctgctg acacgagct tcctgctcag   1680 cgagccggtg gccctgacag gctctgaggc tggctgccga gccagtgcca tcttcctgca   1740
cttctccctg ctcacctgcc tttcctggat gggcctcgag gggtacaacc tctaccgact   1800
cgtggtggag gtctttggca cctatgtccc tggctaccta ctcaagctga gcgccatggg   1860
ctggggcttc cccatctttc tggtgacgct ggtggccctg gtggatgtgg acaactatgg   1920
ccccatcatc ttggctgtgc ataggactcc agagggcgtc atctacccct ccatgtgctg   1980
gatccgggac tccctggtca gctacatcac caacctgggc ctcttcagcc tggtgtttct   2040
gttcaacatg gccatgctag ccaccatggt ggtgcagatc ctgcggctgc gccccacac   2100 ccaaaagtgg tcacatgtgc tgacactgct gggcctcagc ctggtccttg gcctgccctg   2160
ggccttgatc ttcttctcct ttgcttctgg caccttccag cttgtcgtcc tctaccttt   2220 cagcatcatc acctccttcc aaggcttcct catcttcatc tggtactggt ccatgcggct   2280
gcaggcccgg ggtggcccct cccctctgaa gagcaactca gacagcgcca ggctccccat   2340
cagctcgggc agcacctcgt ccagccgcat ctaggcctcc agcccacctg cccatgtgat   2400
gaagcagaga ttcggcctcg tcgcacactg cctgtggccc ccgagccggg cccagcccca   2460
ggccagtcag ccgcagactt tggaaagccc aacgaccatg gagagatggg ccgttgccat   2520
ggtggacgga ctcccgggct gggcttttga attggcttg gggactactc ggctctcact   2580
cagctcccac gggactcaga agtgcgccgc catgctgcct agggtactgt ccccacatct   2640
gtcccaaccc agctggaggc ctggtctctc cttacaaccc ctgggcccag ccctcattgc   2700
tgggggccag gccttggatc ttgagggtct ggcacatcct taatcctgtg ccctgcctg   2760 ggacagaaat gtggctccag ttgctctgtc tctcgtggtc accctgaggg cactctgcat   2820
cctctgtcat tttaacctca ggtggcaccc agggcgaatg gggcccaggg cagaccttca   2880
gggccagagc cctggcggag gagaggccct ttgccaggag cacagcagca gctcgcctac   2940
ctctgagccc aggcccctc cctccctcag cccccagtc ctccctccat ttccctggg   3000 gttctcctcc tctcccaggg cctccttgct ccttcgttca gctgggggg tcccgattc   3060 caatgctgtt ttttggggag tggtttccag gagctgcctg gtgtctgctg taaatgttg   3120 tctactgcac aagcctcggc ctgcccctga ccaggctcg gtaccgatgc gtgggctggg   3180
ctaggtccct ctgtccatct gggcctttgt atgagctgca ttgcccttgc tcaccctgac   3240
caagcacacg cctcagaggg gccctcagcc tctcctgaag ccctcttgtg gcaagaactg   3300
tggaccatgc cagtcccgtc tggtttccat cccaccactc caaggactga gactgacctc   3360
ctctggtgac actggcctag ggcctgacac tctcctaaga ggttctctcc aagcccccaa   3420
atagctccag gcgccctcgg ccgcccatca tggttaattc tgtccaacaa acacacacgg   3480
gtagattgct ggcctgttgt aggtggtagg gacacagatg accgacctgg tcactcctcc   3540
tgccaacatt cagtctggta tgtgaggcgt gcgtgaagca agaactcctg gagctacagg   3600
gacagggagc catcattcct gcctgggaat cctggaagac ttcctgcagg agtcagcgtt   3660
caatcttgac cttgaagatg ggaaggatgt tcttttacg taccaattct tttgtctttt   3720
```

```
gatattaaaa agaagtacat gttcattgta gagaatttgg aaactgtaga agagaatcaa      3780
gaagaaaaat aaaaatcagc tgttgtaatc acctagcaaa ctggcgtaag c               3831
```

<210> SEQ ID NO 22
<211> LENGTH: 693
<212> TYPE: PRT
<213> ORGANISM: Homo sapiens
<220> FEATURE:
<221> NAME/KEY: misc_feature
<222> LOCATION: (1)..(693)
<223> OTHER INFORMATION: G-protein coupled receptor 56 isoform a
      precursor

<400> SEQUENCE: 22

```
Met Thr Pro Gln Ser Leu Leu Gln Thr Thr Leu Phe Leu Leu Ser Leu
1               5                   10                  15

Leu Phe Leu Val Gln Gly Ala His Gly Arg Gly His Arg Glu Asp Phe
            20                  25                  30

Arg Phe Cys Ser Gln Arg Asn Gln Thr His Arg Ser Ser Leu His Tyr
        35                  40                  45

Lys Pro Thr Pro Asp Leu Arg Ile Ser Ile Glu Asn Ser Glu Glu Ala
    50                  55                  60

Leu Thr Val His Ala Pro Phe Pro Ala Ala His Pro Ala Ser Arg Ser
65                  70                  75                  80

Phe Pro Asp Pro Arg Gly Leu Tyr His Phe Cys Leu Tyr Trp Asn Arg
                85                  90                  95

His Ala Gly Arg Leu His Leu Leu Tyr Gly Lys Arg Asp Phe Leu Leu
            100                 105                 110

Ser Asp Lys Ala Ser Ser Leu Leu Cys Phe Gln His Gln Glu Glu Ser
        115                 120                 125

Leu Ala Gln Gly Pro Pro Leu Leu Ala Thr Ser Val Thr Ser Trp Trp
    130                 135                 140

Ser Pro Gln Asn Ile Ser Leu Pro Ser Ala Ala Ser Phe Thr Phe Ser
145                 150                 155                 160

Phe His Ser Pro Pro His Thr Ala Ala His Asn Ala Ser Val Asp Met
                165                 170                 175

Cys Glu Leu Lys Arg Asp Leu Gln Leu Leu Ser Gln Phe Leu Lys His
            180                 185                 190

Pro Gln Lys Ala Ser Arg Arg Pro Ser Ala Ala Pro Ala Ser Gln Gln
        195                 200                 205

Leu Gln Ser Leu Glu Ser Lys Leu Thr Ser Val Arg Phe Met Gly Asp
    210                 215                 220

Met Val Ser Phe Glu Glu Asp Arg Ile Asn Ala Thr Val Trp Lys Leu
225                 230                 235                 240

Gln Pro Thr Ala Gly Leu Gln Asp Leu His Ile His Ser Arg Gln Glu
                245                 250                 255

Glu Glu Gln Ser Glu Ile Met Glu Tyr Ser Val Leu Leu Pro Arg Thr
            260                 265                 270

Leu Phe Gln Arg Thr Lys Gly Arg Ser Gly Glu Ala Glu Lys Arg Leu
        275                 280                 285

Leu Leu Val Asp Phe Ser Ser Gln Ala Leu Phe Gln Asp Lys Asn Ser
    290                 295                 300

Ser Gln Val Leu Gly Glu Lys Val Leu Gly Ile Val Val Gln Asn Thr
305                 310                 315                 320

Lys Val Ala Asn Leu Thr Glu Pro Val Val Leu Thr Phe Gln His Gln
                325                 330                 335
```

Leu Gln Pro Lys Asn Val Thr Leu Gln Cys Val Phe Trp Val Glu Asp
                340                 345                 350

Pro Thr Leu Ser Ser Pro Gly His Trp Ser Ser Ala Gly Cys Glu Thr
                355                 360                 365

Val Arg Arg Glu Thr Gln Thr Ser Cys Phe Cys Asn His Leu Thr Tyr
370                 375                 380

Phe Ala Val Leu Met Val Ser Ser Val Glu Val Asp Ala Val His Lys
385                 390                 395                 400

His Tyr Leu Ser Leu Leu Ser Tyr Val Gly Cys Val Ser Ala Leu
                405                 410                 415

Ala Cys Leu Val Thr Ile Ala Ala Tyr Leu Cys Ser Arg Val Pro Leu
                420                 425                 430

Pro Cys Arg Arg Lys Pro Arg Asp Tyr Thr Ile Lys Val His Met Asn
                435                 440                 445

Leu Leu Leu Ala Val Phe Leu Leu Asp Thr Ser Phe Leu Leu Ser Glu
                450                 455                 460

Pro Val Ala Leu Thr Gly Ser Glu Ala Gly Cys Arg Ala Ser Ala Ile
465                 470                 475                 480

Phe Leu His Phe Ser Leu Leu Thr Cys Leu Ser Trp Met Gly Leu Glu
                485                 490                 495

Gly Tyr Asn Leu Tyr Arg Leu Val Val Glu Val Phe Gly Thr Tyr Val
                500                 505                 510

Pro Gly Tyr Leu Leu Lys Leu Ser Ala Met Gly Trp Gly Phe Pro Ile
                515                 520                 525

Phe Leu Val Thr Leu Val Ala Leu Val Asp Val Asp Asn Tyr Gly Pro
                530                 535                 540

Ile Ile Leu Ala Val His Arg Thr Pro Glu Gly Val Ile Tyr Pro Ser
545                 550                 555                 560

Met Cys Trp Ile Arg Asp Ser Leu Val Ser Tyr Ile Thr Asn Leu Gly
                565                 570                 575

Leu Phe Ser Leu Val Phe Leu Phe Asn Met Ala Met Leu Ala Thr Met
                580                 585                 590

Val Val Gln Ile Leu Arg Leu Arg Pro His Thr Gln Lys Trp Ser His
                595                 600                 605

Val Leu Thr Leu Leu Gly Leu Ser Leu Val Leu Gly Leu Pro Trp Ala
                610                 615                 620

Leu Ile Phe Phe Ser Phe Ala Ser Gly Thr Phe Gln Leu Val Val Leu
625                 630                 635                 640

Tyr Leu Phe Ser Ile Ile Thr Ser Phe Gln Gly Phe Leu Ile Phe Ile
                645                 650                 655

Trp Tyr Trp Ser Met Arg Leu Gln Ala Arg Gly Gly Pro Ser Pro Leu
                660                 665                 670

Lys Ser Asn Ser Asp Ser Ala Arg Leu Pro Ile Ser Ser Gly Ser Thr
                675                 680                 685

Ser Ser Ser Arg Ile
    690

<210> SEQ ID NO 23
<211> LENGTH: 5135
<212> TYPE: DNA
<213> ORGANISM: Homo sapiens
<220> FEATURE:
<221> NAME/KEY: misc_feature
<222> LOCATION: (1)..(5135)
<223> OTHER INFORMATION: WW domain containing transcription regulator 1

(WWTR1), transcript variant 1, mRNA

<400> SEQUENCE: 23

| | | | | | |
|---|---|---|---|---|---|
| ataattcaac | agctcaactt | tcgggcccgc | ctctttcctg | ggggtgggag | tttgctccaa | 60 |
| actttgttta | tgggacagtc | cgggagctgc | tgcggccgcg | ctgtctgctt | ctcctgcgcc | 120 |
| tccttttcgc | ccagcactag | cgccttaggc | cagctcgggg | gatgtgagag | ccgaagccct | 180 |
| tagactgcca | ggcacagagt | cgggtcggga | tttgtcagcc | aagcctcggc | tccagctccg | 240 |
| caatctcggg | actcacccga | gcgacccagg | cccgacggca | agttcgggcg | gacggcggc | 300 |
| cgccgcgcgc | tcaggctcag | cttcgctgcc | cgcccagaag | atgaatccgg | cctcggcgcc | 360 |
| ccctccgctc | ccgccgcctg | ggcagcaagt | gatccacgtc | acgcaggacc | tagacacaga | 420 |
| cctcgaagcc | ctcttcaact | ctgtcatgaa | tccgaagcct | agctcgtggc | ggaagaagat | 480 |
| cctgccggag | tctttctttta | aggagcctga | ttcgggctcg | cactcgcgcc | agtccagcac | 540 |
| cgactcgtcg | ggcggccacc | cggggcctcg | actggctggg | ggtgcccagc | atgtccgctc | 600 |
| gcactcgtcg | cccgcgtccc | tgcagctggg | caccggcgcg | ggtgctgcgg | gtagcccgc | 660 |
| gcagcagcac | gcgcacctcc | gccagcagtc | ctacgacgtg | accgacgagc | tgccactgcc | 720 |
| cccgggctgg | gagatgacct | tcacggccac | tggccagagg | tacttcctca | atcacataga | 780 |
| aaaaatcacc | acatggcaag | accctaggaa | ggcgatgaat | cagcctctga | atcatatgaa | 840 |
| cctccaccct | gccgtcagtt | ccacaccagt | gcctcagagg | tccatggcag | tatcccagcc | 900 |
| aaatctcgtg | atgaatcacc | aacaccagca | gcagatggcc | cccagtaccc | tgagccagca | 960 |
| gaaccacccc | actcagaacc | cacccgcagg | gctcatgagt | atgcccaatg | cgctgaccac | 1020 |
| tcagcagcag | cagcagcaga | aactgcggct | tcagagaatc | cagatggaga | gagaaaggat | 1080 |
| tcgaatgcgc | caagaggagc | tcatgaggca | ggaagctgcc | ctctgtcgac | agctccccat | 1140 |
| ggaagctgag | actcttgccc | cagttcaggc | tgctgtcaac | ccacccacga | tgaccccaga | 1200 |
| catgagatcc | atcactaata | tagctcaga | tccttttcctc | aatggagggc | catatcattc | 1260 |
| gagggagcag | agcactgaca | gtggcctggg | gttagggtgc | tacagtgtcc | ccacaactcc | 1320 |
| ggaggacttc | ctcagcaatg | tggatgagat | ggatacagga | gaaaacgcag | acaaacaccc | 1380 |
| catgaacatc | aatccccaac | agacccgttt | ccctgatttc | cttgactgtc | ttccaggaac | 1440 |
| aaacgttgac | ttaggaactt | tggaatctga | agacctgatc | cccctcttca | atgatgtaga | 1500 |
| gtctgctctg | aacaaaagtg | agcccttttct | aacctggctg | taatcactac | cattgtaact | 1560 |
| tggatgtagc | catgacctta | catttcctgg | gcctcttgga | aaaagtgatg | gagcagagca | 1620 |
| agtctgcagg | tgcaccactt | cccgcctcca | tgactcgtgc | tccctccttt | ttatgttgcc | 1680 |
| agtttaatca | ttgcctggtt | ttgattgaga | gtaacttaag | ttaaacataa | ataaatattc | 1740 |
| tattttcatt | ttctgcaagc | ctgcgttctt | gtgacagatt | atacagaatt | gtgtctgcag | 1800 |
| gattgattat | gcagaatact | tttctctttc | ttctctgctg | ccccatggct | aagctttatg | 1860 |
| ggtgttaatt | gaaatttata | caccaattga | ttttaaacca | taaaaagctg | accacaggca | 1920 |
| gttacttctg | agggcatctt | ggtccaggaa | atgtgcacaa | aattcgacct | gatttacagt | 1980 |
| ttcaaaaact | gtattgatga | cagtagtacc | aaatgcttta | aaaactattt | aacttgagct | 2040 |
| ttaaaaatca | ttgtatggat | agtaaaattc | tactgtatgg | aatacaatgt | aattttgaat | 2100 |
| ccatgctggc | tctgatggct | cttattagtc | tgtatttata | aaggcacaca | gtcctattgt | 2160 |
| agcttatctt | tcgttatttt | actgcagagc | atctagacaa | cttagtccct | ccagcgggaa | 2220 |
| agtagcagca | gcagcattag | tcacaggtct | tacactacag | atcttgtgaa | agagaccagt | 2280 |

```
ttggtactaa ttatgagcat tttattcaaa caaaagtttt tgaaatatta caactgggga    2340
tttaaaaaat tgcagcttag aatctgatgg ttttttttt tcttgatgtt gtttgtttgt     2400
ttttgagatc gagttttgct cttgttgtcc aggctggaat gcaatggcac aatctcggct    2460
cactgcaacc tctgccttct gggttcaagc gattctcctg ccttagcctc ccgagtagct    2520
gggattacag gcacctgcca ccacgtccgg ctaattttt gtattttgag tagagacggg     2580
gtttcaccat aatggtcagg ctgttctcaa actcctgatc tcaggtgatc cacccatctc    2640
ggcctcccaa agtgctggga ttactggcgt gagccaccgc acccggcctt gatgtttatt    2700
ttataaagca ctgtaattt gtagctgatg acaaaaggca gccaaatgtt tttgataaat     2760
cagtggcaac tgtattttg tcttttgaaa taactctgaa aacatcagga caacatagat     2820
ttcaacctga tagcacacca cacacagtga gctgttgctt tttaaattct gaagccttgt    2880
caggtttgct tcctagattt caagtgttta aaataattct atctatgaaa ctgaaggatg    2940
aagcagatct ctgactgaca tgtaaaaaaa aatgcccttt gagggtgtat ggtggagata    3000
aatgtttctg aattcagtaa aattgattcc taagtatatt atcctaatcc tgtttgctac    3060
agttggtata aaaaggcatg aaatatgtat tcaatacctc ttatgtaacc aaaaccattt    3120
ttaattagct tttaaggact gagagagcat catgttcaac tggcatgcag tctgcctgca    3180
ttgccaatga agtcctcaac tgtttaatat tttgaactaa tattatttat aatctatgaa    3240
tttaatcttt tttgaaagac tttaataatt tgagtctctg agaggatact ttcaatttcc    3300 atggggggact tatttgttgg ggatcttaaa taagattcct tttgatctac cggaatatac    3360
atgtacagag tacattggat catgttggaa agaaggcaag tgaaaaggtc agagatgaag    3420
tagcaaagtt atggaatatc gtggaaagga tactagttgt gaaatggaaa agacaagtt     3480 atagtacccc aaaagcaaaa caagcaggag atgcaagaga tgccccaaaa ggacaaagca    3540
acaattttct gttgccacct ttataccgga agactctgtt gtagaagaaa agaaggcttt    3600
ggtgcacctt atgtgggagg aggagggggca gggcatgctg atgctgagcg tacaggcaga    3660
caagagcgta gcctgctgtt gcctccatca ctatgaaatg acttatttta cctgaaggac    3720
ccatggttta tgttcctcta attcctttca ctctccctaa gccctctgag agagatgaag    3780
atagatgatt ttattgctac taaattgaag ggagcactat ttcttttgt cttttgttag     3840 caaaaattg caaaagaat tgtacattct tgctaaaaat aaataataa ataaaaaatt       3900 aaaaaaacaa gggacctaac aaaactcagc agtgttactg tattttaaa aaatattttt     3960 atagactcat tttcaggtta ttaaatgtaa agaaaacaga taccctctct ttttaaagta    4020
ggtaaatcat tgatgattta tattaccaat ttttagaagt aattttctag taagcttgtg    4080
gcatcagaaa atactagaag atttttttag ttaaattagt tagaacattt atgaatgaat    4140
ataataaata tttttcaga ataaaatatg gacccttgt gtttactaat agataaagcc       4200
agatataatt ttttgttttt aaggccacaa aatatggcct ttgttaaaga acactaaagt    4260
tagaaatcta aagttagagc aacttttaa tggctatttc ctattattgt aagtgttaaa     4320 accccctgcag aattcttgat aaggtgctat ttatactata tttcttatta taagataact    4380
gtctttagtc ttcttagtac tagtctttt agtactaaat caatcagtaa acatcatcat     4440 ttcacccccaa aattttgtca cagaaaaggc gtatcaaatg aaaaataatt tcagagatct    4500
ttctttcaag atattttttc ctgataaaat acattgtctt gaagtaaata cattgtcaaa    4560
acctaattgc aattctgtta aatctaagta attttttagac agtgtttcac cgtattattt    4620
```

```
aggatgtgaa atgccatttc tttcactgat tacaccatat acaggaaaca ggtaaaacag    4680
tgaaaacttt attgtgctgg ttgatgccaa cttggttgaa aagctctctg cagaagaagt    4740
gatctagact gacagaagtg ttgctaatta caagttgtgt tctcatgacg taattagaaa    4800
gtaacttctc aaagtacaac ttttatgaaa aaataagct gttaaaaaaa ggaaatcgta     4860
ggttaattta attgggaaaa tgggcaattg acagagacca ttttcctaac acatatatgt    4920
gctagtactt taacttttta aaatttact tctacgtttt gtaatataaa aatttctatt     4980
ttaagtttag aatgttatac gtaccgaaag tatgcagcca aatcgatcag atcaaaccat    5040
tttacctgga gtttggtact ggttttact  tctctgaatc tgtataagaa aaataaagac    5100
aattgaactt ccaaagaaaa aaaaaaaaaa aaaaa                               5135
```

<210> SEQ ID NO 24
<211> LENGTH: 400
<212> TYPE: PRT
<213> ORGANISM: Homo sapiens
<220> FEATURE:
<221> NAME/KEY: misc_feature
<222> LOCATION: (1)..(400)
<223> OTHER INFORMATION: WW domain-containing transcription regulator protein 1

<400> SEQUENCE: 24

```
Met Asn Pro Ala Ser Ala Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Met Ala Pro Ser Thr Leu Ser Gln Gln Asn
        195                 200                 205

His Pro Thr Gln Asn Pro Pro Ala Gly Leu Met Ser Met Pro Asn Ala
    210                 215                 220

Leu Thr Thr Gln Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                245                 250                 255
```

| | | | | | | | | | | | |
|---|---|---|---|---|---|---|---|---|---|---|---|
| Gln | Glu | Ala | Ala | Leu | Cys | Arg | Gln | Leu | Pro | Met | Glu | Ala | Glu | Thr | Leu |
| | | | 260 | | | | | 265 | | | | | 270 | | |
| Ala | Pro | Val | Gln | Ala | Ala | Val | Asn | Pro | Pro | Thr | Met | Thr | Pro | Asp | Met |
| | 275 | | | | | 280 | | | | | 285 | | | | |
| Arg | Ser | Ile | Thr | Asn | Asn | Ser | Ser | Asp | Pro | Phe | Leu | Asn | Gly | Gly | Pro |
| | 290 | | | | | 295 | | | | | 300 | | | | |
| Tyr | His | Ser | Arg | Glu | Gln | Ser | Thr | Asp | Ser | Gly | Leu | Gly | Leu | Gly | Cys |
| 305 | | | | | 310 | | | | | 315 | | | | | 320 |
| Tyr | Ser | Val | Pro | Thr | Thr | Pro | Glu | Asp | Phe | Leu | Ser | Asn | Val | Asp | Glu |
| | | | | 325 | | | | | 330 | | | | | 335 | |
| Met | Asp | Thr | Gly | Glu | Asn | Ala | Gly | Gln | Thr | Pro | Met | Asn | Ile | Asn | Pro |
| | | | 340 | | | | | 345 | | | | | 350 | | |
| Gln | Gln | Thr | Arg | Phe | Pro | Asp | Phe | Leu | Asp | Cys | Leu | Pro | Gly | Thr | Asn |
| | | 355 | | | | | 360 | | | | | 365 | | | |
| Val | Asp | Leu | Gly | Thr | Leu | Glu | Ser | Glu | Asp | Leu | Ile | Pro | Leu | Phe | Asn |
| | 370 | | | | | 375 | | | | | 380 | | | | |
| Asp | Val | Glu | Ser | Ala | Leu | Asn | Lys | Ser | Glu | Pro | Phe | Leu | Thr | Trp | Leu |
| 385 | | | | | 390 | | | | | 395 | | | | | 400 |

<210> SEQ ID NO 25
<211> LENGTH: 4963
<212> TYPE: DNA
<213> ORGANISM: Homo sapiens
<220> FEATURE:
<221> NAME/KEY: misc_feature
<222> LOCATION: (1)..(4963)
<223> OTHER INFORMATION: contactin 3 (CNTN3), mRNA

<400> SEQUENCE: 25

```
gagttactct tgcatttggc aattaaagat gatgtttcca tggaaacagt tgatcctgct      60
ttcattcatt ggctgcttag gaggtgagct tctcttacaa ggccctgtat ttatcaaaga     120
acccagcaac agcattttcc ctgttggttc agaagataaa aaataacttt gcattgtga     180
agcaagaggc aatccatcac ctcattacag atggcagctg aatggaagtg atattgatat     240
gagtatggaa catcgttata agttgaatgg aggaaatctt gtggttatta atcccaacag     300
aaattgggat acaggaactt accaatgttt tgcaacaaat tcacttggaa caattgtcag     360
cagagaagcc aaacttcagt ttgcctatct tgaaattttt aaaaccaaaa tgaggagtac     420
agtgtctgtg cgtgaaggcc agggagttgt gctgctctgc ggccccccac cacactctgg     480
agaactgtca tatgcttgga tcttcaatga atacccatcg tttgttgaag aagatagtcg     540
gagatttgtc tcccaggaga cagggcacct ctacatatct aaggtggagc cgtctgatgt     600
gggaaattac acatgtgtgg tgacaagtat ggtgacaaat gcccgagtgc tgggctctcc     660
aactcctttg gtgctacgtt ctgatggtgt gatgggtgaa tatgaaccta aaatagaagt     720
tcagtttcca gaaactcttc cagcagctaa aggttcgact gtgaaattgg aatgttttgc     780
ccttggaaat cccatacctc agattaattg gagaagaagt gatgggctgc attttccag     840
caaaattaaa ttaaggaagt tcagtggtgt gcttgaaatc cccaacttcc aacaggaaga     900
tgcaggttcc tatgaatgca ttgctgagaa ttcacgagga aaaaatgttg ccagagggcg     960
tctcacttac tatgcaaagc cccattgggt tcaactcata aaggatgtgg aaatagccgt    1020
ggaggacagt ctttattggg aatgcagggc aagcggcaag cccaagcctt cctaccgatg    1080
gctgaaaaat ggagcagccc tggtgctaga ggagagaaca cagatagaaa atggtgccct    1140
tacaatatca aacctaagtg tgactgattc tggcatgttc aatgcatag cagaaaacaa     1200
```

```
acatggcctt gtttattcca gtgctgagct caaagttgtt gcttctgctc cagattttc    1260
aaagaatcca atgaagaagt tggttcaggt gcaggtgggc agcctggtca gcttggattg    1320
taaacccaga gcctcccaa gggcactctc ttcctggaag aagggggatg tgagcgtgca     1380
ggagcatgaa agaatttctt tgttaaacga tggaggactc aaaatagcca atgtgactaa    1440
agctgatgct ggaacttaca cctgcatggc agaaaaccag tttgggaaag caaatggcac    1500
aacacatttg gttgttacgg aaccaacaag aataactttg gcaccatcta acatggatgt    1560
ttctgttggt gaaagcgtca tattgccctg ccaggtacaa catgacccgc tgttagacat    1620
catctttacc tggtatttca atggggccct tgcagatttt aagaaagatg gatctcactt    1680
tgagaaagtt ggtgggagtt catctggtga tttaatgatc agaaacattc agctgaaaca    1740
cagtgggaaa tatgtttgta tggtgcaaac ggggtggac agtgtttcat ctgctgctga     1800
cctcatagta agaggttcac ctggaccacc agaaaatgtg aaggtagatg aaattacaga    1860
cacaacagcc caactctctt ggaaagaagg taaagacaac catagcccag ttatatccta    1920
ttctatccag gctcggacac ctttctccgt gggttggcaa accgtcacaa cagtgcctga    1980
ggtcatcgat gggaagacgc acacagccac tgtagttgag ttaaacccat gggtggaata    2040
tgaatttcgg gttgtagcca gtaacaaaat tggaggtgga gaaccaagtt taccctcaga    2100
aaaagtaaga actgaagagg cagttccaga agtgcctcct tctgaagtca atggaggagg    2160
cggaagccgg tctgaacttg tgataacctg ggatccagtc cctgaagaac tacagaatgg    2220
tgaaggtttt gggtatgttg ttgctttccg ccctcttggg gttaccacct ggatccagac    2280
agtggtgaca tcccctgaca ccccaagata tgtctttagg aatgaaagca tcgtgccata    2340
ttcaccatat gaagttaaag tgggtgttta taataacaaa ggtgaaggac catttagccc    2400
agtgacaaca gtgttctctg cagaagaaga gcctacagtg gccccatctc aagtctctgc    2460
aaatagccta tcttcctcag aaattgaggt ttcatggaac accattcctt ggaagttgag    2520
caatggacat ttactgggct atgaggtgcg gtactgaat gggggtggaa aggaggaatc     2580
atccagtaag atgaaagtgg caggaaatga gacatcagcc agactacggg gcctgaagag    2640
caacctggcc tattcacgg ctgtccgggc ttacaacagt gccggcgctg ggccttttag     2700
cgccacagtt aatgtaacca ccaagaaaac gcctcccagt cagccaccag gaaatgttgt    2760
ttggaatgcc acagacacta agtgttact taattgggag caagttaaag ccatggagaa     2820
tgagtcagaa gtaacaggat ataaagtttt ctataggact agcagtcaaa ataacgtaca    2880
agtactgaac acaaataaaa cttcagctga acttgtgctg cccattaaag aggactacat    2940
tattgaagtc aaggccacaa cagatggagg ggatgggacc agtagtgaac agatcaggat    3000
tccacgaata accagtatgg atgcaagagg atccacttca gccatctcga atgtccaccc    3060
tatgtcaagt tatatgccta gtactgtt cttaattgta tatgtcctgt ggtgatatta      3120
actccttttt attatttatt ggaaagttat ttggttacca aaaaagtgc tttcatgaaa     3180
tgcagtgatt atgcatgttt ttttcaactc ttatttttaa ctttctactt cattataggt    3240
aaatatgaat ataattaaaa aaacagtaaa tccttttagg ggaatctgaa atgccttaat    3300
attaacttga taaccaaag gaatttacat attacatact tcagactttt gatataaatg     3360
ttcttaaact atgagtttaa gcactgccta tggataaaga ctcacacact ctcacatgta    3420
cacacacacg catgagaatt tcttttaca ttgaaaaact ctttcattta attcaaatgc     3480
tatttttccca ttataatagc attatttgga agacttaacc agtatcaatt tgaaatgctg   3540
atttaagtcc ccaaggatga aaaatacatt ttaaaaatta ttttgttgga gaggagtggc    3600
```

```
atgtgattca aaagagcatt gttggaaaat gctactgtgg ggcttagaag aatgatgttt    3660
ggtttggtat gctgctaact agttgtaaga ctttacaaat cactttgcca tctgtacctc    3720
tcaattattc ctctataaaa tatggagata ataataccta tctgatcaga ctttgcccca    3780
tgaattagtt tttaaaagat aaagactgaa gtatgaaagt gcttttgtca ccccaaatgc    3840
aattgaccca tgcaaaatat tagcatgaat ttatttaatc acataaaagt catgaagacc    3900
agccagattt tcaagcttca ttctgtttca ttcagttata ttccaaaatt caaatgatca    3960
cattttattc tttctcaaaa aaaaaagtt tttttaaatt aaaaaaggaa ttgtttcctt    4020
cacagctatg aataagcttt caggttttat taaaacctag aggaaaaaat caggaatgac    4080
ctgaatctca acccaaatat taaacaaaat ccacataatc cctcatttca atttccaatt    4140
ccattaaggg accctctctt tttggatggc agagatggtt ttttaatgaa atcccaccat    4200
ctatctgagt gagtctggca ggcttttag ttcctgagtt aaatttgtaa tagaaccaag    4260
gcaatgctgc tgactttgat atgtatgact cagtctttca atatgtggtt ttcaaaaaat    4320
tgttgaagac gtgacttcat agcaatatat agagaataaa ttaaaatcag cagattgagt    4380
tttcaacatt gcaaaatcag ttttttacct ctttcctacc aatttcacat tttgcagaaa    4440
cttgttcaca tttccaacaa tatcagaatt agaaaacagt tcagataaca agaaagatta    4500
aaaattaggg aaattctgat atcaccataa agcactattt tacatttaga gattacattt    4560
aagataaagt catcatacac aaaaacaata atatttata actttctcta taaggtccgc    4620
atatactgta tatattgaaa caatctgaat gactagtaga tttcatatga ccattgttat    4680
ttccactttc tccaatactt gtattttatg ctacatgtaa tgaagttgga cctttttatt    4740
atttagtaat tcctatatgt tcctatactt ttcattttca agatgattgc tctattgttt    4800
catgttgttt ctagcaatat atctccatga gatatgcact ttgtttcata ttgaaaagta    4860
taaaatttat ctttcaattc ctgtgtgtgt atcctatggt tatctgtatg tattattttc    4920
tattctaata aaatttataa caagcaaaaa aaaaaaaaaa aaa                      4963
```

<210> SEQ ID NO 26
<211> LENGTH: 1028
<212> TYPE: PRT
<213> ORGANISM: Homo sapiens
<220> FEATURE:
<221> NAME/KEY: misc_feature
<222> LOCATION: (1)..(1028)
<223> OTHER INFORMATION: contactin-3 precursor

<400> SEQUENCE: 26

```
Met Met Phe Pro Trp Lys Gln Leu Ile Leu Leu Ser Phe Ile Gly Cys
1               5                   10                  15

Leu Gly Gly Glu Leu Leu Leu Gln Gly Pro Val Phe Ile Lys Glu Pro
            20                  25                  30

Ser Asn Ser Ile Phe Pro Val Gly Ser Glu Asp Lys Lys Ile Thr Leu
        35                  40                  45

His Cys Glu Ala Arg Gly Asn Pro Ser Pro His Tyr Arg Trp Gln Leu
    50                  55                  60

Asn Gly Ser Asp Ile Asp Met Ser Met Glu His Arg Tyr Lys Leu Asn
65                  70                  75                  80

Gly Gly Asn Leu Val Val Ile Asn Pro Asn Arg Asn Trp Asp Thr Gly
                85                  90                  95

Thr Tyr Gln Cys Phe Ala Thr Asn Ser Leu Gly Thr Ile Val Ser Arg
            100                 105                 110
```

```
Glu Ala Lys Leu Gln Phe Ala Tyr Leu Glu Asn Phe Lys Thr Lys Met
            115                 120                 125

Arg Ser Thr Val Ser Val Arg Glu Gly Gln Gly Val Val Leu Leu Cys
        130                 135                 140

Gly Pro Pro His Ser Gly Glu Leu Ser Tyr Ala Trp Ile Phe Asn
145                 150                 155                 160

Glu Tyr Pro Ser Phe Val Glu Glu Asp Ser Arg Arg Phe Val Ser Gln
                165                 170                 175

Glu Thr Gly His Leu Tyr Ile Ser Lys Val Glu Pro Ser Asp Val Gly
            180                 185                 190

Asn Tyr Thr Cys Val Val Thr Ser Met Val Thr Asn Ala Arg Val Leu
        195                 200                 205

Gly Ser Pro Thr Pro Leu Val Leu Arg Ser Asp Gly Val Met Gly Glu
    210                 215                 220

Tyr Glu Pro Lys Ile Glu Val Gln Phe Pro Glu Thr Leu Pro Ala Ala
225                 230                 235                 240

Lys Gly Ser Thr Val Lys Leu Glu Cys Phe Ala Leu Gly Asn Pro Ile
                245                 250                 255

Pro Gln Ile Asn Trp Arg Arg Ser Asp Gly Leu Pro Phe Ser Ser Lys
            260                 265                 270

Ile Lys Leu Arg Lys Phe Ser Gly Val Leu Glu Ile Pro Asn Phe Gln
        275                 280                 285

Gln Glu Asp Ala Gly Ser Tyr Glu Cys Ile Ala Glu Asn Ser Arg Gly
    290                 295                 300

Lys Asn Val Ala Arg Gly Arg Leu Thr Tyr Tyr Ala Lys Pro His Trp
305                 310                 315                 320

Val Gln Leu Ile Lys Asp Val Glu Ile Ala Val Glu Asp Ser Leu Tyr
                325                 330                 335

Trp Glu Cys Arg Ala Ser Gly Lys Pro Lys Pro Ser Tyr Arg Trp Leu
            340                 345                 350

Lys Asn Gly Ala Ala Leu Val Leu Glu Glu Arg Thr Gln Ile Glu Asn
        355                 360                 365

Gly Ala Leu Thr Ile Ser Asn Leu Ser Val Thr Asp Ser Gly Met Phe
    370                 375                 380

Gln Cys Ile Ala Glu Asn Lys His Gly Leu Val Tyr Ser Ser Ala Glu
385                 390                 395                 400

Leu Lys Val Val Ala Ser Ala Pro Asp Phe Ser Lys Asn Pro Met Lys
                405                 410                 415

Lys Leu Val Gln Val Gln Val Gly Ser Leu Val Ser Leu Asp Cys Lys
            420                 425                 430

Pro Arg Ala Ser Pro Arg Ala Leu Ser Ser Trp Lys Lys Gly Asp Val
        435                 440                 445

Ser Val Gln Glu His Glu Arg Ile Ser Leu Leu Asn Asp Gly Gly Leu
    450                 455                 460

Lys Ile Ala Asn Val Thr Lys Ala Asp Ala Gly Thr Tyr Thr Cys Met
465                 470                 475                 480

Ala Glu Asn Gln Phe Gly Lys Ala Asn Gly Thr Thr His Leu Val Val
                485                 490                 495

Thr Glu Pro Thr Arg Ile Thr Leu Ala Pro Ser Asn Met Asp Val Ser
            500                 505                 510

Val Gly Glu Ser Val Ile Leu Pro Cys Gln Val Gln His Asp Pro Leu
        515                 520                 525
```

-continued

Leu Asp Ile Ile Phe Thr Trp Tyr Phe Asn Gly Ala Leu Ala Asp Phe
530                 535                 540

Lys Lys Asp Gly Ser His Phe Glu Lys Val Gly Gly Ser Ser Ser Gly
545                 550                 555                 560

Asp Leu Met Ile Arg Asn Ile Gln Leu Lys His Ser Gly Lys Tyr Val
            565                 570                 575

Cys Met Val Gln Thr Gly Val Asp Ser Val Ser Ala Ala Asp Leu
            580                 585                 590

Ile Val Arg Gly Ser Pro Gly Pro Glu Asn Val Lys Val Asp Glu
    595                 600                 605

Ile Thr Asp Thr Thr Ala Gln Leu Ser Trp Lys Glu Gly Lys Asp Asn
610                 615                 620

His Ser Pro Val Ile Ser Tyr Ser Ile Gln Ala Arg Thr Pro Phe Ser
625                 630                 635                 640

Val Gly Trp Gln Thr Val Thr Val Pro Glu Val Ile Asp Gly Lys
            645                 650                 655

Thr His Thr Ala Thr Val Val Glu Leu Asn Pro Trp Val Glu Tyr Glu
            660                 665                 670

Phe Arg Val Val Ala Ser Asn Lys Ile Gly Gly Gly Glu Pro Ser Leu
    675                 680                 685

Pro Ser Glu Lys Val Arg Thr Glu Glu Ala Val Pro Glu Val Pro Pro
690                 695                 700

Ser Glu Val Asn Gly Gly Gly Gly Ser Arg Ser Glu Leu Val Ile Thr
705                 710                 715                 720

Trp Asp Pro Val Pro Glu Glu Leu Gln Asn Gly Glu Gly Phe Gly Tyr
            725                 730                 735

Val Val Ala Phe Arg Pro Leu Gly Val Thr Thr Trp Ile Gln Thr Val
            740                 745                 750

Val Thr Ser Pro Asp Thr Pro Arg Tyr Val Phe Arg Asn Glu Ser Ile
    755                 760                 765

Val Pro Tyr Ser Pro Tyr Glu Val Lys Val Gly Val Tyr Asn Asn Lys
770                 775                 780

Gly Glu Gly Pro Phe Ser Pro Val Thr Thr Val Phe Ser Ala Glu Glu
785                 790                 795                 800

Glu Pro Thr Val Ala Pro Ser Gln Val Ser Ala Asn Ser Leu Ser Ser
            805                 810                 815

Ser Glu Ile Glu Val Ser Trp Asn Thr Ile Pro Trp Lys Leu Ser Asn
            820                 825                 830

Gly His Leu Leu Gly Tyr Glu Val Arg Tyr Trp Asn Gly Gly Gly Lys
    835                 840                 845

Glu Glu Ser Ser Ser Lys Met Lys Val Ala Gly Asn Glu Thr Ser Ala
850                 855                 860

Arg Leu Arg Gly Leu Lys Ser Asn Leu Ala Tyr Tyr Thr Ala Val Arg
865                 870                 875                 880

Ala Tyr Asn Ser Ala Gly Ala Gly Pro Phe Ser Ala Thr Val Asn Val
            885                 890                 895

Thr Thr Lys Lys Thr Pro Pro Ser Gln Pro Pro Gly Asn Val Val Trp
            900                 905                 910

Asn Ala Thr Asp Thr Lys Val Leu Leu Asn Trp Glu Gln Val Lys Ala
    915                 920                 925

Met Glu Asn Glu Ser Glu Val Thr Gly Tyr Lys Val Phe Tyr Arg Thr
930                 935                 940

Ser Ser Gln Asn Asn Val Gln Val Leu Asn Thr Asn Lys Thr Ser Ala

-continued

```
            945                 950                 955                 960

Glu Leu Val Leu Pro Ile Lys Glu Asp Tyr Ile Ile Glu Val Lys Ala
                965                 970                 975

Thr Thr Asp Gly Gly Asp Gly Thr Ser Ser Glu Gln Ile Arg Ile Pro
                980                 985                 990

Arg Ile Thr Ser Met Asp Ala Arg Gly Ser Thr Ser Ala Ile Ser Asn
            995                 1000                1005

Val His Pro Met Ser Ser Tyr Met Pro Ile Val Leu Phe Leu Ile
    1010                1015                1020

Val Tyr Val Leu Trp
1025
```